United States Patent
Bindschaedler et al.

(10) Patent No.: US 9,732,051 B2
(45) Date of Patent: Aug. 15, 2017

(54) ISOTHIAZOLINE COMPOUNDS FOR COMBATING INVERTEBRATE PESTS

(71) Applicants: Pascal Bindschaedler, Roemerberg (DE); Wolfgang Von Deyn, Neustadt (DE); Karsten Koerber, Eppelheim (DE); Florian Kaiser, Mannheim (DE); Michael Rack, Eppelheim (DE); Deborah L. Culbertson, Fuquay Varina, NC (US); Paul Neese, Apex, NC (US); Franz Josef Braun, Durham, NC (US)

(72) Inventors: Pascal Bindschaedler, Roemerberg (DE); Wolfgang Von Deyn, Neustadt (DE); Karsten Koerber, Eppelheim (DE); Florian Kaiser, Mannheim (DE); Michael Rack, Eppelheim (DE); Deborah L. Culbertson, Fuquay Varina, NC (US); Paul Neese, Apex, NC (US); Franz Josef Braun, Durham, NC (US)

(73) Assignee: BASF SE, Ludwigshafen (DE)

( * ) Notice: Subject to any disclaimer, the term of this patent is extended or adjusted under 35 U.S.C. 154(b) by 7 days.

(21) Appl. No.: 14/366,161

(22) PCT Filed: Dec. 21, 2012

(86) PCT No.: PCT/EP2012/076539
§ 371 (c)(1),
(2) Date: Jun. 17, 2014

(87) PCT Pub. No.: WO2013/092943
PCT Pub. Date: Jun. 27, 2013

(65) Prior Publication Data
US 2014/0364466 A1 Dec. 11, 2014

Related U.S. Application Data

(60) Provisional application No. 61/579,676, filed on Dec. 23, 2011.

(51) Int. Cl.
*C07D 275/02* (2006.01)
*C07D 417/04* (2006.01)
*C07D 275/03* (2006.01)
*A01N 43/80* (2006.01)

(52) U.S. Cl.
CPC ........... *C07D 275/02* (2013.01); *A01N 43/80* (2013.01); *C07D 275/03* (2013.01); *C07D 417/04* (2013.01)

(58) Field of Classification Search
CPC .................................................. C07D 275/02
USPC ....................................................... 548/206
See application file for complete search history.

(56) References Cited

U.S. PATENT DOCUMENTS 3,917,698 A 11/1975 Breslow
6,313,344 B1 11/2001 Trah et al.
6,521,643 B1 2/2003 Tomishima et al.
9,078,444 B2 7/2015 Cassayre et al.
2003/0119806 A1 6/2003 Lindell et al.
2004/0014801 A1 1/2004 Cohen et al.
2004/0110637 A1 6/2004 Ziemer et al.
2009/0023923 A1 1/2009 Mizukoshi et al.
2009/0156643 A1 6/2009 Mita et al.
2010/0144797 A1 6/2010 Mita et al.
2010/0144808 A1 6/2010 Mita et al.
2010/0160683 A1 6/2010 Matoba et al.
2010/0286175 A1 11/2010 Grammenos et al.
2011/0172414 A1 7/2011 Mita et al.

FOREIGN PATENT DOCUMENTS

| CA | 2 547 744 | 12/2006 |
| CH | 577487 | 7/1976 |
| CH | 595365 | 2/1978 |
| CH | 608011 | 12/1978 |
| CN | 1 927 860 | 3/2007 |

(Continued)

OTHER PUBLICATIONS

Chemical Abstracts Registry No. 1187747-84-7, CA 151:381227, 2009.*
Gantla et al., Oriental Journal of Chemistry, (2009), 25(1), pp. 153-157.*
Belen'Kii et al, Database: Beilstein, XP002580907 database accession No. 1988095, Russian Chem. Bull., (1997), pp. 101-104, vol. 46, No. 1.
"DMP 754 Roxifiban Acetate", Drugs of the Future, (1998), pp. 707-711, vol. 23(7).
Hosking, M., et al., "Roxifiban DuPont", Current Opinion in Cardiovascular, Pulmonary & Renal Investigational Drugs, (2000), pp. 165-171, vol. 2(2).
Kaugars, G. et al., "Miticidal activity of benzoyl chloride phenylhydrazones", Journal of Agriculture and Food Chem., (1973), pp. 647-650, vol. 21, No. 4.

(Continued)

*Primary Examiner* — Laura L. Stockton
(74) *Attorney, Agent, or Firm* — Brinks Gilson & Lione

(57) ABSTRACT

The present invention relates to isothiazoline compounds of formula I

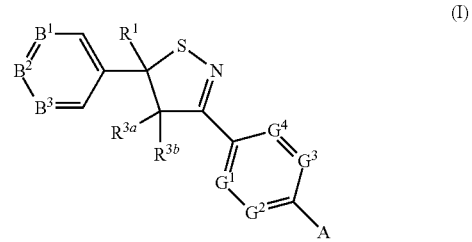

(I)

wherein the variables are as defined in the claims or the description, which are useful for combating or controlling invertebrate pests, in particular arthropod pests and nematodes, and to a method for producing them. The invention also relates to a method for controlling invertebrate pests by using these compounds and to plant propagation material and to an agricultural and a veterinary composition comprising said compounds.

33 Claims, No Drawings

(56) References Cited

FOREIGN PATENT DOCUMENTS

| | | |
|---|---|---|
| DE | 10 2004 010 086 | 9/2004 |
| EP | 0 539 676 | 5/1993 |
| EP | 1 538 138 | 6/2005 |
| EP | 1 731 512 | 12/2006 |
| EP | 1932836 | 6/2008 |
| EP | 1 997 813 | 12/2008 |
| EP | 2 151 437 | 2/2010 |
| EP | 2 186 804 | 5/2010 |
| EP | 2199287 | 6/2010 |
| JP | 8 217754 | 8/1996 |
| JP | 11-505213 | 5/1999 |
| JP | 2007 016017 | 1/2007 |
| JP | 2007 106756 | 4/2007 |
| JP | 2007 308471 | 11/2007 |
| JP | 2008 239611 | 10/2008 |
| JP | 2008-260691 | 10/2008 |
| JP | 2009 108046 | 5/2009 |
| JP | 201024206 | 2/2010 |
| JP | 2010-531893 | 9/2010 |
| JP | 201120955 | 2/2011 |
| JP | 2011212522 | 10/2011 |
| WO | WO 88/05046 | 7/1988 |
| WO | WO 88/06583 | 9/1988 |
| WO | WO 96/33180 | 10/1996 |
| WO | WO 97/23212 | 7/1997 |
| WO | WO 00/61009 | 10/2000 |
| WO | WO 01/17964 | 3/2001 |
| WO | WO 02/068392 | 9/2002 |
| WO | WO 03/022808 | 3/2003 |
| WO | WO 03/062222 | 7/2003 |
| WO | WO 03/067987 | 8/2003 |
| WO | WO 2004/018410 | 3/2004 |
| WO | WO 2004/056735 | 7/2004 |
| WO | WO 2004/060371 | 7/2004 |
| WO | WO 2004/060865 | 7/2004 |
| WO | WO 2005/036961 | 4/2005 |
| WO | WO 2005/085216 | 9/2005 |
| WO | WO 2006/010570 | 2/2006 |
| WO | WO 2006/021833 | 3/2006 |
| WO | WO 2006/065659 | 6/2006 |
| WO | WO 2007/026965 | 3/2007 |
| WO | WO 2007/070606 | 6/2007 |
| WO | WO 2007/074789 | 7/2007 |
| WO | WO 2007/075459 | 7/2007 |
| WO | WO 2007/079162 | 7/2007 |
| WO | WO 2007/081019 | 7/2007 |
| WO | WO 2007/093599 | 8/2007 |
| WO | WO 2007/094313 | 8/2007 |
| WO | WO 2007/105814 | 9/2007 |
| WO | WO 2007/112275 | 10/2007 |
| WO | WO 2007/123855 | 11/2007 |
| WO | WO 2007/125984 | 11/2007 |
| WO | WO 2008/012027 | 1/2008 |
| WO | WO 2008/019760 | 2/2008 |
| WO | WO 2008/022937 | 2/2008 |
| WO | WO 2008/070831 | 6/2008 |
| WO | WO 2008/108448 | 9/2008 |
| WO | WO 2008/122375 | 10/2008 |
| WO | WO 2008/126665 | 10/2008 |
| WO | WO 2008/130651 | 10/2008 |
| WO | WO 2008/154528 | 12/2008 |
| WO | WO 2009/002809 | 12/2008 |
| WO | WO 2009/003075 | 12/2008 |
| WO | WO 2009/005015 | 1/2009 |
| WO | WO 2009/022746 | 2/2009 |
| WO | WO 2009/025983 | 2/2009 |
| WO | WO 2009/035004 | 3/2009 |
| WO | WO 2009/045999 | 4/2009 |
| WO | WO 2009/049846 | 4/2009 |
| WO | WO 2009/051956 | 4/2009 |
| WO | WO 2009/077197 | 6/2009 |
| WO | WO 2009/080250 | 7/2009 |
| WO | WO 2009/112275 | 9/2009 |
| WO | WO 2009/126668 | 10/2009 |
| WO | WO 2010/003877 | 1/2010 |
| WO | WO 2010/003923 | 1/2010 |
| WO | WO 2010/020521 | 2/2010 |
| WO | WO 2010/020522 | 2/2010 |
| WO | WO 2010/072602 | 7/2010 |
| WO | WO 2010/072781 | 7/2010 |
| WO | WO 2010/090344 | 8/2010 |
| WO | WO 2010/112545 | 10/2010 |
| WO | WO 2011/073444 | 6/2011 |
| WO | WO 2011/092287 | 8/2011 |
| WO | WO 2011/067272 | 9/2011 |
| WO | WO 2013/037626 | 3/2013 |

OTHER PUBLICATIONS

Kiriyama, K. et al., "Insecticidal and Neuroblocking Activities of Acetamiprid and Related Compounds", Journal of Pesticide Science, (2003), pp. 8-17, vol. 28.

Wierenga, J. et al., "Insecticidal activity of N-arylalkylbenzhydrolpiperidines", Pest Management Science, (2002), pp. 1266-1272, vol. 58.

Walters, Matthew J. et al., "The preparation of 5-Aryl-5-methyl-4,5-dihydroisoxazoles from dilithiated C($\alpha$), O-oximes and Select Acetyl Ketones", Synthetic Communications, 2003, p. 4163-4171, vol. 33, No. 23.

International Search Report dated Apr. 10, 2013, prepared in International Application No. PCT/EP2012/076539.

International Preliminary Report on Patentability dated Jun. 24, 2014, prepared in International Application No. PCT/EP2012/076539.

* cited by examiner

ISOTHIAZOLINE COMPOUNDS FOR COMBATING INVERTEBRATE PESTS

This application is a National Stage application of International Application No. PCT/EP2012/076539, filed Dec. 21, 2012, which claims the benefit of U.S. Provisional Application No. 61/579,676, filed Dec. 23, 2011, the entire contents of which are hereby incorporated herein by reference.

The present invention relates to isothiazoline compounds which are useful for combating or controlling invertebrate pests, in particular arthropod pests and nematodes, and to a method for producing them. The invention also relates to a method for controlling invertebrate pests by using these compounds and to plant propagation material and to an agricultural and a veterinary composition comprising said compounds.

Invertebrate pests and in particular arthropods and nematodes destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating invertebrate pests, in particular insects, arachnids and nematodes.

Related insecticidal aryl azoline compounds are described in WO 2011/092287, WO 2011/073444, WO 2010/090344, WO 2009/112275 and WO 97/23212. However, these documents do not describe compounds having the characteristic substituents and substituents' arrangement as claimed in the present invention.

It is an object of the present invention to provide compounds that have a good pesticidal activity, in particular insecticidal activity, and show a broad activity spectrum against a large number of different invertebrate pests, especially against difficult to control arthropod pests and/or nematodes.

The object of the present invention was moreover to provide compounds which are less persistent, bioaccumulative and/or toxic than the compounds of the prior art. Especially isoxazoline insecticides show a high persistency in the soil and thus accumulate there.

It has been found that these objectives can be achieved by isothiazoline compounds of the formula I below, by their steroisomers and by their salts, in particular their agriculturally or veterinarily acceptable salts.

Therefore, in a first aspect, the invention relates to isothiazoline compounds of formula I

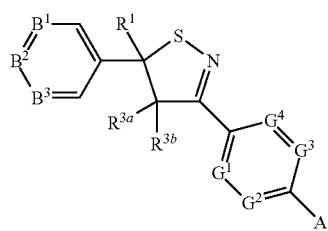

wherein
A is a group $A^1$, $A^2$, $A^3$ or $A^4$;
  wherein
  $A^1$ is selected from the group consisting of —C(=NR$^6$)R$^8$, —S(O)$_n$R$^9$ and —N(R$^5$)R$^6$;

$A^2$ is a group of following formula:

wherein
# denotes the bond to the aromatic ring of formula (I);
W is selected from O and S;
Y is selected from hydrogen, —N(R$^5$)R$^6$ and —OR$^9$;
$A^3$ is a group of following formula:

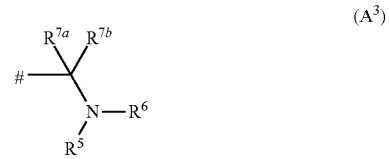

wherein
# denotes the bond to the aromatic ring of formula (I);
$A^4$ is a 3-, 4-, 5-, 6- or 7-membered saturated, partially unsaturated or maximally unsaturated heteromonocyclic ring containing 1, 2, 3 or 4 heteroatoms or heteroatom groups selected from N, O, S, NO, SO and SO$_2$, as ring members, or is a 8-, 9- or 10-membered saturated, partially unsaturated or maximally unsaturated heterobicyclic ring containing 1, 2, 3 or 4 heteroatoms or heteroatom groups selected from N, O, S, NO, SO and SO$_2$, as ring members, where the heteromonocyclic or heterobicyclic ring is optionally substituted with one or more, preferably 1, 2 or 3, in particular 1, substituents R$^{11}$;
$B^1$, $B^2$ and $B^3$ are each independently selected from the group consisting of N and CR$^2$, with the proviso that at most two of $B^1$, $B^2$ and $B^3$ are N;
$G^1$, $G^2$, $G^3$ and $G^4$ are each independently selected from the group consisting of N and CR$^4$, with the proviso that at most two of $G^1$, $G^2$, $G^3$ and $G^4$ are N;
$R^1$ is selected from the group consisting of C$_1$-C$_4$-alkyl, C$_1$-C$_4$-haloalkyl, C$_1$-C$_4$-alkoxy-C$_1$-C$_4$-alkyl, C$_1$-C$_4$-haloalkoxy-C$_1$-C$_4$-alkyl-, C$_2$-C$_4$-alkenyl, C$_2$-C$_4$-haloalkenyl, C$_2$-C$_4$-alkynyl, C$_2$-C$_4$-haloalkynyl, C$_3$-C$_6$-cycloalkyl, C$_3$-C$_6$-halocycloalkyl and —C(=O)OR$^{15}$;
each R$^2$ is independently selected from the group consisting of hydrogen, halogen, cyano, azido, nitro, —SCN, —SF$_5$, C$_1$-C$_6$-alkyl, C$_3$-C$_8$-cycloalkyl, C$_2$-C$_6$-alkenyl, C$_2$-C$_6$-alkynyl, wherein the four last mentioned aliphatic and cycloaliphatic radicals may be partially or fully halogenated and/or may be substituted by one or more, preferably 1, 2 or 3, in particular 1, radicals R$^8$, —Si(R$^{12}$)$_3$, —OR$^9$, —S(O)$_n$R$^9$, —NR$^{10a}$R$^{10b}$,
phenyl which may be substituted by 1, 2, 3, 4 or 5, preferably 1, 2 or 3, in particular 1, radicals R$^{11}$, and a 3-, 4-, 5-, 6- 7-, 8-, 9- or 10-membered saturated, partially unsaturated or maximally unsaturated heteromonocyclic or heterobicyclic ring containing 1, 2, 3 or 4 heteroatoms or heteroatom groups selected from N, O, S, NO, SO and SO$_2$, as ring members, where the heteromono- or heterobicyclic ring may be substituted by one or more, preferably 1, 2 or 3, in particular 1, radicals R$^1$;

$R^{3a}$, $R^{3b}$ are each independently selected from the group consisting of hydrogen, halogen, $-CO_2R^{3d}$, hydroxyl, $C_1$-$C_3$-alkyl, $C_1$-$C_3$-haloalkyl, $C_2$-$C_3$-alkenyl, $C_2$-$C_3$-alkynyl, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkylsulfonyl and $C_1$-$C_3$-haloalkylsulfonyl; or $R^{3a}$ and $R^{3b}$ together form a group $=O$, $=C(R^{3c})_2$, $=NOH$ or $=NOCH_3$;

each $R^{3c}$ is independently selected from the group consisting of hydrogen, halogen, $CH_3$ and $CF_3$;

$R^{3d}$ is selected from the group consisting of hydrogen, $C_1$-$C_6$-alkyl and $C_1$-$C_3$-alkyloxy-$C_1$-$C_3$-alkyl-;

each $R^4$ is independently selected from the group consisting of hydrogen, halogen, cyano, azido, nitro, $-SCN$, $-SF_5$, $C_1$-$C_6$-alkyl which may be partially or fully halogenated and/or may be substituted by one or more, preferably 1, 2 or 3, in particular 1, radicals $R^8$, $C_3$-$C_8$-cycloalkyl which may be partially or fully halogenated and/or may be substituted by one or more, preferably 1, 2 or 3, in particular 1, radicals $R^8$, $C_2$-$C_6$-alkenyl which may be partially or fully halogenated and/or may be substituted by one or more, preferably 1, 2 or 3, in particular 1, radicals $R^8$, $C_2$-$C_6$-alkynyl which may be partially or fully halogenated and/or may be substituted by one or more, preferably 1, 2 or 3, in particular 1, radicals $R^8$, $-Si(R^{12})_3$, $-OR^9$, $-S(O)_nR^9$, $-NR^{10a}R^{10b}$ phenyl which may be substituted by 1, 2, 3, 4 or 5, preferably 1, 2 or 3, in particular 1, radicals $R^{11}$, and a 3-, 4-, 5-, 6- 7-, 8-, 9- or 10-membered saturated, partially unsaturated or maximally unsaturated heteromonocyclic or heterobicyclic ring containing 1, 2, 3 or 4 heteroatoms or heteroatom groups selected from N, O, S, NO, SO and $SO_2$, as ring members, where the heteromonocyclic or heterobicyclic ring may be substituted by one or more, preferably 1, 2 or 3, in particular 1, radicals $R^{11}$;

each $R^5$ is independently selected from the group consisting of hydrogen, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted with one or more, preferably 1, 2 or 3, in particular 1, substituents $R^8$, and $-S(O)_nR^9$, each $R^6$ is independently selected from the group consisting of hydrogen, cyano, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted by one or more, preferably 1, 2 or 3, in particular 1, substituents $R^8$, $-OR^9$, $-NR^{10a}R^{10b}$, $-S(O)_nR^9$, $-C(=O)NR^{10a}N(R^{10a}R^{10b})$, $-Si(R^{12})_3$, $-C(=O)R^8$, phenyl which may be substituted with 1, 2, 3, 4, or 5, preferably 1, 2 or 3, in particular 1, substituents $R^{11}$, and a 3-, 4-, 5-, 6-, 7-, 8-, 9- or 10-membered saturated, partially unsaturated or maximally unsaturated heteromonocyclic or heterobicyclic ring containing 1, 2, 3 or 4 heteroatoms or heteroatom groups independently selected from N, O, S, NO, SO and $SO_2$, as ring members, where the heteromonocyclic or heterobicyclic ring may be substituted with one or more, preferably 1, 2 or 3, in particular 1, substituents $R^{11}$;

or $R^5$ and $R^6$, together with the nitrogen atom to which they are bound, form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O, S, N, SO, $SO_2$, $C=O$ and $C=S$ as ring members, wherein the heterocyclic ring may be substituted with 1, 2, 3, 4 or 5, preferably 1, 2 or 3, in particular 1, substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the aliphatic or cycloaliphatic moieties in the twelve last-mentioned radicals may be substituted by one or more, preferably 1, 2 or 3, in particular 1, radicals $R^8$, and phenyl which may be substituted with 1, 2, 3, 4 or 5 substituents $R^{11}$;

or $R^5$ and $R^6$ together form a group $=C(R^8)_2$, $=S(O)_m(R^9)_2$, $=NR^{10a}$ or $=NOR^9$;

$R^{7a}$, $R^{7b}$ are each independently selected from the group consisting of hydrogen, halogen, cyano, $C_1$-$C_6$-alkyl, $C_3$-$C_8$-cycloalkyl, $C_2$-$C_6$-alkenyl and $C_2$-$C_6$-alkynyl, wherein the four last-mentioned aliphatic and cycloaliphatic radicals may be partially or fully halogenated and/or may be substituted by one or more, preferably 1, 2 or 3, in particular 1, radicals $R^8$;

each $R^8$ is independently selected from the group consisting of cyano, azido, nitro, $-SCN$, $-SF_5$, $C_3$-$C_8$-cycloalkyl, $C_3$-$C_8$-halocycloalkyl, where the cycloaliphatic moieties in the two last-mentioned radicals may be substituted by one or more, preferably 1, 2 or 3, in particular 1, radicals $R^{13}$;

$-Si(R^{12})_3$, $-OR^9$, $-OSO_2R^9$, $-S(O)_nR^9$, $-N(R^{10a})R^{10b}$, $-C(=O)N(R^{10a})R^{10b}$, $-C(=S)N(R^{10a})R^{10b}$, $-C(=O)OR^9$, phenyl, optionally substituted with 1, 2, 3, 4 or 5, preferably 1, 2 or 3, in particular 1, substituents $R^{16}$, and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more, preferably 1, 2 or 3, in particular 1, substituents $R^{16}$, or two $R^8$ present on the same carbon atom of an alkyl, alkenyl, alkynyl or cycloalkyl group together form a group $=O$, $=C(R^{13})_2$; $=S$; $=S(O)_m(R^{15})_2$, $=S(O)_m R^{15}N(R^{14a})R^{14b}$, $=NR^{10a}$, $=NOR^9$; or $=NN(R^{10a})R^{10b}$;

or two radicals $R^8$, together with the carbon atoms of an alkyl, alkenyl, alkynyl or cycloalkyl group which they are bonded to, form a 3-, 4-, 5-, 6-, 7- or 8-membered saturated or partially unsaturated carbocyclic or heterocyclic ring, where the heterocyclic ring comprises 1, 2, 3 or 4 heteroatoms or heteroatom groups independently selected from N, O, S, NO, SO and $SO_2$, as ring members, and where the carbocyclic or heterocyclic ring is optionally substituted with one or more, preferably 1, 2 or 3, in particular 1, substituents $R^{16}$; and $R^8$ as a substituent on a cycloalkyl ring is additionally selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl and $C_2$-$C_6$-haloalkynyl, where the aliphatic moieties in these six radicals may be substituted by one or more, preferably 1, 2 or 3, in particular 1, radicals $R^{13}$; and $R^8$ in the groups $-C(=NR^6)R^8$, $-C(=O)R^8$ and $=C(R^8)_2$ is additionally selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl and $C_2$-$C_6$-haloalkynyl, where the aliphatic moieties in the six last-mentioned radicals may be substituted by one or more, preferably 1, 2 or 3, in particular 1, radicals $R^{13}$;

each $R^9$ is independently selected from the group consisting of hydrogen, cyano, $C_1$-$C_6$-alkyl, $C_1$-$C_6$-haloalkyl, $C_3$-$C_8$-cycloalkyl, $C_3$-$C_8$-cycloalkyl-$C_1$-$C_4$-alkyl-, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, where the aliphatic and cycloaliphatic moieties in the nine last-mentioned radicals may be substituted by one or more, preferably 1, 2 or 3, in particular 1, radicals $R^{13}$
  $-C_1$-$C_6$-alkyl-$C(=O)OR^{15}$,   $-C_1$-$C_6$-alkyl-$C(=O)N(R^{14a})R^{14b}$,
  $-C_1$-$C_6$-alkyl-$C(=S)N(R^{14a})R^{14b}$,   $-C_1$-$C_6$-alkyl-$C(=NR^{14})N(R^{14a})R^{14b}$,
  $-Si(R^{12})_3$,   $-S(O)_nR^{15}$,   $-S(O)_nN(R^{14a})R^{14b}$,
  $-N(R^{10a})R^{10b}$,   $-N=C(R^{13})_2$,   $-C(=O)R^{13}$,
  $-C(=O)N(R^{14a})R^{14b}$,   $-C(=S)N(R^{14a})R^{14b}$,
  $-C(=O)OR^{15}$,
  phenyl, optionally substituted with 1, 2, 3, 4 or 5, preferably 1, 2 or 3, in particular 1, substituents $R^{16}$; and
  a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more, preferably 1, 2 or 3, in particular 1, substituents $R^{16}$; and
  $R^9$ in the groups $-S(O)_nR^9$ and $-OSO_2R^9$ is additionally selected from the group consisting of $C_1$-$C_6$-alkoxy and $C_1$-$C_6$-haloalkoxy;

$R^{10a}$, $R^{10b}$ are selected independently from one another from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, where the aliphatic and cycloaliphatic moieties in the eight last-mentioned radicals may be substituted by one or more radicals $R^{13}$; $C_1$-$C_6$-alkyl-$C(=O)OR^{15}$, $C_1$-$C_6$-alkyl-$C(=O)N(R^{14a})R^{14b}$, $-C_1$-$C_6$-alkyl-$C(=S)N(R^{14a})R^{14b}$, $-C_1$-$C_6$-alkyl-$C(=NR^{14})N(R^{14a})R^{14b}$, $C_1$-$C_6$-alkoxy, $C_1$-$C_6$-haloalkoxy, $C_1$-$C_6$-alkylthio, $C_1$-$C_6$-haloalkylthio,
  $-S(O)_nR^{15}$,   $-S(O)_nN(R^{14a})R^{14b}$,   $-C(=O)R^{13}$,
  $-C(=O)OR^{15}$, $-C(=O)N(R^{14a})R^{14b}$, $-C(=S)R^{13}$,
  $-C(=S)SR^{15}$, $-C(=S)N(R^{14a})R^{14b}$, $-C(=NR^{14})R^{13}$;
  phenyl, optionally substituted with 1, 2, 3 or 4, preferably 1, 2 or 3, in particular 1, substituents $R^{16}$; and
  a 3-, 4-, 5-, 6- or 7-membered saturated, partially unsaturated or maximally unsaturated heterocyclic ring comprising 1, 2, 3 or 4 heteroatoms or heteroatom groups selected from N, O, S, NO, SO and $SO_2$, as ring members, where the heterocyclic ring is optionally substituted with one or more, preferably 1, 2 or 3, in particular 1, substituents $R^{16}$;
or
$R^{10a}$ and $R^{10b}$ form together with the nitrogen atom they are bonded to a 3-, 4-, 5-, 6-, 7- or 8-membered saturated, partially unsaturated or maximally unsaturated heterocyclic ring, wherein the heterocyclic ring may additionally contain one or two heteroatoms or heteroatom groups selected from N, O, S, NO, SO and $SO_2$, as ring members, where the heterocyclic ring optionally carries one or more, preferably 1, 2 or 3, in particular 1, substituents selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, optionally substituted with 1, 2, 3, 4 or 5, preferably 1, 2 or 3, in particular 1, substituents $R^{16}$, and a 3-, 4-, 5-, 6,- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring optionally carries one or more, preferably 1, 2 or 3, in particular 1, substituents $R^{16}$; or $R^{10a}$ and $R^{10b}$ together form a group $=C(R^{13})_2$, $=S(O)_m(R^{15})_2$, $=S(O)_mR^{15}N(R^{14a})R^{14b}$, $=NR^{14}$ or $=NOR^{15}$;

$R^{11}$ is independently selected from the group consisting of halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted with one or more, preferably 1, 2 or 3, in particular 1, radicals $R^8$,
  $-OR^9$, $-NR^{10a}R^{10b}$, $-S(O)_nR^9$, $-Si(R^{12})_3$;
  phenyl, optionally substituted with 1, 2, 3, 4, or 5, preferably 1, 2 or 3, in particular 1, substituents selected independently from $R^{16}$; and
  a 3-, 4-, 5-, 6- or 7-membered saturated, partially unsaturated or maximally unsaturated aromatic heterocyclic ring comprising 1, 2, 3 or 4 heteroatoms or heteroatom groups selected from N, O, S, NO, SO and $SO_2$, as ring members, where the heterocyclic ring is optionally substituted with one or more, preferably 1, 2 or 3, in particular 1, substituents selected independently from $R^{16}$;
or two $R^{11}$ present on the same ring carbon atom of an unsaturated or partially unsaturated heterocyclic ring may together form a group $=O$, $=C(R^{13})_2$; $=S$; $=S(O)_m(R^{15})_2$; $=S(O)_mR^{15}N(R^{14a})R^{14b}$, $=NR^{14}$, $=NOR^{15}$, or $=NN(R^{14a})R^{14b}$;
or two $R^{11}$ bound on adjacent ring atoms form together with the ring atoms to which they are bound a saturated 3-, 4-, 5-, 6-, 7-, 8- or 9-membered ring, wherein the ring may contain 1 or 2 heteroatoms or heteroatom groups selected from O, S, N, $NR^{14}$, NO, SO and $SO_2$ and/or 1 or 2 groups selected from $C=O$, $C=S$ and $C=NR^{14}$ as ring members, and wherein the ring may be substituted by one or more, preferably 1, 2 or 3, in particular 1, radicals selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5, preferably 1, 2 or 3, in particular 1, radicals $R^{16}$, and a 3-, 4-, 5-, 6- or 7-membered saturated, partially unsaturated or maximally unsaturated heterocyclic ring containing 1, 2 or 3 heteroatoms or heteroatom groups selected from N, O, S, NO, SO and $SO_2$, as ring members, where the heterocyclic ring may be substituted by one or more, preferably 1, 2 or 3, in particular 1, radicals $R^{16}$;

each $R^{12}$ is independently selected from the group consisting of hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$- alkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, and phenyl, optionally substituted with 1, 2, 3, 4, or 5, preferably 1, 2 or 3, preferably 1 or 2, in particular 1, substituents $R^{16}$;

each $R^{13}$ is independently selected from the group consisting of cyano, nitro, —OH, —SH, —SCN, —$SF_5$, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, trimethylsilyl, triethylsilyl, tert-butyldimethylsilyl, $C_3$-$C_8$-cycloalkyl which may be unsubstituted, partially or fully halogenated and/or may carry 1 or 2, in particular 1, radicals selected from $C_1$-$C_4$-alkyl, $C_3$-$C_4$-cycloalkyl, $C_1$-$C_4$-alkoxy, $C_1$-$C_4$-haloalkoxy and oxo; phenyl, benzyl, phenoxy, where the phenyl moiety in the three last-mentioned radicals may be unsubstituted, partially or fully halogenated and/or carry 1, 2, 3, 4 or 5, preferably 1, 2 or 3, more preferably 1 or 2, in particular 1, substituents $R^{16}$; and a 3-, 4-, 5-, 6- or 7-membered saturated, partially unsaturated or maximally unsaturated heterocyclic ring containing 1, 2 or 3 heteroatoms or heteroatom groups selected from N, O, S, NO, SO and $SO_2$, as ring members, where the heterocyclic ring may be substituted by 1, 2 or 3, preferably 1 or 2, in particular 1, substituents $R^{16}$;

or two $R^{13}$ present on the same carbon atom (of an alkyl, alkenyl, alkynyl or cycloalkyl group) may together be =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl); and $R^{13}$ as a substituent on a cycloalkyl ring is additionally selected from the group consisting of $C_1$-$C_6$-alkyl, $C_2$-$C_6$-alkenyl and $C_2$-$C_6$-alkynyl, wherein the three last-mentioned aliphatic radicals may be unsubstituted, partially or fully halogenated and/or may carry 1 or 2, in particular 1, substituents selected from CN, $C_3$-$C_4$-cycloalkyl, $C_1$-$C_4$-alkoxy, $C_1$-$C_4$-haloalkoxy and oxo; and $R^{13}$ in the groups =C($R^{13}$)$_2$, —N=C($R^{13}$)$_2$, —C(=O)$R^{13}$, —C(=S)$R^{13}$ and —C(=N$R^{14}$)$R^{13}$ is additionally selected from the group consisting of hydrogen, halogen, $C_1$-$C_6$-alkyl, $C_2$-$C_6$-alkenyl and $C_2$-$C_6$-alkynyl, wherein the three last-mentioned aliphatic radicals may be unsubstituted, partially or fully halogenated and/or may carry 1 or 2, in particular 1, radicals selected from CN, $C_3$-$C_4$-cycloalkyl, $C_1$-$C_4$-alkoxy, $C_1$-$C_4$-haloalkoxy and oxo;

each $R^{14}$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2, in particular 1, radicals selected from CN, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_3$-$C_4$-cycloalkyl which may be substituted by 1 or 2, in particular 1, substituents selected from halogen and cyano; and oxo;

$C_3$-$C_8$-cycloalkyl which may be unsubstituted, partially or fully halogenated and/or may carry 1 or 2, in particular 1, radicals selected from $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_3$-$C_4$-cycloalkyl, $C_3$-$C_4$-cycloalkyl-$C_1$-$C_4$-alkyl-, where the cycloalkyl moiety in the two last-mentioned radicals may be substituted by 1 or 2, in particular 1, substituents selected from halogen and cyano; and oxo;

phenyl, benzyl, pyridyl, phenoxy, wherein the cyclic moieties in the four last-mentioned radicals may be unsubstituted and/or carry 1, 2 or 3, in particular 1, substituents selected from halogen, $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl; and a 3-, 4-, 5- or 6-membered saturated, partially unsaturated or maximally unsaturated heterocyclic ring comprising 1 or 2 heteroatoms or heteroatom groups selected from N, O, S, NO, SO and $SO_2$, as ring members, where the heterocyclic ring is optionally substituted with one or more substituents $R^{16}$;

$R^{14a}$ and $R^{14b}$, independently of each other, have one of the meanings given for $R^{14}$;

or $R^{14a}$ and $R^{14b}$, together with the nitrogen atom to which they are bound, form a 3-, 4-, 5-, 6- or 7-membered saturated, partially unsaturated or maximally unsaturated heterocyclic ring, wherein the heterocyclic ring may additionally contain 1 or 2 heteroatoms or heteroatom groups selected from N, O, S, NO, SO and $SO_2$, as ring members, where the heterocyclic ring optionally carries one or more, preferably 1, 2 or 3, in particular 1, substitutents selected from halogen, $C_1$-$C_4$-alkyl, $C_1$-$C_4$-haloalkyl, $C_1$-$C_4$-alkoxy and $C_1$-$C_4$-haloalkoxy;

or $R^{14a}$ and $R^{14}$ or $R^{14b}$ and $R^{14}$, together with the nitrogen atoms to which they are bound in the group —C(=N$R^{14}$)N($R^{14a}$)$R^{14b}$, form a 3-, 4-, 5-, 6- or 7-membered partially unsaturated or maximally unsaturated heterocyclic ring, wherein the heterocyclic ring may additionally contain 1 or 2 heteroatoms or heteroatom groups selected from N, O, S, NO, SO and $SO_2$, as ring members, where the heterocyclic ring optionally carries one or more, preferably 1, 2 or 3, in particular 1, substitutents selected from halogen, $C_1$-$C_4$-haloalkyl, $C_1$-$C_4$-alkoxy and $C_1$-$C_4$-haloalkoxy;

each $R^{15}$ is independently selected from the group consisting of hydrogen, cyano, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2, in particular 1, radicals selected from $C_3$-$C_4$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl and oxo; $C_3$-$C_8$-cycloalkyl which may be unsubstituted, partially or fully halogenated and/or may carry 1 or 2, in particular 1, radicals selected from $C_1$-$C_4$-alkyl, $C_3$-$C_4$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl and oxo;

phenyl, benzyl, pyridyl and phenoxy, wherein the four last-mentioned radicals may be unsubstituted, partially or fully halogenated and/or carry 1, 2 or 3, preferably 1 or 2 in particular 1, substituents selected from $C_1$-$C_6$- alkyl, $C_1$-$C_6$-haloalkyl, $C_1$-$C_6$-alkoxy, $C_1$-$C_6$-haloalkoxy and ($C_1$-$C_6$-alkoxy)carbonyl;

each $R^{16}$ is independently selected from the group consisting of halogen, nitro, cyano, —OH, —SH, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, trimethylsilyl, triethylsilyl, tert-butyldimethylsilyl;

$C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2, in particular 1, radicals selected from $C_3$-$C_4$-cycloalkyl, $C_1$-$C_4$-alkoxy, $C_1$-$C_4$-haloalkoxy and oxo;

$C_3$-$C_8$-cycloalkyl which may be unsubstituted, partially or fully halogenated and/or may carry 1 or 2, in particular 1, radicals selected from $C_1$-$C_4$-alkyl, $C_3$-$C_4$-cycloalkyl, $C_1$-$C_4$-alkoxy, $C_1$-$C_4$-haloalkoxy and oxo;

phenyl, benzyl, pyridyl and phenoxy, wherein the four last mentioned radicals may be unsubstituted, partially or fully halogenated and/or carry 1, 2 or 3, in particular 1, substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl;

or two $R^{16}$ present together on the same atom of an unsaturated or partially unsaturated ring may be =O, =S, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

or two $R^{16}$ on two adjacent carbon atoms form together with the carbon atoms they are bonded to a 4-, 5-, 6-, 7- or 8-membered saturated, partially unsaturated or maximally unsaturated ring, wherein the ring may contain 1 or 2 heteroatoms or heteroatom groups selected from N, O, S, NO, SO and $SO_2$, as ring members, and wherein the ring optionally carries one or more, preferably 1, 2 or 3, in particular 1, substituents selected from halogen, $C_1$-$C_4$-haloalkyl, $C_1$-$C_4$-alkoxy and $C_1$-$C_4$-haloalkoxy;

each n is independently 0, 1 or 2; and
each m is independently 0 or 1;
and the N-oxides, stereoisomers and agriculturally or veterinarily acceptable salts thereof.

The present invention also provides an agricultural composition comprising at least one compound of the formula I as defined herein and/or an agriculturally acceptable salt thereof and at least one liquid or solid carrier.

The present invention also provides a veterinary composition comprising at least one compound of the formula I as defined herein and/or a veterinarily acceptable salt thereof and at least one liquid or solid carrier.

The present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula I or a salt thereof as defined herein.

The present invention also relates to plant propagation material, in particular seed, comprising at least one compound of formula I and/or an agriculturally acceptable salt thereof as defined herein.

The present invention further relates to a method for treating or protecting an animal from infestation or infection by parasites which comprises bringing the animal in contact with a parasiticidally effective amount of a compound of the formula I or a veterinarily acceptable salt thereof as defined herein. Bringing the animal in contact with the compound I, its salt or the veterinary composition of the invention means applying or administering it to the animal.

The term "steroisomers" encompasses both optical isomers, such as enantiomers or diastereomers, the latter existing due to more than one center of chirality in the molecule, as well as geometrical isomers (cis/trans isomers).

Depending on the substitution pattern, the compounds of the formula I may have one or more centers of chirality, in which case they are present as mixtures of enantiomers or diastereomers. One center of chirality is the carbon ring atom of the isothiazoline ring carrying radical $R^1$. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof.

The term N-oxides relates to a form of compounds I in which at least one nitrogen atom is present in oxidized form (as NO).

The compounds of the present invention may be amorphous or may exist in one or more different crystalline states (polymorphs) which may have a different macroscopic properties such as stability or show different biological properties such as activities. The present invention includes both amorphous and crystalline compounds of the formula I, mixtures of different crystalline states of the respective compound I, as well as amorphous or crystalline salts thereof.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally acceptable salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH^{4+}$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy) ethylammonium, bis(2-hydroxyethyl)ammonium, benzyltrimethylammonium and benzl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

By the term "veterinarily acceptable salts" is meant salts of those cations or anions which are known and accepted in the art for the formation of salts for veterinary use. Suitable acid addition salts, e.g. formed by compounds of formula I containing a basic nitrogen atom, e.g. an amino group, include salts with inorganic acids, for example hydrochlorids, sulphates, phosphates, and nitrates and salts of organic acids for example acetic acid, maleic acid, dimaleic acid, fumaric acid, difumaric acid, methane sulfenic acid, methane sulfonic acid, and succinic acid.

The term "invertebrate pest" as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. The plant propagation materials may be treated prophylactically with a plant protection compound either at or before planting or transplanting. Said young plants may also be protected before transplantation by a total or partial treatment by immersion or pouring.

The term "plants" comprises any types of plants including "non-cultivated plants" and in particular "cultivated plants".

The term "non-cultivated plants" refers to any wild type species or related species or related genera of a cultivated plant.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyl-phenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e.g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); BtXtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the CryIF toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The organic moieties mentioned in the above definitions of the variables are—like the term halogen—collective terms for individual listings of the individual group members.

The prefix $C_n$-$C_m$ indicates in each case the possible number of carbon atoms in the group.

The term halogen denotes in each case fluorine, bromine, chlorine or iodine, in particular fluorine, chlorine or bromine.

The term "alkyl" as used herein and in the alkyl moieties of alkoxy, alkylthio, alkylsulfinyl, alkylsulfonyl, alkylcarbonyl, alkoxycarbonyl and the like refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl"), 1 to 6 ("$C_1$-$C_6$-alkyl"), 1 to 8 ("$C_1$-$C_8$-alkyl") or 1 to 10 ("$C_1$-$C_{10}$-alkyl") carbon atoms. $C_1$-$C_2$-Alkyl is methyl or ethyl. $C_1$-$C_3$-Alkyl is additionally propyl and isopropyl. $C_1$-$C_4$-Alkyl is additionally butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. $C_1$-$C_8$-Alkyl is additionally also, for example, heptyl, octyl, 2-ethylhexyl and positional isomers thereof. $C_1$-$C_{10}$-Alkyl is additionally also, for example, nonyl, decyl and positional isomers thereof.

The term "haloalkyl" as used herein, which is also expressed as "alkyl which is partially or fully halogenated", refers to straight-chain or branched alkyl groups having 1 to 2 ("$C_1$-$C_2$-haloalkyl"), 1 to 3 ("$C_1$-$C_3$-haloalkyl"), 1 to 4 ("$C_1$-$C_4$-haloalkyl"), 1 to 6 ("$C_1$-$C_6$-haloalkyl"), 1 to 8 ("$C_1$-$C_8$-haloalkyl") or 1 to 10 ("$C_1$-$C_{10}$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. $C_1$-$C_3$-haloalkyl is additionally, for example, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoropropyl, 1,1,1-trifluoroprop-2-yl, 3-chloropropyl and the like. Examples for $C_1$-$C_4$-haloalkyl are, apart those mentioned for $C_1$-$C_3$-haloalkyl, 4-chlorobutyl and the like.

"Halomethyl" is methyl in which 1, 2 or 3 of the hydrogen atoms are replaced by halogen atoms. Examples are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl"), 2 to 6 ("$C_2$-$C_6$-alkenyl"), 2 to 8 ("$C_2$-$C_8$-alkenyl") or 2 to 10 ("$C_2$-$C_{10}$-alkenyl") carbon atoms and a double bond in any position, for example $C_2$-$C_3$-alkenyl, such as ethenyl, 1-propenyl, 2-propenyl or 1-methylethenyl; $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like, or $C_2$-$C_{10}$-alkenyl, such as the radicals mentioned for $C_2$-$C_6$-alkenyl and additionally 1-heptenyl, 2-heptenyl, 3-heptenyl, 1-octenyl, 2-octenyl, 3-octenyl, 4-octenyl, 1-nonenyl, 2-nonenyl, 3-nonenyl, 4-nonenyl, 1-decenyl, 2-decenyl, 3-decenyl, 4-decenyl, 5-decenyl and the positional isomers thereof.

The term "haloalkenyl" as used herein, which is also expressed as "alkenyl which is partially or fully halogenated", refers to unsaturated straight-chain or branched hydrocarbon radicals having 2 to 4 ("$C_2$-$C_4$-haloalkenyl"), 2 to 6 ("$C_2$-$C_6$-haloalkenyl"), 2 to 8 ("$C_2$-$C_6$-haloalkenyl") or 2 to 10 ("$C_2$-$C_{10}$-haloalkenyl") carbon atoms and a double bond in any position (as mentioned above), where some or all of the hydrogen atoms in these groups are replaced by halogen atoms as mentioned above, in particular fluorine, chlorine and bromine, for example chlorovinyl, chloroallyl and the like.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl"), 2 to 6 ("$C_2$-$C_6$-alkynyl"), 2 to 8 ("$C_2$-$C_8$-alkynyl"), or 2 to 10 ("$C_2$-$C_{10}$-alkynyl") carbon atoms and one or two triple bonds in any position, for example $C_2$-$C_3$-alkynyl, such as ethynyl, 1-propynyl or 2-propynyl; $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "haloalkynyl" as used herein, which is also expressed as "alkynyl which is partially or fully halogenated", refers to unsaturated straight-chain or branched hydrocarbon radicals having 2 to 4 ("$C_2$-$C_4$-haloalkynyl"), 3 to 4 ("$C_3$-$C_4$-haloalkynyl"), 2 to 6 ("$C_2$-$C_6$-haloalkynyl"), 2 to 8 ("$C_2$-$C_8$-haloalkynyl") or 2 to 10 ("$C_2$-$C_{10}$-haloalkynyl") carbon atoms and one or two triple bonds in any position (as mentioned above), where some or all of the hydrogen atoms in these groups are replaced by halogen atoms as mentioned above, in particular fluorine, chlorine and bromine;

The term "cycloalkyl" as used herein refers to mono- or bi- or polycyclic saturated hydrocarbon radicals having 3 to 8 ("$C_3$-$C_8$-cycloalkyl"), in particular 3 to 6 carbon atoms ("$C_3$-$C_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl. Preferably, the term cycloalkyl denotes a monocyclic saturated hydrocarbon radical.

The term "halocycloalkyl" as used herein, which is also expressed as "cycloalkyl which is partially or fully halogenated", refers to mono- or bi- or polycyclic saturated hydrocarbon groups having 3 to 8 ("$C_3$-$C_8$-halocycloalkyl") or preferably 3 to 6 ("$C_3$-$C_6$-halocycloalkyl") carbon ring members (as mentioned above) in which some or all of the hydrogen atoms are replaced by halogen atoms as mentioned above, in particular fluorine, chlorine and bromine.

The term "cycloalkyl-$C_1$-$C_4$-alkyl" refers to a $C_3$-$C_8$-cycloalkyl group ("$C_3$-$C_8$-cycloalkyl-$C_1$-$C_4$-alkyl"), preferably a $C_3$-$C_6$-cycloalkyl group ("$C_3$-$C_6$-cycloalkyl-$C_1$-$C_4$-alkyl"), more preferably a $C_3$-$C_4$-cycloalkyl group ("$C_3$-$C_4$-cycloalkyl-$C_1$-$C_4$-alkyl") as defined above (preferably a monocyclic cycloalkyl group) which is bound to the remainder of the molecule via a $C_1$-$C_4$-alkyl group, as defined above. Examples for $C_3$-$C_4$-cycloalkyl-$C_1$-$C_4$-alkyl are cyclopropylmethyl, cyclopropylethyl, cyclopropylpropyl, cyclobutylmethyl, cyclobutylethyl and cyclobutylpropyl, Examples for $C_3$-$C_6$-cycloalkyl-$C_1$-$C_4$-alkyl, apart those mentioned for $C_3$-$C_4$-cycloalkyl-$C_1$-$C_4$-alkyl, are cyclopentylmethyl, cyclopentylethyl, cyclopentylpropyl, cyclohexylmethyl, cyclohexylethyl and cyclohexylpropyl. Examples for $C_3$-$C_8$-cycloalkyl-$C_1$-$C_4$-alkyl, apart those mentioned for $C_3$-$C_6$-cycloalkyl-$C_1$-$C_4$-alkyl, are cycloheptylmethyl, cycloheptylethyl, cyclooctylmethyl and the like.

The term "$C_3$-$C_8$-halocycloalkyl-$C_1$-$C_4$-alkyl" refers to a $C_3$-$C_8$-halocycloalkyl group as defined above which is bound to the remainder of the molecule via a $C_1$-$C_4$-alkyl group, as defined above.

The term "$C_1$-$C_2$-alkoxy" is a $C_1$-$C_2$-alkyl group, as defined above, attached via an oxygen atom. The term "$C_1$-$C_3$-alkoxy" is a $C_1$-$C_3$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom. $C_1$-$C_2$-Alkoxy is methoxy or ethoxy. $C_1$-$C_3$-Alkoxy is additionally, for example, n-propoxy and 1-methylethoxy (isopropoxy). $C_1$-$C_4$-Alkoxy is additionally, for example, butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

The term "$C_1$-$C_2$-haloalkoxy" is a $C_1$-$C_2$-haloalkyl group, as defined above, attached via an oxygen atom. The term "$C_1$-$C_3$-haloalkoxy" is a $C_1$-$C_3$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. The term "$C_1$-$C_{10}$-haloalkoxy" is a $C_1$-$C_{10}$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_3$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy or 1-($CH_2Br$)-2-bromoethoxy. $C_1$-$C_4$-Haloalkoxy is additionally, for example, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "$C_1$-$C_4$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_4$-alkoxy group, as defined above. The term "$C_1$-$C_6$-alkoxy-$C_1$-$C_6$-alkyl" as used herein, refers to a straight-chain or branched alkyl group having 1 to 6 carbon atoms, as defined above, where one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

The term "$C_1$-$C_6$-alkoxy-methyl" as used herein, refers to methyl in which one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, pentyloxymethyl, hexyloxymethyl and the like.

$C_1$-$C_6$-Haloalkoxy-$C_1$-$C_6$-alkyl is a straight-chain or branched alkyl group having from 1 to 6, especially 1 to 4 carbon atoms (═$C_1$-$C_6$-haloalkoxy-$C_1$-$C_4$-alkyl), wherein one of the hydrogen atoms is replaced by a $C_1$-$C_6$-alkoxy group and wherein at least one, e.g. 1, 2, 3, 4 or all of the remaining hydrogen atoms (either in the alkoxy moiety or in the alkyl moiety or in both) are replaced by halogen atoms. $C_1$-$C_4$-Haloalkoxy-$C_1$-$C_4$-alkyl is a straight-chain or branched alkyl group having from 1 to 4 carbon atoms, wherein one of the hydrogen atoms is replaced by a $C_1$-$C_4$-alkoxy group and wherein at least one, e.g. 1, 2, 3, 4 or all of the remaining hydrogen atoms (either in the alkoxy moiety or in the alkyl moiety or in both) are replaced by halogen atoms. Examples are difluoromethoxy-methyl ($CHF_2OCH_2$), trifluoromethoxymethyl, 1-difluoromethoxyethyl, 1-trifluoromethoxyethyl, 2-difluoromethoxyethyl, 2-trifluoromethoxyethyl, difluoromethoxy-methyl ($CH_3OCF_2$), 1,1-difluoro-2-methoxyethyl, 2,2-difluoro-2-methoxyethyl and the like.

The term "$C_1$-$C_2$-alkylthio" is a $C_1$-$C_2$-alkyl group, as defined above, attached via a sulfur atom. The term "$C_1$-$C_3$-alkylthio" is a $C_1$-$C_3$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" is a $C_1$-$C_6$-alkyl group, as defined above, attached via a sulfur atom. The term "$C_1$-$C_{10}$-alkylthio" is a $C_1$-$C_{10}$-alkyl group, as defined above, attached via a sulfur atom. $C_1$-$C_2$-Alkylthio is methylthio or ethylthio. $C_1$-$C_3$-Alkylthio is additionally, for example, n-propylthio or 1-methylethylthio (isopropylthio). $C_1$-$C_4$-Alkylthio is additionally, for example, butylthio, 1-methylpropylthio (sec-butylthio), 2-methylpropylthio (isobutylthio) or 1,1-dimethylethylthio (tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof. $C_1$-$C_{10}$-Alkylthio is additionally, for example, nonylthio, decylthio and positional isomers thereof.

The term "$C_1$-$C_2$-haloalkylthio" is a $C_1$-$C_2$-haloalkyl group, as defined above, attached via a sulfur atom. The term "$C_1$-$C_3$-haloalkylthio" is a $C_1$-$C_3$-haloalkyl group, as defined above, attached via a sulfur atom. The term "$C_1$-$C_4$-haloalkylthio" is a $C_1$-$C_4$-haloalkyl group, as defined above, attached via a sulfur atom. The term "$C_1$-$C_6$-haloalkylthio" is a $C_1$-$C_6$-haloalkyl group, as defined above, attached via a sulfur atom. The term "$C_1$-$C_{10}$-haloalkylthio" is a $C_1$-$C_{10}$-haloalkyl group, as defined above, attached via a sulfur atom. $C_1$-$C_2$-Haloalkylthio is, for example, $SCH_2F$, $SCHF_2$, $SCF_3$, $SCH_2Cl$, $SCHC_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_3$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio or 1-($CH_2Br$)-2-bromoethylthio. $C_1$-$C_4$-Haloalkylthio is additionally, for example, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The term "$C_1$-$C_2$-alkylsulfinyl" is a $C_1$-$C_2$-alkyl group, as defined above, attached via a sulfinyl [S(O)] group. The term "$C_1$-$C_4$-alkylsulfinyl" is a $C_1$-$C_4$-alkyl group, as defined above, attached via a sulfinyl [S(O)] group. The term "$C_1$-$C_6$-alkylsulfinyl" is a $C_1$-$C_6$-alkyl group, as defined above, attached via a sulfinyl [S(O)] group. The term "$C_1$-$C_{10}$-alkylsulfinyl" is a $C_1$-$C_{10}$-alkyl group, as defined above, attached via a sulfinyl [S(O)] group. $C_1$-$C_2$-Alkylsulfinyl is methylsulfinyl or ethylsulfinyl. $C_1$-$C_4$-Alkylsulfinyl is additionally, for example, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl. $C_1$-$C_8$-Alkylsulfinyl is additionally, for example, heptylsulfinyl, octylsulfinyl, 2-ethylhexylsulfinyl and positional isomers thereof. $C_1$-$C_{10}$-Alkylsulfinyl is additionally, for example, nonylsulfinyl, decylsulfinyl and positional isomers thereof.

The term "$C_1$-$C_2$-haloalkylsulfinyl" is a $C_1$-$C_2$-haloalkyl group, as defined above, attached via a sulfinyl [S(O)] group. The term "$C_1$-$C_4$-haloalkylsulfinyl" is a $C_1$-$C_4$-haloalkyl group, as defined above, attached via a sulfinyl [S(O)] group. The term "$C_1$-$C_6$-haloalkylsulfinyl" is a $C_1$-$C_6$-haloalkyl group, as defined above, attached via a sulfinyl [S(O)] group. The term "$C_1$-$C_{10}$-haloalkylsulfinyl" is a $C_1$-$C_{10}$-haloalkyl group, as defined above, attached via a sulfinyl [S(O)] group. $C_1$-$C_2$-Haloalkylsulfinyl is, for example, S(O)$CH_2F$, S(O)$CHF_2$, S(O)$CF_3$, S(O)$CH_2Cl$, S(O)$CHCl_2$, S(O)$CCl_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl or S(O)$C_2F_5$. $C_1$-$C_4$-Haloalkylsulfinyl is additionally, for example, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, S(O)$CH_2$—$C_2F_5$, S(O)$CF_2$—$C_2F_5$, 1-($CH_2F$)-2-fluoroethylsulfinyl, 1-($CH_2Cl$)-2-chloroethylsulfinyl, 1-($CH_2Br$)-2-bromoethylsulfinyl, 4-fluorobutylsulfinyl, 4-chlorobutylsulfinyl, 4-bromobutylsulfinyl or nonafluorobutylsulfinyl. $C_1$-$C_6$-Haloalkylsulfinyl is additionally, for example, 5-fluoropentylsulfinyl, 5-chloropentylsulfinyl, 5-brompentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl.

The term "$C_1$-$C_2$-alkylsulfonyl" is a $C_1$-$C_2$-alkyl group, as defined above, attached via a sulfonyl [S(O)$_2$] group. The term "$C_1$-$C_3$-alkylsulfonyl" is a $C_1$-$C_3$-alkyl group, as defined above, attached via a sulfonyl [S(O)$_2$] group. The term "$C_1$-$C_4$-alkylsulfonyl" is a $C_1$-$C_4$-alkyl group, as defined above, attached via a sulfonyl [S(O)$_2$] group. The term "$C_1$-$C_6$-alkylsulfonyl" is a $C_1$-$C_6$-alkyl group, as defined above, attached via a sulfonyl [S(O)$_2$] group. The term "$C_1$-$C_{10}$-alkylsulfonyl" is a $C_1$-$C_{10}$-alkyl group, as defined above, attached via a sulfonyl [S(O)$_2$] group. $C_1$-$C_2$-Alkylsulfonyl is methylsulfonyl or ethylsulfonyl. $C_1$-$C_3$-Alkylsulfonyl is additionally, for example, n-propylsulfonyl or 1-methylethylsulfonyl (isopropylsulfonyl). $C_1$-$C_4$-Alkylsulfonyl is additionally, for example, butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl. $C_1$-$C_8$-Alkylsulfonyl is additionally, for example, heptylsulfonyl, octylsulfonyl, 2-ethylhexylsulfonyl and positional isomers thereof. $C_1$-$C_{10}$-Alkylsulfonyl is additionally, for example, nonylsulfonyl, decylsulfonyl and positional isomers thereof.

The term "$C_1$-$C_2$-haloalkylsulfonyl" is a $C_1$-$C_2$-haloalkyl group, as defined above, attached via a sulfonyl [S(O)$_2$] group. The term "$C_1$-$C_3$-haloalkylsulfonyl" is a $C_1$-$C_3$-haloalkyl group, as defined above, attached via a sulfonyl [S(O)$_2$] group. The term "$C_1$-$C_4$-haloalkylsulfonyl" is a $C_1$-$C_4$-haloalkyl group, as defined above, attached via a sulfonyl [S(O)$_2$] group. The term "$C_1$-$C_6$-haloalkylsulfonyl" is a $C_1$-$C_6$-haloalkyl group, as defined above, attached via a sulfonyl [S(O)$_2$] group. The term "$C_1$-$C_{10}$-haloalkylsulfonyl" is a $C_1$-$C_{10}$-haloalkyl group, as defined above, attached via a sulfonyl [S(O)$_2$] group. $C_1$-$C_2$-Haloalkylsulfonyl is, for example, S(O)$_2CH_2F$, S(O)$_2CHF_2$, S(O)$_2CF_3$, S(O)$_2CH_2Cl$, S(O)$_2CHCl_2$, S(O)$_2CCO_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or S(O)$_2CF_5$. $C_1$-$C_3$-Haloalkylsulfonyl is additionally, for example, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, S(O)$_2$CH$_2$—C$_2$F$_5$, S(O)$_2$CF$_2$—C$_2$F$_5$, 1-(CH$_2$F)-2-fluoroethylsulfonyl, 1-(CH$_2$Cl)-2-chloroethylsulfonyl or 1-(CH$_2$Br)-2-bromoethylsulfonyl. C$_1$-C$_4$-Haloalkylsulfonyl is additionally, for example, 4-fluorobutylsulfonyl, 4-chlorobutylsulfonyl, 4-bromobutylsulfonyl or nonafluorobutylsulfonyl. C$_1$-C$_6$-Haloalkylsulfonyl is additionally, for example, 5-fluoropentylsulfonyl, 5-chloropentylsulfonyl, 5-brompentylsulfonyl, 5-iodopentylsulfonyl, undecafluoropentylsulfonyl, 6-fluorohexylsulfonyl, 6-chlorohexylsulfonyl, 6-bromohexylsulfonyl, 6-iodohexylsulfonyl or dodecafluorohexylsulfonyl.

The substituent "oxo" replaces a CH$_2$ group by a C(=O) group.

The term "alkylcarbonyl" is a C$_1$-C$_6$-alkyl ("C$_1$-C$_6$-alkylcarbonyl"), preferably a C$_1$-C$_4$-alkyl ("C$_1$-C$_4$-alkylcarbonyl") group, as defined above, attached via a carbonyl [C(=O)] group. Examples are acetyl (methylcarbonyl), propionyl (ethylcarbonyl), propylcarbonyl, isopropylcarbonyl, n-butylcarbonyl and the like.

The term "haloalkylcarbonyl" is a C$_1$-C$_6$-haloalkyl ("C$_1$-C$_6$-haloalkylcarbonyl"), preferably a C$_1$-C$_4$-haloalkyl ("C$_1$-C$_4$-haloalkylcarbonyl") group, as defined above, attached via a carbonyl [C(=O)] group. Examples are trifluoromethylcarbonyl, 2,2,2-trifluoroethylcarbonyl and the like.

The term "alkoxycarbonyl" is a C$_1$-C$_6$-alkoxy ("C$_1$-C$_6$-alkoxycarbonyl"), preferably a C$_1$-C$_4$-alkoxy ("C$_1$-C$_4$-alkoxycarbonyl") group, as defined above, attached via a carbonyl [C(=O)] group. Examples are methoxycarbonyl), ethoxycarbonyl, propoxycarbonyl, isopropoxycarbonyl, n-butoxycarbonyl and the like.

The term "haloalkoxycarbonyl" is a C$_1$-C$_6$-haloalkoxy ("C$_1$-C$_6$-haloalkoxycarbonyl"), preferably a C$_1$-C$_4$-haloalkoxy ("C$_1$-C$_4$-haloalkoxycarbonyl") group, as defined above, attached via a carbonyl [C(=O)] group. Examples are trifluoromethoxycarbonyl, 2,2,2-trifluoroethoxycarbonyl and the like.

The term "C$_1$-C$_6$-alkylamino" is a group —N(H)C$_1$-C$_6$-alkyl. Examples are methylamino, ethylamino, propylamino, isopropylamino, butylamino and the like.

The term "di-(C$_1$-C$_6$-alkyl)amino" is a group —N(C$_1$-C$_6$-alkyl)$_2$. Examples are dimethylamino, diethylamino, ethylmethylamino, dipropylamino, diisopropylamino, methylpropylamino, methylisopropylamino, ethylpropylamino, ethylisopropylamino, dibutylamino and the like.

The term "3-, 4-, 5-, 6-, 7-, 8-, 9- or 10-membered saturated, partially unsaturated or maximally unsaturated heterocyclic ring containing 1, 2 or 3 (or 4) heteroatoms or heteroatom groups selected from N, O, S, NO, SO and SO$_2$, as ring members" denotes a 3-, 4-, 5-, 6- or 7-membered saturated, partially unsaturated or maximum unsaturated heteromonocyclic ring or a 8-, 9- or 10-membered saturated, partially unsaturated or maximally unsaturated heterobicyclic ring containing 1, 2 or 3 (or 4) heteroatoms or heteroatom groups selected from N, O, S, NO, SO and SO$_2$, as ring members.

Unsaturated rings contain at least one C—C and/or C—N and/or N—N double bond(s). Maximally unsaturated rings contain as many conjugated C—C and/or C—N and/or N—N double bonds as allowed by the ring size. Maximally unsaturated 5- or 6-membered heterocyclic rings are aromatic. The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

The term "3-, 4-, 5-, 6- or 7-membered saturated, partially unsaturated or maximum unsaturated heterocyclic ring containing 1, 2 or 3 (or 4) heteroatoms or heteroatom groups selected from N, O, S, NO, SO and SO$_2$, as ring members" [wherein "maximum unsaturated" includes also "aromatic"] as used herein denotes monocyclic radicals, the monocyclic radicals being saturated, partially unsaturated or maximum unsaturated (including aromatic). The term "3-, 4-, 5-, 6-, 7- or 8-membered saturated, partially unsaturated or maximum unsaturated heterocyclic ring containing 1, 2 or 3 (or 4) heteroatoms or heteroatom groups selected from N, O, S, NO, SO and SO$_2$, as ring members" [wherein "maximum unsaturated" includes also "aromatic"] as used herein further also encompasses 8-membered heteromonocyclic radicals containing 1, 2 or 3 (or 4) heteroatoms or heteroatom groups selected from N, O, S, NO, SO and SO$_2$, as ring members, the monocyclic radicals being saturated, partially unsaturated or maximum unsaturated (including aromatic). Unsaturated rings contain at least one C—C and/or C—N and/or N—N double bond(s). Maximum unsaturated rings contain as many conjugated C—C and/or C—N and/or N—N double bonds as allowed by the ring size. Maximum unsaturated 5- or 6-membered heterocyclic rings are aromatic. 7- and 8-membered rings cannot be aromatic. They are homoaromatic (7-membered ring, 3 double bonds) or have 4 double bonds (8-membered ring). The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

Examples of a 3-, 4-, 5-, 6- or 7-membered saturated heterocyclic ring include: Oxiranyl, thiiranyl, aziridinyl, oxetanyl, thietanyl, azetidinyl, tetrahydrofuran-2-yl, tetrahydrofuran-3-yl, tetrahydrothien-2-yl, tetrahydrothien-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2-tetrahydropyranyl, 4-tetrahydropyranyl, 1,3-dioxan-5-yl, 1,4-dioxan-2-yl, piperidin-1-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl and 1,2,4-hexahydrotriazin-3-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of a 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples for a 3-, 4-, 5-, 6- or 7-membered maximally unsaturated (including aromatic) heterocyclic ring are 5- or 6-membered heteroaromatic rings, such as 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl and 2-pyrazinyl, and also homoaromatic radicals, such as 1H-azepine, 1H-[1,3]-diazepine and 1H-[1,4]-diazepine.

Examples for a 8-, 9- or 10-membered saturated heterobicyclic ring containing 1, 2 or 3 (or 4) heteroatoms or heteroatom groups selected from N, O, S, NO, SO and SO$_2$, as ring members are:

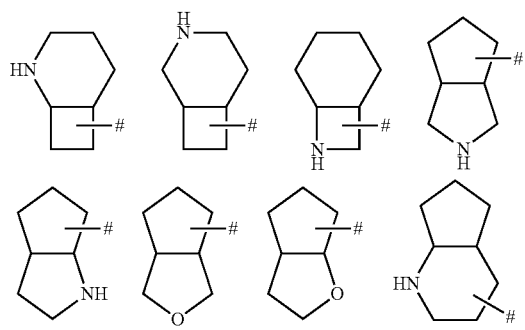

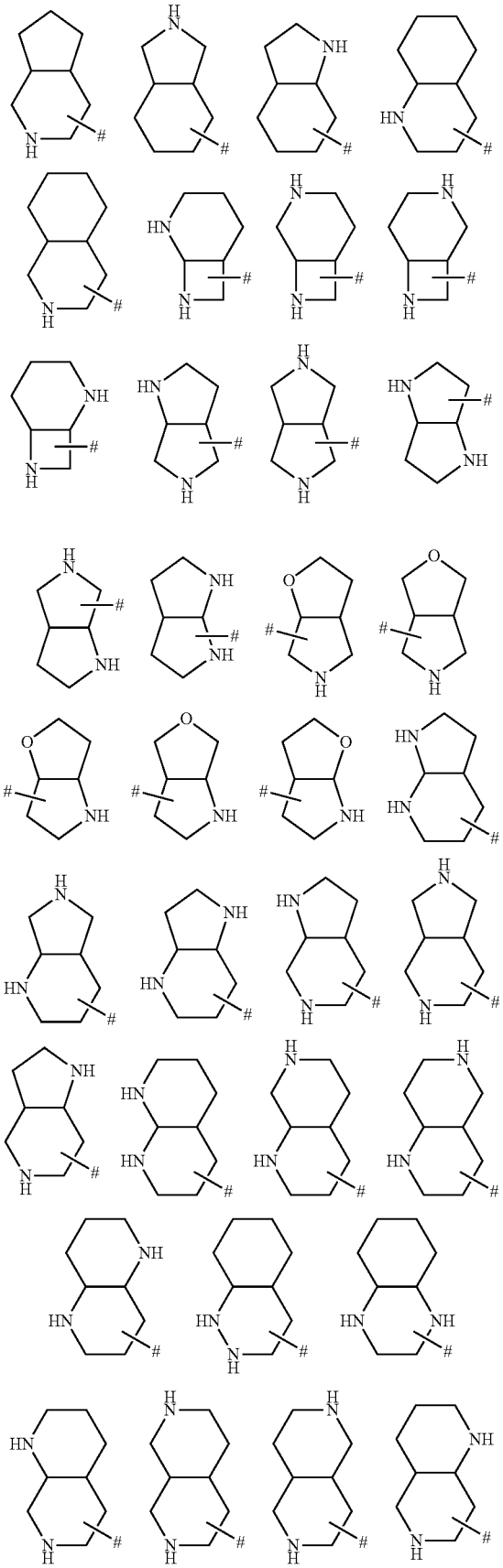

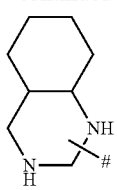

Examples for a 8-, 9- or 10-membered partially unsaturated heterobicyclic ring containing 1, 2 or 3 (or 4) heteroatoms or heteroatom groups selected from N, O, S, NO, SO and SO₂, as ring members are:

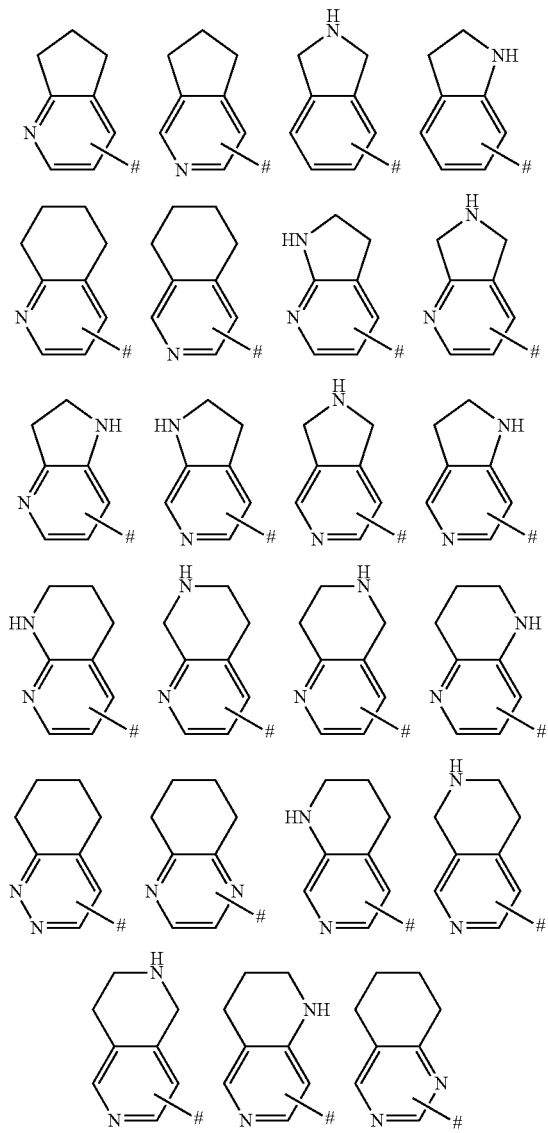

Examples for a 8-, 9- or 10-membered maximally unsaturated heterobicyclic ring containing 1, 2 or 3 (or 4) heteroatoms or heteroatom groups selected from N, O, S, NO, SO and SO₂, as ring members are:

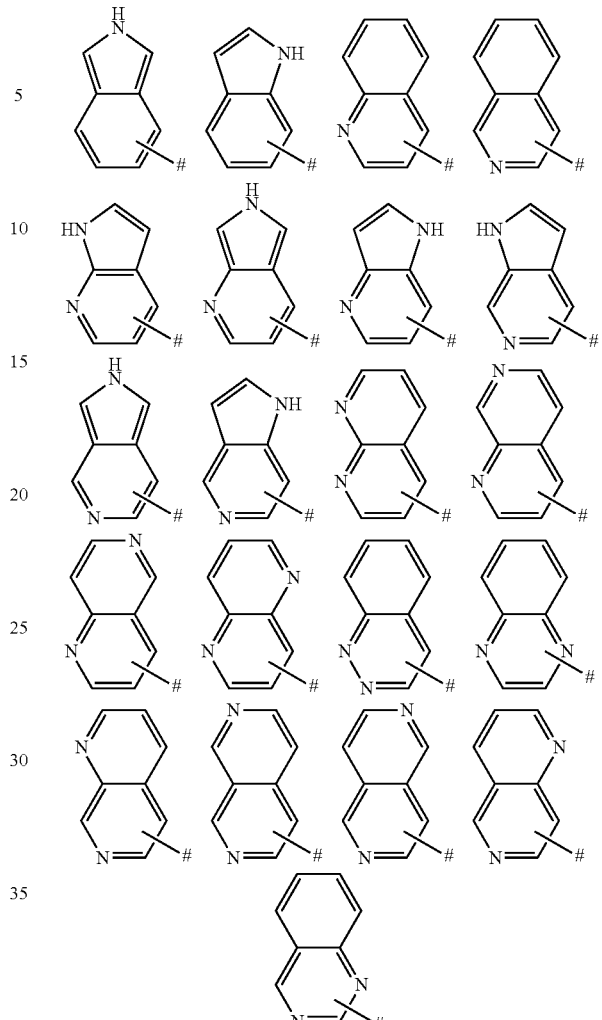

In the above structures # denotes the attachment point to the remainder of the molecule. The attachment point is not restricted to the ring on which is shown, but can be on either of the fused rings, and may be on a carbon or on a nitrogen ring atom. If the rings carry one or more substituents, these may be bound to carbon and/or to nitrogen ring atoms (if the latter are not part of a double bond).

A saturated 3-, 4-, 5-, 6-, 7-, 8- or 9-membered ring, wherein the ring may contain 1 or 2 heteroatoms or heteroatom groups selected from O, S, N, NR$^{14}$, NO, SO and SO$_2$ and/or 1 or 2 groups selected from C=O, C=S and C=NR$^{14}$ as ring members is either carbocyclic or heterocyclic. Examples are, in addition to the saturated heteromonocyclic rings mentioned above, carbocyclic rings, such as cyclopropyl, cyclopropanonyl, cyclobutyl, cyclobutanonyl, cyclopentyl, cyclopentanonyl, cyclohexyl, cyclohexanonyl, cyclohexadienonyl, cycloheptyl, cycloheptanonyl, cyclooctyl, cyclooctanonyl, furan-2-onyl, pyrrolidine-2-onyl, pyrrolidine-2,5-dionyl, piperidine-2-only, piperidine-2,6-dionyl and the like.

The remarks made below concerning preferred embodiments of the variables of the compounds of formula I, especially with respect to their substituents A, A$^1$, A$^2$, A$^3$, A$^4$, B$^1$, B$^2$, B$^3$, G$^1$, G$^2$, G$^3$, G$^4$, R$^1$, R$^2$, R$^{3a}$, R$^{3b}$, R$^{3c}$, R$^4$, R$^5$, R$^6$, R$^7$, R$^8$, R$^9$, R$^{10a}$, R$^{10b}$, R$^{11}$, R$^{12}$, R$^{13}$, R$^{14}$, R$^{14a}$, $R^{14b}$, $R^{15}$, $R^{16}$, m and n, the features of the use and method according to the invention and of the composition of the invention are valid both on their own and, in particular, in every possible combination with each other.

In one embodiment of the invention, A is $A^1$.

In one preferred embodiment, $A^1$ is selected from —C(=NR$^6$)R$^8$ and —N(R$^5$)R$^6$ and is more preferably —C(=NR$^6$)R$^8$; wherein R$^5$, R$^6$ and R$^8$ have one of the above general meanings, or, in particular, one of the below preferred meanings.

$R^6$ as a radical in the group —C(=NR$^6$)R$^8$ is preferably selected from hydrogen, cyano, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals each independently may be partially or fully halogenated and/or may be substituted with 1, 2, 3, 4, 5 or 6, preferably 1, 2 or 3, in particular 1, substituents $R^8$; OR$^9$ and NR$^{10a}$R$^{10b}$; wherein $R^8$, $R^9$, $R^{10a}$ and $R^{10b}$ have one of the above general meanings, or, in particular, one of the below preferred meanings.

More preferably, $R^6$ in —C(=NR$^6$)R$^8$ is selected from hydrogen, $C_1$-$C_{10}$-alkyl, $C_3$-$C_8$-cycloalkyl, wherein the two last-mentioned aliphatic and cycloaliphatic radicals each independently may be partially or fully halogenated and/or may be substituted with 1, 2 or 3, preferably 1 or 2, in particular 1, substituents $R^8$; OR$^9$ and NR$^{10a}$R$^{10b}$; wherein $R^8$, $R^9$, $R^{10a}$ and $R^{10b}$ have one of the above general meanings, or, in particular, one of the below preferred meanings.

Even more preferably, $R^6$ in —C(=NR$^6$)R$^8$ is selected from OR$^9$ and NR$^{10a}$R$^{10b}$; wherein $R^8$, $R^9$, $R^{10a}$ and $R^{10b}$ have one of the above general meanings, or, in particular, one of the below preferred meanings.

In OR$^9$ as a preferred meaning of $R^6$ in —C(=NR$^6$)R$^8$, $R^9$ is preferably selected from hydrogen, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl-, $C_2$-$C_6$-alkenyl, $C_2$-$C_6$-haloalkenyl, $C_2$-$C_6$-alkynyl and $C_2$-$C_6$-haloalkynyl, and more preferably from hydrogen, $C_1$-$C_6$-alkyl, $C_1$-$C_6$-haloalkyl, $C_3$-$C_8$-cycloalkyl, $C_3$-$C_8$-halocycloalkyl and $C_3$-$C_8$-cycloalkyl-$C_1$-$C_4$-alkyl-.

In NR$^{10a}$R$^{10b}$ as a preferred meaning of $R^6$ in —C(=NR$^6$)R$^8$, $R^{10a}$ and $R^{10b}$, independently of each other, are selected from the group consisting of hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkylcarbonyl, $C_1$-$C_6$-haloalkylcarbonyl, —C(=O)OR$^{15}$, —C(=O)N(R$^{14a}$)R$^{14b}$, —C(=S)N(R$^{14a}$)R$^{14b}$, phenyl which is optionally substituted with 1, 2, 3 or 4, substituents $R^{16}$, and a 3-, 4-, 5-, 6- or 7-membered saturated, partially unsaturated or maximally unsaturated heterocyclic ring comprising 1, 2, 3 or 4 heteroatoms or heteroatom groups selected from N, O, S, NO, SO and SO$_2$, as ring members, where the heterocyclic ring is optionally substituted with one or more substituents $R^{16}$; or $R^{10a}$ and $R^{10b}$ form together with the nitrogen atom they are bonded to a 3-, 4-, 5-, 6-, 7- or 8-membered saturated, partially unsaturated or maximally unsaturated heterocyclic ring, wherein the heterocyclic ring may additionally contain one or two heteroatoms or heteroatom groups selected from N, O, S, NO, SO and SO$_2$, as ring members, where the heterocyclic ring optionally carries one or more substituents selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl and $C_2$-$C_6$-haloalkynyl; wherein $R^{14a}$, $R^{14b}$ and $R^{16}$ have one of the above general meanings, or, in particular, one of the below preferred meanings.

More preferably, $R^{10a}$ is selected from hydrogen, $C_1$-$C_6$-alkyl and $C_1$-$C_6$-haloalkyl; and $R^{10b}$ is selected from $C_1$-$C_6$-alkyl, $C_1$-$C_6$-haloalkyl, $C_1$-$C_6$-alkylcarbonyl, $C_1$-$C_6$-haloalkylcarbonyl, —C(=O)OR$^{15}$, —C(=O)N(R$^{14a}$)R$^{14b}$, —C(=S)N(R$^{14a}$)R$^{14b}$, phenyl which is optionally substituted with 1, 2, 3 or 4, substituents $R^{16}$, and a 5- or 6-membered heteroaromatic ring comprising 1, 2 or 3 heteroatoms selected from N, O and S, as ring members, where the heteroaromatic ring is optionally substituted with one or more substituents $R^{16}$; wherein $R^{14a}$, $R^{14b}$ and $R^{16}$ have one of the above general meanings, or, in particular, one of the below preferred meanings.

In the above radicals $R^{10a}$ and $R^{10b}$, $R^{14a}$ is selected from hydrogen, $C_1$-$C_6$-alkyl and $C_1$-$C_6$-haloalkyl; and $R^{14b}$ is selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_3$-$C_6$-cycloalkyl-$C_1$-$C_4$-alkyl-, $C_1$-$C_6$-alkyl substituted with a CN group, $C_1$-$C_6$-alkoxyl, $C_1$-$C_6$-haloalkoxy, phenyl which is optionally substituted with 1, 2, 3 or 4, substituents each independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; and a heterocyclic ring selected from rings of formulae E-1 to E-51 defined below.

In an alternatively preferred embodiment, $R^{11a}$ and $R^{10b}$, independently of each other, are selected from the group consisting of hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkylcarbonyl, $C_1$-$C_6$-haloalkylcarbonyl, —C(=O)N(R$^{14a}$)R$^{14b}$, —C(=S)N(R$^{14a}$)R$^{14b}$, phenyl which is optionally substituted with 1, 2, 3 or 4, preferably 1, 2 or 3, in particular 1, substituents $R^{16}$, and a 3-, 4-, 5-, 6- or 7-membered saturated, partially unsaturated or maximally unsaturated heterocyclic ring comprising 1, 2, 3 or 4 heteroatoms or heteroatom groups selected from N, O, S, NO, SO and SO$_2$, as ring members, where the heterocyclic ring is optionally substituted with one or more, preferably 1, 2 or 3, in particular 1, substituents $R^{16}$;

or $R^{10a}$ and $R^{10b}$ form together with the nitrogen atom they are bonded to a 3-, 4-, 5-, 6-, 7- or 8-membered saturated, partially unsaturated or maximally unsaturated heterocyclic ring, wherein the heterocyclic ring may additionally contain one or two heteroatoms or heteroatom groups selected from N, O, S, NO, SO and SO$_2$, as ring members, where the heterocyclic ring optionally carries one or more, preferably 1, 2 or 3, in particular 1, substituents selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl and $C_2$-$C_6$-haloalkynyl; wherein $R^{14a}$, $R^{14b}$ and $R^{16}$ have one of the above general meanings, or, in particular, one of the below preferred meanings.

In an alternatively more preferred embodiment, $R^{10a}$ is selected from hydrogen, $C_1$-$C_6$-alkyl and $C_1$-$C_6$-haloalkyl; and $R^{10b}$ is selected from —C(=O)N($R^{14a}$)$R^{14b}$, —C(=S)N($R^{14a}$)$R^{14b}$, phenyl which is optionally substituted with 1, 2, 3 or 4, preferably 1, 2 or 3, in particular 1, substituents $R^{16}$, and a 5- or 6-membered heteroaromatic ring comprising 1, 2 or 3 heteroatoms selected from N, O and S, as ring members, where the heteroaromatic ring is optionally substituted with one or more, preferably 1, 2 or 3, in particular 1, substituents $R^{16}$;

wherein $R^{14a}$, $R^{14b}$ and $R^{16}$ have one of the above general meanings, or, in particular, one of the below preferred meanings.

In the above radicals $R^{10a}$ and $R^{10b}$ of the above alternatively preferred and more preferred embodiments, $R^{14a}$ is preferably selected from hydrogen, $C_1$-$C_6$-alkyl and $C_1$-$C_6$-haloalkyl; and $R^{14b}$ is preferably selected from hydrogen, $C_1$-$C_6$-alkyl, $C_1$-$C_6$-haloalkyl, $C_1$-$C_6$-alkenyl, $C_1$-$C_6$-haloalkenyl, $C_3$-$C_6$-cycloalkyl, $C_3$-$C_6$-halocycloalkyl, $C_3$-$C_6$-cycloalkyl-$C_1$-$C_4$-alkyl-, $C_1$-$C_6$-alkyl substituted with a CN group, phenyl which is optionally substituted with 1, 2, 3 or 4, preferably 1, 2 or 3, in particular 1, substituents $R^{16}$, which are each independently preferably selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; and a heterocyclic ring selected from rings of following formulae E-1 to E-51:

E-1

E-2

E-3

E-4

E-5

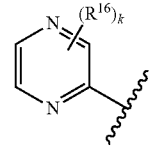

E-6

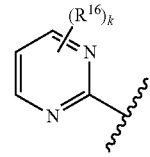

E-7

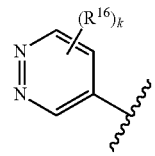

E-8

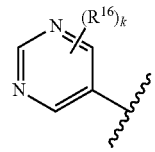

E-9

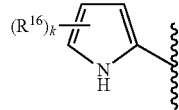

E-10

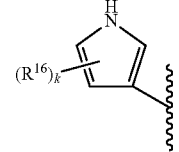

E-11

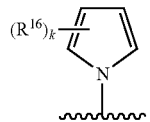

E-12

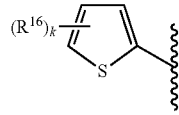

E-13

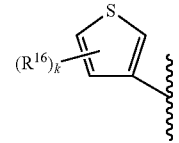

E-14

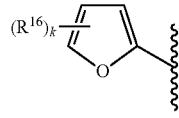

E-15

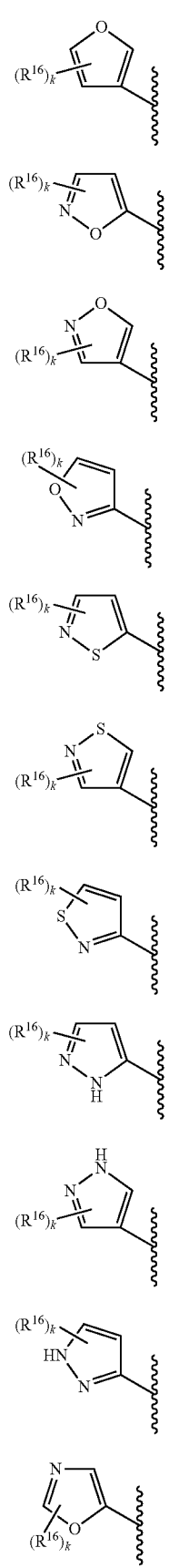
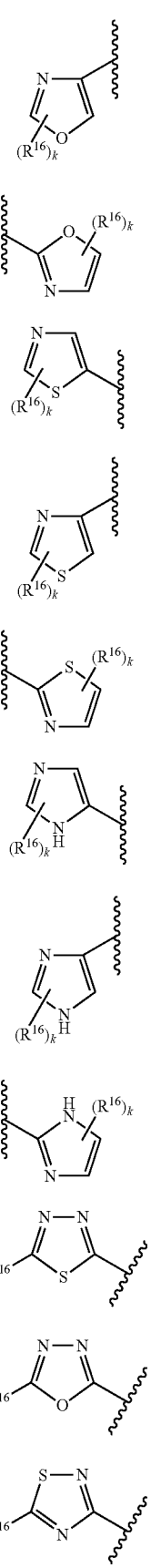
E-16
E-17
E-18
E-19
E-20
E-21
E-22
E-23
E-24
E-25
E-26
E-27
E-28
E-29
E-30
E-31
E-32
E-33
E-34
E-35
E-36
E-37

-continued

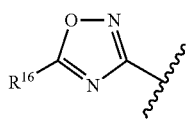

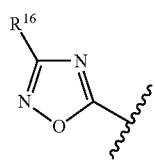

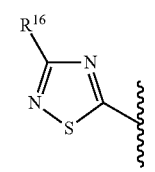

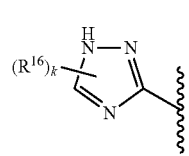

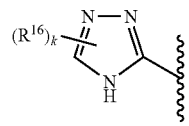

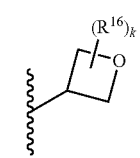

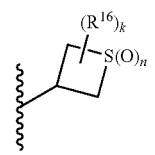

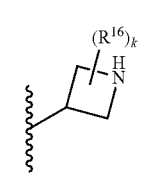

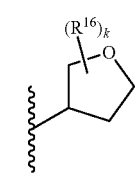

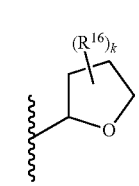

-continued

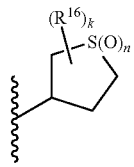

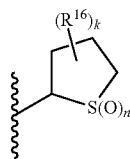

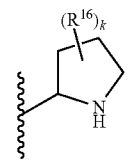

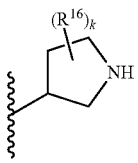

wherein
k is 0, 1, 2 or 3, n is 0, 1 or 2,
n is 0, 1 or 2; and
each $R^{16}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or two $R^{16}$ present on the same carbon atom of a saturated ring may form together a group =O or =S.

More preferably, in the above radicals $R^{10a}$ and $R^{10b}$,
$R^{14a}$ is selected from hydrogen and methyl; and
$R^{14b}$ is selected from hydrogen, $C_1$-$C_4$-alkyl, $C_1$-$C_4$-haloalkyl, $C_2$-$C_4$-alkenyl, $C_2$-$C_4$-haloalkenyl, $C_3$-$C_6$-cycloalkyl, $C_3$-$C_6$-halocycloalkyl, $C_3$-$C_6$-cycloalkyl-methyl-, $C_1$-$C_6$-alkyl substituted with a CN group, phenyl which is optionally substituted with 1, 2, 3 or 4, preferably 1, 2 or 3, in particular 1, substituents $R^{16}$ selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; and a 4-membered saturated heterocyclic ring comprising one heteroatom or heteroatom group selected from S, SO and $SO_2$ as ring member (ring E-44), where the heterocyclic ring is optionally substituted with one or more, preferably 1 or 2, in particular 1, substituents $R^{16}$;
wherein each $R^{16}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or two $R^{16}$ present on the same carbon atom may form together a group =O or =S.

Preferably, in the above radicals, each $R^{16}$ is independently selected from halogen, CN, $C_1$-$C_4$-alkyl, $C_1$-$C_4$-haloalkyl, $C_1$-$C_4$-alkoxy and $C_1$-$C_4$-haloalkoxy.

Specifically, in the above radicals $R^{11a}$ and $R^{10b}$, $R^{14a}$ is selected from hydrogen and methyl, and is specifically hydrogen; and $R^{14b}$ is selected from hydrogen, $C_1$-$C_4$-alkyl, $C_1$-$C_4$-haloalkyl and $C_3$-$C_6$-cycloalkyl-methyl-.

$R^8$ as a radical in the group —C(=NR$^6$)R$^8$ is preferably selected from hydrogen, $C_1$-$C_4$-alkyl, $C_1$-$C_4$-haloalkyl and $NR^{10a}R^{10b}$, and more preferably from hydrogen and $NR^{10a}R^{10b}$, and is specifically hydrogen.

In this case (i.e. in $NR^{10a}R^{10b}$ as a meaning of $R^8$), $R^{10a}$ and $R^{10b}$ are preferably selected, independently of each other, from hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkylcarbonyl, $C_1$-$C_4$-haloalkylcarbonyl, $C_1$-$C_4$-alkylaminocarbonyl, $C_1$-$C_4$-haloalkylaminocarbonyl, $C_3$-$C_6$-cycloalkylaminocarbonyl and $C_3$-$C_6$-halocycloalkylaminocarbonyl, or, together with the nitrogen atom to which they are bound, form a 5- or 6-membered saturated, partially unsaturated or aromatic heterocyclic ring, which additionally may contain 1 or 2 further heteroatoms or heteroatom groups selected from N, O, S, NO, SO and $SO_2$, as ring members, where the heterocyclic ring may carry 1 or 2, in particular 1, substituents selected from halogen, CN, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio.

More preferably, $R^{10a}$ and $R^{10b}$ are in this case selected, independently of each other, from hydrogen, $C_1$-$C_4$-alkyl, $C_1$-$C_4$-haloalkyl, $C_3$-$C_6$-cycloalkyl, $C_3$-$C_6$-halocycloalkyl, $C_1$-$C_4$-alkylaminocarbonyl and $C_1$-$C_4$-haloalkylaminocarbonyl.

In an alternative embodiment of the invention, A is $A^2$.

In $A^2$, W is preferably O.

In $A^2$, Y is preferably N(R$^5$)R$^6$; wherein $R^5$ and $R^6$ have one of the above general meanings, or, in particular, one of the below preferred meanings.

In an alternatively preferred embodiment, in $A^2$Y is hydrogen.

In an alternatively preferred embodiment, in $A^2$Y is —OR$^9$. $R^9$ has one of the above general meanings, or, in particular, is selected from hydrogen, $C_1$-$C_6$-alkyl, $C_1$-$C_6$-haloalkyl and $C_1$-$C_6$-alkyl substituted by one radical $R^{13}$, where $R^{13}$ has one of the above general meanings, or, in particular, one of the below preferred meanings.

More preferably, in $A^2$, W is O and Y is N(R$^5$)R$^6$; wherein $R^5$ and $R^6$ have one of the above general meanings, or, in particular, one of the below preferred meanings.

In alternatively more preferred embodiment, in $A^2$, W is O and Y H.

In alternatively more preferred embodiment, in $A^2$, W is O and Y is —OR$^9$, where $R^9$ has one of the above general meanings, or, in particular, is selected from hydrogen, $C_1$-$C_6$-alkyl, $C_1$-$C_6$-haloalkyl and $C_1$-$C_6$-alkyl substituted by one radical $R^{13}$, where $R^{13}$ has one of the above general meanings, or, in particular, one of the below preferred meanings.

In N(R$^5$)R$^6$ as a radical Y, $R^5$ is preferably selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl and $C_3$-$C_8$-halocycloalkyl, where the aforementioned aliphatic and cycloaliphatic radicals may be substituted by 1, 2 or 3, preferably 1, radicals $R^8$; and $R^6$ is preferably selected from hydrogen, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted by one or more, preferably 1, 2 or 3, in particular 1, substituents $R^8$, $OR^9$, $NR^{10a}R^{10b}$, $S(O)_nR^9$, $C(=O)NR^{10a}N(R^{10a}R^{10b})$, $C(=O)R^8$, phenyl which may be substituted with 1, 2, 3, 4, or 5, preferably 1, 2 or 3, in particular 1, substituents $R^{11}$, and a 3-, 4-, 5-, 6-, 7-, 8-, 9- or 10-membered saturated, partially unsaturated or maximally unsaturated heteromonocyclic or heterobicyclic ring containing 1, 2, 3 or 4 heteroatoms or heteroatom groups independently selected from N, O, S, NO, SO and $SO_2$, as ring members, where the heteromonocyclic or heterobicyclic ring may be substituted with one or more, preferably 1, 2 or 3, in particular 1, substituents $R^{11}$;

or $R^5$ and $R^6$, together with the nitrogen atom to which they are bound, form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O, S, SO, $SO_2$, N, NH, C=O and C=S as ring members, wherein the heterocyclic ring may be substituted with 1, 2, 3, 4 or 5, preferably 1, 2 or 3, in particular 1, substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the aliphatic or cycloaliphatic moieties in the twelve last-mentioned radicals may be substituted by one or more, preferably 1, 2 or 3, in particular 1, radicals $R^8$, and phenyl which may be substituted with 1, 2, 3, 4 or 5, preferably 1, 2 or 3, in particular 1, substituents $R^{11}$;

or $R^5$ and $R^6$ together form a group =C(R$^8$)$_2$, =S(O)$_m$(R$^9$)$_2$, =NR$^{10a}$ or =NOR$^9$;

wherein $R^8$, $R^9$, $R^{10a}$, $R^{10b}$ and $R^{11}$ have one of the above general meanings, or, in particular, one of the below preferred meanings.

More preferably, in N(R$^5$)R$^6$ as a radical Y, $R^5$ is selected from hydrogen, $C_1$-$C_6$-alkyl, $C_2$-$C_3$-alkynyl and —CH$_2$—CN; and $R^6$ is selected from hydrogen, $C_1$-$C_6$-alkyl, $C_1$-$C_6$-haloalkyl, $C_2$-$C_6$-alkenyl, $C_2$-$C_{10}$-haloalkenyl, $C_2$-$C_6$-alkynyl, $C_3$-$C_6$-cycloalkyl, $C_3$-$C_6$-halocycloalkyl, where the four last-mentioned aliphatic and cycloaliphatic radicals may carry 1, 2 or 3 radicals $R^8$; $C_1$-$C_6$-alkoxy, $C_1$-$C_6$-haloalkoxy, $N(R^{10a})R^{10b}$, phenyl which may be substituted with 1, 2, 3, 4, or 5 substituents $R^{11}$, and a 3-, 4-, 5-, 6- or 7-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more substituents $R^{11}$;

wherein $R^8$ and $R^{11}$ are as defined in claim 1;
or $R^5$ and $R^6$, together with the nitrogen atom to which they are bound, form a 3-, 4-, 5- or 6-membered saturated heterocyclic ring, where the ring may further contain 1 or 2 heteroatoms or heteroatom-containing groups selected from O, S, SO, $SO_2$, NH and C=O as ring members, wherein the heterocyclic ring may be substituted with 1, 2, 3, 4 or 5 substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy;
or $R^5$ and $R^6$, together with the nitrogen atom to which they are bound, form a group =$S(R^9)_2$, where $R^9$ is selected from $C_1$-$C_6$-alkyl and $C_1$-$C_6$-haloalkyl.

Even more preferably, in $N(R^5)R^6$ as a radical Y, $R^5$ is selected from hydrogen, $C_1$-$C_6$-alkyl, $C_2$-$C_3$-alkynyl and $CH_2$—CN; and $R^6$ is selected from $C_1$-$C_6$-alkyl, $C_1$-$C_6$-haloalkyl, $C_1$-$C_4$-alkyl which carries one radical $R^8$, $C_2$-$C_6$-alkenyl, $C_2$-$C_{10}$-haloalkenyl, $C_2$-$C_6$-alkynyl, $C_3$-$C_6$-cycloalkyl which may be substituted by 1 or 2 substituents selected from F, CN and pyridyl;

$C_1$-$C_6$-alkoxy, $C_1$-$C_6$-haloalkoxy, $N(R^{10a})R^{10b}$, phenyl which may be substituted with 1, 2, 3, 4, or 5 substituents $R^{11}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more substituents $R^{11}$;

wherein $R^8$ and $R^{11}$ are as defined in claim 1;
or $R^5$ and $R^6$, together with the nitrogen atom to which they are bound, form a 3-, 4-, 5- or 6-membered saturated heterocyclic ring, where the ring may further contain 1 or 2 heteroatoms or heteroatom-containing groups selected from O, S, SO, $SO_2$, NH and C=O as ring members, wherein the heterocyclic ring may be substituted with 1, 2 or 3 substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy;
or $R^5$ and $R^6$, together with the nitrogen atom to which they are bound, form a group =$S(R^9)_2$, where $R^9$ is selected from $C_1$-$C_6$-alkyl and $C_1$-$C_6$-haloalkyl.

Particularly preferably, in $N(R^5)R^6$ as a radical Y, $R^5$ selected from hydrogen, $C_1$-$C_6$-alkyl, $C_2$-$C_3$-alkynyl and $CH_2$—CN; and $R^6$ is selected from $C_1$-$C_6$-alkyl, $C_1$-$C_6$-haloalkyl, $C_1$-$C_4$-alkyl which carries one radical $R^8$, $C_2$-$C_6$-alkenyl, $C_2$-$C_{10}$-haloalkenyl, $C_2$-$C_6$-alkynyl, $C_3$-$C_6$-cycloalkyl which may be substituted by 1 or 2 substituents selected from F, CN and pyridyl;

$C_1$-$C_6$-alkoxy, $C_1$-$C_6$-haloalkoxy, $N(R^{10a})R^{10b}$, wherein RiG$^a$ is selected from hydrogen and $C_1$-$C_6$-alkyl and $R^{10b}$ is selected from a 5- or 6-membered heteroaromatic ring containing 1, 2 or 3 heteroatoms selected from N, O and S as ring members, where the heteroaromatic ring may be substituted with one or more substituents $R^{16}$;

phenyl which may be substituted with 1, 2, 3, 4, or 5 substituents $R^{11}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more substituents $R^{11}$;

wherein each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or two $R^{11}$ present on the same carbon atom of a saturated heterocyclic ring may form together =O or =S;

$R^8$ is selected from OH, CN, $C_3$-$C_8$-cycloalkyl which optionally carries a CN substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfonyl, $C_1$-$C_6$-haloalkylsulfonyl, —C(=O)$N(R^{10a})R^{10b}$, phenyl, optionally substituted with 1, 2, 3, 4 or 5 substituents $R^{16}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more substituents $R^{16}$;

wherein $R^{10a}$ is selected from the group consisting of hydrogen and $C_1$-$C_6$-alkyl;

$R^{10b}$ is selected from the group consisting of hydrogen, $C_1$-$C_6$-alkyl, $C_2$-$C_4$-alkynyl, $CH_2$—CN, $C_1$-$C_6$-haloalkyl, $C_3$-$C_6$-cycloalkyl, $C_3$-$C_6$-halocycloalkyl, $C_1$-$C_4$-alkoxy and $C_1$-$C_4$-haloalkoxy, and each $R^{16}$ as a substituent on phenyl or the heterocyclic rings is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or two $R^{16}$ present on the same carbon atom of a saturated heterocyclic ring may form together =O or =S;
or $R^5$ and $R^6$, together with the nitrogen atom to which they are bound, form a 5- or 6-membered saturated heterocyclic ring, where the ring may further contain 1 or 2 heteroatoms or heteroatom-containing groups selected from O, S, SO, $SO_2$, NH and C=O as ring members, wherein the heterocyclic ring may be substituted with 1, 2 or 3 substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy;
or $R^5$ and $R^6$, together with the nitrogen atom to which they are bound, form a group =$S(R^9)_2$, where $R^9$ is selected from $C_1$-$C_6$-alkyl and $C_1$-$C_6$-haloalkyl.

Alternatively, more preferably, in $N(R^5)R^6$ as a radical Y, $R^5$ is selected from hydrogen, $C_1$-$C_6$-alkyl, $C_2$-$C_3$-alkynyl, $CH_2$—CN and $C_1$-$C_6$-alkoxy-methyl-; and $R^6$ is selected from hydrogen, $C_1$-$C_6$-alkyl, $C_1$-$C_6$-haloalkyl, $C_3$-$C_6$-cycloalkyl, $C_3$-$C_6$-halocycloalkyl, where the four last-mentioned aliphatic and cycloaliphatic radicals may carry 1, 2 or 3, preferably 1, radicals $R^8$; C(=O)$R^8$, phenyl which may be substituted with 1, 2, 3, 4, or 5 substituents $R^{11}$, and a 3-, 4-, 5-, 6- or 7-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more, preferably 1, 2 or 3, in particular 1, substituents $R^{11}$;

wherein $R^8$ and $R^{11}$ have one of the above general meanings, or, in particular, one of the below preferred meanings;

or $R^5$ and $R^6$, together with the nitrogen atom to which they are bound, form a 5- or 6-membered saturated heterocyclic ring, where the ring may further contain 1 or 2 heteroatoms or heteroatom-containing groups selected from O, S, SO, $SO_2$, NH and C=O, preferably from O, NH and C=O, as ring members, wherein the heterocyclic ring may be substituted with 1, 2, 3, 4 or 5 substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy.

Preferably, the 3-, 4-, 5-, 6- or 7-membered saturated, partially unsaturated or maximally unsaturated heteromonocyclic ring $R^6$ containing 1, 2 or 3 heteroatoms or heteroatom groups independently selected from N, O, S, NO, SO and $SO_2$, as ring members is selected from rings D-1 to D-173 listed below in context with $A^4$. The ring may be substituted with one or more, preferably 1, 2 or 3, in particular 1, substituents $R^{11}$.

Alternatively, particularly preferably, in $N(R^5)R^6$ as a radical Y, $R^5$ is selected from hydrogen, $C_1$-$C_6$-alkyl, $C_2$-$C_3$-alkynyl, $CH_2$—CN and $C_1$-$C_6$-alkoxy-methyl-; and $R^6$ is selected from hydrogen, $C_1$-$C_6$-alkyl, $C_1$-$C_6$-haloalkyl, $C_3$-$C_6$-cycloalkyl which may be substituted by 1 or 2 substituents selected from F, CN, methyl and oxo;

$C_1$-$C_4$-alkyl which carries one radical $R^8$; C(=O)$R^8$, phenyl which may be substituted with 1, 2, 3, 4, or 5 substituents $R^{11}$, and a 3-, 4-, 5-, 6- or 7-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more, preferably 1, 2 or 3, in particular 1, substituents $R^{11}$;

wherein $R^8$ and $R^{11}$ have one of the above general meanings, or, in particular, one of the below preferred meanings;

or $R^5$ and $R^6$, together with the nitrogen atom to which they are bound, form a 5- or 6-membered saturated heterocyclic ring, where the ring may further contain 1 or 2 heteroatoms or heteroatom-containing groups selected from O, S, SO, $SO_2$, NH and C=O, preferably from O, NH and C=O, as ring members, wherein the heterocyclic ring may be substituted with 1, 2 or 3 substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy.

Alternatively, even more preferably, in $N(R^5)R^6$ as a radical Y, $R^5$ is selected from hydrogen and $C_1$-$C_6$-alkyl; and $R^6$ is selected from $C_1$-$C_6$-alkyl, $C_1$-$C_6$-haloalkyl, $C_1$-$C_4$-alkyl which carries one radical $R^8$, $C_3$-$C_6$-cycloalkyl which may be substituted by 1 or 2 substituents selected from F, CN, methyl and oxo, C(=O)$R^8$, phenyl which may be substituted with 1, 2, 3, 4, or 5 substituents $R^{11}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more substituents $R^{11}$;

wherein $R^8$ and $R^{11}$ have one of the above general meanings, or, in particular, one of the below preferred meanings;

or $R^5$ and $R^6$, together with the nitrogen atom to which they are bound, form a 5- or 6-membered saturated heterocyclic ring, where the ring may further contain 1 or 2 heteroatoms or heteroatom-containing groups selected from O, S, SO, $SO_2$, NH and C=O, preferably from O, NH and C=O, as ring members, wherein the heterocyclic ring may be substituted with 1, 2 or 3 substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy.

Preferably the 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members is selected from rings D-1 to D-173 listed below in context with $A^4$, and more preferably from rings F-1 to F-51 listed below. The ring may be substituted with one or more, preferably 1, 2 or 3, in particular 1, substituents $R^1$.

In particular, in $N(R^5)R^6$ as a radical Y, $R^5$ is selected from hydrogen and methyl, preferably hydrogen; and $R^6$ is selected from $C_1$-$C_4$-alkyl which carries one radical $R^8$, preferably methyl which carries one radical $R^8$, $C_1$-$C_4$-haloalkyl, and a 4-, 5- or 6-membered saturated heteromonocyclic ring containing 1 heteroatom or heteroatom group selected from S, SO and $SO_2$, as ring member, where the heteromonocyclic ring may be substituted with one or more substituents $R^{11}$;

wherein $R^8$ and $R^{11}$ have one of the above general meanings, or, in particular, one of the below preferred meanings;

or $R^5$ and $R^6$, together with the nitrogen atom to which they are bound, form a 5- or 6-membered saturated heterocyclic ring (i.e. $R^5$ and $R^6$ form together —$(CH_2)_4$— or —$(CH_2)_5$—), wherein the heterocyclic ring may be substituted with 1, 2 or 3 substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy.

Preferably the 4-, 5- or 6-membered saturated heteromonocyclic ring containing 1 heteroatom or heteroatom group selected from S, SO and $SO_2$, as ring member is selected from rings D-72, D-77, D-78 and D-100 to D-102 listed below in context with $A^4$. The ring may be substituted with one or more, preferably 1, 2 or 3, in particular 1, substituents $R^{11}$. More preference is given to ring D-72 with n=0 (thietan-3-yl) and its oxidized analogs with n=1 and n=2 (1-oxo-thietan-3-yl and 1,1-dioxo-thietan-3-yl)

In $N(R^5)R^6$ as a radical Y, $R^8$ as a substituent on an aliphatic or cycloaliphatic group is preferably selected from cyano, $C_3$-$C_8$-cycloalkyl which may be substituted by 1 or 2 substituents selected from CN, methyl and oxo, $C_3$-$C_8$-halocycloalkyl, $OR^9$, $S(O)_n R^9$, $N(R^{10a})R^{10b}$ $C(=O)N(R^{10a})R^{10b}$, $C(=O)OR^9$, phenyl, optionally substituted with 1, 2, 3, 4 or 5, preferably 1, 2 or 3, in particular 1, substituents $R^{16}$, and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more, preferably 1, 2 or 3, in particular 1, substituents $R^{16}$; and $R^8$ in the group $C(=O)R^8$ is selected from hydrogen, $C_1$-$C_6$-alkyl, $C_1$-$C_6$-haloalkyl, $OR^9$ and $N(R^{10a})R^{10b}$;

wherein $R^9$, $R^{10a}$, $R^{10b}$ and $R^{16}$ have one of the above general meanings, or, in particular, one of the below preferred meanings.

More preferably, in $N(R^5)R^6$ as a radical Y, $R^8$ as a substituent on an aliphatic or cycloaliphatic group is selected from $C_3$-$C_8$-cycloalkyl, $C_3$-$C_8$-halocycloalkyl, —$C(=O)N(R^{10a})R^{10b}$, —$C(=S)N(R^{10a})R^{10b}$, —$C(=O)OR^9$, phenyl, optionally substituted with 1, 2, 3, 4 or 5, preferably 1, 2 or 3, in particular 1, substituents $R^{16}$, and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more, preferably 1, 2 or 3, in particular 1, substituents $R^{16}$;

or two $R^8$ present on the same carbon atom together form a group =O, =C($R^{13}$)$_2$; =S; =S(O)$_m$($R^{15}$)$_2$, =S(O)$_m$ $R^{15}$N($R^{14a}$)$R^{14b}$, =$NR^{10a}$, =$NOR^9$; or =NN$R^{10a}R^{10b}$;

and $R^8$ in the group $C(=O)R^8$ is selected from hydrogen, $C_1$-$C_6$-alkyl, $C_1$-$C_6$-haloalkyl, $OR^9$ and $N(R^{10a})R^{10b}$;

wherein $R^9$, $R^{10a}$, $R^{10b}$ and $R^{16}$ have one of the above general meanings, or, in particular, one of the below preferred meanings.

Even more preferably, in $N(R^5)R^6$ as a radical Y, $R^8$ as a substituent on an aliphatic or cycloaliphatic group is selected from —$C(=O)N(R^{10a})R^{10b}$, phenyl and a 5- or 6-membered heteroaromatic ring comprising 1, 2 or 3 heteroatoms selected from N, O and S, as ring members, where the heteroaromatic ring is optionally substituted with one or more, preferably 1, 2 or 3, in particular 1, substituents $R^{16}$.

In this case, $R^{11a}$ and $R^{10b}$ are preferably selected, independently of each other, from hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkylcarbonyl, $C_1$-$C_4$-haloalkylcarbonyl, $C_1$-$C_4$-alkylaminocarbonyl, $C_1$-$C_4$-haloalkylaminocarbonyl, $C_3$-$C_6$-cycloalkylaminocarbonyl and $C_3$-$C_6$-halocycloalkylaminocarbonyl, or, together with the nitrogen atom to which they are bound, form a 5- or 6-membered saturated, partially unsaturated or aromatic heterocyclic ring, which additionally may contain 1 or 2 further heteroatoms or heteroatom groups selected from N, O, S, NO, SO and $SO_2$, as ring members, where the heterocyclic ring may carry 1 or 2, in particular 1, substituents selected from halogen, CN, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio.

More preferably, $R^{10a}$ and $R^{10b}$ are in this case selected, independently of each other, from hydrogen, $C_1$-$C_4$-alkyl, $C_1$-$C_4$-haloalkyl, $C_3$-$C_6$-cycloalkyl, $C_3$-$C_6$-halocycloalkyl, $C_1$-$C_4$-alkylaminocarbonyl and $C_1$-$C_4$-haloalkylaminocarbonyl. Specifically, they are selected, independently of each other, from hydrogen, $C_1$-$C_4$-alkyl, $C_1$-$C_4$-haloalkyl and $C_3$-$C_6$-cycloalkyl. Very specifically, one of $R^{10a}$ and $R^{10b}$ is hydrogen and the other is $C_1$-$C_4$-alkyl, $C_1$-$C_4$-haloalkyl or $C_3$-$C_6$-cycloalkyl.

In an alternative particular embodiment, in $N(R^5)R^6$ as Y, $R^5$ is hydrogen;

$R^6$ is selected from $C_1$-$C_6$-alkyl, $C_1$-$C_6$-haloalkyl, $C_1$-$C_4$-alkyl which carries one radical $R^8$, $C_3$-$C_6$-cycloalkyl, phenyl which may be substituted with 1, 2, 3, 4, or 5 substituents $R^{11}$, and a 4-, 5- or 6-membered saturated heteromonocyclic ring containing 1 heteroatom or heteroatom group selected from N, O, S, SO and $SO_2$, as ring member or a 5- or 6-membered heteromonocyclic aromatic ring containing 1, 2 or 3 heteroatoms selected from O, N and S as ring members, where the heteromonocyclic ring may be substituted with one or more substituents $R^{11}$, where the heteromonocyclic ring is preferably selected from rings of formulae F-1 to F-51:

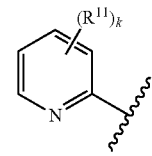
F-1

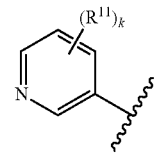
F-2

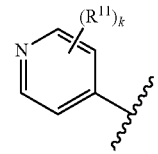
F-3

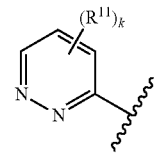
F-4

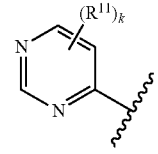
F-5

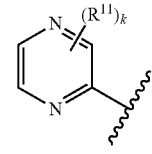
F-6

-continued
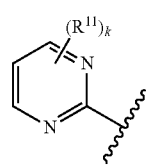 F-7
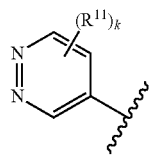 F-8
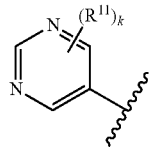 F-9
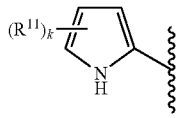 F-10
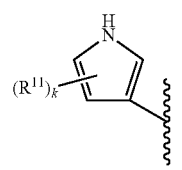 F-11
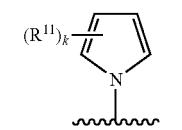 F-12
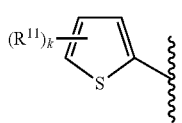 F-13
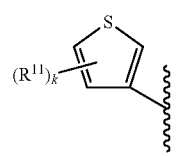 F-14
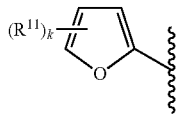 F-15
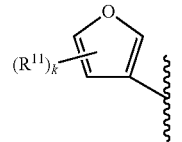 F-16
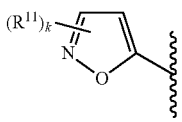 F-17
-continued
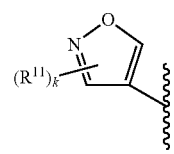 F-18
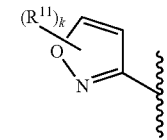 F-19
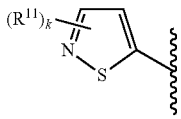 F-20
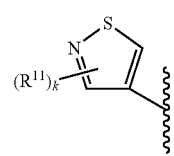 F-21
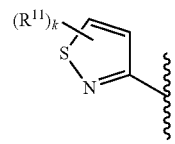 F-22
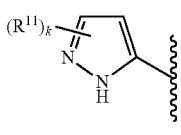 F-23
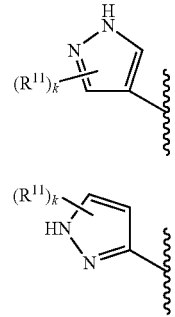 F-24
F-25
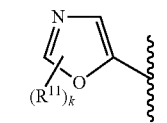 F-26
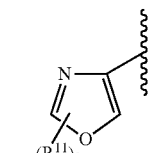 F-27
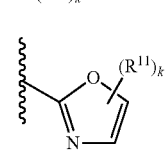 F-28

-continued
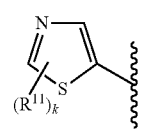 F-29
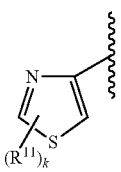 F-30
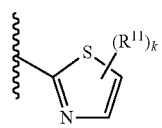 F-31
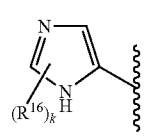 F-32
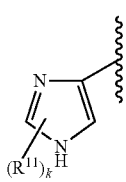 F-33
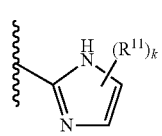 F-34
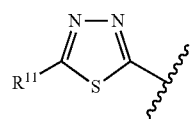 F-35
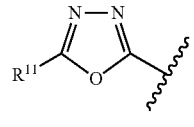 F-36
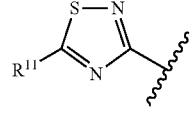 F-37
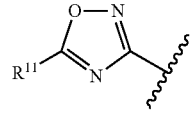 F-38
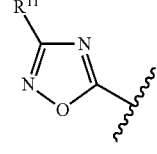 F-39
-continued
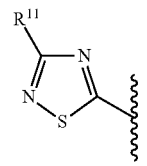 F-40
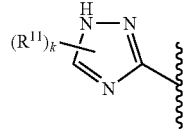 F-41
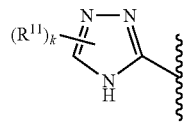 F-42
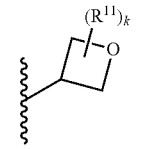 F-43
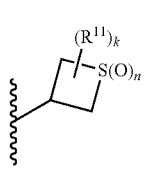 F-44
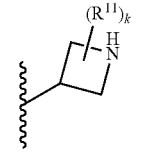 F-45
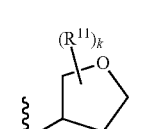 F-46
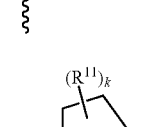 F-47
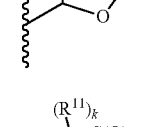 F-48
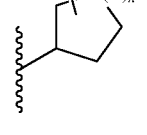 F-49

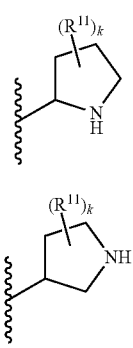

wherein
k is 0, 1, 2 or 3,
n is 0, 1 or 2, and
each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or two $R^{11}$ present on the same carbon atom of a saturated ring may form together =O or =S;
$R^8$ is selected from $C_3$-$C_8$-cycloalkyl, $C_3$-$C_8$-halocycloalkyl, $C_1$-$C_6$-alkylthio, $C_1$-$C_6$-haloalkylthio, —C(=O)N($R^{10a}$)$R^{10b}$, phenyl, optionally substituted with 1, 2, 3, 4 or 5 substituents $R^{16}$, and a heterocyclic ring selected from rings of formulae E-1 to E-51 as defined above;
wherein
$R^{10a}$ is selected from the group consisting of hydrogen, $C_1$-$C_6$-alkyl, $C_2$-$C_3$-alkynyl, —$CH_2$—CN and $C_1$-$C_6$-alkoxy-methyl;
$R^{11b}$ is selected from the group consisting of hydrogen, $C_1$-$C_6$-alkyl, $C_1$-$C_6$-haloalkyl, $C_3$-$C_6$-cycloalkyl, $C_3$-$C_6$-cyclohaloalkyl, phenyl which is optionally substituted with 1, 2, 3, 4 or 5 substituents selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; and a heterocyclic ring selected from rings of formulae E-1 to E-51 as defined above; and
each $R^{16}$ as a substituent on phenyl or a heterocyclic ring E-1 to E-51 is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or
two $R^{16}$ present on the same carbon atom of a saturated heterocyclic ring may form together =O or =S;
or
$R^5$ and $R^6$, together with the nitrogen atom to which they are bound, form a 5- or 6-membered saturated heterocyclic ring, where the ring may further contain 1 or 2 heteroatoms or heteroatom-containing groups selected from O, S, SO, $SO_2$, NH and C=O as ring members, wherein the heterocyclic ring may be substituted with 1, 2 or 3 substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy, and preferably form a 5- or 6-membered saturated heterocyclic ring, wherein the heterocyclic ring may be substituted with 1, 2 or 3 substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy.

Among the above rings, preference is given to F-44, F-48 and F-49. Particular preference is given to ring F-44 with n=0 (thietan-3-yl) and its oxidized analogs with n=1 and n=2 (1-oxo-thietan-3-yl and 1,1-dioxo-thietan-3-yl).

Specifically, in $A^2$, W is O and Y is N($R^5$)$R^6$, wherein
$R^5$ is selected from hydrogen and methyl, preferably hydrogen; and
$R^6$ is selected from $C_1$-$C_4$-alkyl which carries one radical $R^8$, preferably methyl which carries one radical $R^8$; $C_1$-$C_4$-haloalkyl, and a 4-, 5- or 6-membered saturated heteromonocyclic ring containing 1 heteroatom or heteroatom group selected from S, SO and $SO_2$, as ring member, where the heteromonocyclic ring may be substituted with one or more substituents $R^{11}$;
wherein
$R^8$ is selected from —C(=O)N($R^{10a}$)$R^{10b}$, phenyl and a 5- or 6-membered heteroaromatic ring comprising 1, 2 or 3 heteroatoms selected from N, O and S, as ring members, where the heteroaromatic ring is optionally substituted with one or more, preferably 1, 2 or 3, in particular 1, substituents $R^{16}$,
wherein
$R^{10a}$ and $R^{10b}$ are selected, independently of each other, from hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkylcarbonyl, $C_1$-$C_4$-haloalkylcarbonyl, $C_1$-$C_4$-alkylaminocarbonyl, $C_1$-$C_4$-haloalkylaminocarbonyl, $C_3$-$C_6$-cycloalkylaminocarbonyl and $C_3$-$C_6$-halocycloalkylaminocarbonyl, and preferably from hydrogen, $C_1$-$C_4$-alkyl, $C_1$-$C_4$-haloalkyl and $C_3$-$C_6$-cycloalkyl, where it is preferred that one of $R^{10a}$ and $R^{10b}$ is hydrogen and the other is $C_1$-$C_4$-alkyl, $C_1$-$C_4$-haloalkyl or $C_3$-$C_6$-cycloalkyl;
each $R^{11}$ is independently selected from halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; and
each $R^{16}$ is independently selected from halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl;
or
$R^5$ and $R^6$, together with the nitrogen atom to which they are bound, form a 5- or 6-membered saturated, partially unsaturated or aromatic heterocyclic ring, which additionally may contain 1 or 2 further heteroatoms or heteroatom groups selected from N, O, S, NO, SO and $SO_2$, as ring members, where the heterocyclic ring may carry 1 or 2, in particular 1, substituents selected from halogen, CN, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio, and form preferably a 5- or 6-membered saturated heterocyclic ring (i.e. $R^5$ and $R^6$ form together —(CH$_2$)$_4$— or —(CH$_2$)$_5$—), wherein the heterocyclic ring may be substituted with 1, 2 or 3 substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy.

Preferably the 4-, 5- or 6-membered saturated heteromonocyclic ring $R^6$ containing 1 heteroatom or heteroatom group selected from S, SO and SO$_2$, as ring member is selected from rings D-72 (=F-44), D-77 (=F-48), D-78 (=F-49) and D-100 to D-102 listed below in context with $A^4$. The ring may be substituted with one or more, preferably 1, 2 or 3, in particular 1, substituents $R^{11}$ as defined above. More preference is given to rings D-72 (=F-44), D-77 (=F-48) and D-78 (=F-49). Particular preference is given to ring D-72 (=F-44) with n=0 (thietan-3-yl) and its oxidized analogs with n=1 and n=2 (1-oxo-thietan-3-yl and 1,1-dioxo-thietan-3-yl).

Preferably the 5- or 6-membered heteroaromatic ring comprising 1, 2 or 3 heteroatoms selected from N, O and S, as ring members is selected from rings E-1 to E-42 as defined above. The ring may be substituted with one or more, preferably 1, 2 or 3, in particular 1, substituents $R^{16}$ selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl.

In an alternative embodiment of the invention, A is $A^3$.

Preferably, $R^{7a}$ and $R^{7b}$ in the group $A^3$ are independently of each other selected from hydrogen, $C_1$-$C_4$-alkyl and $C_1$-$C_4$-haloalkyl, and more preferably one of $R^{7a}$ and $R^{7b}$ is hydrogen and the other is hydrogen or methyl. Specifically, both are hydrogen.

In the group $A^3$, $R^5$ is preferably selected from hydrogen, $C_1$-$C_6$-alkyl, $C_3$-$C_6$-cycloalkyl, $C_2$-$C_6$-alkenyl, $C_2$-$C_6$-alkynyl, wherein the four last-mentioned aliphatic and cycloaliphatic radicals may be partially or fully halogenated and/or may be substituted with one or more, preferably 1, 2 or 3, in particular 1, substituents $R^8$; and $R^6$ is preferably selected from hydrogen, $C_1$-$C_6$-alkyl, $C_3$-$C_6$-cycloalkyl, $C_2$-$C_6$-alkenyl, $C_2$-$C_6$-alkynyl, wherein the four last-mentioned aliphatic and cycloaliphatic radicals may be partially or fully halogenated and/or may be substituted by one or more, preferably 1, 2 or 3, in particular 1, substituents $R^8$, —$OR^9$, —$NR^{10a}R^{10b}$, —$S(O)_nR^9$, —$C(=O)NR^{10a}N(R^{10a}R^{10b})$, —$C(=O)R^8$, and a 3-, 4-, 5-, 6- or 7-membered saturated, partially unsaturated or maximally unsaturated heteromonocyclic or heterobicyclic ring containing 1, 2, 3 or 4 heteroatoms or heteroatom groups independently selected from N, O, S, NO, SO and SO$_2$, as ring members, where the heteromonocyclic or heterobicyclic ring may be substituted with one or more, preferably 1, 2 or 3, in particular 1, substituents $R^{11}$;

or $R^5$ and $R^6$, together with the nitrogen atom to which they are bound, form a 3-, 4-, 5- or 6-membered saturated, partially unsaturated or maximally unsaturated heterocyclic ring, where the ring may further contain 1, 2, 3 or 4 heteroatoms or heteroatom-containing groups selected from O, S, N, SO, SO$_2$, C=O and C=S as ring members, wherein the heterocyclic ring may be substituted with 1, 2, 3, 4 or 5, preferably 1, 2 or 3, in particular 1, substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the aliphatic or cycloaliphatic moieties in the twelve last-mentioned radicals may be substituted by one or more, preferably 1, 2 or 3, in particular 1, radicals $R^8$, and phenyl which may be substituted with 1, 2, 3, 4 or 5, preferably 1, 2 or 3, in particular 1, substituents $R^{11}$;

or $R^5$ and $R^6$ together form a group =$C(R^8)_2$, =$S(O)_m(R^9)_2$, =$NR^{10a}$ or =$NOR^9$ wherein $R^8$, $R^9$, $R^{10a}$, $R^{10b}$ and $R^{11}$ have one of the above general meanings, or, in particular, one of the below preferred meanings.

More preferably, in the group $A^3$, $R^5$ is selected from hydrogen, $C_1$-$C_4$-alkyl, which may be partially or fully halogenated and/or may be substituted with one or more, preferably 1, 2 or 3, in particular 1, substituents $R^8$ selected from cyano and $C_1$-$C_6$-alkoxy; and $C_2$-$C_4$-alkynyl; and $R^6$ is selected from —$S(O)_nR^9$ and —$C(=O)R^8$, or $R^5$ and $R^6$, together with the nitrogen atom to which they are bound, form a 3-, 4-, 5- or 6-membered saturated, partially unsaturated or maximally unsaturated heterocyclic ring, where the ring may further contain 1, 2, 3 or 4 heteroatoms or heteroatom-containing groups selected from O, S, N, SO, SO$_2$, C=O and C=S as ring members, wherein the heterocyclic ring may be substituted with 1, 2, 3, 4 or 5, preferably 1, 2 or 3, in particular 1, substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the aliphatic or cycloaliphatic moieties in the twelve last-mentioned radicals may be substituted by one or more, preferably 1, 2 or 3, in particular 1, radicals $R^8$, and phenyl which may be substituted with 1, 2, 3, 4 or 5, preferably 1, 2 or 3, in particular 1, substituents $R^{11}$;

wherein $R^8$, $R^9$, $R^{10a}$, $R^{10b}$ and $R^{11}$ have one of the above general meanings, or, in particular, one of the below preferred meanings.

Even more preferably, in the group $A^3$, $R^5$ is selected from hydrogen, $C_1$-$C_4$-alkyl, $C_2$-$C_3$-alkynyl, CH$_2$—CN and $C_1$-$C_6$-alkoxy-methyl-, preferably from hydrogen and $C_1$-$C_4$-alkyl; and $R^6$ is —$C(=O)R^8$;

wherein $R^8$ has one of the above general meanings, or, in particular, one of the below preferred meanings.

$R^8$ in —$C(=O)R^8$ as a meaning of the radicals $R^5$ and $R^6$ of the group $A^3$ is preferably selected from the group consisting of $C_1$-$C_6$-alkyl, $C_1$-$C_6$-haloalkyl, $C_3$-$C_8$-cycloalkyl, $C_3$-$C_8$-halocycloalkyl, where the aliphatic and cycloaliphatic moieties in the four last-mentioned radicals may be substituted by one or more, preferably 1, 2 or 3, in particular 1, radicals $R^{13}$;

—$OR^9$, —$S(O)_nR^9$, —$N(R^{10a})R^{10b}$, phenyl, optionally substituted with 1, 2, 3, 4 or 5, preferably 1, 2 or 3, in particular 1, substituents $R^{16}$, and a 3-, 4-, 5- or 6-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more, preferably 1, 2 or 3, in particular 1, substituents $R^{16}$, wherein $R^9$, $R^{10a}$, $R^{10b}$, $R^{13}$ and $R^{16}$ have one of the above general meanings, or, in particular, one of the below preferred meanings.

More preferably, $R^8$ in $-C(=O)R^8$ as a meaning of the radicals $R^5$ and $R^6$ of the group $A^3$ is selected from the group consisting of $C_1$-$C_6$-alkyl, $C_1$-$C_6$-haloalkyl, $C_1$-$C_4$-alkyl substituted by one radical $R^{13}$, $C_3$-$C_8$-cycloalkyl, $C_3$-$C_8$-halocycloalkyl, $-N(R^{10a})R^{10b}$, phenyl which is optionally substituted with 1, 2, 3, 4 or 5 substituents each independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; and a heterocyclic ring selected from rings of formulae E-1 to E-51 as defined above.

$R^9$ in $-OR^9$ as a meaning of $R^8$ in the group $-C(=O)R^8$ as a meaning of the radicals $R^5$ and $R^6$ of the group $A^3$ is preferably selected from $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl and $C_3$-$C_8$-cycloalkyl-$C_1$-$C_4$-alkyl-, and more preferably from $C_1$-$C_6$-alkyl, $C_1$-$C_6$-haloalkyl, $C_3$-$C_8$-cycloalkyl, $C_3$-$C_8$-halocycloalkyl and $C_3$-$C_8$-cycloalkyl-$C_1$-$C_4$-alkyl-.

$R^{10a}$ and $R^{10b}$ in $-N(R^{10a})R^{10b}$ as a meaning of $R^8$ in the group $-C(=O)R^8$ as a meaning of the radicals $R^5$ and $R^6$ of the group $A^3$ are, independently of each other, preferably selected from hydrogen, $C_1$-$C_4$-alkyl, $C_1$-$C_4$-haloalkyl, $C_1$-$C_4$-alkyl substituted by one radical $R^{13}$, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkylcarbonyl, $C_1$-$C_4$-haloalkylcarbonyl, $C_1$-$C_4$-alkylaminocarbonyl, $C_1$-$C_4$-haloalkylaminocarbonyl, $C_3$-$C_6$-cycloalkylaminocarbonyl, $C_3$-$C_6$-halocycloalkylaminocarbonyl, and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more, preferably 1, 2 or 3, in particular 1, substituents selected from halogen, CN, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio;

or, $R^{10a}$ and $R^{10b}$, together with the nitrogen atom to which they are bound, form a 5- or 6-membered saturated, partially unsaturated or aromatic heterocyclic ring, which additionally may contain 1 or 2 further heteroatoms or heteroatom groups selected from N, O, S, NO, SO and $SO_2$, as ring members, where the heterocyclic ring may carry 1 or 2, in particular 1, substituents selected from halogen, CN, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio.

More preferably, $R^{10a}$ and $R^{10b}$ in $R^8$ in the radicals $R^5$ and $R^6$ of the group $A^3$ are, independently of each other, selected from hydrogen, $C_1$-$C_4$-alkyl, $C_1$-$C_4$-haloalkyl, $C_1$-$C_4$-alkyl substituted by one radical $R^{13}$, $C_3$-$C_6$-cycloalkyl, $C_3$-$C_6$-halocycloalkyl, and a 3- or 4-membered saturated heterocyclic ring comprising 1 heteroatom or heteroatom group selected from N, O, S, NO, SO and $SO_2$, as ring member, where the heterocyclic ring is optionally substituted with one or more, preferably 1, 2 or 3, in particular 1, substituents selected from halogen, CN, $C_1$-$C_4$-alkyl, $C_1$-$C_4$-haloalkyl, $C_1$-$C_4$-alkoxy and $C_1$-$C_4$-haloalkoxy; and are specifically, independently of each other, selected from hydrogen, $C_1$-$C_4$-alkyl and $C_1$-$C_4$-haloalkyl.

$R^{13}$ in $R^8$ in the radicals $R^5$ and $R^6$ of the group $A^3$ is preferably selected from CN, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl and $C_1$-$C_6$-haloalkylsulfonyl.

$R^{16}$ in $R^8$ in the radicals $R^5$ and $R^6$ of the group $A^3$ is preferably selected from halogen, $C_1$-$C_4$-alkyl, $C_1$-$C_4$-haloalkyl, $C_1$-$C_4$-alkoxy and $C_1$-$C_4$-haloalkoxy.

Specifically, $R^8$ in the group $-C(=O)R^8$ in the radicals $R^5$ and $R^6$ of the group $A^3$ is selected from the group consisting of $C_1$-$C_6$-alkyl, $C_1$-$C_6$-haloalkyl, $C_1$-$C_4$-alkyl substituted by one radical $R^{13}$, $C_3$-$C_8$-cycloalkyl, $C_3$-$C_8$-halocycloalkyl, $-N(R^{10a})R^{10b}$, phenyl which is optionally substituted with 1, 2, 3, 4 or 5, preferably 1, 2 or 3 and in particular 1, substituents each independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl, and a heterocyclic ring selected from rings of formulae E-1 to E-51 as defined above, wherein $R^{10a}$ and $R^{10b}$, independently of each other, are selected from hydrogen, $C_1$-$C_4$-alkyl, $C_1$-$C_4$-haloalkyl and $C_3$-$C_6$-cycloalkyl;

$R^{13}$ is selected from CN, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl and a heterocyclic ring selected from rings of formulae E-1 to E-51 as defined above and preferably from $C_1$-$C_6$-alkylthio, $C_1$-$C_6$-haloalkylthio, $C_1$-$C_6$-alkylsulfonyl and $C_1$-$C_6$-haloalkylsulfonyl; and each $R^{16}$ as a substituent on heterocyclic rings of formulae E-1 to E-51 is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or two $R^{16}$ present on the same carbon atom of a saturated heterocyclic ring may form together =O or =S.

More specifically, $R^8$ in the group $-C(=O)R^8$ in the radicals $R^5$ and $R^6$ of the group $A^3$ is selected from the group consisting of $C_1$-$C_6$-alkyl, $C_1$-$C_6$-haloalkyl, $C_1$-$C_4$-alkyl substituted by one radical $R^{13}$, $C_3$-$C_8$-cycloalkyl and $C_3$-$C_8$-halocycloalkyl, where $R^{13}$ is selected from CN, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, preferably from $C_1$-$C_6$-alkylthio, $C_1$-$C_6$-haloalkylthio, $C_1$-$C_6$-alkylsulfonyl and $C_1$-$C_6$-haloalkylsulfonyl and in particular from $C_1$-$C_6$-alkylthio, $C_1$-$C_6$-haloalkylthio, $C_1$-$C_6$-alkylsulfonyl and $C_1$-$C_6$-haloalkylsulfonyl.

Alternatively, in the group $A^3$, $R^5$ and $R^6$ are in particular hydrogen.

In an alternative embodiment of the invention, A is $A^4$.

$A^4$ is preferably selected from a 3-, 4-, 5-, 6- or 7-membered saturated, partially unsaturated or maximally unsaturated heteromonocyclic ring containing 1, 2, 3 or 4 heteroatoms or heteroatom groups selected from N, O, S, NO and SO$_2$, as ring members, where the heteromonocyclic ring is optionally substituted with one or more, preferably 1, 2 or 3, in particular 1, substituents R$^{11}$, where R$^{11}$ has one of the above general meanings, or, in particular, one of the below preferred meanings.

More preferably, A$^4$ is selected from a 3-, 4-, 5-, 6- or 7-membered saturated heteromonocyclic ring containing 1 or 2 heteroatoms or heteroatom groups selected from N, O, S, NO, SO and SO$_2$, as ring members, a 5-, 6- or 7-membered partially unsaturated heteromonocyclic ring containing 1, 2 or 3 heteroatoms or heteroatom groups selected from N, O, S, NO, SO and SO$_2$, as ring members, and a 5- or 6-membered aromatic heteromonocyclic ring containing 1, 2, 3 or 4 heteroatoms selected from N, O and S as ring members, where the heteromonocyclic ring is optionally substituted with one or more, preferably 1, 2 or 3, in particular 1, substituents R$^{11}$, where R$^{11}$ has one of the above general meanings, or, in particular, one of the below preferred meanings.

A$^4$ is even more preferably selected from rings of formulae D-1 to D-173

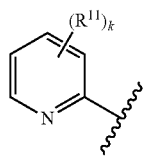
D-1

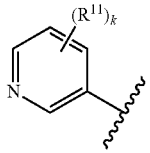
D-2

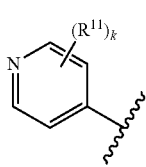
D-3

D-4

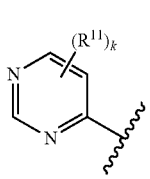
D-5

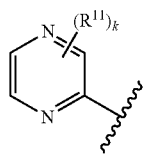
D-6

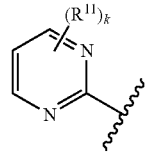
D-7

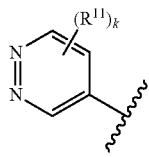
D-8

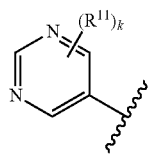
D-9

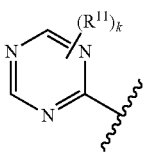
D-10

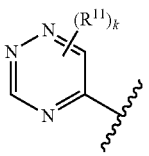
D-11

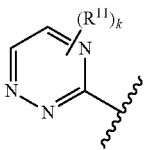
D-12

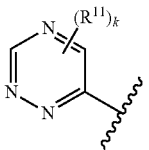
D-13

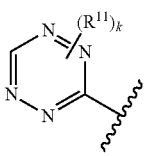
D-14

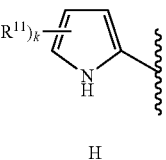
D-15

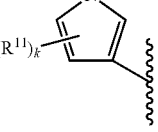
D-16

| | |
|---|---|
| 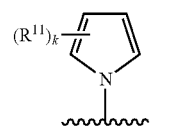 D-17 | 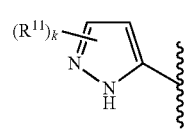 D-28 |
| 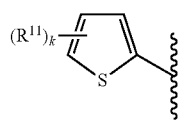 D-18 | 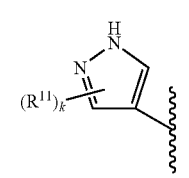 D-29 |
| 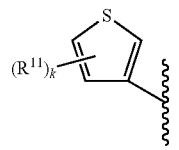 D-19 | 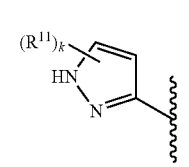 D-30 |
| 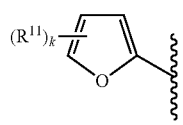 D-20 | 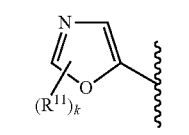 D-31 |
| 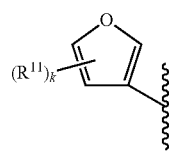 D-21 | 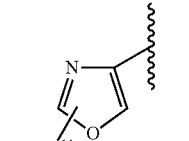 D-32 |
| 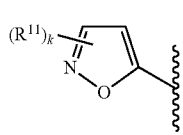 D-22 | 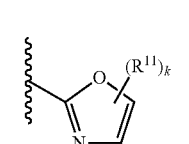 D-33 |
| 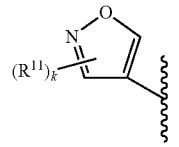 D-23 | 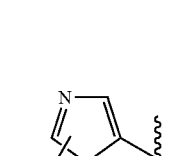 D-34 |
| 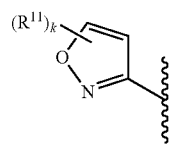 D-24 | 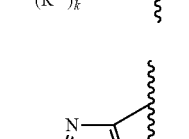 D-35 |
| 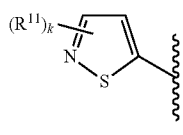 D-25 | 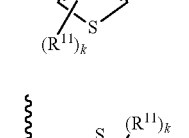 D-36 |
| 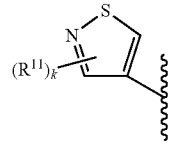 D-26 | 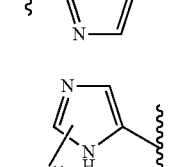 D-37 |
| 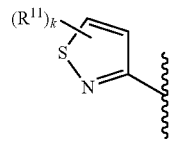 D-27 | |

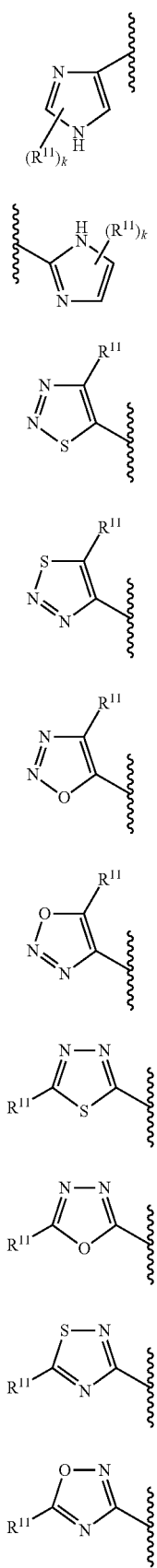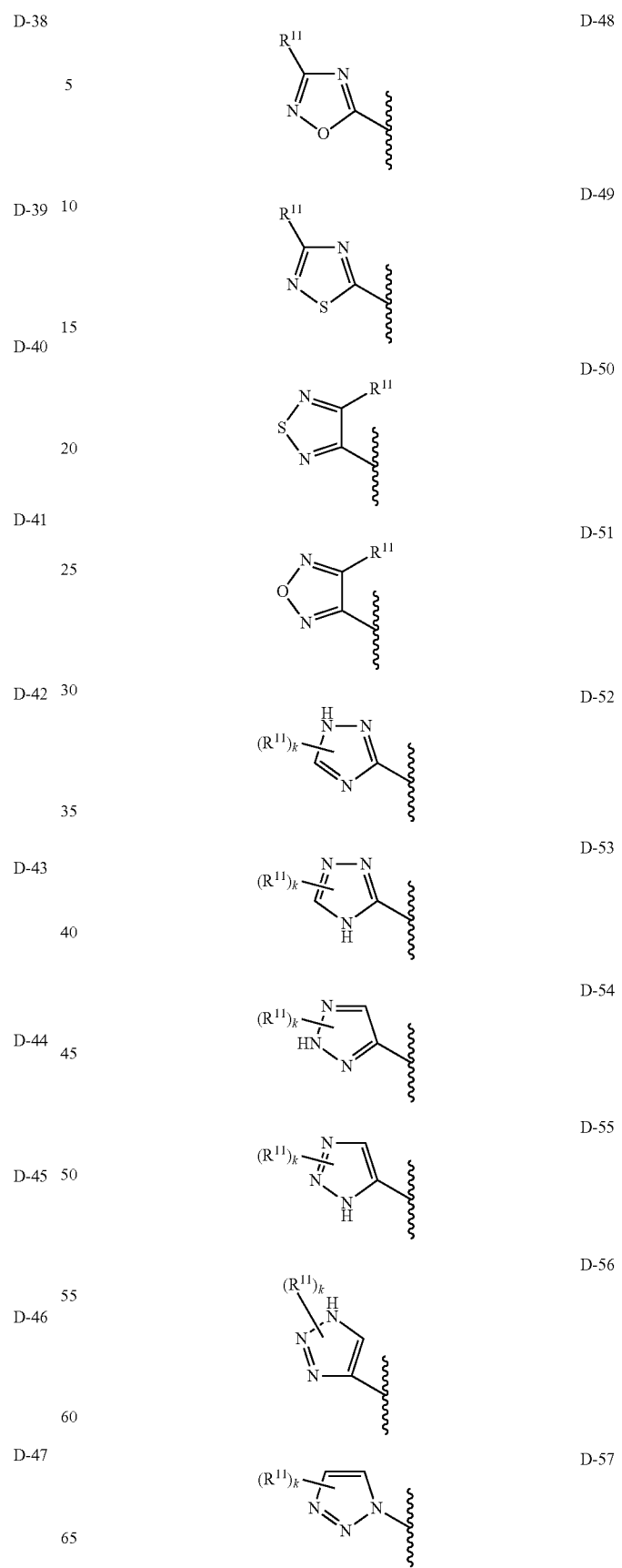

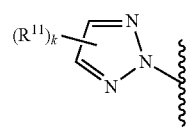 D-58
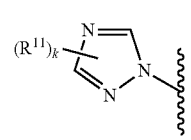 D-59
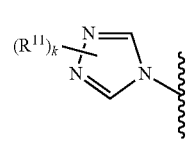 D-60
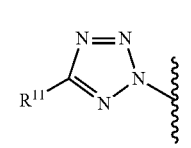 D-61
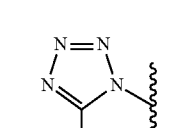 D-62
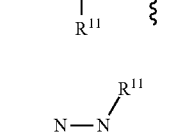 D-63
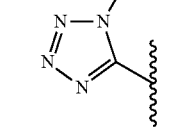 D-64
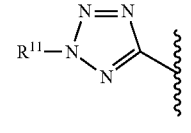 D-65
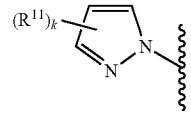 D-66
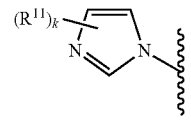 D-67
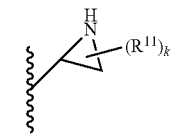 D-68
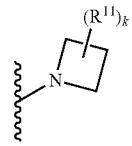 D-69
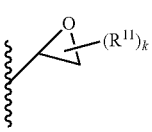 D-70
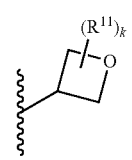 D-71
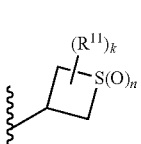 D-72
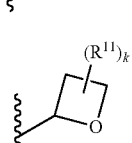 D-73
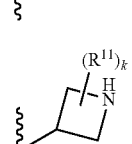 D-74
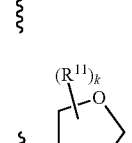 D-75
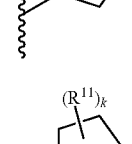 D-76
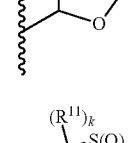 D-77
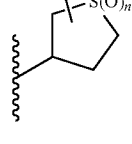 D-78

-continued
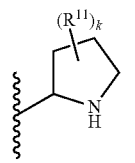 D-79
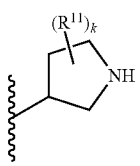 D-80
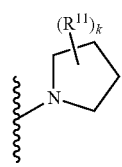 D-81
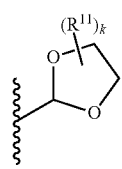 D-82
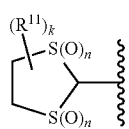 D-83
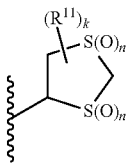 D-84
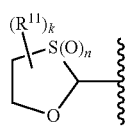 D-85
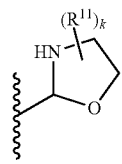 D-86
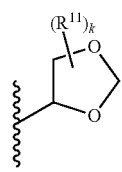 D-87
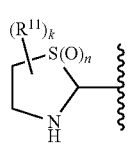 D-88
-continued
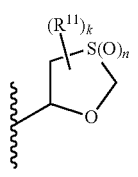 D-89
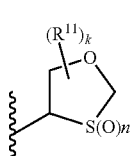 D-90
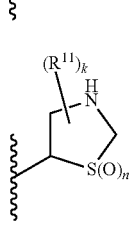 D-91
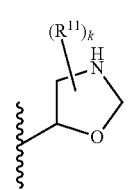 D-92
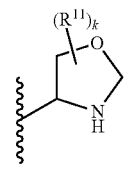 D-93
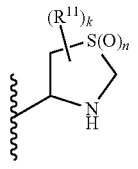 D-94
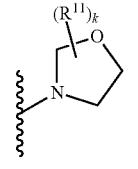 D-95
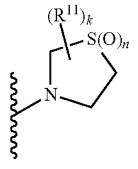 D-96
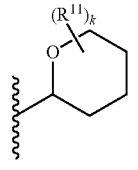 D-97

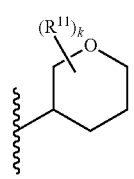 D-98
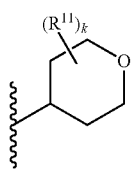 D-99
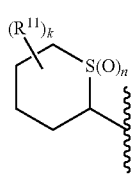 D-100
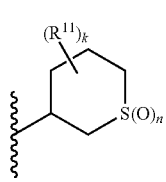 D-101
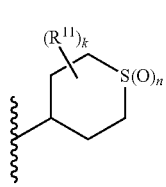 D-102
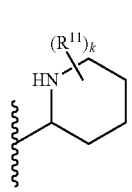 D-103
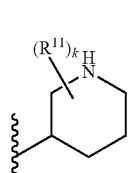 D-104
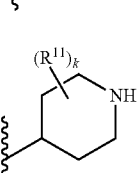 D-105
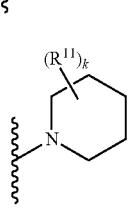 D-106
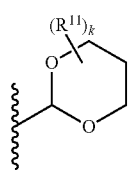 D-107
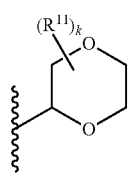 D-108
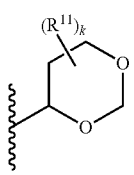 D-109
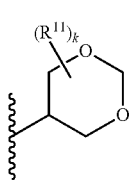 D-110
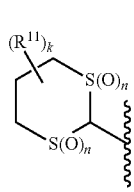 D-111
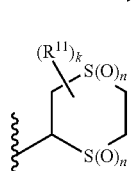 D-112
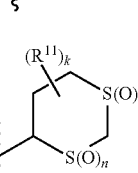 D-113
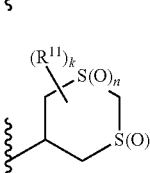 D-114
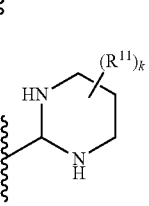 D-115

-continued
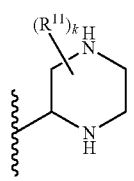 D-116
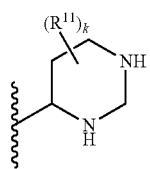 D-117
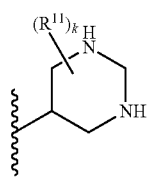 D-118
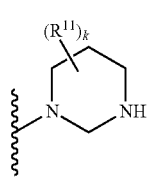 D-119
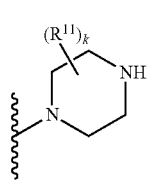 D-120
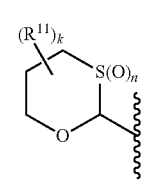 D-121
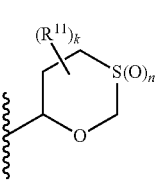 D-122
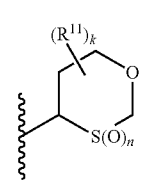 D-123
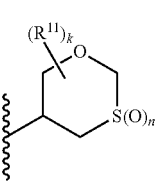 D-124
-continued
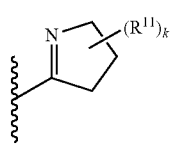 D-125
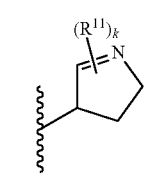 D-126
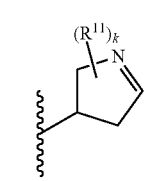 D-127
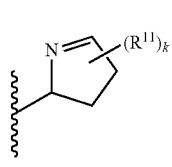 D-128
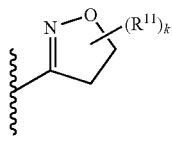 D-129
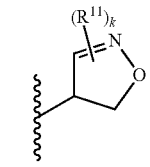 D-130
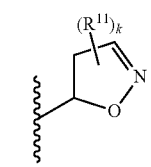 D-131
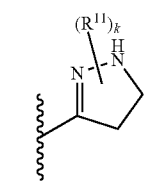 D-132
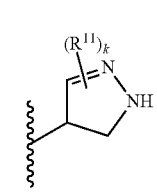 D-133

-continued
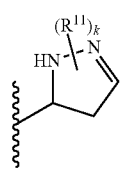 D-134
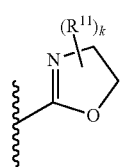 D-135
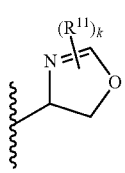 D-136
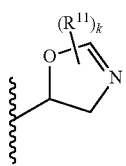 D-137
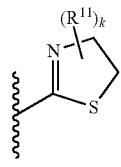 D-138
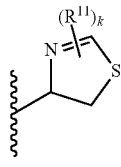 D-139
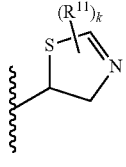 D-140
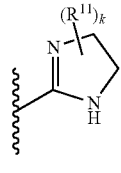 D-141
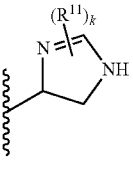 D-142
-continued
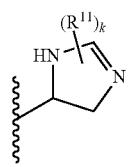 D-143
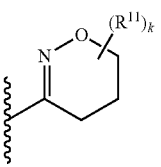 D-144
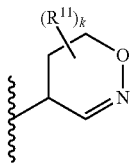 D-145
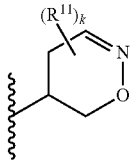 D-146
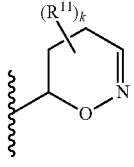 D-147
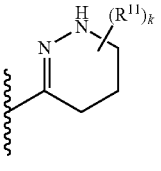 D-148
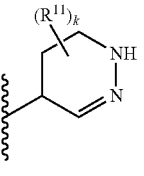 D-149
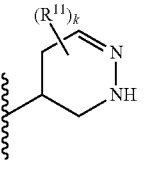 D-150
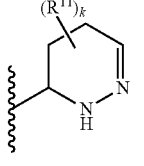 D-151

-continued

D-152

D-153

D-154

D-155

D-156

D-157

D-158

D-159

D-160

-continued

D-161

D-162

D-163

D-164

D-165

D-166

D-167

D-168

D-169

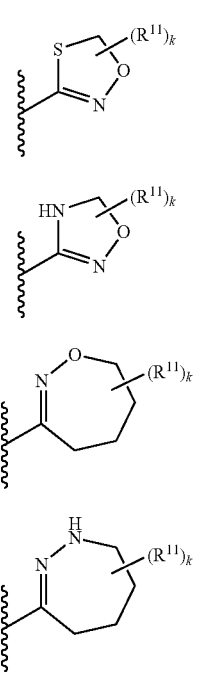

wherein k is 0, 1, 2 or 3, n is 0, 1 or 2 and $R^{11}$ has one of the above general meanings, or, in particular, one of the below preferred meanings;
and is in particular selected from D-59, D-65 and D-66 and is specifically D-59.

Preferably, in the above rings D-1 to D-173,
each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or
two $R^{11}$ present on the same carbon atom of a saturated or partially unsaturated ring may form together =O or =S.

Among the radicals $A^1$, $A^2$, $A^3$ and $A^4$, preference is given to $A^2$.

Preferably, $B^1$, $B^2$ and $B^3$ are $CR^2$.

More preferably, $B^1$ and $B^3$ are $CR^2$, where $R^2$ is not hydrogen, and $B^2$ is $CR^2$, where $R^2$ has one of the meanings given above.

Preferably, $R^2$ is selected from hydrogen, halogen, cyano, azido, nitro, —SCN, $SF_5$, $C_1$-$C_6$-alkyl, $C_3$-$C_8$-cycloalkyl, $C_2$-$C_6$-alkenyl, $C_2$-$C_6$-alkynyl, wherein the four last mentioned aliphatic and cycloaliphatic radicals may be partially or fully halogenated and/or may be substituted by one or more, preferably 1, 2 or 3, in particular 1, radicals $R^8$, —$OR^9$, —$S(O)_nR^9$ and —$NR^{10a}R^{10b}$,
wherein $R^8$, $R^9$, $R^{10a}$ and $R^{10b}$ have one of the above general meanings, or, in particular, one of the below preferred meanings.

More preferably, $R^2$ is selected from hydrogen, halogen and $C_1$-$C_2$-haloalkyl, even more preferably from hydrogen, F, Cl, Br and $CF_3$, even more preferably from hydrogen, F, $C_1$ and $CF_3$, and in particular from hydrogen and Cl.

Specifically, $B^2$ is CH and $B^1$ and $B^3$ have one of the general or one of the preferred meanings given above for $R^2$ (with the proviso that they are not hydrogen) and are preferably selected from halogen and $C_1$-$C_2$-haloalkyl, even more preferably from F, Cl, Br and $CF_3$, particularly preferably from hydrogen, F, $C_1$ and $CF_3$, and are in particular Cl.

Alternatively, $B^2$ is CF or CCl and $B^1$ and $B^3$ have one of the general or one of the preferred meanings given above for $R^2$ (with the proviso that they are not hydrogen) and are preferably selected from halogen and $C_1$-$C_2$-haloalkyl, such as F, $C_1$ and $CF_3$, even more preferably from F and Cl, and are in particular Cl.

Preferably, $G^1$, $G^3$ and $G^4$ are $CR^4$ and $G^2$ is N or $CR^4$, where $R^4$ has one of the meanings given above or below; or $G^2$, $G^3$ and $G^4$ are $CR^4$ and $G^1$ is N or $CR^4$, where $R^4$ has one of the meanings given above or below.

Preferably, $R^4$ is selected from hydrogen, halogen, cyano, azido, nitro, $C_1$-$C_6$-alkyl which may be partially or fully halogenated and/or may be substituted by one or more, preferably 1, 2 or 3, in particular 1, radicals $R^8$, $C_3$-$C_8$-cycloalkyl which may be partially or fully halogenated and/or may be substituted by one or more, preferably 1, 2 or 3, in particular 1, radicals $R^8$, $C_2$-$C_6$-alkenyl which may be partially or fully halogenated and/or may be substituted by one or more, preferably 1, 2 or 3, in particular 1, radicals $R^8$, $C_2$-$C_6$-alkynyl which may be partially or fully halogenated and/or may be substituted by one or more, preferably 1, 2 or 3, in particular 1, radicals $R^8$, —$OR^9$, —$S(O)_nR^9$, and —$NR^{10a}R^{10b}$. More preferably, $R^4$ is selected from hydrogen, halogen, cyano, $C_1$-$C_6$-alkyl, $C_1$-$C_6$-haloalkyl, $C_3$-$C_5$-cycloalkyl, $C_3$-$C_5$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, and even more preferably from hydrogen, halogen, cyano, $C_1$-$C_4$-alkyl, $C_1$-$C_4$-haloalkyl, $C_3$-$C_5$-cycloalkyl, $C_3$-$C_5$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio and $C_1$-$C_4$-haloalkylthio, and specifically from hydrogen, methyl and $CF_3$.

More preferably, $G^1$, $G^3$ and $G^4$ are CH and $G^2$ is $CR^4$, where $R^4$ has one of the above general or preferred meanings; or $G^1$ is N, $G^3$ and $G^4$ are CH and $G^2$ is $CR^4$.

In another embodiment, $G^1$ and $G^4$ are $CR^4$ and $G^2$ and $G^3$ are CH, where $R^4$ has one of the meanings given above or below.

Even more preferably, $G^1$, $G^3$ and $G^4$ are CH and $G^2$ is $CR^4$, where $R^4$ is selected from hydrogen, halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, preferably from hydrogen, F, Cl, CN, methyl, $CF_3$, methoxy and methylthio, and specifically from hydrogen, F, Cl, CN, methyl methoxy and methylthio.

Alternatively, even more preferably, $G^1$ is N, $G^2$ is $CR^4$ and $G^3$ and $G^4$ are CH, where $R^4$ is selected from hydrogen, halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, preferably from hydrogen, F, Cl, CN, methyl, $CF_3$, methoxy and methylthio, and specifically from hydrogen and methyl.

Preferably, $R^1$ is selected from $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_3$-$C_6$-cycloalkyl $C_3$-$C_6$-halocycloalkyl or C(=O)$OR^{13}$; more preferably, from $C_1$-$C_4$-alkyl, $C_1$-$C_4$-haloalkyl, $C_3$-$C_6$-cycloalkyl, $C_3$-$C_6$-halocycloalkyl and C(=O)$OR^{15}$, even more preferably from $C_1$-$C_4$-alkyl, $C_1$-$C_4$-haloalkyl and —C(=O)$OR^{15}$, and particularly preferably from $C_1$-$C_4$-haloalkyl and —C(=O)$OR^{15}$, wherein $R^{15}$ is preferably $C_1$-$C_4$-alkyl. In particular, $R^1$ is $C_1$-$C_4$-haloalkyl, specifically $C_1$-$C_2$-haloalkyl and more specifically halomethyl, in particular fluoromethyl, such as fluoromethyl, difluoromethyl and trifluoromethyl, and is very specifically trifluoromethyl.

Preferably, $R^{3a}$ and $R^{3b}$ are selected, independently of each other, from hydrogen, halogen, hydroxyl, $C_1$-$C_3$-alkyl, $C_1$-$C_3$-alkenyl, $C_1$-$C_3$-alkynyl, $C_1$-$C_3$-haloalkyl, $C_1$-$C_3$-alkoxy, $C_1$-$C_3$-alkylthio and $C_1$-$C_3$-alkylsulfonyl, more preferably from hydrogen and halogen, in particular from hydrogen and fluorine and are specifically hydrogen.

If not specified otherwise above, $R^8$, $R^9$, $R^{10a}$, $R^{10b}$, $R^{11}$, $R^{12}$, $R^{13}$, $R^{14}$, $R^{14a}$, $R^{14b}$, $R^{15}$ and $R^{16}$ have following preferred meanings:

In case $R^8$ is a substituent on an alkyl, alkenyl or alkynyl group, it is preferably selected from the group consisting of cyano, $C_3$-$C_8$-cycloalkyl, $C_3$-$C_8$-halocycloalkyl, $-OR^9$, $-SR^9$, $-C(=O)N(R^{10a})R^{10b}$, $-C(=S)N(R^{10a})R^{10b}$, $-C(=O)OR^9$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^9$, $R^{10a}$, $R^{10b}$ and $R^{16}$ have one of the meanings given above or in particular one of the preferred meanings given below.

In case $R^8$ is a substituent on an alkyl, alkenyl or alkynyl group, it is even more preferably selected from the group consisting of cyano, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-haloalkylthio, $-C(=O)N(R^{10a})R^{10b}$, $-C(=S)N(R^{10a})R^{10b}$, $-C(=O)OR^9$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^9$, $R^{10a}$, $R^{10b}$ and $R^{16}$ have one of the meanings given above or in particular one of the preferred meanings given below. In particular it is selected from the group consisting of cyano, $C_3$-$C_6$-cycloalkyl, $C_3$-$C_6$-halocycloalkyl, $-C(=O)N(R^{10a})R^{10b}$, $-C(=S)N(R^{10a})R^{10b}$, $-C(=O)OR^9$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^9$, $R^{10a}$, $R^{10b}$ and $R^{16}$ have one of the meanings given above or in particular one of the preferred meanings given below.

In case $R^8$ is a substituent on a cycloalkyl group, it is preferably selected from the group consisting of cyano, $C_1$-$C_6$-alkyl, $C_1$-$C_6$-haloalkyl, $C_1$-$C_6$-alkoxy-$C_1$-$C_6$-alkyl, $-OR^9$, $-OSO_2R^9$, $-SR^9$, $-N(R^{10a})R^{10b}$, $-C(=O)N(R^{10a})R^{10b}$, $-C(=S)N(R^{10a})R^{10b}$, $-C(=O)OR^9$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^9$, $R^{10a}$, $R^{10b}$ and $R^{16}$ have one of the meanings given above or in particular one of the preferred meanings given below.

In case $R^8$ is a substituent on a cycloalkyl group, it is even more preferably selected from the group consisting of halogen, $C_1$-$C_4$-alkyl, $C_1$-$C_3$-haloalkyl, $C_1$-$C_4$-alkoxy and $C_1$-$C_3$-haloalkoxy. In particular, $R^8$ as a substituent on a cycloalkyl group is selected from halogen, $C_1$-$C_4$-alkyl and $C_1$-$C_3$-haloalkyl.

In case of $R^8$ in a group $-C(=O)R^8$, $=C(R^8)_2$ or $-C(=NR^6)R^8$, $R^8$ is preferably selected from the group consisting of hydrogen, $C_1$-$C_6$-alkyl, $C_1$-$C_6$-haloalkyl, $C_1$-$C_6$-alkoxy-$C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, $-OR^9$, $-SR^9$, $-N(R^{10a})R^{10b}$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^9$, $R^{10a}$, $R^{10b}$ and $R^{16}$ have one of the meanings given above or in particular one of the preferred meanings given below.

In case of $R^8$ in a group $-C(=O)R^8$, $=C(R^8)_2$ or $-C(=NR^6)R^8$, $R^8$ is more preferably selected from the group consisting of $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, $-N(R^{10a})R^{10b}$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $RiG^a$, $R^{10b}$ and $R^{16}$ have has one of the meanings given above or in particular one of the preferred meanings given below.

Preferably, each $R^9$ is independently selected from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl, phenyl which may be substituted by 1, 2, 3, 4 or 5 radicals $R^{16}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{16}$, where $R^{16}$ has one of the meanings given above or in particular one of the preferred meanings given below.

More preferably, each $R^9$ is independently selected from the group consisting of hydrogen, $C_1$-$C_6$-alkyl, $C_1$-$C_6$-haloalkyl, phenyl which may be substituted by 1, 2, 3, 4 or 5 radicals $R^{16}$; and a 5- or 6-membered heteroaromatic ring containing 1, 2 or 3 heteroatoms selected from N, O and S, as ring members, where the heteroaromatic ring may be substituted by one or more radicals $R^{16}$; where $R^{16}$ has one of the meanings given above or in particular one of the preferred meanings given below.

$R^{10a}$ and $R^{10b}$ are, independently of each other, preferably selected from hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkylcarbonyl, $C_1$-$C_4$-haloalkylcarbonyl, $C_1$-$C_4$-alkylaminocarbonyl, $C_1$-$C_4$-haloalkylaminocarbonyl, $C_3$-$C_6$-cycloalkylaminocarbonyl, $C_3$-$C_6$-halocycloalkylaminocarbonyl, and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more, preferably 1, 2 or 3, in particular 1, substituents selected from halogen, CN, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio;

or, $R^{10a}$ and $R^{10b}$, together with the nitrogen atom to which they are bound, form a 5- or 6-membered saturated, partially unsaturated or aromatic heterocyclic ring, which additionally may contain 1 or 2 further heteroatoms or heteroatom groups selected from N, O, S, NO, SO and $SO_2$, as ring members, where the heterocyclic ring may carry 1 or 2, in particular 1, substituents selected from halogen, CN, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio.

More preferably, $R^{10a}$ and $R^{10b}$ are, independently of each other, selected from hydrogen, $C_1$-$C_4$-alkyl, $C_1$-$C_4$-haloalkyl, $C_3$-$C_6$-cycloalkyl, $C_3$-$C_6$-halocycloalkyl, and a 3- or 4-membered saturated heterocyclic ring comprising 1 heteroatom or heteroatom group selected from N, O, S, NO, SO and $SO_2$, as ring member, where the heterocyclic ring is optionally substituted with one or more, preferably 1, 2 or 3, in particular 1, substituents selected from halogen, CN, $C_1$-$C_4$-alkyl, $C_1$-$C_4$-haloalkyl, $C_1$-$C_4$-alkoxy and $C_1$-$C_4$-haloalkoxy; and are specifically, independently of each other, selected from hydrogen, $C_1$-$C_4$-alkyl and $C_1$-$C_4$-haloalkyl.

Each $R^{11}$ and each $R^{16}$ are independently of each occurrence and independently of each other preferably selected from halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl and $C_1$-$C_4$-haloalkylsulfonyl, and more preferably from halogen, CN, $C_1$-$C_4$-alkyl, $C_1$-$C_4$-haloalkyl, $C_1$-$C_4$-alkoxy and $C_1$-$C_4$-haloalkoxy.

Each $R^{12}$ is preferably selected from $C_1$-$C_4$-alkyl and is in particular methyl.

In case $R^{13}$ is a substituent on an alkyl, alkenyl or alkynyl group, it is preferably selected from the group consisting of cyano, $C_3$-$C_8$-cycloalkyl, $C_3$-$C_8$-halocycloalkyl, —OH, —SH, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl and phenyl which may be substituted by 1, 2 or 3 radicals selected from halogen, $C_1$-$C_4$-alkyl, $C_1$-$C_4$-haloalkyl, $C_1$-$C_4$-alkoxy and $C_1$-$C_4$-haloalkoxy.

In case $R^{13}$ is a substituent on a cycloalkyl group, it is preferably selected from the group consisting of cyano, $C_1$-$C_6$-alkyl, $C_1$-$C_6$-haloalkyl, $C_3$-$C_8$-cycloalkyl, $C_3$-$C_8$-halocycloalkyl, —OH, —SH, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl and phenyl which may be substituted by 1, 2 or 3 radicals selected from halogen, $C_1$-$C_4$-alkyl, $C_1$-$C_4$-haloalkyl, $C_1$-$C_4$-alkoxy and $C_1$-$C_4$-haloalkoxy.

In case $R^{13}$ is a substituent on a cycloalkyl group, it is even more preferably selected from the group consisting of halogen, $C_1$-$C_4$-alkyl, $C_1$-$C_3$-haloalkyl, $C_1$-$C_4$-alkoxy and $C_1$-$C_3$-haloalkoxy. In particular, $R^{13}$ as a substituent on a cycloalkyl group is selected from halogen, $C_1$-$C_4$-alkyl and $C_1$-$C_3$-haloalkyl.

In case of $R^{13}$ in a group —C(=O)$R^{13}$, —C(=S)$R^{13}$, =C($R^{13}$)$_2$ or —C(=N$R^{14}$)$R^{13}$, $R^8$ is preferably selected from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, —OH, —SH, $C_1$-$C_6$-alkoxy, $C_1$-$C_6$-haloalkoxy and phenyl which may be substituted by 1, 2 or 3 radicals selected from halogen, $C_1$-$C_4$-alkyl, $C_1$-$C_4$-haloalkyl, $C_1$-$C_4$-alkoxy and $C_1$-$C_4$-haloalkoxy.

$R^{14}$, $R^{14a}$ and $R^{14b}$ are, independently of each other, preferably selected from hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl and benzyl, where the phenyl ring in benzyl is optionally substituted 1, 2 or 3, in particular 1, substituents selected from halogen, $C_1$-$C_4$-alkyl, $C_1$-$C_4$-haloalkyl, $C_1$-$C_4$-alkoxy and $C_1$-$C_4$-haloalkoxy;

or, $R^{14a}$ and $R^{14b}$, together with the nitrogen atom to which they are bound, form a 5- or 6-membered saturated, partially unsaturated or aromatic heterocyclic ring, which additionally may contain 1 or 2 further heteroatoms or heteroatom groups selected from N, O, S, NO, SO and $SO_2$, as ring members, where the heterocyclic ring may carry 1 or 2, in particular 1, substituents selected from halogen, $C_1$-$C_4$-alkyl, $C_1$-$C_4$-haloalkyl, $C_1$-$C_4$-alkoxy and $C_1$-$C_4$-haloalkoxy.

More preferably, $R^{14}$, $R^{14a}$ and $R^{14b}$ are, independently of each other, selected from hydrogen, $C_1$-$C_4$-alkyl, $C_1$-$C_4$-haloalkyl, $C_3$-$C_6$-cycloalkyl, $C_3$-$C_6$-halocycloalkyl and benzyl, where the phenyl ring in benzyl is optionally substituted 1, 2 or 3, in particular 1, substituents selected from halogen, $C_1$-$C_4$-alkyl, $C_1$-$C_4$-haloalkyl, $C_1$-$C_4$-alkoxy and $C_1$-$C_4$-haloalkoxy;

or, $R^{14a}$ and $R^{14b}$, together with the nitrogen atom to which they are bound, form a 5- or 6-membered saturated, partially unsaturated or aromatic heterocyclic ring, which additionally may contain 1 or 2 further heteroatoms or heteroatom groups selected from N, O, S, NO, SO and $SO_2$, as ring members, where the heterocyclic ring may carry 1 or 2, in particular 1, substituents selected from halogen, $C_1$-$C_4$-alkyl, $C_1$-$C_4$-haloalkyl, $C_1$-$C_4$-alkoxy and $C_1$-$C_4$-haloalkoxy.

Each $R^{15}$ is preferably selected from hydrogen, $C_1$-$C_6$-alkyl, $C_1$-$C_6$-haloalkyl, phenyl, benzyl, pyridyl and phenoxy, wherein the four last-mentioned radicals may be unsubstituted and/or carry 1, 2 or 3 substituents selected from $C_1$-$C_6$-alkyl, $C_1$-$C_6$-haloalkyl, $C_1$-$C_6$-alkoxy and $C_1$-$C_6$-haloalkoxy.

In a particular embodiment of the invention, compound I is a compound of formula IA

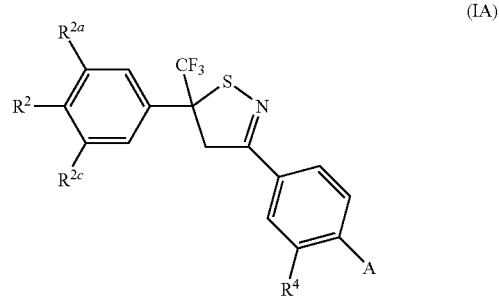

(IA)

where A, $R^2$ and $R^4$ have one of the above-given general or, in particular, one of the above-given preferred meanings, and $R^{2a}$ and $R^{2c}$, independently of each other, have one of the general or, in particular, one of the preferred meanings given above for $R^2$, with the proviso that they are not hydrogen, and are specifically Cl or $CF_3$ and are very specifically Cl.

Examples of preferred compounds are compounds of the following formulae Ia.1 to Ia.31, where the variables have one of the general or preferred meanings given above. Examples of preferred compounds are the individual compounds compiled in the tables 1 to 2082 below, Moreover, the meanings mentioned below for the individual variables in the tables are per se, independently of the combination in which they are mentioned, a particularly preferred embodiment of the substituents in question.

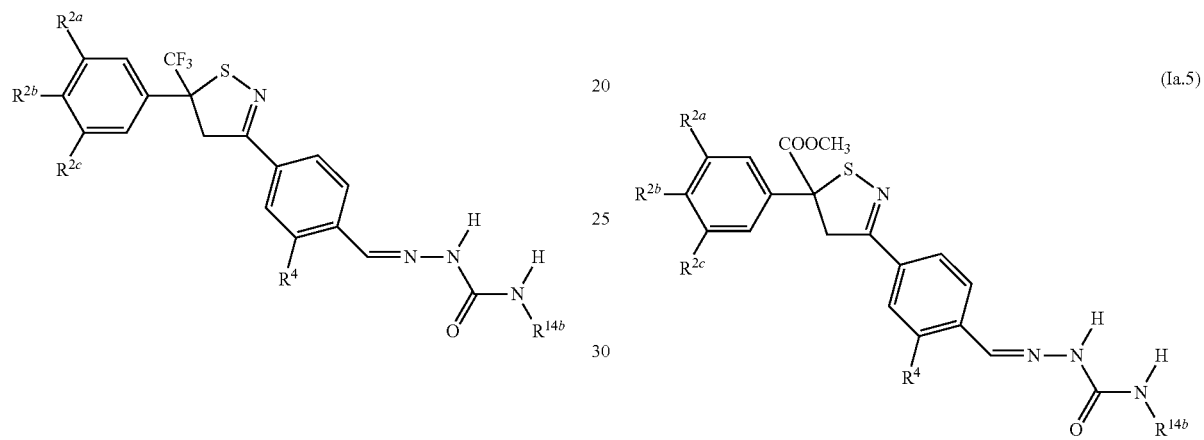

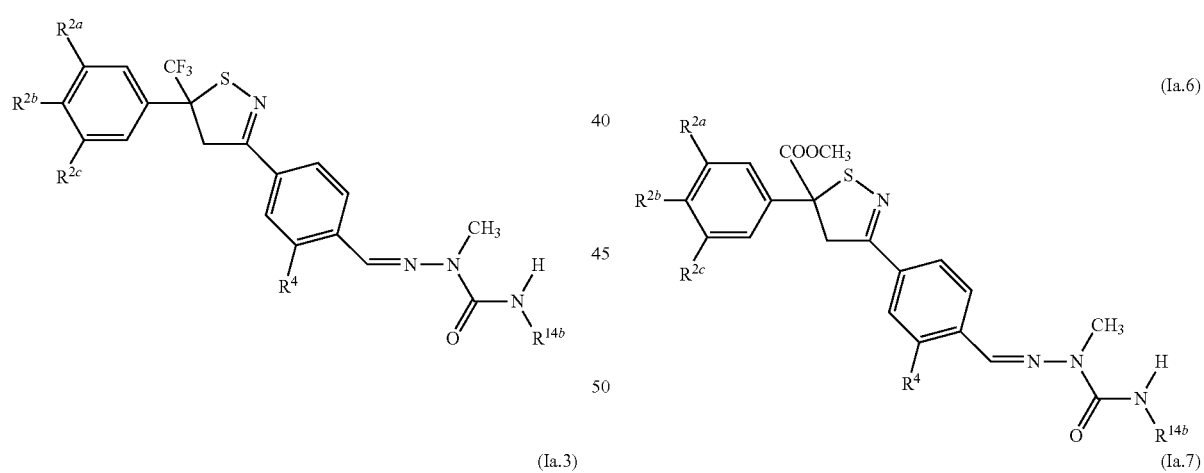

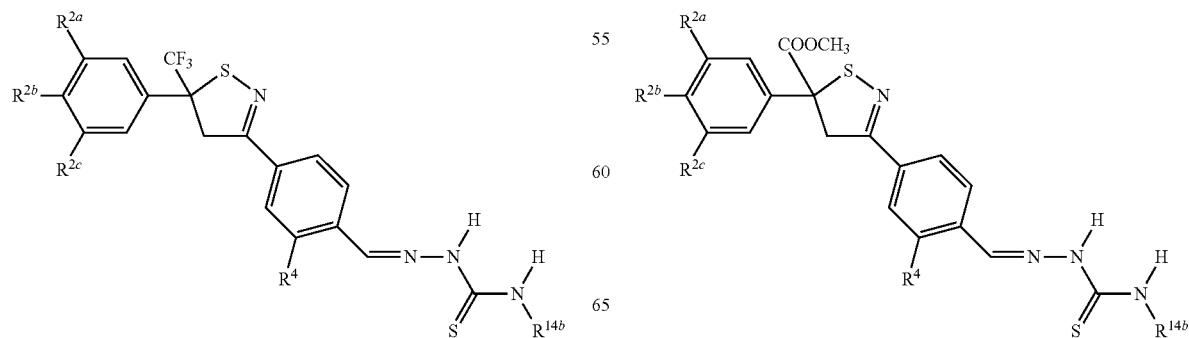

-continued

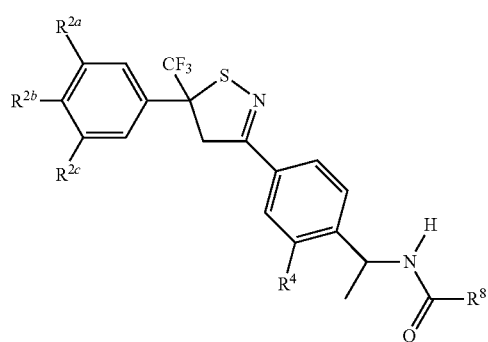
(Ia.18)
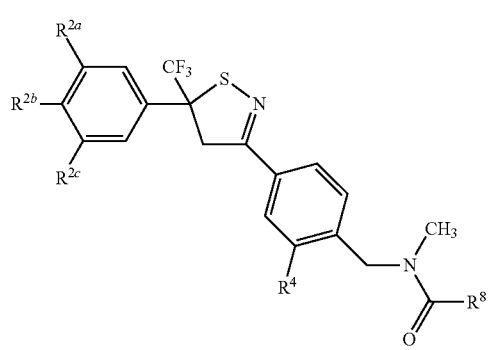
(Ia.19)
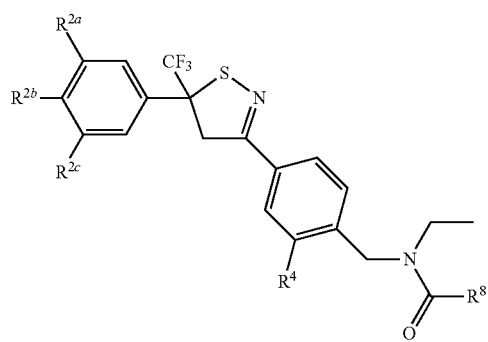
(Ia.20)
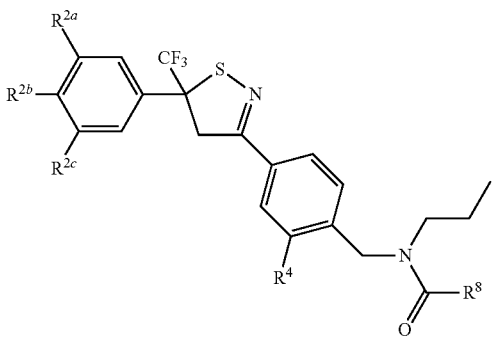
(Ia.21)
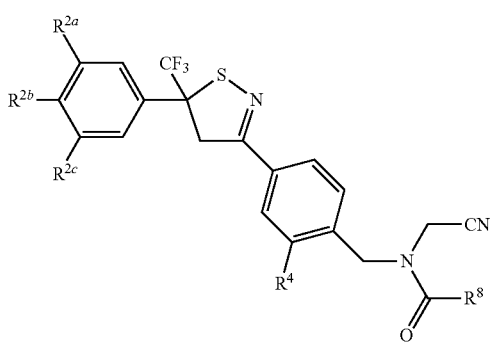
(Ia.22)
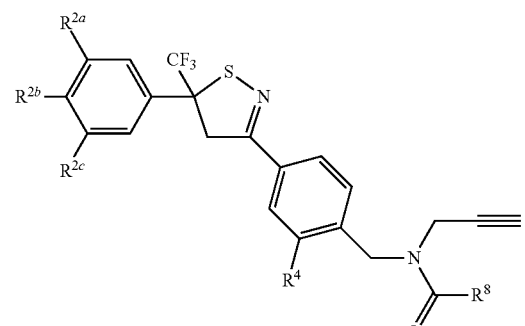
(Ia.23)
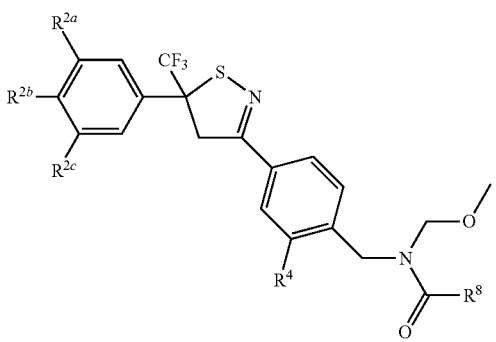
(Ia.24)
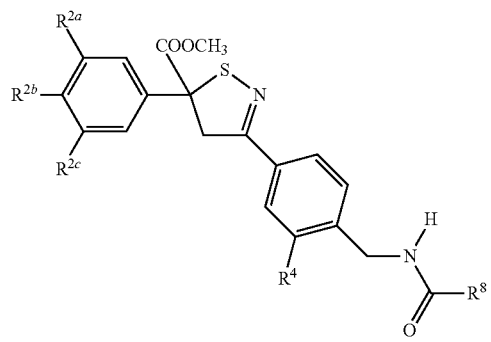
(Ia.25)

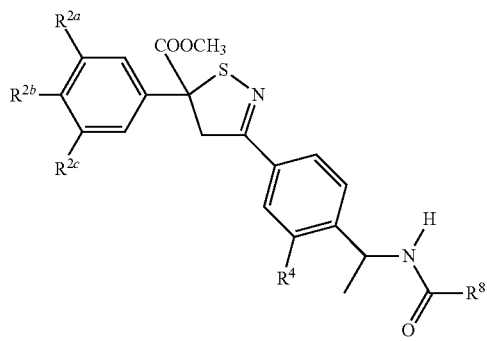
(Ia.26)

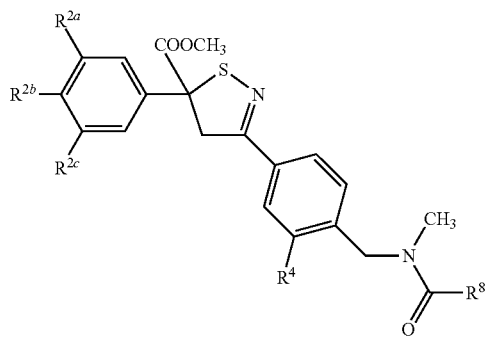
(Ia.27)

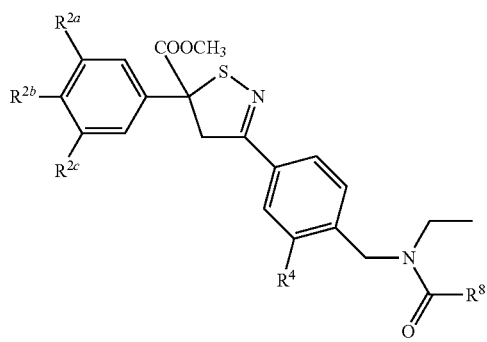
(Ia.28)

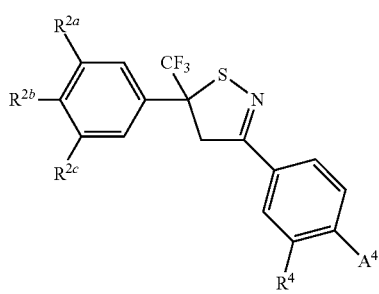
(Ia.29)

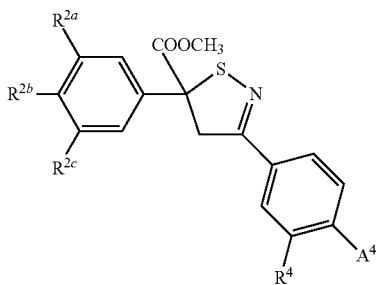
(Ia.30)

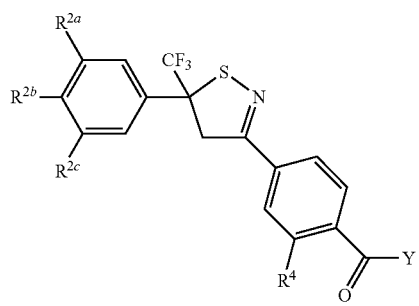
(Ia.31)

Table 1

Compounds of the formula Ia.1 in which $R^{14b}$ is hydrogen, and the combination of $R^{2a}$, $R^{2b}$, $R^{2c}$ and $R^4$ for a compound corresponds in each case to one row of Table A Table 2

Compounds of the formula Ia.1 in which $R^{14b}$ is methyl, and the combination of $R^{2a}$, $R^{2b}$, $R^{2c}$ and $R^4$ for a compound corresponds in each case to one row of Table A Table 3

Compounds of the formula Ia.1 in which $R^{14b}$ is ethyl, and the combination of $R^{2a}$, $R^{2b}$, $R^{2c}$ and $R^4$ for a compound corresponds in each case to one row of Table A Table 4

Compounds of the formula Ia.1 in which $R^{14b}$ is propyl, and the combination of $R^{2a}$, $R^{2b}$, $R^{2c}$ and $R^4$ for a compound corresponds in each case to one row of Table A Table 5

Compounds of the formula Ia.1 in which $R^{14b}$ is isopropyl, and the combination of $R^{2a}$, $R^{2b}$, $R^{2c}$ and $R^4$ for a compound corresponds in each case to one row of Table A Table 6

Compounds of the formula Ia.1 in which $R^{14b}$ is n-butyl, and the combination of $R^{2a}$, $R^{2b}$, $R^{2c}$ and $R^4$ for a compound corresponds in each case to one row of Table A Table 7

Compounds of the formula Ia.1 in which $R^{14b}$ is sec-butyl, and the combination of $R^{2a}$, $R^{2b}$, $R^{2c}$ and $R^4$ for a compound corresponds in each case to one row of Table A Table 8

Compounds of the formula Ia.1 in which $R^{14b}$ is isobutyl, and the combination of $R^{2a}$, $R^{2b}$, $R^{2c}$ and $R^4$ for a compound corresponds in each case to one row of Table A Table 9

Compounds of the formula Ia.1 in which $R^{14b}$ is tert-butyl, and the combination of $R^{2a}$, $R^{2b}$, $R^{2c}$ and $R^4$ for a compound corresponds in each case to one row of Table A Table 10

Compounds of the formula Ia.1 in which $R^{14b}$ is isopropenyl, and the combination of $R^{2a}$, $R^{2b}$, $R^{2c}$ and $R^4$ for a compound corresponds in each case to one row of Table A Table 11
Compounds of the formula Ia.1 in which $R^{14b}$ is cyclopropyl, and the combination of $R^{2a}$, $R^{2b}$, $R^{2c}$ and $R^4$ for a compound corresponds in each case to one row of Table A Table 12
Compounds of the formula Ia.1 in which $R^{14b}$ is 2,2-difluoroethyl, and the combination of $R^{2a}$, $R^{2b}$, $R^{2c}$ and $R^4$ for a compound corresponds in each case to one row of Table A Table 13
Compounds of the formula Ia.1 in which $R^{14b}$ is 2,2,2-trifluoroethyl, and the combination of $R^{2a}$, $R^{2b}$, $R^{2c}$ and $R^4$ for a compound corresponds in each case to one row of Table A Table 14
Compounds of the formula Ia.1 in which $R^{14b}$ is 3,3,3-trifluoropropyl, and the combination of $R^{2a}$, $R^{2b}$, $R^{2c}$ and $R^4$ for a compound corresponds in each case to one row of Table A Table 15
Compounds of the formula Ia.1 in which $R^{14b}$ is $CH_2$—CN, and the combination of $R^{2a}$, $R^{2b}$, $R^{2c}$ and $R^4$ for a compound corresponds in each case to one row of Table A Table 16
Compounds of the formula Ia.1 in which $R^{14b}$ is $CH_2$-isopropenyl, and the combination of $R^{2a}$, $R^{2b}$, $R^{2c}$ and $R^4$ for a compound corresponds in each case to one row of Table A Table 17
Compounds of the formula Ia.1 in which $R^{14b}$ is $CH_2$-cyclopropyl, and the combination of $R^{2a}$, $R^{2b}$, $R^{2c}$ and $R^4$ for a compound corresponds in each case to one row of Table A Table 18
Compounds of the formula Ia.1 in which $R^{14b}$ is thietan-3-yl, and the combination of $R^{2a}$, $R^{2b}$, $R^{2c}$ and $R^4$ for a compound corresponds in each case to one row of Table A Table 19
Compounds of the formula Ia.1 in which $R^{14b}$ is 1-oxo-thietan-3-yl, and the combination of $R^{2a}$, $R^{2b}$, $R^{2c}$ and $R^4$ for a compound corresponds in each case to one row of Table A Table 20
Compounds of the formula Ia.1 in which $R^{14b}$ is 1,1-dioxo-thietan-3-yl, and the combination of $R^{2a}$, $R^{2b}$, $R^{2c}$ and $R^4$ for a compound corresponds in each case to one row of Table A Table 21
Compounds of the formula Ia.1 in which $R^{14b}$ is allyl, and the combination of $R^{2a}$, $R^{2b}$, $R^{2c}$ and $R^4$ for a compound corresponds in each case to one row of Table A Table 22
Compounds of the formula Ia.1 in which $R^{14b}$ is propargyl, and the combination of $R^{2a}$, $R^{2b}$, $R^{2c}$ and $R^4$ for a compound corresponds in each case to one row of Table A Table 23
Compounds of the formula Ia.1 in which $R^{14b}$ is methoxy, and the combination of $R^{2a}$, $R^{2b}$, $R^{2c}$ and $R^4$ for a compound corresponds in each case to one row of Table A Table 24
Compounds of the formula Ia.1 in which $R^{14b}$ is ethoxy, and the combination of $R^{2a}$, $R^{2b}$, $R^{2c}$ and $R^4$ for a compound corresponds in each case to one row of Table A Table 25
Compounds of the formula Ia.1 in which $R^{14b}$ is isopropoxy, and the combination of $R^{2a}$, $R^{2b}$, $R^{2c}$ and $R^4$ for a compound corresponds in each case to one row of Table A Tables 26 to 50
Compounds of the formula Ia.2 in which $R^{14b}$ is as defined in any of tables 1 to 25 and the combination of $R^{2a}$, $R^{2b}$, $R^{2c}$ and $R^4$ for a compound corresponds in each case to one row of Table A Tables 51 to 75
Compounds of the formula Ia.3 in which $R^{14b}$ is as defined in any of tables 1 to 25 and the combination of $R^{2a}$, $R^{2b}$, $R^{2c}$ and $R^4$ for a compound corresponds in each case to one row of Table A Tables 76 to 100
Compounds of the formula Ia.4 in which $R^{14b}$ is as defined in any of tables 1 to 25 and the combination of $R^{2a}$, $R^{2b}$, $R^{2c}$ and $R^4$ for a compound corresponds in each case to one row of Table A Tables 101 to 125
Compounds of the formula Ia.5 in which $R^{14b}$ is as defined in any of tables 1 to 25 and the combination of $R^{2a}$, $R^{2b}$, $R^{2c}$ and $R^4$ for a compound corresponds in each case to one row of Table A Tables 126 to 150
Compounds of the formula Ia.6 in which $R^{14b}$ is as defined in any of tables 1 to 25 and the combination of $R^{2a}$, $R^{2b}$, $R^{2c}$ and $R^4$ for a compound corresponds in each case to one row of Table A Tables 151 to 175
Compounds of the formula Ia.7 in which $R^{14b}$ is as defined in any of tables 1 to 25 and the combination of $R^{2a}$, $R^{2b}$, $R^{2c}$ and $R^4$ for a compound corresponds in each case to one row of Table A Tables 176 to 200
Compounds of the formula Ia.8 in which $R^{14b}$ is as defined in any of tables 1 to 25 and the combination of $R^{2a}$, $R^{2b}$, $R^{2c}$ and $R^4$ for a compound corresponds in each case to one row of Table A Table 201
Compounds of the formula Ia.9 in which $R^{10b}$ is phenyl, and the combination of $R^{2a}$, $R^{2b}$, $R^{2c}$ and $R^4$ for a compound corresponds in each case to one row of Table A Table 202
Compounds of the formula Ia.9 in which $R^{10b}$ is 2-fluorophenyl, and the combination of $R^{2a}$, $R^{2b}$, $R^{2c}$ and $R^4$ for a compound corresponds in each case to one row of Table A Table 203
Compounds of the formula Ia.9 in which $R^{10b}$ is 3-fluorophenyl, and the combination of $R^{2a}$, $R^{2b}$, $R^{2c}$ and $R^4$ for a compound corresponds in each case to one row of Table A Table 204
Compounds of the formula Ia.9 in which $R^{10b}$ is 4-fluorophenyl, and the combination of $R^{2a}$, $R^{2b}$, $R^{2c}$ and $R^4$ for a compound corresponds in each case to one row of Table A Table 205
Compounds of the formula Ia.9 in which $R^{10b}$ is 2-chlorophenyl, and the combination of $R^{2a}$, $R^{2b}$, $R^{2c}$ and $R^4$ for a compound corresponds in each case to one row of Table A Table 206
Compounds of the formula Ia.9 in which $R^{10b}$ is 3-chlorophenyl, and the combination of $R^{2a}$, $R^{2b}$, $R^{2c}$ and $R^4$ for a compound corresponds in each case to one row of Table A Table 207
Compounds of the formula Ia.9 in which $R^{10b}$ is 4-chlorophenyl, and the combination of $R^{2a}$, $R^{2b}$, $R^{2c}$ and $R^4$ for a compound corresponds in each case to one row of Table A Table 208
Compounds of the formula Ia.9 in which $R^{10b}$ is 2,3-difluorophenyl, and the combination of $R^{2a}$, $R^{2b}$, $R^{2c}$ and $R^4$ for a compound corresponds in each case to one row of Table A Table 209
Compounds of the formula Ia.9 in which $R^{10b}$ is 2,4-difluorophenyl, and the combination of $R^{2a}$, $R^{2b}$, $R^{2c}$ and $R^4$ for a compound corresponds in each case to one row of Table A Table 210
Compounds of the formula Ia.9 in which $R^{10b}$ is 2,5-difluorophenyl, and the combination of $R^{2a}$, $R^{2b}$, $R^{2c}$ and $R^4$ for a compound corresponds in each case to one row of Table A Table 211
Compounds of the formula Ia.9 in which $R^{10b}$ is 2,6-difluorophenyl, and the combination of $R^{2a}$, $R^{2b}$, $R^{2c}$ and $R^4$ for a compound corresponds in each case to one row of Table A Table 212
Compounds of the formula Ia.9 in which $R^{10b}$ is 3,4-difluorophenyl, and the combination of $R^{2a}$, $R^{2b}$, $R^{2c}$ and $R^4$ for a compound corresponds in each case to one row of Table A Table 213
Compounds of the formula Ia.9 in which $R^{10b}$ is 3,5-difluorophenyl, and the combination of $R^{2a}$, $R^{2b}$, $R^{2c}$ and $R^4$ for a compound corresponds in each case to one row of Table A Table 214
Compounds of the formula Ia.9 in which $R^{10b}$ is 3,4,5-trifluorophenyl, and the combination of $R^{2a}$, $R^{2b}$, $R^{2c}$ and $R^4$ for a compound corresponds in each case to one row of Table A Table 215
Compounds of the formula Ia.9 in which $R^{10b}$ is 2,4-dichlorophenyl, and the combination of $R^{2a}$, $R^{2b}$, $R^{2c}$ and $R^4$ for a compound corresponds in each case to one row of Table A Table 216
Compounds of the formula Ia.9 in which $R^{10b}$ is 3,5-dichlorophenyl, and the combination of $R^{2a}$, $R^{2b}$, $R^{2c}$ and $R^4$ for a compound corresponds in each case to one row of Table A Table 217
Compounds of the formula Ia.9 in which $R^{10b}$ is 2-methylphenyl, and the combination of $R^{2a}$, $R^{2b}$, $R^{2c}$ and $R^4$ for a compound corresponds in each case to one row of Table A Table 218
Compounds of the formula Ia.9 in which $R^{10b}$ is 3-methylphenyl, and the combination of $R^{2a}$, $R^{2b}$, $R^{2c}$ and $R^4$ for a compound corresponds in each case to one row of Table A Table 219
Compounds of the formula Ia.9 in which $R^{10b}$ is 4-methylphenyl, and the combination of $R^{2a}$, $R^{2b}$, $R^{2c}$ and $R^4$ for a compound corresponds in each case to one row of Table A Table 220
Compounds of the formula Ia.9 in which $R^{10b}$ is 2-methoxyphenyl, and the combination of $R^{2a}$, $R^{2b}$, $R^{2c}$ and $R^4$ for a compound corresponds in each case to one row of Table A Table 221
Compounds of the formula Ia.9 in which $R^{10b}$ is 3-methoxyphenyl, and the combination of $R^{2a}$, $R^{2b}$, $R^{2c}$ and $R^4$ for a compound corresponds in each case to one row of Table A Table 222
Compounds of the formula Ia.9 in which $R^{10b}$ is 4-methoxyphenyl, and the combination of $R^{2a}$, $R^{2b}$, $R^{2c}$ and $R^4$ for a compound corresponds in each case to one row of Table A Table 223
Compounds of the formula Ia.9 in which $R^{10b}$ is pyridin-2-yl, and the combination of $R^{2a}$, $R^{2b}$, $R^{2c}$ and $R^4$ for a compound corresponds in each case to one row of Table A Table 224
Compounds of the formula Ia.9 in which $R^{10b}$ is 3-chloropyridin-2-yl, and the combination of $R^{2a}$, $R^{2b}$, $R^{2c}$ and $R^4$ for a compound corresponds in each case to one row of Table A Table 225
Compounds of the formula Ia.9 in which $R^{10b}$ is 4-chloropyridin-2-yl, and the combination of $R^{2a}$, $R^{2b}$, $R^{2c}$ and $R^4$ for a compound corresponds in each case to one row of Table A Table 226
Compounds of the formula Ia.9 in which $R^{10b}$ is 5-chloropyridin-2-yl, and the combination of $R^{2a}$, $R^{2b}$, $R^{2c}$ and $R^4$ for a compound corresponds in each case to one row of Table A Table 227
Compounds of the formula Ia.9 in which $R^{10b}$ is 6-chloropyridin-2-yl, and the combination of $R^{2a}$, $R^{2b}$, $R^{2c}$ and $R^4$ for a compound corresponds in each case to one row of Table A Table 228
Compounds of the formula Ia.9 in which $R^{10b}$ is 3-methoxypyridin-2-yl, and the combination of $R^{2a}$, $R^{2b}$, $R^{2c}$ and $R^4$ for a compound corresponds in each case to one row of Table A Table 229
Compounds of the formula Ia.9 in which $R^{10b}$ is 4-methoxypyridin-2-yl, and the combination of $R^{2a}$, $R^{2b}$, $R^{2c}$ and $R^4$ for a compound corresponds in each case to one row of Table A Table 230
Compounds of the formula Ia.9 in which $R^{10b}$ is 5-methoxypyridin-2-yl, and the combination of $R^{2a}$, $R^{2b}$, $R^{2c}$ and $R^4$ for a compound corresponds in each case to one row of Table A Table 231
Compounds of the formula Ia.9 in which $R^{10b}$ is 6-methoxypyridin-2-yl, and the combination of $R^{2a}$, $R^{2b}$, $R^{2c}$ and $R^4$ for a compound corresponds in each case to one row of Table A Table 232
Compounds of the formula Ia.9 in which $R^{10b}$ is pyridin-3-yl, and the combination of $R^{2a}$, $R^{2b}$, $R^{2c}$ and $R^4$ for a compound corresponds in each case to one row of Table A Table 233
Compounds of the formula Ia.9 in which $R^{10b}$ is 2-chloropyridin-3-yl, and the combination of $R^{2a}$, $R^{2b}$, $R^{2c}$ and $R^4$ for a compound corresponds in each case to one row of Table A Table 234
Compounds of the formula Ia.9 in which $R^{10b}$ is 4-chloropyridin-3-yl, and the combination of $R^{2a}$, $R^{2b}$, $R^{2c}$ and $R^4$ for a compound corresponds in each case to one row of Table A Table 235
Compounds of the formula Ia.9 in which $R^{10b}$ is 5-chloropyridin-3-yl, and the combination of $R^{2a}$, $R^{2b}$, $R^{2c}$ and $R^4$ for a compound corresponds in each case to one row of Table A Table 236

Compounds of the formula Ia.9 in which $R^{10b}$ is 6-chloropyridin-3-yl, and the combination of $R^{2a}$, $R^{2b}$, $R^{2c}$ and $R^4$ for a compound corresponds in each case to one row of Table A Table 237

Compounds of the formula Ia.9 in which $R^{10b}$ is 2-methoxypyridin-3-yl, and the combination of $R^{2a}$, $R^{2b}$, $R^{2c}$ and $R^4$ for a compound corresponds in each case to one row of Table A Table 238

Compounds of the formula Ia.9 in which $R^{10b}$ is 4-methoxypyridin-3-yl, and the combination of $R^{2a}$, $R^{2b}$, $R^{2c}$ and $R^4$ for a compound corresponds in each case to one row of Table A Table 239

Compounds of the formula Ia.9 in which $R^{10b}$ is 5-methoxypyridin-3-yl, and the combination of $R^{2a}$, $R^{2b}$, $R^{2c}$ and $R^4$ for a compound corresponds in each case to one row of Table A Table 240

Compounds of the formula Ia.9 in which $R^{10b}$ is 6-methoxypyridin-3-yl, and the combination of $R^{2a}$, $R^{2b}$, $R^{2c}$ and $R^4$ for a compound corresponds in each case to one row of Table A Table 241

Compounds of the formula Ia.9 in which $R^{10b}$ is pyridin-4-yl, and the combination of $R^{2a}$, $R^{2b}$, $R^{2c}$ and $R^4$ for a compound corresponds in each case to one row of Table A Table 242

Compounds of the formula Ia.9 in which $R^{10b}$ is 2-chloropyridin-4-yl, and the combination of $R^{2a}$, $R^{2b}$, $R^{2c}$ and $R^4$ for a compound corresponds in each case to one row of Table A Table 243

Compounds of the formula Ia.9 in which $R^{10b}$ is 3-chloropyridin-4-yl, and the combination of $R^{2a}$, $R^{2b}$, $R^{2c}$ and $R^4$ for a compound corresponds in each case to one row of Table A Table 244

Compounds of the formula Ia.9 in which $R^{10b}$ is 2-methoxypyridin-4-yl, and the combination of $R^{2a}$, $R^{2b}$, $R^{2c}$ and $R^4$ for a compound corresponds in each case to one row of Table A Table 245

Compounds of the formula Ia.9 in which $R^{10b}$ is 3-methoxypyridin-4-yl, and the combination of $R^{2a}$, $R^{2b}$, $R^{2c}$ and $R^4$ for a compound corresponds in each case to one row of Table A Table 246

Compounds of the formula Ia.9 in which $R^{10b}$ is pyrimidin-2-yl, and the combination of $R^{2a}$, $R^{2b}$, $R^{2c}$ and $R^4$ for a compound corresponds in each case to one row of Table A Table 247

Compounds of the formula Ia.9 in which $R^{10b}$ is pyrimidin-4-yl, and the combination of $R^{2a}$, $R^{2b}$, $R^{2c}$ and $R^4$ for a compound corresponds in each case to one row of Table A Table 248

Compounds of the formula Ia.9 in which $R^{10b}$ is pyrimidin-5-yl, and the combination of $R^{2a}$, $R^{2b}$, $R^{2c}$ and $R^4$ for a compound corresponds in each case to one row of Table A Table 249

Compounds of the formula Ia.9 in which $R^{10b}$ is pyrrol-2-yl, and the combination of $R^{2a}$, $R^{2b}$, $R^{2c}$ and $R^4$ for a compound corresponds in each case to one row of Table A Table 250

Compounds of the formula Ia.9 in which $R^{10b}$ is pyrrol-3-yl, and the combination of $R^{2a}$, $R^{2b}$, $R^{2c}$ and $R^4$ for a compound corresponds in each case to one row of Table A Table 251

Compounds of the formula Ia.9 in which $R^{10b}$ is hydrogen, and the combination of $R^{2a}$, $R^{2b}$, $R^{2c}$ and $R^4$ for a compound corresponds in each case to one row of Table A Table 252

Compounds of the formula Ia.9 in which $R^{10b}$ is methyl, and the combination of $R^{2a}$, $R^{2b}$, $R^{2c}$ and $R^4$ for a compound corresponds in each case to one row of Table A Table 253

Compounds of the formula Ia.9 in which $R^{10b}$ is ethyl, and the combination of $R^{2a}$, $R^{2b}$, $R^{2c}$ and $R^4$ for a compound corresponds in each case to one row of Table A Table 254

Compounds of the formula Ia.9 in which $R^{10b}$ is isopropyl, and the combination of $R^{2a}$, $R^{2b}$, $R^{2c}$ and $R^4$ for a compound corresponds in each case to one row of Table A Table 255

Compounds of the formula Ia.9 in which $R^{10b}$ is methylcarbonyl, and the combination of $R^{2a}$, $R^{2b}$, $R^{2c}$ and $R^4$ for a compound corresponds in each case to one row of Table A Table 256

Compounds of the formula Ia.9 in which $R^{10b}$ is ethylcarbonyl, and the combination of $R^{2a}$, $R^{2b}$, $R^{2c}$ and $R^4$ for a compound corresponds in each case to one row of Table A Table 257

Compounds of the formula Ia.9 in which $R^{10b}$ is isopropylcarbonyl, and the combination of $R^{2a}$, $R^{2b}$, $R^{2c}$ and $R^4$ for a compound corresponds in each case to one row of Table A Table 258

Compounds of the formula Ia.9 in which $R^{10b}$ is methoxycarbonyl, and the combination of $R^{2a}$, $R^{2b}$, $R^{2c}$ and $R^4$ for a compound corresponds in each case to one row of Table A Table 259

Compounds of the formula Ia.9 in which $R^{10b}$ is ethoxycarbonyl, and the combination of $R^{2a}$, $R^{2b}$, $R^{2c}$ and $R^4$ for a compound corresponds in each case to one row of Table A Table 260

Compounds of the formula Ia.9 in which $R^{10b}$ is isopropoxycarbonyl, and the combination of $R^{2a}$, $R^{2b}$, $R^{2c}$ and $R^4$ for a compound corresponds in each case to one row of Table A Tables 261 to 320

Compounds of the formula Ia.10 in which $R^{10b}$ is as defined in any of tables 201 to 260 and the combination of $R^{2a}$, $R^{2b}$, $R^{2c}$ and $R^4$ for a compound corresponds in each case to one row of Table A Tables 321 to 380

Compounds of the formula Ia.11 in which $R^{10b}$ is as defined in any of tables 201 to 260 and the combination of $R^{2a}$, $R^{2b}$, $R^{2c}$ and $R^4$ for a compound corresponds in each case to one row of Table A Tables 381 to 440

Compounds of the formula Ia.12 in which $R^{10b}$ is as defined in any of tables 201 to 260 and the combination of $R^{2a}$, $R^{2b}$, $R^{2c}$ and $R^4$ for a compound corresponds in each case to one row of Table A Table 441

Compounds of the formula Ia.13 in which $R^6$ is hydrogen and the combination of $R^{2a}$, $R^{2b}$, $R^{2c}$ and $R^4$ for a compound corresponds in each case to one row of Table A Table 442

Compounds of the formula Ia.13 in which $R^6$ is methyl and the combination of $R^{2a}$, $R^{2b}$, $R^{2c}$ and $R^4$ for a compound corresponds in each case to one row of Table A Table 443

Compounds of the formula Ia.13 in which $R^6$ is ethyl and the combination of $R^{2a}$, $R^{2b}$, $R^{2c}$ and $R^4$ for a compound corresponds in each case to one row of Table A Table 444

Compounds of the formula Ia.13 in which $R^6$ is propyl and the combination of $R^{2a}$, $R^{2b}$, $R^{2c}$ and $R^4$ for a compound corresponds in each case to one row of Table A Table 445

Compounds of the formula Ia.13 in which $R^6$ is isopropyl and the combination of $R^{2a}$, $R^{2b}$, $R^{2c}$ and $R^4$ for a compound corresponds in each case to one row of Table A Table 446

Compounds of the formula Ia.13 in which $R^6$ is n-butyl and the combination of $R^{2a}$, $R^{2b}$, $R^{2c}$ and $R^4$ for a compound corresponds in each case to one row of Table A Table 447

Compounds of the formula Ia.13 in which $R^6$ is sec-butyl and the combination of $R^{2a}$, $R^{2b}$, $R^{2c}$ and $R^4$ for a compound corresponds in each case to one row of Table A Table 448

Compounds of the formula Ia.13 in which $R^6$ is isobutyl and the combination of $R^{2a}$, $R^{2b}$, $R^{2c}$ and $R^4$ for a compound corresponds in each case to one row of Table A Table 449

Compounds of the formula Ia.13 in which $R^6$ is tert-butyl and the combination of $R^{2a}$, $R^{2b}$, $R^{2c}$ and $R^4$ for a compound corresponds in each case to one row of Table A Table 450

Compounds of the formula Ia.13 in which $R^6$ is $CH_2$—$C(CH_3)_3$ and the combination of $R^{2a}$, $R^{2b}$, $R^{2c}$ and $R^4$ for a compound corresponds in each case to one row of Table A Table 451

Compounds of the formula Ia.13 in which $R^6$ is —$CH_2CN$ and the combination of $R^{2a}$, $R^{2b}$, $R^{2c}$ and $R^4$ for a compound corresponds in each case to one row of Table A Table 452

Compounds of the formula Ia.13 in which $R^6$ is —$CH_2$—$CH=CH_2$ and the combination of $R^{2a}$, $R^{2b}$, $R^{2c}$ and $R^4$ for a compound corresponds in each case to one row of Table A Table 453

Compounds of the formula Ia.13 in which $R^6$ is —$CH_2C\equiv CH$ and the combination of $R^{2a}$, $R^{2b}$, $R^{2c}$ and $R^4$ for a compound corresponds in each case to one row of Table A Table 454

Compounds of the formula Ia.13 in which $R^6$ is $CH_2CH_2OH$ and the combination of $R^{2a}$, $R^{2b}$, $R^{2c}$ and $R^4$ for a compound corresponds in each case to one row of Table A Table 455

Compounds of the formula Ia.13 in which $R^6$ is —$CH_2CH_2OCH_3$ and the combination of $R^{2a}$, $R^{2b}$, $R^{2c}$ and $R^4$ for a compound corresponds in each case to one row of Table A Table 456

Compounds of the formula Ia.13 in which $R^6$ is —$CH_2CH_2OCH_2CH_3$ and the combination of $R^{2a}$, $R^{2b}$, $R^{2c}$ and $R^4$ for a compound corresponds in each case to one row of Table A Table 457

Compounds of the formula Ia.13 in which $R^6$ is —$CH_2CH_2OCF_3$ and the combination of $R^{2a}$, $R^{2b}$, $R^{2c}$ and $R^4$ for a compound corresponds in each case to one row of Table A Table 458

Compounds of the formula Ia.13 in which $R^6$ is —$CH_2CH_2OCH_2CF_3$ and the combination of $R^{2a}$, $R^{2b}$, $R^{2c}$ and $R^4$ for a compound corresponds in each case to one row of Table A Table 459

Compounds of the formula Ia.13 in which $R^6$ is —$CH(CH_3)CH_2OCH_3$ and the combination of $R^{2a}$, $R^{2b}$, $R^{2c}$ and $R^4$ for a compound corresponds in each case to one row of Table A Table 460

Compounds of the formula Ia.13 in which $R^6$ is —$CH(CH_3)CH_2OCH_2CH_3$ and the combination of $R^{2a}$, $R^{2b}$, $R^{2c}$ and $R^4$ for a compound corresponds in each case to one row of Table A Table 461

Compounds of the formula Ia.13 in which $R^6$ is —$CH_2CH_2SCH_3$ and the combination of $R^{2a}$, $R^{2b}$, $R^{2c}$ and $R^4$ for a compound corresponds in each case to one row of Table A Table 462

Compounds of the formula Ia.13 in which $R^6$ is —$CH_2CH_2S(O)CH_3$ and the combination of $R^{2a}$, $R^{2b}$, $R^{2c}$ and $R^4$ for a compound corresponds in each case to one row of Table A Table 463

Compounds of the formula Ia.13 in which $R^6$ is —$CH_2CH_2S(O)_2CH_3$ and the combination of $R^{2a}$, $R^{2b}$, $R^{2c}$ and $R^4$ for a compound corresponds in each case to one row of Table A Table 464

Compounds of the formula Ia.13 in which $R^6$ is —$CH_2CH_2SCH_2CH_3$ and the combination of $R^{2a}$, $R^{2b}$, $R^{2c}$ and $R^4$ for a compound corresponds in each case to one row of Table A Table 465

Compounds of the formula Ia.13 in which $R^6$ is —$CH_2CH_2S(O)CH_2CH_3$ and the combination of $R^{2a}$, $R^{2b}$, $R^{2c}$ and $R^4$ for a compound corresponds in each case to one row of Table A Table 466

Compounds of the formula Ia.13 in which $R^6$ is —$CH_2CH_2S(O)_2CH_2CH_3$ and the combination of $R^{2a}$, $R^{2b}$, $R^{2c}$ and $R^4$ for a compound corresponds in each case to one row of Table A Table 467

Compounds of the formula Ia.13 in which $R^6$ is —$CH(CH_3)CH_2SCH_3$ and the combination of $R^{2a}$, $R^{2b}$, $R^{2c}$ and $R^4$ for a compound corresponds in each case to one row of Table A Table 468

Compounds of the formula Ia.13 in which $R^6$ is —$CH(CH_3)CH_2S(O)CH_3$ and the combination of $R^{2a}$, $R^{2b}$, $R^{2c}$ and $R^4$ for a compound corresponds in each case to one row of Table A Table 469

Compounds of the formula Ia.13 in which $R^6$ is —$CH(CH_3)CH_2S(O)_2CH_3$ and the combination of $R^{2a}$, $R^{2b}$, $R^{2c}$ and $R^4$ for a compound corresponds in each case to one row of Table A Table 470

Compounds of the formula Ia.13 in which $R^6$ is —$C(CH_3)_2CH_2SCH_3$ and the combination of $R^{2a}$, $R^{2b}$, $R^{2c}$ and $R^4$ for a compound corresponds in each case to one row of Table A Table 471
Compounds of the formula Ia.13 in which $R^6$ is —C($CH_3$)$_2CH_2S(O)CH_3$ and the combination of $R^{2a}$, $R^{2b}$, $R^{2c}$ and $R^4$ for a compound corresponds in each case to one row of Table A Table 472
Compounds of the formula Ia.13 in which $R^6$ is —C($CH_3$)$_2CH_2S(O)_2CH_3$ and the combination of $R^{2a}$, $R^{2b}$, $R^{2c}$ and $R^4$ for a compound corresponds in each case to one row of Table A Table 473
Compounds of the formula Ia.13 in which $R^6$ is —$CH_2CH_2SCF_3$ and the combination of $R^{2a}$, $R^{2b}$, $R^{2c}$ and $R^4$ for a compound corresponds in each case to one row of Table A Table 474
Compounds of the formula Ia.13 in which $R^6$ is $CF_3$ and the combination of $R^{2a}$, $R^{2b}$, $R^{2c}$ and $R^4$ for a compound corresponds in each case to one row of Table A Table 475
Compounds of the formula Ia.13 in which $R^6$ is $CH_2CHF_2$ and the combination of $R^{2a}$, $R^{2b}$, $R^{2c}$ and $R^4$ for a compound corresponds in each case to one row of Table A Table 476
Compounds of the formula Ia.13 in which $R^6$ is $CH_2CF_3$ and the combination of $R^{2a}$, $R^{2b}$, $R^{2c}$ and $R^4$ for a compound corresponds in each case to one row of Table A Table 477
Compounds of the formula Ia.13 in which $R^6$ is $CH_2CH_2CF_3$ and the combination of $R^{2a}$, $R^{2b}$, $R^{2c}$ and $R^4$ for a compound corresponds in each case to one row of Table A Table 478
Compounds of the formula Ia.13 in which $R^6$ is $CH(CH_3)CF_3$ and the combination of $R^{2a}$, $R^{2b}$, $R^{2c}$ and $R^4$ for a compound corresponds in each case to one row of Table A Table 479
Compounds of the formula Ia.13 in which $R^6$ is $CH(CF_3)_2$ and the combination of $R^{2a}$, $R^{2b}$, $R^{2c}$ and $R^4$ for a compound corresponds in each case to one row of Table A Table 480
Compounds of the formula Ia.13 in which $R^6$ is $CH_2CH_2CH_2CF_3$ and the combination of $R^{2a}$, $R^{2b}$, $R^{2c}$ and $R^4$ for a compound corresponds in each case to one row of Table A Table 481
Compounds of the formula Ia.13 in which $R^6$ is $CH_2CH_2CH=CF_2$ and the combination of $R^{2a}$, $R^{2b}$, $R^{2c}$ and $R^4$ for a compound corresponds in each case to one row of Table A Table 482
Compounds of the formula Ia.13 in which $R^6$ is $CH_2CH_2CF=CF_2$ and the combination of $R^{2a}$, $R^{2b}$, $R^{2c}$ and $R^4$ for a compound corresponds in each case to one row of Table A Table 483
Compounds of the formula Ia.13 in which $R^6$ is cyclopropyl and the combination of $R^{2a}$, $R^{2b}$, $R^{2c}$ and $R^4$ for a compound corresponds in each case to one row of Table A Table 484
Compounds of the formula Ia.13 in which $R^6$ is 1-cyano-cyclopropyl and the combination of $R^{2a}$, $R^{2b}$, $R^{2c}$ and $R^4$ for a compound corresponds in each case to one row of Table A Table 485
Compounds of the formula Ia.13 in which $R^6$ is 1-(pyridin-2-yl)-cyclopropyl and the combination of $R^{2a}$, $R^{2b}$, $R^{2c}$ and $R^4$ for a compound corresponds in each case to one row of Table A Table 486
Compounds of the formula Ia.13 in which $R^6$ is cyclobutyl and the combination of $R^{2a}$, $R^{2b}$, $R^{2c}$ and $R^4$ for a compound corresponds in each case to one row of Table A Table 487
Compounds of the formula Ia.13 in which $R^6$ is cyclopentyl and the combination of $R^{2a}$, $R^{2b}$, $R^{2c}$ and $R^4$ for a compound corresponds in each case to one row of Table A Table 488
Compounds of the formula Ia.13 in which $R^6$ is cyclohexyl and the combination of $R^{2a}$, $R^{2b}$, $R^{2c}$ and $R^4$ for a compound corresponds in each case to one row of Table A Table 489
Compounds of the formula Ia.13 in which $R^6$ is —$CH_2$-cyclopropyl and the combination of $R^{2a}$, $R^{2b}$, $R^{2c}$ and $R^4$ for a compound corresponds in each case to one row of Table A Table 490
Compounds of the formula Ia.13 in which $R^6$ is —$CH_2$-(1-cyano-cyclopropyl) and the combination of $R^{2a}$, $R^{2b}$, $R^{2c}$ and $R^4$ for a compound corresponds in each case to one row of Table A Table 491
Compounds of the formula Ia.13 in which $R^6$ is —$CH_2$-(2,2-difluorocyclopropyl) and the combination of $R^{2a}$, $R^{2b}$, $R^{2c}$ and $R^4$ for a compound corresponds in each case to one row of Table A Table 492
Compounds of the formula Ia.13 in which $R^6$ is —$CH_2$-(2,2-dichlorocyclopropyl) and the combination of $R^{2a}$, $R^{2b}$, $R^{2c}$ and $R^4$ for a compound corresponds in each case to one row of Table A Table 493
Compounds of the formula Ia.13 in which $R^6$ is —$CH_2$-cyclobutyl and the combination of $R^{2a}$, $R^{2b}$, $R^{2c}$ and $R^4$ for a compound corresponds in each case to one row of Table A Table 494
Compounds of the formula Ia.13 in which $R^6$ is —$CH_2$-(2,2-difluorocyclobutyl) and the combination of $R^{2a}$, $R^{2b}$, $R^{2c}$ and $R^4$ for a compound corresponds in each case to one row of Table A Table 495
Compounds of the formula Ia.13 in which $R^6$ is —$CH_2$-cyclopentyl and the combination of $R^{2a}$, $R^{2b}$, $R^{2c}$ and $R^4$ for a compound corresponds in each case to one row of Table A Table 496
Compounds of the formula Ia.13 in which $R^6$ is —$CH_2$-cyclohexyl and the combination of $R^{2a}$, $R^{2b}$, $R^{2c}$ and $R^4$ for a compound corresponds in each case to one row of Table A Table 497
Compounds of the formula Ia.13 in which $R^6$ is 1,1-difluorocyclobut-3-yl and the combination of $R^{2a}$, $R^{2b}$, $R^{2c}$ and $R^4$ for a compound corresponds in each case to one row of Table A Table 498
Compounds of the formula Ia.13 in which $R^6$ is —$CH_2$-1,1-difluorocyclobut-3-yl and the combination of $R^{2a}$, $R^{2b}$, $R^{2c}$ and $R^4$ for a compound corresponds in each case to one row of Table A Table 499
Compounds of the formula Ia.13 in which $R^6$ is thietan-3-yl and the combination of $R^{2a}$, $R^{2b}$, $R^{2c}$ and $R^4$ for a compound corresponds in each case to one row of Table A Table 500
Compounds of the formula Ia.13 in which $R^6$ is 1-oxo-thietan-3-yl and the combination of $R^{2a}$, $R^{2b}$, $R^{2c}$ and $R^4$ for a compound corresponds in each case to one row of Table A Table 501
Compounds of the formula Ia.13 in which $R^6$ is 1,1-dioxo-thietan-3-yl and the combination of $R^{2a}$, $R^{2b}$, $R^{2c}$ and $R^4$ for a compound corresponds in each case to one row of Table A Table 502
Compounds of the formula Ia.13 in which $R^6$ is 3-methyl-thietan-3-yl and the combination of $R^{2a}$, $R^{2b}$, $R^{2c}$ and $R^4$ for a compound corresponds in each case to one row of Table A Table 503
Compounds of the formula Ia.13 in which $R^6$ is 3-methyl-1-oxo-thietan-3-yl and the combination of $R^{2a}$, $R^{2b}$, $R^{2c}$ and $R^4$ for a compound corresponds in each case to one row of Table A Table 504
Compounds of the formula Ia.13 in which $R^6$ is 3-methyl-1,1-dioxo-thietan-3-yl and the combination of $R^{2a}$, $R^{2b}$, $R^{2c}$ and $R^4$ for a compound corresponds in each case to one row of Table A Table 505
Compounds of the formula Ia.13 in which $R^6$ is —$CH_2$-thietan-3-yl and the combination of $R^{2a}$, $R^{2b}$, $R^{2c}$ and $R^4$ for a compound corresponds in each case to one row of Table A Table 506
Compounds of the formula Ia.13 in which $R^6$ is —$CH_2$-(1-oxo-thietan-3-yl) and the combination of $R^{2a}$, $R^{2b}$, $R^{2c}$ and $R^4$ for a compound corresponds in each case to one row of Table A Table 507
Compounds of the formula Ia.13 in which $R^6$ is —$CH_2$-(1,1-dioxo-thietan-3-yl) and the combination of $R^{2a}$, $R^{2b}$, $R^{2c}$ and $R^4$ for a compound corresponds in each case to one row of Table A Table 508
Compounds of the formula Ia.13 in which $R^6$ is tetrahydrothiophen-3-yl and the combination of $R^{2a}$, $R^{2b}$, $R^{2c}$ and $R^4$ for a compound corresponds in each case to one row of Table A Table 509
Compounds of the formula Ia.13 in which $R^6$ is 1-oxo-tetrahydrothiophen-3-yl and the combination of $R^{2a}$, $R^{2b}$, $R^{2c}$ and $R^4$ for a compound corresponds in each case to one row of Table A Table 510
Compounds of the formula Ia.13 in which $R^6$ is 1,1-dioxo-tetrahydrothiophen-3-yl and the combination of $R^{2a}$, $R^{2b}$, $R^{2c}$ and $R^4$ for a compound corresponds in each case to one row of Table A Table 511
Compounds of the formula Ia.13 in which $R^6$ is phenyl and the combination of $R^{2a}$, $R^{2b}$, $R^{2c}$ and $R^4$ for a compound corresponds in each case to one row of Table A Table 512
Compounds of the formula Ia.13 in which $R^6$ is 2-nitrophenyl and the combination of $R^{2a}$, $R^{2b}$, $R^{2c}$ and $R^4$ for a compound corresponds in each case to one row of Table A Table 513
Compounds of the formula Ia.13 in which $R^6$ is pyridin-2-yl and the combination of $R^{2a}$, $R^{2b}$, $R^{2c}$ and $R^4$ for a compound corresponds in each case to one row of Table A Table 514
Compounds of the formula Ia.13 in which $R^6$ is pyridin-3-yl and the combination of $R^{2a}$, $R^{2b}$, $R^{2c}$ and $R^4$ for a compound corresponds in each case to one row of Table A Table 515
Compounds of the formula Ia.13 in which $R^6$ is pyridin-4-yl and the combination of $R^{2a}$, $R^{2b}$, $R^{2c}$ and $R^4$ for a compound corresponds in each case to one row of Table A Table 516
Compounds of the formula Ia.13 in which $R^6$ is pyrimidin-2-yl and the combination of $R^{2a}$, $R^{2b}$, $R^{2c}$ and $R^4$ for a compound corresponds in each case to one row of Table A Table 517
Compounds of the formula Ia.13 in which $R^6$ is pyrimidin-4-yl and the combination of $R^{2a}$, $R^{2b}$, $R^{2c}$ and $R^4$ for a compound corresponds in each case to one row of Table A Table 518
Compounds of the formula Ia.13 in which $R^6$ is pyrimidin-5-yl and the combination of $R^{2a}$, $R^{2b}$, $R^{2c}$ and $R^4$ for a compound corresponds in each case to one row of Table A Table 519
Compounds of the formula Ia.13 in which $R^6$ is thiazol-2-yl and the combination of $R^{2a}$, $R^{2b}$, $R^{2c}$ and $R^4$ for a compound corresponds in each case to one row of Table A Table 520
Compounds of the formula Ia.13 in which $R^6$ is 4-trifluoromethylthiazol-2-yl and the combination of $R^{2a}$, $R^{2b}$, $R^{2c}$ and $R^4$ for a compound corresponds in each case to one row of Table A Table 521
Compounds of the formula Ia.13 in which $R^6$ is oxetan-3-yl and the combination of $R^{2a}$, $R^{2b}$, $R^{2c}$ and $R^4$ for a compound corresponds in each case to one row of Table A Table 522
Compounds of the formula Ia.13 in which $R^6$ is tetrahydrofuran-2-yl and the combination of $R^{2a}$, $R^{2b}$, $R^{2c}$ and $R^4$ for a compound corresponds in each case to one row of Table A Table 523
Compounds of the formula Ia.13 in which $R^6$ is tetrahydrofuran-3-yl and the combination of $R^{2a}$, $R^{2b}$, $R^{2c}$ and $R^4$ for a compound corresponds in each case to one row of Table A Table 524
Compounds of the formula Ia.13 in which $R^6$ is 2-oxo-tetrahydrofuran-3-yl and the combination of $R^{2a}$, $R^{2b}$, $R^{2c}$ and $R^4$ for a compound corresponds in each case to one row of Table A Table 525
Compounds of the formula Ia.13 in which $R^6$ is 2-oxopyrrolidin-3-yl and the combination of $R^{2a}$, $R^{2b}$, $R^{2c}$ and $R^4$ for a compound corresponds in each case to one row of Table A Table 526
Compounds of the formula Ia.13 in which $R^6$ is 1-methyl-2-oxopyrrolidin-3-yl and the combination of $R^{2a}$, $R^{2b}$, $R^{2c}$ and $R^4$ for a compound corresponds in each case to one row of Table A Table 527
Compounds of the formula Ia.13 in which $R^6$ is 2-oxo-1-(2,2,2-trifluoroethyl)-pyrrolidin-3-yl and the combination of $R^{2a}$, $R^{2b}$, $R^{2c}$ and $R^4$ for a compound corresponds in each case to one row of Table A Table 528
Compounds of the formula Ia.13 in which $R^6$ is azetidin-3-yl and the combination of $R^{2a}$, $R^{2b}$, $R^{2c}$ and $R^4$ for a compound corresponds in each case to one row of Table A Table 529
Compounds of the formula Ia.13 in which $R^6$ is 1-acetyl-azetidin-3-yl and the combination of $R^{2a}$, $R^{2b}$, $R^{2c}$ and $R^4$ for a compound corresponds in each case to one row of Table A Table 530
Compounds of the formula Ia.13 in which $R^6$ is —NH-phenyl and the combination of $R^{2a}$, $R^{2b}$, $R^{2c}$ and $R^4$ for a compound corresponds in each case to one row of Table A Table 531

Compounds of the formula Ia.13 in which $R^6$ is —NH-pyridin-2-yl and the combination of $R^{2a}$, $R^{2b}$, $R^{2c}$ and $R^4$ for a compound corresponds in each case to one row of Table A Table 532

Compounds of the formula Ia.13 in which $R^6$ is —NH-pyridin-3-yl and the combination of $R^{2a}$, $R^{2b}$, $R^{2c}$ and $R^4$ for a compound corresponds in each case to one row of Table A Table 533

Compounds of the formula Ia.13 in which $R^6$ is —NH-pyridin-4-yl and the combination of $R^{2a}$, $R^{2b}$, $R^{2c}$ and $R^4$ for a compound corresponds in each case to one row of Table A Table 534

Compounds of the formula Ia.13 in which $R^6$ is —N(CH$_3$)-pyridin-2-yl and the combination of $R^{2a}$, $R^{2b}$, $R^{2c}$ and $R^4$ for a compound corresponds in each case to one row of Table A Table 535

Compounds of the formula Ia.13 in which $R^6$ is —NH-pyrimidin-2-yl and the combination of $R^{2a}$, $R^{2b}$, $R^{2c}$ and $R^4$ for a compound corresponds in each case to one row of Table A Table 536

Compounds of the formula Ia.13 in which $R^6$ is —NH-pyrimidin-4-yl and the combination of $R^{2a}$, $R^{2b}$, $R^{2c}$ and $R^4$ for a compound corresponds in each case to one row of Table A Table 537

Compounds of the formula Ia.13 in which $R^6$ is —NH-pyrimidin-5-yl and the combination of $R^{2a}$, $R^{2b}$, $R^{2c}$ and $R^4$ for a compound corresponds in each case to one row of Table A Table 538

Compounds of the formula Ia.13 in which $R^6$ is —CH$_2$—COOCH$_3$ and the combination of $R^{2a}$, $R^{2b}$, $R^{2c}$ and $R^4$ for a compound corresponds in each case to one row of Table A Table 539

Compounds of the formula Ia.13 in which $R^6$ is —CH$_2$—COO—CH$_2$CH$_3$ and the combination of $R^{2a}$, $R^{2b}$, $R^{2c}$ and $R^4$ for a compound corresponds in each case to one row of Table A Table 540

Compounds of the formula Ia.13 in which $R^6$ is —CH$_2$—CONH—CH$_3$ and the combination of $R^{2a}$, $R^{2b}$, $R^{2c}$ and $R^4$ for a compound corresponds in each case to one row of Table A Table 541

Compounds of the formula Ia.13 in which $R^6$ is —CH$_2$—CONH—CH$_2$CH$_3$ and the combination of $R^{2a}$, $R^{2b}$, $R^{2c}$ and $R^4$ for a compound corresponds in each case to one row of Table A Table 542

Compounds of the formula Ia.13 in which $R^6$ is —CH$_2$—CONH—CF$_3$ and the combination of $R^{2a}$, $R^{2b}$, $R^{2c}$ and $R^4$ for a compound corresponds in each case to one row of Table A Table 543

Compounds of the formula Ia.13 in which $R^6$ is —CH$_2$—CONH—CH$_2$CF$_3$ and the combination of $R^{2a}$, $R^{2b}$, $R^{2c}$ and $R^4$ for a compound corresponds in each case to one row of Table A Table 544

Compounds of the formula Ia.13 in which $R^6$ is —CH$_2$—CONH-cyclopropyl and the combination of $R^{2a}$, $R^{2b}$, $R^{2c}$ and $R^4$ for a compound corresponds in each case to one row of Table A Table 545

Compounds of the formula Ia.13 in which $R^6$ is —CH$_2$—CONH-isopropyl and the combination of $R^{2a}$, $R^{2b}$, $R^{2c}$ and $R^4$ for a compound corresponds in each case to one row of Table A Table 546

Compounds of the formula Ia.13 in which $R^6$ is —CH$_2$—CONH—CH(CF$_3$)CH$_3$ and the combination of $R^{2a}$, $R^{2b}$, $R^{2c}$ and $R^4$ for a compound corresponds in each case to one row of Table A Table 547

Compounds of the formula Ia.13 in which $R^6$ is —CH$_2$—CONH—CH(CF$_3$)$_2$ and the combination of $R^{2a}$, $R^{2b}$, $R^{2c}$ and $R^4$ for a compound corresponds in each case to one row of Table A Table 548

Compounds of the formula Ia.13 in which $R^6$ is —CH$_2$—CONH—CH$_2$CH$_2$CF$_3$ and the combination of $R^{2a}$, $R^{2b}$, $R^{2c}$ and $R^4$ for a compound corresponds in each case to one row of Table A Table 549

Compounds of the formula Ia.13 in which $R^6$ is —CH$_2$—CONH—CH$_2$CN and the combination of $R^{2a}$, $R^{2b}$, $R^{2c}$ and $R^4$ for a compound corresponds in each case to one row of Table A Table 550

Compounds of the formula Ia.13 in which $R^6$ is —CH$_2$—CONH—CH$_2$C—CH and the combination of $R^{2a}$, $R^{2b}$, $R^{2c}$ and $R^4$ for a compound corresponds in each case to one row of Table A Table 551

Compounds of the formula Ia.13 in which $R^6$ is —CH$_2$—CON(CH$_3$)—CH$_2$CF$_3$ and the combination of $R^{2a}$, $R^{2b}$, $R^{2c}$ and $R^4$ for a compound corresponds in each case to one row of Table A Table 552

Compounds of the formula Ia.13 in which $R^6$ is —CH(CH$_3$)—CONH—CH$_2$CF$_3$ and the combination of $R^{2a}$, $R^{2b}$, $R^{2c}$ and $R^4$ for a compound corresponds in each case to one row of Table A Table 553

Compounds of the formula Ia.13 in which $R^6$ is —CH$_2$—CONH—CH$_2$-cyclopropyl and the combination of $R^{2a}$, $R^{2b}$, $R^{2c}$ and $R^4$ for a compound corresponds in each case to one row of Table A Table 554

Compounds of the formula Ia.13 in which $R^6$ is —CH$_2$—CONH-thietan-3-yl and the combination of $R^{2a}$, $R^{2b}$, $R^{2c}$ and $R^4$ for a compound corresponds in each case to one row of Table A Table 555

Compounds of the formula Ia.13 in which $R^6$ is —CH$_2$—CONH-1-oxo-thietan-3-yl and the combination of $R^{2a}$, $R^{2b}$, $R^{2c}$ and $R^4$ for a compound corresponds in each case to one row of Table A Table 556

Compounds of the formula Ia.13 in which $R^6$ is —CH$_2$—CONH-1,1-dioxo-thietan-3-yl and the combination of $R^{2a}$, $R^{2b}$, $R^{2c}$ and $R^4$ for a compound corresponds in each case to one row of Table A Table 557

Compounds of the formula Ia.13 in which $R^6$ is benzyl and the combination of $R^{2a}$, $R^{2b}$, $R^{2c}$ and $R^4$ for a compound corresponds in each case to one row of Table A Table 558

Compounds of the formula Ia.13 in which $R^6$ is 2-fluorobenzyl and the combination of $R^{2a}$, $R^{2b}$, $R^{2c}$ and $R^4$ for a compound corresponds in each case to one row of Table A Table 559
Compounds of the formula Ia.13 in which $R^6$ is 3-fluorobenzyl and the combination of $R^{2a}$, $R^{2b}$, $R^{2c}$ and $R^4$ for a compound corresponds in each case to one row of Table A Table 560
Compounds of the formula Ia.13 in which $R^6$ is 4-fluorobenzyl and the combination of $R^{2a}$, $R^{2b}$, $R^{2c}$ and $R^4$ for a compound corresponds in each case to one row of Table A Table 561
Compounds of the formula Ia.13 in which $R^6$ is 2-chlorobenzyl and the combination of $R^{2a}$, $R^{2b}$, $R^{2c}$ and $R^4$ for a compound corresponds in each case to one row of Table A Table 562
Compounds of the formula Ia.13 in which $R^6$ is 3-chlorobenzyl and the combination of $R^{2a}$, $R^{2b}$, $R^{2c}$ and $R^4$ for a compound corresponds in each case to one row of Table A Table 563
Compounds of the formula Ia.13 in which $R^6$ is 4-chlorobenzyl and the combination of $R^{2a}$, $R^{2b}$, $R^{2c}$ and $R^4$ for a compound corresponds in each case to one row of Table A Table 564
Compounds of the formula Ia.13 in which $R^6$ is 2-methoxybenzyl and the combination of $R^{2a}$, $R^{2b}$, $R^{2c}$ and $R^4$ for a compound corresponds in each case to one row of Table A Table 565
Compounds of the formula Ia.13 in which $R^6$ is 3-methoxybenzyl and the combination of $R^{2a}$, $R^{2b}$, $R^{2c}$ and $R^4$ for a compound corresponds in each case to one row of Table A Table 566
Compounds of the formula Ia.13 in which $R^6$ is 4-methoxybenzyl and the combination of $R^{2a}$, $R^{2b}$, $R^{2c}$ and $R^4$ for a compound corresponds in each case to one row of Table A Table 567
Compounds of the formula Ia.13 in which $R^6$ is 2-methylsulfanylbenzyl and the combination of $R^{2a}$, $R^{2b}$, $R^{2c}$ and $R^4$ for a compound corresponds in each case to one row of Table A Table 568
Compounds of the formula Ia.13 in which $R^6$ is 3-methylsulfanylbenzyl and the combination of $R^{2a}$, $R^{2b}$, $R^{2c}$ and $R^4$ for a compound corresponds in each case to one row of Table A Table 569
Compounds of the formula Ia.13 in which $R^6$ is 4-methylsulfanylbenzyl and the combination of $R^{2a}$, $R^{2b}$, $R^{2c}$ and $R^4$ for a compound corresponds in each case to one row of Table A Table 570
Compounds of the formula Ia.13 in which $R^6$ is 2-methylsulfonylbenzyl and the combination of $R^{2a}$, $R^{2b}$, $R^{2c}$ and $R^4$ for a compound corresponds in each case to one row of Table A Table 571
Compounds of the formula Ia.13 in which $R^6$ is 3-methylsulfonylbenzyl and the combination of $R^{2a}$, $R^{2b}$, $R^{2c}$ and $R^4$ for a compound corresponds in each case to one row of Table A Table 572
Compounds of the formula Ia.13 in which $R^6$ is 4-methylsulfonylbenzyl and the combination of $R^{2a}$, $R^{2b}$, $R^{2c}$ and $R^4$ for a compound corresponds in each case to one row of Table A Table 573
Compounds of the formula Ia.13 in which $R^6$ is pyridin-2-yl-methyl and the combination of $R^{2a}$, $R^{2b}$, $R^{2c}$ and $R^4$ for a compound corresponds in each case to one row of Table A Table 574
Compounds of the formula Ia.13 in which $R^6$ is pyridin-3-yl-methyl and the combination of $R^{2a}$, $R^{2b}$, $R^{2c}$ and $R^4$ for a compound corresponds in each case to one row of Table A Table 575
Compounds of the formula Ia.13 in which $R^6$ is 6-chloro-pyridin-3-yl-methyl and the combination of $R^{2a}$, $R^{2b}$, $R^{2c}$ and $R^4$ for a compound corresponds in each case to one row of Table A Table 576
Compounds of the formula Ia.13 in which $R^6$ is pyridin-4-yl-methyl and the combination of $R^{2a}$, $R^{2b}$, $R^{2c}$ and $R^4$ for a compound corresponds in each case to one row of Table A Table 577
Compounds of the formula Ia.13 in which $R^6$ is 5-chloro-pyridin-2-yl-methyl and the combination of $R^{2a}$, $R^{2b}$, $R^{2c}$ and $R^4$ for a compound corresponds in each case to one row of Table A Table 578
Compounds of the formula Ia.13 in which $R^6$ is 6-(trifluoromethyl)-pyridin-2-yl-methyl and the combination of $R^{2a}$, $R^{2b}$, $R^{2c}$ and $R^4$ for a compound corresponds in each case to one row of Table A Table 579
Compounds of the formula Ia.13 in which $R^6$ is 6-(trifluoromethyl)-pyridin-3-yl-methyl and the combination of $R^{2a}$, $R^{2b}$, $R^{2c}$ and $R^4$ for a compound corresponds in each case to one row of Table A Table 580
Compounds of the formula Ia.13 in which $R^6$ is pyrimidin-2-yl-methyl and the combination of $R^{2a}$, $R^{2b}$, $R^{2c}$ and $R^4$ for a compound corresponds in each case to one row of Table A Table 581
Compounds of the formula Ia.13 in which $R^6$ is pyrimidin-4-yl-methyl and the combination of $R^{2a}$, $R^{2b}$, $R^{2c}$ and $R^4$ for a compound corresponds in each case to one row of Table A Table 582
Compounds of the formula Ia.13 in which $R^6$ is pyrimidin-5-yl-methyl and the combination of $R^{2a}$, $R^{2b}$, $R^{2c}$ and $R^4$ for a compound corresponds in each case to one row of Table A Table 583
Compounds of the formula Ia.13 in which $R^6$ is pyridazin-3-yl-methyl and the combination of $R^{2a}$, $R^{2b}$, $R^{2c}$ and $R^4$ for a compound corresponds in each case to one row of Table A Table 584
Compounds of the formula Ia.13 in which $R^6$ is pyrazin-2-yl-methyl and the combination of $R^{2a}$, $R^{2b}$, $R^{2c}$ and $R^4$ for a compound corresponds in each case to one row of Table A Table 585
Compounds of the formula Ia.13 in which $R^6$ is thien-2-yl-methyl and the combination of $R^{2a}$, $R^{2b}$, $R^{2c}$ and $R^4$ for a compound corresponds in each case to one row of Table A Table 586
Compounds of the formula Ia.13 in which $R^6$ is thien-3-yl-methyl and the combination of $R^{2a}$, $R^{2b}$, $R^{2c}$ and $R^4$ for a compound corresponds in each case to one row of Table A Table 587
Compounds of the formula Ia.13 in which $R^6$ is thiazol-2-yl-methyl and the combination of $R^{2a}$, $R^{2b}$, $R^{2c}$ and $R^4$ for a compound corresponds in each case to one row of Table A Table 588
Compounds of the formula Ia.13 in which $R^6$ is thiazol-4-yl-methyl and the combination of $R^{2a}$, $R^{2b}$, $R^{2c}$ and $R^4$ for a compound corresponds in each case to one row of Table A Table 589
Compounds of the formula Ia.13 in which $R^6$ is thiazol-5-yl-methyl and the combination of $R^{2a}$, $R^{2b}$, $R^{2c}$ and $R^4$ for a compound corresponds in each case to one row of Table A Table 590
Compounds of the formula Ia.13 in which $R^6$ is 2-chloro-thiazol-5-yl-methyl and the combination of $R^{2a}$, $R^{2b}$, $R^{2c}$ and $R^4$ for a compound corresponds in each case to one row of Table A Table 591
Compounds of the formula Ia.13 in which $R^6$ is isothiazol-3-yl-methyl and the combination of $R^{2a}$, $R^{2b}$, $R^{2c}$ and $R^4$ for a compound corresponds in each case to one row of Table A Table 592
Compounds of the formula Ia.13 in which $R^6$ is isothiazol-4-yl-methyl and the combination of $R^{2a}$, $R^{2b}$, $R^{2c}$ and $R^4$ for a compound corresponds in each case to one row of Table A Table 593
Compounds of the formula Ia.13 in which $R^6$ is isothiazol-5-yl-methyl and the combination of $R^{2a}$, $R^{2b}$, $R^{2c}$ and $R^4$ for a compound corresponds in each case to one row of Table A Table 594
Compounds of the formula Ia.13 in which $R^6$ is oxazol-2-yl-methyl and the combination of $R^{2a}$, $R^{2b}$, $R^{2c}$ and $R^4$ for a compound corresponds in each case to one row of Table A Table 595
Compounds of the formula Ia.13 in which $R^6$ is oxazol-4-yl-methyl and the combination of $R^{2a}$, $R^{2b}$, $R^{2c}$ and $R^4$ for a compound corresponds in each case to one row of Table A Table 596
Compounds of the formula Ia.13 in which $R^6$ is oxazol-5-yl-methyl and the combination of $R^{2a}$, $R^{2b}$, $R^{2c}$ and $R^4$ for a compound corresponds in each case to one row of Table A Table 597
Compounds of the formula Ia.13 in which $R^6$ is isoxazol-3-yl-methyl and the combination of $R^{2a}$, $R^{2b}$, $R^{2c}$ and $R^4$ for a compound corresponds in each case to one row of Table A Table 598
Compounds of the formula Ia.13 in which $R^6$ is isoxazol-4-yl-methyl and the combination of $R^{2a}$, $R^{2b}$, $R^{2c}$ and $R^4$ for a compound corresponds in each case to one row of Table A Table 599
Compounds of the formula Ia.13 in which $R^6$ is isoxazol-5-yl-methyl and the combination of $R^{2a}$, $R^{2b}$, $R^{2c}$ and $R^4$ for a compound corresponds in each case to one row of Table A Table 600
Compounds of the formula Ia.13 in which $R^6$ is [1,2,3]-thiadiazol-4-yl-methyl and the combination of $R^{2a}$, $R^{2b}$, $R^{2c}$ and $R^4$ for a compound corresponds in each case to one row of Table A Table 601
Compounds of the formula Ia.13 in which $R^6$ is [1,3,4]-thiadiazol-2-yl-methyl and the combination of $R^{2a}$, $R^{2b}$, $R^{2c}$ and $R^4$ for a compound corresponds in each case to one row of Table A Table 602
Compounds of the formula Ia.13 in which $R^6$ is 1-methyl-imidazol-2-yl-methyl and the combination of $R^{2a}$, $R^{2b}$, $R^{2c}$ and $R^4$ for a compound corresponds in each case to one row of Table A Table 603
Compounds of the formula Ia.13 in which $R^6$ is 1-methyl-imidazol-4-yl-methyl and the combination of $R^{2a}$, $R^{2b}$, $R^{2c}$ and $R^4$ for a compound corresponds in each case to one row of Table A Table 604
Compounds of the formula Ia.13 in which $R^6$ is 1-methyl-imidazol-5-yl-methyl and the combination of $R^{2a}$, $R^{2b}$, $R^{2c}$ and $R^4$ for a compound corresponds in each case to one row of Table A Table 605
Compounds of the formula Ia.13 in which $R^6$ is 1-methyl-pyrazol-3-yl-methyl and the combination of $R^{2a}$, $R^{2b}$, $R^{2c}$ and $R^4$ for a compound corresponds in each case to one row of Table A Table 606
Compounds of the formula Ia.13 in which $R^6$ is 2-methyl-pyrazol-3-yl-methyl and the combination of $R^{2a}$, $R^{2b}$, $R^{2c}$ and $R^4$ for a compound corresponds in each case to one row of Table A Table 607
Compounds of the formula Ia.13 in which $R^6$ is tetrahydrofuran-3-yl-methyl and the combination of $R^{2a}$, $R^{2b}$, $R^{2c}$ and $R^4$ for a compound corresponds in each case to one row of Table A Table 608
Compounds of the formula Ia.13 in which $R^6$ is 1,3-dioxolan-2-yl-methyl and the combination of $R^{2a}$, $R^{2b}$, $R^{2c}$ and $R^4$ for a compound corresponds in each case to one row of Table A Table 609
Compounds of the formula Ia.13 in which $R^6$ is 2-pyridyl-eth-1-yl and the combination of $R^{2a}$, $R^{2b}$, $R^{2c}$ and $R^4$ for a compound corresponds in each case to one row of Table A Table 610
Compounds of the formula Ia.13 in which $R^6$ is (1R)-2-pyridyl-eth-1-yl and the combination of $R^{2a}$, $R^{2b}$, $R^{2c}$ and $R^4$ for a compound corresponds in each case to one row of Table A Table 611
Compounds of the formula Ia.13 in which $R^6$ is (1S)-2-pyridyl-eth-1-yl and the combination of $R^{2a}$, $R^{2b}$, $R^{2c}$ and $R^4$ for a compound corresponds in each case to one row of Table A Table 612
Compounds of the formula Ia.13 in which $R^6$ is —$CONH_2$ and the combination of $R^{2a}$, $R^{2b}$, $R^{2c}$ and $R^4$ for a compound corresponds in each case to one row of Table A Table 613
Compounds of the formula Ia.13 in which $R^6$ is —CONH—$CH_3$ and the combination of $R^{2a}$, $R^{2b}$, $R^{2c}$ and $R^4$ for a compound corresponds in each case to one row of Table A Table 614
Compounds of the formula Ia.13 in which $R^6$ is —CONH—$CH_2CH_3$ and the combination of $R^{2a}$, $R^{2b}$, $R^{2c}$ and $R^4$ for a compound corresponds in each case to one row of Table A Table 615
Compounds of the formula Ia.13 in which $R^6$ is —CONH—$CH_2CH_2CH_3$ and the combination of $R^{2a}$, $R^{2b}$, $R^{2c}$ and $R^4$ for a compound corresponds in each case to one row of Table A Table 616
Compounds of the formula Ia.13 in which $R^6$ is —CONH-cyclopropyl and the combination of $R^{2a}$, $R^{2b}$, $R^{2c}$ and $R^4$ for a compound corresponds in each case to one row of Table A Table 617
Compounds of the formula Ia.13 in which $R^6$ is —CONH—$CH_2$-cyclopropyl and the combination of $R^{2a}$, $R^{2b}$, $R^{2c}$ and $R^4$ for a compound corresponds in each case to one row of Table A Table 618
Compounds of the formula Ia.13 in which $R^6$ is —CONH-phenyl and the combination of $R^{2a}$, $R^{2b}$, $R^{2c}$ and $R^4$ for a compound corresponds in each case to one row of Table A Table 619
Compounds of the formula Ia.13 in which $R^6$ is —CONH-benzyl and the combination of $R^{2a}$, $R^{2b}$, $R^{2c}$ and $R^4$ for a compound corresponds in each case to one row of Table A Table 620
Compounds of the formula Ia.13 in which $R^6$ is —NHCO—NH—$CH_2CF_3$ and the combination of $R^{2a}$, $R^{2b}$, $R^{2c}$ and $R^4$ for a compound corresponds in each case to one row of Table A Table 621
Compounds of the formula Ia.13 in which $R^6$ is —NHCO—NH—$CH_2CHF_2$ and the combination of $R^{2a}$, $R^{2b}$, $R^{2c}$ and $R^4$ for a compound corresponds in each case to one row of Table A Table 622
Compounds of the formula Ia.13 in which $R^6$ is —CH=$NOCH_3$ and the combination of $R^{2a}$, $R^{2b}$, $R^{2c}$ and $R^4$ for a compound corresponds in each case to one row of Table A Table 623
Compounds of the formula Ia.13 in which $R^6$ is —CH=$NOCH_2CF_3$ and the combination of $R^{2a}$, $R^{2b}$, $R^{2c}$ and $R^4$ for a compound corresponds in each case to one row of Table A Table 624
Compounds of the formula Ia.13 in which $R^6$ is 3-oxo-isoxazolidin-4-yl and the combination of $R^{2a}$, $R^{2b}$, $R^{2c}$ and $R^4$ for a compound corresponds in each case to one row of Table A Table 625
Compounds of the formula Ia.13 in which $R^6$ is 2-methyl-3-oxo-isoxazolidin-4-yl and the combination of $R^{2a}$, $R^{2b}$, $R^{2c}$ and $R^4$ for a compound corresponds in each case to one row of Table A Table 626
Compounds of the formula Ia.13 in which $R^6$ is 2-ethyl-3-oxo-isoxazolidin-4-yl and the combination of $R^{2a}$, $R^{2b}$, $R^{2c}$ and $R^4$ for a compound corresponds in each case to one row of Table A Table 627
Compounds of the formula Ia.13 in which $R^6$ is 2-propyl-3-oxo-isoxazolidin-4-yl and the combination of $R^{2a}$, $R^{2b}$, $R^{2c}$ and $R^4$ for a compound corresponds in each case to one row of Table A Table 628
Compounds of the formula Ia.13 in which $R^6$ is 2-butyl-3-oxo-isoxazolidin-4-yl and the combination of $R^{2a}$, $R^{2b}$, $R^{2c}$ and $R^4$ for a compound corresponds in each case to one row of Table A Table 629
Compounds of the formula Ia.13 in which $R^6$ is 2-(but-2-yl)-3-oxo-isoxazolidin-4-yl and the combination of $R^{2a}$, $R^{2b}$, $R^{2c}$ and $R^4$ for a compound corresponds in each case to one row of Table A Table 630
Compounds of the formula Ia.13 in which $R^6$ is 2-(3-bromopropyl)-3-oxo-isoxazolidin-4-yl and the combination of $R^{2a}$, $R^{2b}$, $R^{2c}$ and $R^4$ for a compound corresponds in each case to one row of Table A Table 631
Compounds of the formula Ia.13 in which $R^6$ is 2-(2-fluoroethyl)-3-oxo-isoxazolidin-4-yl and the combination of $R^{2a}$, $R^{2b}$, $R^{2c}$ and $R^4$ for a compound corresponds in each case to one row of Table A Table 632
Compounds of the formula Ia.13 in which $R^6$ is 2-(2,2-difluoroethyl)-3-oxo-isoxazolidin-4-yl and the combination of $R^{2a}$, $R^{2b}$, $R^{2c}$ and $R^4$ for a compound corresponds in each case to one row of Table A Table 633
Compounds of the formula Ia.13 in which $R^6$ is 2-(2,2,2-trifluoroethyl)-3-oxo-isoxazolidin-4-yl and the combination of $R^{2a}$, $R^{2b}$, $R^{2c}$ and $R^4$ for a compound corresponds in each case to one row of Table A Table 634
Compounds of the formula Ia.13 in which $R^6$ is 2-(3,3,3-trifluoropropyl)-3-oxo-isoxazolidin-4-yl and the combination of $R^{2a}$, $R^{2b}$, $R^{2c}$ and $R^4$ for a compound corresponds in each case to one row of Table A Table 635
Compounds of the formula Ia.13 in which $R^6$ is 2-(2-methoxyethyl)-3-oxo-isoxazolidin-4-yl and the combination of $R^{2a}$, $R^{2b}$, $R^{2c}$ and $R^4$ for a compound corresponds in each case to one row of Table A Table 636
Compounds of the formula Ia.13 in which $R^6$ is 2-(1-methoxy-prop-2-yl)-3-oxo-isoxazolidin-4-yl and the combination of $R^{2a}$, $R^{2b}$, $R^{2c}$ and $R^4$ for a compound corresponds in each case to one row of Table A Table 637
Compounds of the formula Ia.13 in which $R^6$ is 2-cyclobutyl-3-oxo-isoxazolidin-4-yl and the combination of $R^{2a}$, $R^{2b}$, $R^{2c}$ and $R^4$ for a compound corresponds in each case to one row of Table A Table 638
Compounds of the formula Ia.13 in which $R^6$ is 2-(2-methylcyclohex-1-yl)-3-oxo-isoxazolidin-4-yl and the combination of $R^{2a}$, $R^{2b}$, $R^{2c}$ and $R^4$ for a compound corresponds in each case to one row of Table A Table 639
Compounds of the formula Ia.13 in which $R^6$ is 2-(phenylmethyl)-3-oxo-isoxazolidin-4-yl and the combination of $R^{2a}$, $R^{2b}$, $R^{2c}$ and $R^4$ for a compound corresponds in each case to one row of Table A Table 640
Compounds of the formula Ia.13 in which $R^6$ is 2-(1-phenyl-eth-1-yl)-3-oxo-isoxazolidin-4-yl and the combination of $R^{2a}$, $R^{2b}$, $R^{2c}$ and $R^4$ for a compound corresponds in each case to one row of Table A Table 641
Compounds of the formula Ia.13 in which $R^6$ is 2-(2-phenyl-eth-1-yl)-3-oxo-isoxazolidin-4-yl and the combination of $R^{2a}$, $R^{2b}$, $R^{2c}$ and $R^4$ for a compound corresponds in each case to one row of Table A Table 642
Compounds of the formula Ia.13 in which $R^6$ is 2-[(3-chlorophenyl)-methyl]-3-oxo-isoxazolidin-4-yl and the combination of $R^{2a}$, $R^{2b}$, $R^{2c}$ and $R^4$ for a compound corresponds in each case to one row of Table A Table 643
Compounds of the formula Ia.13 in which $R^6$ is 2-[(2-fluorophenyl)-methyl]-3-oxo-isoxazolidin-4-yl and the combination of $R^{2a}$, $R^{2b}$, $R^{2c}$ and $R^4$ for a compound corresponds in each case to one row of Table A Table 644
Compounds of the formula Ia.13 in which $R^6$ is 2-[(4-methoxyphenyl)-methyl]-3-oxo-isoxazolidin-4-yl and the combination of $R^{2a}$, $R^{2b}$, $R^{2c}$ and $R^4$ for a compound corresponds in each case to one row of Table A Table 645
Compounds of the formula Ia.13 in which $R^6$ is 2-[(2-trifluoromethylphenyl)-methyl]-3-oxo-isoxazolidin-4-yl and the combination of $R^{2a}$, $R^{2b}$, $R^{2c}$ and $R^4$ for a compound corresponds in each case to one row of Table A Table 646
Compounds of the formula Ia.13 in which $R^6$ is 2-[(2-trifluoromethoxyphenyl)-methyl]-3-oxo-isoxazolidin-4-yl and the combination of $R^{2a}$, $R^{2b}$, $R^{2c}$ and $R^4$ for a compound corresponds in each case to one row of Table A Table 647
Compounds of the formula Ia.13 in which $R^6$ is 2-(pyridin-2-yl-methyl)-3-oxo-isoxazolidin-4-yl and the combination of $R^{2a}$, $R^{2b}$, $R^{2c}$ and $R^4$ for a compound corresponds in each case to one row of Table A Table 648
Compounds of the formula Ia.13 in which $R^6$ is 2-(pyridin-3-yl-methyl)-3-oxo-isoxazolidin-4-yl and the combination of $R^{2a}$, $R^{2b}$, $R^{2c}$ and $R^4$ for a compound corresponds in each case to one row of Table A Table 649
Compounds of the formula Ia.13 in which $R^6$ is 2-[(2-chloropyridin-5-yl)-methyl]-3-oxo-isoxazolidin-4-yl and the combination of $R^{2a}$, $R^{2b}$, $R^{2c}$ and $R^4$ for a compound corresponds in each case to one row of Table A Table 650
Compounds of the formula Ia.13 in which $R^6$ is 2-[(1-methyl-1H-imidazol-4-yl)-methyl]-3-oxo-isoxazolidin-4-yl and the combination of $R^{2a}$, $R^{2b}$, $R^{2c}$ and $R^4$ for a compound corresponds in each case to one row of Table A Table 651
Compounds of the formula Ia.13 in which $R^6$ is 2-[(furan-2-yl)-methyl]-3-oxo-isoxazolidin-4-yl and the combination of $R^{2a}$, $R^{2b}$, $R^{2c}$ and $R^4$ for a compound corresponds in each case to one row of Table A Table 652
Compounds of the formula Ia.13 in which $R^6$ is 2-[(2-thiophen-2'-yl)-eth-1-yl]-3-oxo-isoxazolidin-4-yl and the combination of $R^{2a}$, $R^{2b}$, $R^{2c}$ and $R^4$ for a compound corresponds in each case to one row of Table A Table 653
Compounds of the formula Ia.13 in which $R^6$ is 2-[2-(indol-3'-yl)-eth-1-yl]-3-oxo-isoxazolidin-4-yl and the combination of $R^{2a}$, $R^{2b}$, $R^{2c}$ and $R^4$ for a compound corresponds in each case to one row of Table A Table 654
Compounds of the formula Ia.13 in which $R^6$ is 2-[(1H-benzimidazol-2-yl)-methyl]-3-oxo-isoxazolidin-4-yl and the combination of $R^{2a}$, $R^{2b}$, $R^{2c}$ and $R^4$ for a compound corresponds in each case to one row of Table A Table 655
Compounds of the formula Ia.13 in which $R^6$ is 2-[(oxetan-2-yl)-methyl]-3-oxo-isoxazolidin-4-yl and the combination of $R^{2a}$, $R^{2b}$, $R^{2c}$ and $R^4$ for a compound corresponds in each case to one row of Table A Table 656
Compounds of the formula Ia.13 in which $R^6$ is 2-[(tetrahydrofuran-2-yl)-methyl]-3-oxo-isoxazolidin-4-yl and the combination of $R^{2a}$, $R^{2b}$, $R^{2c}$ and $R^4$ for a compound corresponds in each case to one row of Table A Table 657
Compounds of the formula Ia.13 in which $R^6$ is 2-[(2-[1',3']dioxolan-2'-yl)-eth-1-yl]-3-oxo-isoxazolidin-4-yl and the combination of $R^{2a}$, $R^{2b}$, $R^{2c}$ and $R^4$ for a compound corresponds in each case to one row of Table A Table 658
Compounds of the formula Ia.13 in which $R^6$ is 2-[(2-morpholin-4'-yl)-eth-1-yl]-3-oxo-isoxazolidin-4-yl and the combination of $R^{2a}$, $R^{2b}$, $R^{2c}$ and $R^4$ for a compound corresponds in each case to one row of Table A Table 659
Compounds of the formula Ia.13 in which $R^6$ is 2-[(2-benzo[1',3']dioxol-5'-yl)-eth-1-yl]-3-oxo-isoxazolidin-4-yl and the combination of $R^{2a}$, $R^{2b}$, $R^{2c}$ and $R^4$ for a compound corresponds in each case to one row of Table A Table 660
Compounds of the formula Ia.13 in which $R^6$ is 2-[(2,3-dihydro-benzo[1,4]dioxin-6-yl)methyl]-3-oxo-isoxazolidin-4-yl and the combination of $R^{2a}$, $R^{2b}$, $R^{2c}$ and $R^4$ for a compound corresponds in each case to one row of Table A Table 661
Compounds of the formula Ia.13 in which $R^6$ is 2-(2-chlorophenyl)-3-oxo-isoxazolidin-4-yl and the combination of $R^{2a}$, $R^{2b}$, $R^{2c}$ and $R^4$ for a compound corresponds in each case to one row of Table A Table 662
Compounds of the formula Ia.13 in which $R^6$ is 2-(3-fluorophenyl)-3-oxo-isoxazolidin-4-yl and the combination of $R^{2a}$, $R^{2b}$, $R^{2c}$ and $R^4$ for a compound corresponds in each case to one row of Table A Table 663
Compounds of the formula Ia.13 in which $R^6$ is 2-(2-methylphenyl)-3-oxo-isoxazolidin-4-yl and the combination of $R^{2a}$, $R^{2b}$, $R^{2c}$ and $R^4$ for a compound corresponds in each case to one row of Table A Table 664
Compounds of the formula Ia.13 in which $R^6$ is 2-(2-chloro-6-methylphenyl)-3-oxo-isoxazolidin-4-yl and the combination of $R^{2a}$, $R^{2b}$, $R^{2c}$ and $R^4$ for a compound corresponds in each case to one row of Table A Table 665
Compounds of the formula Ia.13 in which $R^6$ is 2-(2-trifluoromethylphenyl)-3-oxo-isoxazolidin-4-yl and the combination of $R^{2a}$, $R^{2b}$, $R^{2c}$ and $R^4$ for a compound corresponds in each case to one row of Table A Table 666
Compounds of the formula Ia.13 in which $R^6$ is 2-(2,4-dimethoxyphenyl)-3-oxo-isoxazolidin-4-yl and the combination of $R^{2a}$, $R^{2b}$, $R^{2c}$ and $R^4$ for a compound corresponds in each case to one row of Table A Table 667
Compounds of the formula Ia.13 in which $R^6$ is 2-(3-methylpyrid-2-yl)-3-oxo-isoxazolidin-4-yl and the combination of $R^{2a}$, $R^{2b}$, $R^{2c}$ and $R^4$ for a compound corresponds in each case to one row of Table A Table 668
Compounds of the formula Ia.13 in which $R^6$ is 2-(1,3-dimethyl-1H-pyrazol-5-yl)-3-oxo-isoxazolidin-4-yl and the combination of $R^{2a}$, $R^{2b}$, $R^{2c}$ and $R^4$ for a compound corresponds in each case to one row of Table A Table 669
Compounds of the formula Ia.13 in which $R^6$ is 2-(4-methylthiazol-2-yl)-3-oxo-isoxazolidin-4-yl and the combination of $R^{2a}$, $R^{2b}$, $R^{2c}$ and $R^4$ for a compound corresponds in each case to one row of Table A Table 670

Compounds of the formula Ia.13 in which $R^6$ is 2-(5-methylthiadiazol-2-yl)-3-oxo-isoxazolidin-4-yl and the combination of $R^{2a}$, $R^{2b}$, $R^{2c}$ and $R^4$ for a compound corresponds in each case to one row of Table A Table 671

Compounds of the formula Ia.13 in which $R^6$ is 2-(quinolin-2-yl)-3-oxo-isoxazolidin-4-yl and the combination of $R^{2a}$, $R^{2b}$, $R^{2c}$ and $R^4$ for a compound corresponds in each case to one row of Table A Table 672

Compounds of the formula Ia.13 in which $R^6$ is 2-(quinolin-5-yl)-3-oxo-isoxazolidin-4-yl and the combination of $R^{2a}$, $R^{2b}$, $R^{2c}$ and $R^4$ for a compound corresponds in each case to one row of Table A Table 673

Compounds of the formula Ia.13 in which $R^6$ is 2-(benzothiazol-6-yl)-3-oxo-isoxazolidin-4-yl and the combination of $R^{2a}$, $R^{2b}$, $R^{2c}$ and $R^4$ for a compound corresponds in each case to one row of Table A Table 674

Compounds of the formula Ia.13 in which $R^6$ is 2-(4-methylbenzothiazol-2-yl)-3-oxo-isoxazolidin-4-yl and the combination of $R^{2a}$, $R^{2b}$, $R^{2c}$ and $R^4$ for a compound corresponds in each case to one row of Table A Table 675

Compounds of the formula Ia.13 in which $R^6$ is 2-(thietan-3-yl)-3-oxo-isoxazolidin-4-yl and the combination of $R^{2a}$, $R^{2b}$, $R^{2c}$ and $R^4$ for a compound corresponds in each case to one row of Table A Table 676

Compounds of the formula Ia.13 in which $R^6$ is 2-(1-oxo-thietan-3-yl)-3-oxo-isoxazolidin-4-yl and the combination of $R^{2a}$, $R^{2b}$, $R^{2c}$ and $R^4$ for a compound corresponds in each case to one row of Table A Table 677

Compounds of the formula Ia.13 in which $R^6$ is 2-(1,1-dioxo-thietan-3-yl)-3-oxo-isoxazolidin-4-yl and the combination of $R^{2a}$, $R^{2b}$, $R^{2c}$ and $R^4$ for a compound corresponds in each case to one row of Table A Table 678

Compounds of the formula Ia.13 in which $R^6$ is 2-(3-methylthietan-3-yl)-3-oxo-isoxazolidin-4-yl and the combination of $R^{2a}$, $R^{2b}$, $R^{2c}$ and $R^4$ for a compound corresponds in each case to one row of Table A Table 679

Compounds of the formula Ia.13 in which $R^6$ is 2-(oxetan-3-yl)-3-oxo-isoxazolidin-4-yl and the combination of $R^{2a}$, $R^{2b}$, $R^{2c}$ and $R^4$ for a compound corresponds in each case to one row of Table A Table 680

Compounds of the formula Ia.13 in which $R^6$ is 2-(tetrahydropyran-4-yl)-3-oxo-isoxazolidin-4-yl and the combination of $R^{2a}$, $R^{2b}$, $R^{2c}$ and $R^4$ for a compound corresponds in each case to one row of Table A Tables 681 to 920

Compounds of the formula Ia.14 in which $R^6$ is as defined in any of tables 441 to 680 and the combination of $R^{2a}$, $R^{2b}$, $R^{2c}$ and $R^4$ for a compound corresponds in each case to one row of Table A Tables 921 to 1160

Compounds of the formula Ia.15 in which $R^6$ is as defined in any of tables 441 to 680 and the combination of $R^{2a}$, $R^{2b}$, $R^{2c}$ and $R^4$ for a compound corresponds in each case to one row of Table A Tables 1161 to 1400

Compounds of the formula Ia.16 in which $R^6$ is as defined in any of tables 441 to 680 and the combination of $R^{2a}$, $R^{2b}$, $R^{2c}$ and $R^4$ for a compound corresponds in each case to one row of Table A Table 1401

Compounds of the formula Ia.17 in which $R^8$ is methyl and the combination of $R^{2a}$, $R^{2b}$, $R^{2c}$ and $R^4$ for a compound corresponds in each case to one row of Table A Table 1402

Compounds of the formula Ia.17 in which $R^8$ is ethyl and the combination of $R^{2a}$, $R^{2b}$, $R^{2c}$ and $R^4$ for a compound corresponds in each case to one row of Table A Table 1403

Compounds of the formula Ia.17 in which $R^8$ is propyl and the combination of $R^{2a}$, $R^{2b}$, $R^{2c}$ and $R^4$ for a compound corresponds in each case to one row of Table A Table 1404

Compounds of the formula Ia.17 in which $R^8$ is isopropyl and the combination of $R^{2a}$, $R^{2b}$, $R^{2c}$ and $R^4$ for a compound corresponds in each case to one row of Table A Table 1405

Compounds of the formula Ia.17 in which $R^8$ is n-butyl and the combination of $R^{2a}$, $R^{2b}$, $R^{2c}$ and $R^4$ for a compound corresponds in each case to one row of Table A Table 1406

Compounds of the formula Ia.17 in which $R^8$ is sec-butyl and the combination of $R^{2a}$, $R^{2b}$, $R^{2c}$ and $R^4$ for a compound corresponds in each case to one row of Table A Table 1407

Compounds of the formula Ia.17 in which $R^8$ is isobutyl and the combination of $R^{2a}$, $R^{2b}$, $R^{2c}$ and $R^4$ for a compound corresponds in each case to one row of Table A Table 1408

Compounds of the formula Ia.17 in which $R^8$ is tert-butyl and the combination of $R^{2a}$, $R^{2b}$, $R^{2c}$ and $R^4$ for a compound corresponds in each case to one row of Table A Table 1409

Compounds of the formula Ia.17 in which $R^8$ is $CF_3$ and the combination of $R^{2a}$, $R^{2b}$, $R^{2c}$ and $R^4$ for a compound corresponds in each case to one row of Table A Table 1410

Compounds of the formula Ia.17 in which $R^8$ is $CH_2CHF_2$ and the combination of $R^{2a}$, $R^{2b}$, $R^{2c}$ and $R^4$ for a compound corresponds in each case to one row of Table A Table 1411

Compounds of the formula Ia.17 in which $R^8$ is $CH_2CF_3$ and the combination of $R^{2a}$, $R^{2b}$, $R^{2c}$ and $R^4$ for a compound corresponds in each case to one row of Table A Table 1412

Compounds of the formula Ia.17 in which $R^8$ is $CH_2CH_2CF_3$ and the combination of $R^{2a}$, $R^{2b}$, $R^{2c}$ and $R^4$ for a compound corresponds in each case to one row of Table A Table 1413

Compounds of the formula Ia.17 in which $R^8$ is cyclopropyl and the combination of $R^{2a}$, $R^{2b}$, $R^{2c}$ and $R^4$ for a compound corresponds in each case to one row of Table A Table 1414

Compounds of the formula Ia.17 in which $R^8$ is methylthiomethyl and the combination of $R^{2a}$, $R^{2b}$, $R^{2c}$ and $R^4$ for a compound corresponds in each case to one row of Table A Table 1415

Compounds of the formula Ia.17 in which $R^8$ is ethylthiomethyl and the combination of $R^{2a}$, $R^{2b}$, $R^{2c}$ and $R^4$ for a compound corresponds in each case to one row of Table A Table 1416
Compounds of the formula Ia.17 in which $R^8$ is methylsulfinylmethyl and the combination of $R^{2a}$, $R^{2b}$, $R^{2c}$ and $R^4$ for a compound corresponds in each case to one row of Table A Table 1417
Compounds of the formula Ia.17 in which $R^8$ is ethylsulfinylmethyl and the combination of $R^{2a}$, $R^{2b}$, $R^{2c}$ and $R^4$ for a compound corresponds in each case to one row of Table A Table 1418
Compounds of the formula Ia.17 in which $R^8$ is methylsulfonylmethyl and the combination of $R^{2a}$, $R^{2b}$, $R^{2c}$ and $R^4$ for a compound corresponds in each case to one row of Table A Table 1419
Compounds of the formula Ia.17 in which $R^8$ is ethylsulfonylmethyl and the combination of $R^{2a}$, $R^{2b}$, $R^{2c}$ and $R^4$ for a compound corresponds in each case to one row of Table A Table 1420
Compounds of the formula Ia.17 in which $R^8$ is phenyl and the combination of $R^{2a}$, $R^{2b}$, $R^{2c}$ and $R^4$ for a compound corresponds in each case to one row of Table A Table 1421
Compounds of the formula Ia.17 in which $R^8$ is 2-fluorophenyl and the combination of $R^{2a}$, $R^{2b}$, $R^{2c}$ and $R^4$ for a compound corresponds in each case to one row of Table A Table 1422
Compounds of the formula Ia.17 in which $R^8$ is 3-fluorophenyl and the combination of $R^{2a}$, $R^{2b}$, $R^{2c}$ and $R^4$ for a compound corresponds in each case to one row of Table A Table 1423
Compounds of the formula Ia.17 in which $R^8$ is 4-fluorophenyl and the combination of $R^{2a}$, $R^{2b}$, $R^{2c}$ and $R^4$ for a compound corresponds in each case to one row of Table A Table 1424
Compounds of the formula Ia.17 in which $R^8$ is 2,3-difluorophenyl and the combination of $R^{2a}$, $R^{2b}$, $R^{2c}$ and $R^4$ for a compound corresponds in each case to one row of Table A Table 1425
Compounds of the formula Ia.17 in which $R^8$ is 2,4-difluorophenyl and the combination of $R^{2a}$, $R^{2b}$, $R^{2c}$ and $R^4$ for a compound corresponds in each case to one row of Table A Table 1426
Compounds of the formula Ia.17 in which $R^8$ is 2,5-difluorophenyl and the combination of $R^{2a}$, $R^{2b}$, $R^{2c}$ and $R^4$ for a compound corresponds in each case to one row of Table A Table 1427
Compounds of the formula Ia.17 in which $R^8$ is 2,6-difluorophenyl and the combination of $R^{2a}$, $R^{2b}$, $R^{2c}$ and $R^4$ for a compound corresponds in each case to one row of Table A Table 1428
Compounds of the formula Ia.17 in which $R^8$ is 3,4-difluorophenyl and the combination of $R^{2a}$, $R^{2b}$, $R^{2c}$ and $R^4$ for a compound corresponds in each case to one row of Table A Table 1429
Compounds of the formula Ia.17 in which $R^8$ is 3,5-difluorophenyl and the combination of $R^{2a}$, $R^{2b}$, $R^{2c}$ and $R^4$ for a compound corresponds in each case to one row of Table A Table 1430
Compounds of the formula Ia.17 in which $R^8$ is 2-chlorophenyl and the combination of $R^{2a}$, $R^{2b}$, $R^{2c}$ and $R^4$ for a compound corresponds in each case to one row of Table A Table 1431
Compounds of the formula Ia.17 in which $R^8$ is 3-chlorophenyl and the combination of $R^{2a}$, $R^{2b}$, $R^{2c}$ and $R^4$ for a compound corresponds in each case to one row of Table A Table 1432
Compounds of the formula Ia.17 in which $R^8$ is 4-chlorophenyl and the combination of $R^{2a}$, $R^{2b}$, $R^{2c}$ and $R^4$ for a compound corresponds in each case to one row of Table A Table 1433
Compounds of the formula Ia.17 in which $R^8$ is 2-methoxyphenyl and the combination of $R^{2a}$, $R^{2b}$, $R^{2c}$ and $R^4$ for a compound corresponds in each case to one row of Table A Table 1434
Compounds of the formula Ia.17 in which $R^8$ is 3-methoxyphenyl and the combination of $R^{2a}$, $R^{2b}$, $R^{2c}$ and $R^4$ for a compound corresponds in each case to one row of Table A Table 1435
Compounds of the formula Ia.17 in which $R^8$ is 4-methoxyphenyl and the combination of $R^{2a}$, $R^{2b}$, $R^{2c}$ and $R^4$ for a compound corresponds in each case to one row of Table A Table 1436
Compounds of the formula Ia.17 in which $R^8$ is thietan-3-yl and the combination of $R^{2a}$, $R^{2b}$, $R^{2c}$ and $R^4$ for a compound corresponds in each case to one row of Table A Table 1437
Compounds of the formula Ia.17 in which $R^8$ is 1-oxothietan-3-yl and the combination of $R^{2a}$, $R^{2b}$, $R^{2c}$ and $R^4$ for a compound corresponds in each case to one row of Table A Table 1438
Compounds of the formula Ia.17 in which $R^8$ is 1,1-dioxothietan-3-yl and the combination of $R^{2a}$, $R^{2b}$, $R^{2c}$ and $R^4$ for a compound corresponds in each case to one row of Table A Table 1439
Compounds of the formula Ia.17 in which $R^8$ is pyridin-2-yl and the combination of $R^{2a}$, $R^{2b}$, $R^{2c}$ and $R^4$ for a compound corresponds in each case to one row of Table A Table 1440
Compounds of the formula Ia.17 in which $R^8$ is pyridin-3-yl and the combination of $R^{2a}$, $R^{2b}$, $R^{2c}$ and $R^4$ for a compound corresponds in each case to one row of Table A Table 1441
Compounds of the formula Ia.17 in which $R^8$ is pyridin-4-yl and the combination of $R^{2a}$, $R^{2b}$, $R^{2c}$ and $R^4$ for a compound corresponds in each case to one row of Table A Table 1442
Compounds of the formula Ia.17 in which $R^8$ is 4-chloropyridin-3-yl and the combination of $R^{2a}$, $R^{2b}$, $R^{2c}$ and $R^4$ for a compound corresponds in each case to one row of Table A Table 1443
Compounds of the formula Ia.17 in which $R^8$ is —NH—$CH_3$ and the combination of $R^{2a}$, $R^{2b}$, $R^{2c}$ and $R^4$ for a compound corresponds in each case to one row of Table A Table 1444
Compounds of the formula Ia.17 in which $R^8$ is —NH—$CH_2CH_3$ and the combination of $R^{2a}$, $R^{2b}$, $R^{2c}$ and $R^4$ for a compound corresponds in each case to one row of Table A Table 1445

Compounds of the formula Ia.17 in which $R^8$ is —NH—$CH_2CH_2CH_3$ and the combination of $R^{2a}$, $R^{2b}$, $R^{2c}$ and $R^4$ for a compound corresponds in each case to one row of Table A Table 1446

Compounds of the formula Ia.17 in which $R^8$ is —NH—$CF_3$ and the combination of $R^{2a}$, $R^{2b}$, $R^{2c}$ and $R^4$ for a compound corresponds in each case to one row of Table A Table 1447

Compounds of the formula Ia.17 in which $R^8$ is —NH—$CH_2CHF_2$ and the combination of $R^{2a}$, $R^{2b}$, $R^{2c}$ and $R^4$ for a compound corresponds in each case to one row of Table A Table 1448

Compounds of the formula Ia.17 in which $R^8$ is —NH—$CH_2CF_3$ and the combination of $R^{2a}$, $R^{2b}$, $R^{2c}$ and $R^4$ for a compound corresponds in each case to one row of Table A Table 1449

Compounds of the formula Ia.17 in which $R^8$ is —NH-phenyl and the combination of $R^{2a}$, $R^{2b}$, $R^{2c}$ and $R^4$ for a compound corresponds in each case to one row of Table A Table 1450

Compounds of the formula Ia.17 in which $R^8$ is —NH-benzyl and the combination of $R^{2a}$, $R^{2b}$, $R^{2c}$ and $R^4$ for a compound corresponds in each case to one row of Table A Tables 1451 to 1500

Compounds of the formula Ia.18 in which $R^8$ is as defined in any of tables 1401 to 1450 and the combination of $R^{2a}$, $R^{2b}$, $R^{2c}$ and $R^4$ for a compound corresponds in each case to one row of Table A Tables 1501 to 1550

Compounds of the formula Ia.19 in which $R^8$ is as defined in any of tables 1401 to 1450 and the combination of $R^{2a}$, $R^{2b}$, $R^{2c}$ and $R^4$ for a compound corresponds in each case to one row of Table A Tables 1551 to 1600

Compounds of the formula Ia.20 in which $R^8$ is as defined in any of tables 1401 to 1450 and the combination of $R^{2a}$, $R^{2b}$, $R^{2c}$ and $R^4$ for a compound corresponds in each case to one row of Table A Tables 1601 to 1650

Compounds of the formula Ia.21 in which $R^8$ is as defined in any of tables 1401 to 1450 and the combination of $R^{2a}$, $R^{2b}$, $R^{2c}$ and $R^4$ for a compound corresponds in each case to one row of Table A Tables 1651 to 1700

Compounds of the formula Ia.22 in which $R^8$ is as defined in any of tables 1401 to 1450 and the combination of $R^{2a}$, $R^{2b}$, $R^{2c}$ and $R^4$ for a compound corresponds in each case to one row of Table A Tables 1701 to 1750

Compounds of the formula Ia.23 in which $R^8$ is as defined in any of tables 1401 to 1450 and the combination of $R^{2a}$, $R^{2b}$, $R^{2c}$ and $R^4$ for a compound corresponds in each case to one row of Table A Tables 1751 to 1800

Compounds of the formula Ia.24 in which $R^8$ is as defined in any of tables 1401 to 1450 and the combination of $R^{2a}$, $R^{2b}$, $R^{2c}$ and $R^4$ for a compound corresponds in each case to one row of Table A Tables 1801 to 1850

Compounds of the formula Ia.25 in which $R^8$ is as defined in any of tables 1401 to 1450 and the combination of $R^{2a}$, $R^{2b}$, $R^{2c}$ and $R^4$ for a compound corresponds in each case to one row of Table A Tables 1851 to 1900

Compounds of the formula Ia.26 in which $R^8$ is as defined in any of tables 1401 to 1450 and the combination of $R^{2a}$, $R^{2b}$, $R^{2c}$ and $R^4$ for a compound corresponds in each case to one row of Table A Tables 1901 to 1950

Compounds of the formula Ia.27 in which $R^8$ is as defined in any of tables 1401 to 1450 and the combination of $R^{2a}$, $R^{2b}$, $R^{2c}$ and $R^4$ for a compound corresponds in each case to one row of Table A Tables 1951 to 2000

Compounds of the formula Ia.28 in which $R^8$ is as defined in any of tables 1401 to 1450 and the combination of $R^{2a}$, $R^{2b}$, $R^{2c}$ and $R^4$ for a compound corresponds in each case to one row of Table A Table 2001

Compounds of the formula Ia.29 in which $A^4$ is 1H-pyrrol-1-yl and the combination of $R^{2a}$, $R^{2b}$, $R^{2c}$ and $R^4$ for a compound corresponds in each case to one row of Table A Table 2002

Compounds of the formula Ia.29 in which $A^4$ is 1H-3-chloro-pyrrol-1-yl and the combination of $R^{2a}$, $R^{2b}$, $R^{2c}$ and $R^4$ for a compound corresponds in each case to one row of Table A Table 2003

Compounds of the formula Ia.29 in which $A^4$ is 1H-3-cyano-pyrrol-1-yl and the combination of $R^{2a}$, $R^{2b}$, $R^{2c}$ and $R^4$ for a compound corresponds in each case to one row of Table A Table 2004

Compounds of the formula Ia.29 in which $A^4$ is 1H-pyrazol-1-yl and the combination of $R^{2a}$, $R^{2b}$, $R^{2c}$ and $R^4$ for a compound corresponds in each case to one row of Table A Table 2005

Compounds of the formula Ia.29 in which $A^4$ is 1H-4-cloro-pyrazol-1-yl and the combination of $R^{2a}$, $R^{2b}$, $R^{2c}$ and $R^4$ for a compound corresponds in each case to one row of Table A Table 2006

Compounds of the formula Ia.29 in which $A^4$ is 1H-4-cyano-pyrazol-1-yl and the combination of $R^{2a}$, $R^{2b}$, $R^{2c}$ and $R^4$ for a compound corresponds in each case to one row of Table A Table 2007

Compounds of the formula Ia.29 in which $A^4$ is 1H-imidazol-1-yl and the combination of $R^{2a}$, $R^{2b}$, $R^{2c}$ and $R^4$ for a compound corresponds in each case to one row of Table A Table 2008

Compounds of the formula Ia.29 in which $A^4$ is 1H-4-chloro-imidazol-1-yl and the combination of $R^{2a}$, $R^{2b}$, $R^{2c}$ and $R^4$ for a compound corresponds in each case to one row of Table A Table 2009

Compounds of the formula Ia.29 in which $A^4$ is 1H-4-cyano-imidazol-1-yl and the combination of $R^{2a}$, $R^{2b}$, $R^{2c}$ and $R^4$ for a compound corresponds in each case to one row of Table A Table 2010

Compounds of the formula Ia.29 in which $A^4$ is 1H-[1,2,4]-triazol-1-yl and the combination of $R^{2a}$, $R^{2b}$, $R^{2c}$ and $R^4$ for a compound corresponds in each case to one row of Table A Table 2011

Compounds of the formula Ia.29 in which $A^4$ is 1H-[1,2,4]-3-chloro-triazol-1-yl and the combination of $R^{2a}$, $R^{2b}$, $R^{2c}$ and $R^4$ for a compound corresponds in each case to one row of Table A Table 2012
Compounds of the formula Ia.29 in which $A^4$ is 1H-[1,2,4]-3-cyano-triazol-1-yl and the combination of $R^{2a}$, $R^{2b}$, $R^{2c}$ and $R^4$ for a compound corresponds in each case to one row of Table A Table 2013
Compounds of the formula Ia.29 in which $A^4$ is 1H-1-methyl-pyrrol-2-yl and the combination of $R^{2a}$, $R^{2b}$, $R^{2c}$ and $R^4$ for a compound corresponds in each case to one row of Table A Table 2014
Compounds of the formula Ia.29 in which $A^4$ is 1H-1-methyl-pyrrol-3-yl and the combination of $R^{2a}$, $R^{2b}$, $R^{2c}$ and $R^4$ for a compound corresponds in each case to one row of Table A Table 2015
Compounds of the formula Ia.29 in which $A^4$ is 1H-1-methyl-pyrazol-4-yl and the combination of $R^{2a}$, $R^{2b}$, $R^{2c}$ and $R^4$ for a compound corresponds in each case to one row of Table A Table 2016
Compounds of the formula Ia.29 in which $A^4$ is 1H-1-methyl-pyrazol-5-yl and the combination of $R^{2a}$, $R^{2b}$, $R^{2c}$ and $R^4$ for a compound corresponds in each case to one row of Table A Table 2017
Compounds of the formula Ia.29 in which $A^4$ is 1H-1,3-dimethyl-pyrazol-5-yl and the combination of $R^{2a}$, $R^{2b}$, $R^{2c}$ and $R^4$ for a compound corresponds in each case to one row of Table A Table 2018
Compounds of the formula Ia.29 in which $A^4$ is 1H-1-methyl-3-trifluoromethyl-pyrazol-5-yl and the combination of $R^{2a}$, $R^{2b}$, $R^{2c}$ and $R^4$ for a compound corresponds in each case to one row of Table A Table 2019
Compounds of the formula Ia.29 in which $A^4$ is 1H-1-[1,2,3]-triazol-5-yl and the combination of $R^{2a}$, $R^{2b}$, $R^{2c}$ and $R^4$ for a compound corresponds in each case to one row of Table A Table 2020
Compounds of the formula Ia.29 in which $A^4$ is pyridin-2-yl and the combination of $R^{2a}$, $R^{2b}$, $R^{2c}$ and $R^4$ for a compound corresponds in each case to one row of Table A Table 2021
Compounds of the formula Ia.29 in which $A^4$ is pyridin-3-yl and the combination of $R^{2a}$, $R^{2b}$, $R^{2c}$ and $R^4$ for a compound corresponds in each case to one row of Table A Table 2022
Compounds of the formula Ia.29 in which $A^4$ is pyridin-4-yl and the combination of $R^{2a}$, $R^{2b}$, $R^{2c}$ and $R^4$ for a compound corresponds in each case to one row of Table A Table 2023
Compounds of the formula Ia.29 in which $A^4$ is pyrimidin-2-yl and the combination of $R^{2a}$, $R^{2b}$, $R^{2c}$ and $R^4$ for a compound corresponds in each case to one row of Table A Table 2024
Compounds of the formula Ia.29 in which $A^4$ is pyrimidin-4-yl and the combination of $R^{2a}$, $R^{2b}$, $R^{2c}$ and $R^4$ for a compound corresponds in each case to one row of Table A Table 2025
Compounds of the formula Ia.29 in which $A^4$ is pyrimidin-5-yl and the combination of $R^{2a}$, $R^{2b}$, $R^{2c}$ and $R^4$ for a compound corresponds in each case to one row of Table A Table 2026
Compounds of the formula Ia.29 in which $A^4$ is pyrazin-2-yl and the combination of $R^{2a}$, $R^{2b}$, $R^{2c}$ and $R^4$ for a compound corresponds in each case to one row of Table A Tables 2027 to 2052
Compounds of the formula Ia.30 in which $A^4$ is as defined in any of tables 2001 to 2026 and the combination of $R^{2a}$, $R^{2b}$, $R^{2c}$ and $R^4$ for a compound corresponds in each case to one row of Table A Table 2053
Compounds of the formula Ia.31 in which Y is H and the combination of $R^{2a}$, $R^{2b}$, $R^{2c}$ and $R^4$ for a compound corresponds in each case to one row of Table A Table 2054
Compounds of the formula Ia.31 in which Y is OH and the combination of $R^{2a}$, $R^{2b}$, $R^{2c}$ and $R^4$ for a compound corresponds in each case to one row of Table A Table 2055
Compounds of the formula Ia.31 in which Y is $OCH_3$ and the combination of $R^{2a}$, $R^{2b}$, $R^{2c}$ and $R^4$ for a compound corresponds in each case to one row of Table A Table 2056
Compounds of the formula Ia.31 in which Y is $OC_2H_5$ and the combination of $R^{2a}$, $R^{2b}$, $R^{2c}$ and $R^4$ for a compound corresponds in each case to one row of Table A Table 2057
Compounds of the formula Ia.31 in which Y is $OC(CH_3)_3$ and the combination of $R^{2a}$, $R^{2b}$, $R^{2c}$ and $R^4$ for a compound corresponds in each case to one row of Table A Table 2058
Compounds of the formula Ia.31 in which Y is $OCH_2CF_3$ and the combination of $R^{2a}$, $R^{2b}$, $R^{2c}$ and $R^4$ for a compound corresponds in each case to one row of Table A Table 2059
Compounds of the formula Ia.31 in which Y is $OCH_2CH_2CF_3$ and the combination of $R^{2a}$, $R^{2b}$, $R^{2c}$ and $R^4$ for a compound corresponds in each case to one row of Table A Table 2060
Compounds of the formula Ia.31 in which Y is $OCH_2$-(pyridine-2-yl) and the combination of $R^{2a}$, $R^{2b}$, $R^{2c}$ and $R^4$ for a compound corresponds in each case to one row of Table A Table 2061
Compounds of the formula Ia.31 in which Y is aziridin-1-yl and the combination of $R^{2a}$, $R^{2b}$, $R^{2c}$ and $R^4$ for a compound corresponds in each case to one row of Table A Table 2062
Compounds of the formula Ia.31 in which Y is azetidin-1-yl and the combination of $R^{2a}$, $R^{2b}$, $R^{2c}$ and $R^4$ for a compound corresponds in each case to one row of Table A Table 2063
Compounds of the formula Ia.31 in which Y is pyrrolidin-1-yl and the combination of $R^{2a}$, $R^{2b}$, $R^{2c}$ and $R^4$ for a compound corresponds in each case to one row of Table A Table 2064
Compounds of the formula Ia.31 in which Y is piperidin-1-yl and the combination of $R^{2a}$, $R^{2b}$, $R^{2c}$ and $R^4$ for a compound corresponds in each case to one row of Table A Table 2065
Compounds of the formula Ia.31 in which Y is morpholin-4-yl and the combination of $R^{2a}$, $R^{2b}$, $R^{2c}$ and $R^4$ for a compound corresponds in each case to one row of Table A Table 2066
Compounds of the formula Ia.31 in which Y is thiomorpholin-4-yl and the combination of $R^{2a}$, $R^{2b}$, $R^{2c}$ and $R^4$ for a compound corresponds in each case to one row of Table A Table 2067

Compounds of the formula Ia.31 in which Y is thiazinan-4-yl and the combination of $R^{2a}$, $R^{2b}$, $R^{2c}$ and $R^4$ for a compound corresponds in each case to one row of Table A Table 2068

Compounds of the formula Ia.31 in which Y is 1-oxo-thiazinan-4-yl and the combination of $R^{2a}$, $R^{2b}$, $R^{2c}$ and $R^4$ for a compound corresponds in each case to one row of Table A Table 2069

Compounds of the formula Ia.31 in which Y is 1,1-dioxo-thiazinan-4-yl and the combination of $R^{2a}$, $R^{2b}$, $R^{2c}$ and $R^4$ for a compound corresponds in each case to one row of Table A Table 2070

Compounds of the formula Ia.31 in which Y is thiazolidin-3-yl and the combination of $R^{2a}$, $R^{2b}$, $R^{2c}$ and $R^4$ for a compound corresponds in each case to one row of Table A Table 2071

Compounds of the formula Ia.31 in which Y is —N=S(CH$_3$)$_2$ and the combination of $R^{2a}$, $R^{2b}$, $R^{2c}$ and $R^4$ for a compound corresponds in each case to one row of Table A Table 2072

Compounds of the formula Ia.31 in which Y is —N=S(C$_2$H$_5$)$_2$ and the combination of $R^{2a}$, $R^{2b}$, $R^{2c}$ and $R^4$ for a compound corresponds in each case to one row of Table A Table 2073

Compounds of the formula Ia.31 in which Y is —N=S[CH(CH$_3$)$_2$]$_2$ and the combination of $R^{2a}$, $R^{2b}$, $R^{2c}$ and $R^4$ for a compound corresponds in each case to one row of Table A Table 2074

Compounds of the formula Ia.31 in which Y is —N(CH$_3$)—CH$_2$— (thiazol-4-yl) and the combination of $R^{2a}$, $R^{2b}$, $R^{2c}$ and $R^4$ for a compound corresponds in each case to one row of Table A Table 2075

Compounds of the formula Ia.31 in which Y is —N(C$_2$H$_5$)—CH$_2$— (thiazol-4-yl) and the combination of $R^{2a}$, $R^{2b}$, $R^{2c}$ and $R^4$ for a compound corresponds in each case to one row of Table A Table 2076

Compounds of the formula Ia.31 in which Y is —N(CH$_3$)—CH$_2$— (pyridin-2-yl) and the combination of $R^{2a}$, $R^{2b}$, $R^{2c}$ and $R^4$ for a compound corresponds in each case to one row of Table A Table 2077

Compounds of the formula Ia.31 in which Y is —N(C$_2$H$_5$)—CH$_2$— (pyridin-2-yl) and the combination of $R^{2a}$, $R^{2b}$, $R^{2c}$ and $R^4$ for a compound corresponds in each case to one row of Table A Table 2078

Compounds of the formula Ia.31 in which Y is —N(CH$_2$CN)—CH$_2$— (pyridin-2-yl) and the combination of $R^{2a}$, $R^{2b}$, $R^{2c}$ and $R^4$ for a compound corresponds in each case to one row of Table A Table 2079

Compounds of the formula Ia.31 in which Y is —N(CH$_2$—C—CH)—CH$_2$— (pyridin-2-yl) and the combination of $R^{2a}$, $R^{2b}$, $R^{2c}$ and $R^4$ for a compound corresponds in each case to one row of Table A Table 2080

Compounds of the formula Ia.31 in which Y is —N(CH$_3$)—CH$_2$—CONH—CH$_2$CF$_3$ and the combination of $R^{2a}$, $R^{2b}$, $R^{2c}$ and $R^4$ for a compound corresponds in each case to one row of Table A Table 2081

Compounds of the formula Ia.31 in which Y is —N(C$_2$H$_5$)—CH$_2$—CONH—CH$_2$CF$_3$ and the combination of $R^{2a}$, $R^{2b}$, $R^{2c}$ and $R^4$ for a compound corresponds in each case to one row of Table A Table 2082

Compounds of the formula Ia.31 in which Y is —N(CH$_3$)—OCH$_3$ and the combination of $R^{2a}$, $R^{2b}$, $R^{2c}$ and $R^4$ for a compound corresponds in each case to one row of Table A

TABLE A

| No. | $R^{2a}$ | $R^{2b}$ | $R^{2c}$ | $R^4$ |
|---|---|---|---|---|
| A-1 | F | H | F | H |
| A-2 | F | F | F | H |
| A-3 | F | Cl | F | H |
| A-4 | F | Br | F | H |
| A-5 | F | H | Cl | H |
| A-6 | F | H | Br | H |
| A-7 | Cl | H | Cl | H |
| A-8 | Cl | Cl | Cl | H |
| A-9 | Cl | F | Cl | H |
| A-10 | Cl | Br | Cl | H |
| A-11 | Cl | H | Br | H |
| A-12 | Br | H | Br | H |
| A-13 | Br | F | Br | H |
| A-14 | Br | Cl | Br | H |
| A-15 | CF$_3$ | H | F | H |
| A-16 | CF$_3$ | H | Cl | H |
| A-17 | CF$_3$ | H | Br | H |
| A-18 | CF$_3$ | H | CF$_3$ | H |
| A-19 | CF$_3$ | F | F | H |
| A-20 | CF$_3$ | Cl | Cl | H |
| A-21 | CF$_3$ | Br | Br | H |
| A-22 | SF$_5$ | H | F | H |
| A-23 | SF$_5$ | H | Cl | H |
| A-24 | SF$_5$ | H | Br | H |
| A-25 | SF$_5$ | H | CF$_3$ | H |
| A-26 | F | H | F | CH$_3$ |
| A-27 | F | F | F | CH$_3$ |
| A-28 | F | Cl | F | CH$_3$ |
| A-29 | F | Br | F | CH$_3$ |
| A-30 | F | H | Cl | CH$_3$ |
| A-31 | F | H | Br | CH$_3$ |
| A-32 | Cl | H | Cl | CH$_3$ |
| A-33 | Cl | Cl | Cl | CH$_3$ |
| A-34 | Cl | F | Cl | CH$_3$ |
| A-35 | Cl | Br | Cl | CH$_3$ |
| A-36 | Cl | H | Br | CH$_3$ |
| A-37 | Br | H | Br | CH$_3$ |
| A-38 | Br | F | Br | CH$_3$ |
| A-39 | Br | Cl | Br | CH$_3$ |
| A-40 | CF$_3$ | H | F | CH$_3$ |
| A-41 | CF$_3$ | H | Cl | CH$_3$ |
| A-42 | CF$_3$ | H | Br | CH$_3$ |
| A-43 | CF$_3$ | H | CF$_3$ | CH$_3$ |
| A-44 | CF$_3$ | F | F | CH$_3$ |
| A-45 | CF$_3$ | Cl | Cl | CH$_3$ |
| A-46 | CF$_3$ | Br | Br | CH$_3$ |
| A-47 | SF$_5$ | H | F | CH$_3$ |
| A-48 | SF$_5$ | H | Cl | CH$_3$ |
| A-49 | SF$_5$ | H | Br | CH$_3$ |
| A-50 | SF$_5$ | H | CF$_3$ | CH$_3$ |
| A-51 | F | H | F | CH$_2$CH$_3$ |
| A-52 | F | F | F | CH$_2$CH$_3$ |
| A-53 | F | Cl | F | CH$_2$CH$_3$ |
| A-54 | F | Br | F | CH$_2$CH$_3$ |
| A-55 | F | H | Cl | CH$_2$CH$_3$ |
| A-56 | F | H | Br | CH$_2$CH$_3$ |
| A-57 | Cl | H | Cl | CH$_2$CH$_3$ |
| A-58 | Cl | Cl | Cl | CH$_2$CH$_3$ |
| A-59 | Cl | F | Cl | CH$_2$CH$_3$ |
| A-60 | Cl | Br | Cl | CH$_2$CH$_3$ |
| A-61 | Cl | H | Br | CH$_2$CH$_3$ |
| A-62 | Br | H | Br | CH$_2$CH$_3$ |
| A-63 | Br | F | Br | CH$_2$CH$_3$ |
| A-64 | Br | Cl | Br | CH$_2$CH$_3$ |
| A-65 | CF$_3$ | H | F | CH$_2$CH$_3$ |
| A-66 | CF$_3$ | H | Cl | CH$_2$CH$_3$ |

TABLE A-continued

| No. | $R^{2a}$ | $R^{2b}$ | $R^{2c}$ | $R^4$ |
|---|---|---|---|---|
| A-67 | $CF_3$ | H | Br | $CH_2CH_3$ |
| A-68 | $CF_3$ | H | $CF_3$ | $CH_2CH_3$ |
| A-69 | $CF_3$ | F | F | $CH_2CH_3$ |
| A-70 | $CF_3$ | Cl | Cl | $CH_2CH_3$ |
| A-71 | $CF_3$ | Br | Br | $CH_2CH_3$ |
| A-72 | $SF_5$ | H | F | $CH_2CH_3$ |
| A-73 | $SF_5$ | H | Cl | $CH_2CH_3$ |
| A-74 | $SF_5$ | H | Br | $CH_2CH_3$ |
| A-75 | $SF_5$ | H | $CF_3$ | $CH_2CH_3$ |
| A-76 | F | H | F | $CH(CH_3)_2$ |
| A-77 | F | F | F | $CH(CH_3)_2$ |
| A-78 | F | Cl | F | $CH(CH_3)_2$ |
| A-79 | F | Br | F | $CH(CH_3)_2$ |
| A-80 | F | H | Cl | $CH(CH_3)_2$ |
| A-81 | F | H | Br | $CH(CH_3)_2$ |
| A-82 | Cl | H | Cl | $CH(CH_3)_2$ |
| A-83 | Cl | Cl | Cl | $CH(CH_3)_2$ |
| A-84 | Cl | F | Cl | $CH(CH_3)_2$ |
| A-85 | Cl | Br | Cl | $CH(CH_3)_2$ |
| A-86 | Cl | H | Br | $CH(CH_3)_2$ |
| A-87 | Br | H | Br | $CH(CH_3)_2$ |
| A-88 | Br | F | Br | $CH(CH_3)_2$ |
| A-89 | Br | Cl | Br | $CH(CH_3)_2$ |
| A-90 | $CF_3$ | H | F | $CH(CH_3)_2$ |
| A-91 | $CF_3$ | H | Cl | $CH(CH_3)_2$ |
| A-92 | $CF_3$ | H | Br | $CH(CH_3)_2$ |
| A-93 | $CF_3$ | H | $CF_3$ | $CH(CH_3)_2$ |
| A-94 | $CF_3$ | F | F | $CH(CH_3)_2$ |
| A-95 | $CF_3$ | Cl | Cl | $CH(CH_3)_2$ |
| A-96 | $CF_3$ | Br | Br | $CH(CH_3)_2$ |
| A-97 | $SF_5$ | H | F | $CH(CH_3)_2$ |
| A-98 | $SF_5$ | H | Cl | $CH(CH_3)_2$ |
| A-99 | $SF_5$ | H | Br | $CH(CH_3)_2$ |
| A-100 | $SF_5$ | H | $CF_3$ | $CH(CH_3)_2$ |
| A-101 | F | H | F | $CHF_2$ |
| A-102 | F | F | F | $CHF_2$ |
| A-103 | F | Cl | F | $CHF_2$ |
| A-104 | F | Br | F | $CHF_2$ |
| A-105 | F | H | Cl | $CHF_2$ |
| A-106 | F | H | Br | $CHF_2$ |
| A-107 | Cl | H | Cl | $CHF_2$ |
| A-108 | Cl | Cl | Cl | $CHF_2$ |
| A-109 | Cl | F | Cl | $CHF_2$ |
| A-110 | Cl | Br | Cl | $CHF_2$ |
| A-111 | Cl | H | Br | $CHF_2$ |
| A-112 | Br | H | Br | $CHF_2$ |
| A-113 | Br | F | Br | $CHF_2$ |
| A-114 | Br | Cl | Br | $CHF_2$ |
| A-115 | $CF_3$ | H | F | $CHF_2$ |
| A-116 | $CF_3$ | H | Cl | $CHF_2$ |
| A-117 | $CF_3$ | H | Br | $CHF_2$ |
| A-118 | $CF_3$ | H | $CF_3$ | $CHF_2$ |
| A-119 | $CF_3$ | F | F | $CHF_2$ |
| A-120 | $CF_3$ | Cl | Cl | $CHF_2$ |
| A-121 | $CF_3$ | Br | Br | $CHF_2$ |
| A-122 | $SF_5$ | H | F | $CHF_2$ |
| A-123 | $SF_5$ | H | Cl | $CHF_2$ |
| A-124 | $SF_5$ | H | Br | $CHF_2$ |
| A-125 | $SF_5$ | H | $CF_3$ | $CHF_2$ |
| A-126 | F | H | F | $CF_3$ |
| A-127 | F | F | F | $CF_3$ |
| A-128 | F | Cl | F | $CF_3$ |
| A-129 | F | Br | F | $CF_3$ |
| A-130 | F | H | Cl | $CF_3$ |
| A-131 | F | H | Br | $CF_3$ |
| A-132 | Cl | H | Cl | $CF_3$ |
| A-133 | Cl | Cl | Cl | $CF_3$ |
| A-134 | Cl | F | Cl | $CF_3$ |
| A-135 | Cl | Br | Cl | $CF_3$ |
| A-136 | Cl | H | Br | $CF_3$ |
| A-137 | Br | H | Br | $CF_3$ |
| A-138 | Br | F | Br | $CF_3$ |
| A-139 | Br | Cl | Br | $CF_3$ |
| A-140 | $CF_3$ | H | F | $CF_3$ |
| A-141 | $CF_3$ | H | Cl | $CF_3$ |
| A-142 | $CF_3$ | H | Br | $CF_3$ |
| A-143 | $CF_3$ | H | $CF_3$ | $CF_3$ |
| A-144 | $CF_3$ | F | F | $CF_3$ |
| A-145 | $CF_3$ | Cl | Cl | $CF_3$ |
| A-146 | $CF_3$ | Br | Br | $CF_3$ |
| A-147 | $SF_5$ | H | F | $CF_3$ |
| A-148 | $SF_5$ | H | Cl | $CF_3$ |
| A-149 | $SF_5$ | H | Br | $CF_3$ |
| A-150 | $SF_5$ | H | $CF_3$ | $CF_3$ |
| A-151 | F | H | F | $CH_2-CH=CH_2$ |
| A-152 | F | F | F | $CH_2-CH=CH_2$ |
| A-153 | F | Cl | F | $CH_2-CH=CH_2$ |
| A-154 | F | Br | F | $CH_2-CH=CH_2$ |
| A-155 | F | H | Cl | $CH_2-CH=CH_2$ |
| A-156 | F | H | Br | $CH_2-CH=CH_2$ |
| A-157 | Cl | H | Cl | $CH_2-CH=CH_2$ |
| A-158 | Cl | Cl | Cl | $CH_2-CH=CH_2$ |
| A-159 | Cl | F | Cl | $CH_2-CH=CH_2$ |
| A-160 | Cl | Br | Cl | $CH_2-CH=CH_2$ |
| A-161 | Cl | H | Br | $CH_2-CH=CH_2$ |
| A-162 | Br | H | Br | $CH_2-CH=CH_2$ |
| A-163 | Br | F | Br | $CH_2-CH=CH_2$ |
| A-164 | Br | Cl | Br | $CH_2-CH=CH_2$ |
| A-165 | $CF_3$ | H | F | $CH_2-CH=CH_2$ |
| A-166 | $CF_3$ | H | Cl | $CH_2-CH=CH_2$ |
| A-167 | $CF_3$ | H | Br | $CH_2-CH=CH_2$ |
| A-168 | $CF_3$ | H | $CF_3$ | $CH_2-CH=CH_2$ |
| A-169 | $CF_3$ | F | F | $CH_2-CH=CH_2$ |
| A-170 | $CF_3$ | Cl | Cl | $CH_2-CH=CH_2$ |
| A-171 | $CF_3$ | Br | Br | $CH_2-CH=CH_2$ |
| A-172 | $SF_5$ | H | F | $CH_2-CH=CH_2$ |
| A-173 | $SF_5$ | H | Cl | $CH_2-CH=CH_2$ |
| A-174 | $SF_5$ | H | Br | $CH_2-CH=CH_2$ |
| A-175 | $SF_5$ | H | $CF_3$ | $CH_2-CH=CH_2$ |
| A-176 | F | H | F | $CH=CH_2$ |
| A-177 | F | F | F | $CH=CH_2$ |
| A-178 | F | Cl | F | $CH=CH_2$ |
| A-179 | F | Br | F | $CH=CH_2$ |
| A-180 | F | H | Cl | $CH=CH_2$ |
| A-181 | F | H | Br | $CH=CH_2$ |
| A-182 | Cl | H | Cl | $CH=CH_2$ |
| A-183 | Cl | Cl | Cl | $CH=CH_2$ |
| A-184 | Cl | F | Cl | $CH=CH_2$ |
| A-185 | Cl | Br | Cl | $CH=CH_2$ |
| A-186 | Cl | H | Br | $CH=CH_2$ |
| A-187 | Br | H | Br | $CH=CH_2$ |
| A-188 | Br | F | Br | $CH=CH_2$ |
| A-189 | Br | Cl | Br | $CH=CH_2$ |
| A-190 | $CF_3$ | H | F | $CH=CH_2$ |
| A-191 | $CF_3$ | H | Cl | $CH=CH_2$ |
| A-192 | $CF_3$ | H | Br | $CH=CH_2$ |
| A-193 | $CF_3$ | H | $CF_3$ | $CH=CH_2$ |
| A-194 | $CF_3$ | F | F | $CH=CH_2$ |
| A-195 | $CF_3$ | Cl | Cl | $CH=CH_2$ |
| A-196 | $CF_3$ | Br | Br | $CH=CH_2$ |
| A-197 | $SF_5$ | H | F | $CH=CH_2$ |
| A-198 | $SF_5$ | H | Cl | $CH=CH_2$ |
| A-199 | $SF_5$ | H | Br | $CH=CH_2$ |
| A-200 | $SF_5$ | H | $CF_3$ | $CH=CH_2$ |
| A-201 | F | H | F | $C\equiv CH$ |
| A-202 | F | F | F | $C\equiv CH$ |
| A-203 | F | Cl | F | $C\equiv CH$ |
| A-204 | F | Br | F | $C\equiv CH$ |
| A-205 | F | H | Cl | $C\equiv CH$ |
| A-206 | F | H | Br | $C\equiv CH$ |
| A-207 | Cl | H | Cl | $C\equiv CH$ |
| A-208 | Cl | Cl | Cl | $C\equiv CH$ |
| A-209 | Cl | F | Cl | $C\equiv CH$ |
| A-210 | Cl | Br | Cl | $C\equiv CH$ |
| A-211 | Cl | H | Br | $C\equiv CH$ |
| A-212 | Br | H | Br | $C\equiv CH$ |
| A-213 | Br | F | Br | $C\equiv CH$ |
| A-214 | Br | Cl | Br | $C\equiv CH$ |
| A-215 | $CF_3$ | H | F | $C\equiv CH$ |
| A-216 | $CF_3$ | H | Cl | $C\equiv CH$ |
| A-217 | $CF_3$ | H | Br | $C\equiv CH$ |
| A-218 | $CF_3$ | H | $CF_3$ | $C\equiv CH$ |
| A-219 | $CF_3$ | F | F | $C\equiv CH$ |
| A-220 | $CF_3$ | Cl | Cl | $C\equiv CH$ |
| A-221 | $CF_3$ | Br | Br | $C\equiv CH$ |
| A-222 | $SF_5$ | H | F | $C\equiv CH$ |

TABLE A-continued

| No. | $R^{2a}$ | $R^{2b}$ | $R^{2c}$ | $R^4$ |
|---|---|---|---|---|
| A-223 | SF$_5$ | H | Cl | C≡CH |
| A-224 | SF$_5$ | H | Br | C≡CH |
| A-225 | SF$_5$ | H | CF$_3$ | C≡CH |
| A-226 | F | H | F | $^cC_3H_5$* |
| A-227 | F | F | F | $^cC_3H_5$* |
| A-228 | F | Cl | F | $^cC_3H_5$* |
| A-229 | F | Br | F | $^cC_3H_5$* |
| A-230 | F | H | Cl | $^cC_3H_5$* |
| A-231 | F | H | Br | $^cC_3H_5$* |
| A-232 | Cl | H | Cl | $^cC_3H_5$* |
| A-233 | Cl | Cl | Cl | $^cC_3H_5$* |
| A-234 | Cl | F | Cl | $^cC_3H_5$* |
| A-235 | Cl | Br | Cl | $^cC_3H_5$* |
| A-236 | Cl | H | Br | $^cC_3H_5$* |
| A-237 | Br | H | Br | $^cC_3H_5$* |
| A-238 | Br | F | Br | $^cC_3H_5$* |
| A-239 | Br | Cl | Br | $^cC_3H_5$* |
| A-240 | CF$_3$ | H | F | $^cC_3H_5$* |
| A-241 | CF$_3$ | H | Cl | $^cC_3H_5$* |
| A-242 | CF$_3$ | H | Br | $^cC_3H_5$* |
| A-243 | CF$_3$ | H | CF$_3$ | $^cC_3H_5$* |
| A-244 | CF$_3$ | F | F | $^cC_3H_5$* |
| A-245 | CF$_3$ | Cl | Cl | $^cC_3H_5$* |
| A-246 | CF$_3$ | Br | Br | $^cC_3H_5$* |
| A-247 | SF$_5$ | H | F | $^cC_3H_5$* |
| A-248 | SF$_5$ | H | Cl | $^cC_3H_5$* |
| A-249 | SF$_5$ | H | Br | $^cC_3H_5$* |
| A-250 | SF$_5$ | H | CF$_3$ | $^cC_3H_5$* |
| A-251 | F | H | F | F |
| A-252 | F | F | F | F |
| A-253 | F | Cl | F | F |
| A-254 | F | Br | F | F |
| A-255 | F | H | Cl | F |
| A-256 | F | H | Br | F |
| A-257 | Cl | H | Cl | F |
| A-258 | Cl | Cl | Cl | F |
| A-259 | Cl | F | Cl | F |
| A-260 | Cl | Br | Cl | F |
| A-261 | Cl | H | Br | F |
| A-262 | Br | H | Br | F |
| A-263 | Br | F | Br | F |
| A-264 | Br | Cl | Br | F |
| A-265 | CF$_3$ | H | F | F |
| A-266 | CF$_3$ | H | Cl | F |
| A-267 | CF$_3$ | H | Br | F |
| A-268 | CF$_3$ | H | CF$_3$ | F |
| A-269 | CF$_3$ | F | F | F |
| A-270 | CF$_3$ | Cl | Cl | F |
| A-271 | CF$_3$ | Br | Br | F |
| A-272 | SF$_5$ | H | F | F |
| A-273 | SF$_5$ | H | Cl | F |
| A-274 | SF$_5$ | H | Br | F |
| A-275 | SF$_5$ | H | CF$_3$ | F |
| A-276 | F | H | F | Cl |
| A-277 | F | F | F | Cl |
| A-278 | F | Cl | F | Cl |
| A-279 | F | Br | F | Cl |
| A-280 | F | H | Cl | Cl |
| A-281 | F | H | Br | Cl |
| A-282 | Cl | H | Cl | Cl |
| A-283 | Cl | Cl | Cl | Cl |
| A-284 | Cl | F | Cl | Cl |
| A-285 | Cl | Br | Cl | Cl |
| A-286 | Cl | H | Br | Cl |
| A-287 | Br | H | Br | Cl |
| A-288 | Br | F | Br | Cl |
| A-289 | Br | Cl | Br | Cl |
| A-290 | CF$_3$ | H | F | Cl |
| A-291 | CF$_3$ | H | Cl | Cl |
| A-292 | CF$_3$ | H | Br | Cl |
| A-293 | CF$_3$ | H | CF$_3$ | Cl |
| A-294 | CF$_3$ | F | F | Cl |
| A-295 | CF$_3$ | Cl | Cl | Cl |
| A-296 | CF$_3$ | Br | Br | Cl |
| A-297 | SF$_5$ | H | F | Cl |
| A-298 | SF$_5$ | H | Cl | Cl |
| A-299 | SF$_5$ | H | Br | Cl |
| A-300 | SF$_5$ | H | CF$_3$ | Cl |
| A-301 | F | H | F | Br |
| A-302 | F | F | F | Br |
| A-303 | F | Cl | F | Br |
| A-304 | F | Br | F | Br |
| A-305 | F | H | Cl | Br |
| A-306 | F | H | Br | Br |
| A-307 | Cl | H | Cl | Br |
| A-308 | Cl | Cl | Cl | Br |
| A-309 | Cl | F | Cl | Br |
| A-310 | Cl | Br | Cl | Br |
| A-311 | Cl | H | Br | Br |
| A-312 | Br | H | Br | Br |
| A-313 | Br | F | Br | Br |
| A-314 | Br | Cl | Br | Br |
| A-315 | CF$_3$ | H | F | Br |
| A-316 | CF$_3$ | H | Cl | Br |
| A-317 | CF$_3$ | H | Br | Br |
| A-318 | CF$_3$ | H | CF$_3$ | Br |
| A-319 | CF$_3$ | F | F | Br |
| A-320 | CF$_3$ | Cl | Cl | Br |
| A-321 | CF$_3$ | Br | Br | Br |
| A-322 | SF$_5$ | H | F | Br |
| A-323 | SF$_5$ | H | Cl | Br |
| A-324 | SF$_5$ | H | Br | Br |
| A-325 | SF$_5$ | H | CF$_3$ | Br |
| A-326 | F | H | F | CN |
| A-327 | F | F | F | CN |
| A-328 | F | Cl | F | CN |
| A-329 | F | Br | F | CN |
| A-330 | F | H | Cl | CN |
| A-331 | F | H | Br | CN |
| A-332 | Cl | H | Cl | CN |
| A-333 | Cl | Cl | Cl | CN |
| A-334 | Cl | F | Cl | CN |
| A-335 | Cl | Br | Cl | CN |
| A-336 | Cl | H | Br | CN |
| A-337 | Br | H | Br | CN |
| A-338 | Br | F | Br | CN |
| A-339 | Br | Cl | Br | CN |
| A-340 | CF$_3$ | H | F | CN |
| A-341 | CF$_3$ | H | Cl | CN |
| A-342 | CF$_3$ | H | Br | CN |
| A-343 | CF$_3$ | H | CF$_3$ | CN |
| A-344 | CF$_3$ | F | F | CN |
| A-345 | CF$_3$ | Cl | Cl | CN |
| A-346 | CF$_3$ | Br | Br | CN |
| A-347 | SF$_5$ | H | F | CN |
| A-348 | SF$_5$ | H | Cl | CN |
| A-349 | SF$_5$ | H | Br | CN |
| A-350 | SF$_5$ | H | CF$_3$ | CN |
| A-351 | F | H | F | OCH$_3$ |
| A-352 | F | F | F | OCH$_3$ |
| A-353 | F | Cl | F | OCH$_3$ |
| A-354 | F | Br | F | OCH$_3$ |
| A-355 | F | H | Cl | OCH$_3$ |
| A-356 | F | H | Br | OCH$_3$ |
| A-357 | Cl | H | Cl | OCH$_3$ |
| A-358 | Cl | Cl | Cl | OCH$_3$ |
| A-359 | Cl | F | Cl | OCH$_3$ |
| A-360 | Cl | Br | Cl | OCH$_3$ |
| A-361 | Cl | H | Br | OCH$_3$ |
| A-362 | Br | H | Br | OCH$_3$ |
| A-363 | Br | F | Br | OCH$_3$ |
| A-364 | Br | Cl | Br | OCH$_3$ |
| A-365 | CF$_3$ | H | F | OCH$_3$ |
| A-366 | CF$_3$ | H | Cl | OCH$_3$ |
| A-367 | CF$_3$ | H | Br | OCH$_3$ |
| A-368 | CF$_3$ | H | CF$_3$ | OCH$_3$ |
| A-369 | CF$_3$ | F | F | OCH$_3$ |
| A-370 | CF$_3$ | Cl | Cl | OCH$_3$ |
| A-371 | CF$_3$ | Br | Br | OCH$_3$ |
| A-372 | SF$_5$ | H | F | OCH$_3$ |
| A-373 | SF$_5$ | H | Cl | OCH$_3$ |
| A-374 | SF$_5$ | H | Br | OCH$_3$ |
| A-375 | SF$_5$ | H | CF$_3$ | OCH$_3$ |
| A-376 | F | H | F | OCH$_2$CH$_3$ |
| A-377 | F | F | F | OCH$_2$CH$_3$ |
| A-378 | F | Cl | F | OCH$_2$CH$_3$ |

TABLE A-continued

| No. | R$^{2a}$ | R$^{2b}$ | R$^{2c}$ | R$^4$ |
|---|---|---|---|---|
| A-379 | F | Br | F | OCH$_2$CH$_3$ |
| A-380 | F | H | Cl | OCH$_2$CH$_3$ |
| A-381 | F | H | Br | OCH$_2$CH$_3$ |
| A-382 | Cl | H | Cl | OCH$_2$CH$_3$ |
| A-383 | Cl | Cl | Cl | OCH$_2$CH$_3$ |
| A-384 | Cl | F | Cl | OCH$_2$CH$_3$ |
| A-385 | Cl | Br | Cl | OCH$_2$CH$_3$ |
| A-386 | Cl | H | Br | OCH$_2$CH$_3$ |
| A-387 | Br | H | Br | OCH$_2$CH$_3$ |
| A-388 | Br | F | Br | OCH$_2$CH$_3$ |
| A-389 | Br | Cl | Br | OCH$_2$CH$_3$ |
| A-390 | CF$_3$ | H | F | OCH$_2$CH$_3$ |
| A-391 | CF$_3$ | H | Cl | OCH$_2$CH$_3$ |
| A-392 | CF$_3$ | H | Br | OCH$_2$CH$_3$ |
| A-393 | CF$_3$ | H | CF$_3$ | OCH$_2$CH$_3$ |
| A-394 | CF$_3$ | F | F | OCH$_2$CH$_3$ |
| A-395 | CF$_3$ | Cl | Cl | OCH$_2$CH$_3$ |
| A-396 | CF$_3$ | Br | Br | OCH$_2$CH$_3$ |
| A-397 | SF$_5$ | H | F | OCH$_2$CH$_3$ |
| A-398 | SF$_5$ | H | Cl | OCH$_2$CH$_3$ |
| A-399 | SF$_5$ | H | Br | OCH$_2$CH$_3$ |
| A-400 | SF$_5$ | H | CF$_3$ | OCH$_2$CH$_3$ |
| A-401 | F | H | F | OCH(CH$_3$)$_2$ |
| A-402 | F | F | F | OCH(CH$_3$)$_2$ |
| A-403 | F | Cl | F | OCH(CH$_3$)$_2$ |
| A-404 | F | Br | F | OCH(CH$_3$)$_2$ |
| A-405 | F | H | Cl | OCH(CH$_3$)$_2$ |
| A-406 | F | H | Br | OCH(CH$_3$)$_2$ |
| A-407 | Cl | H | Cl | OCH(CH$_3$)$_2$ |
| A-408 | Cl | Cl | Cl | OCH(CH$_3$)$_2$ |
| A-409 | Cl | F | Cl | OCH(CH$_3$)$_2$ |
| A-410 | Cl | Br | Cl | OCH(CH$_3$)$_2$ |
| A-411 | Cl | H | Br | OCH(CH$_3$)$_2$ |
| A-412 | Br | H | Br | OCH(CH$_3$)$_2$ |
| A-413 | Br | F | Br | OCH(CH$_3$)$_2$ |
| A-414 | Br | Cl | Br | OCH(CH$_3$)$_2$ |
| A-415 | CF$_3$ | H | F | OCH(CH$_3$)$_2$ |
| A-416 | CF$_3$ | H | Cl | OCH(CH$_3$)$_2$ |
| A-417 | CF$_3$ | H | Br | OCH(CH$_3$)$_2$ |
| A-418 | CF$_3$ | H | CF$_3$ | OCH(CH$_3$)$_2$ |
| A-419 | CF$_3$ | F | F | OCH(CH$_3$)$_2$ |
| A-420 | CF$_3$ | Cl | Cl | OCH(CH$_3$)$_2$ |
| A-421 | CF$_3$ | Br | Br | OCH(CH$_3$)$_2$ |
| A-422 | SF$_5$ | H | F | OCH(CH$_3$)$_2$ |
| A-423 | SF$_5$ | H | Cl | OCH(CH$_3$)$_2$ |
| A-424 | SF$_5$ | H | Br | OCH(CH$_3$)$_2$ |
| A-425 | SF$_5$ | H | CF$_3$ | OCH(CH$_3$)$_2$ |
| A-426 | F | H | F | OCH$_2$CH=CH$_2$ |
| A-427 | F | F | F | OCH$_2$CH=CH$_2$ |
| A-428 | F | Cl | F | OCH$_2$CH=CH$_2$ |
| A-429 | F | Br | F | OCH$_2$CH=CH$_2$ |
| A-430 | F | H | Cl | OCH$_2$CH=CH$_2$ |
| A-431 | F | H | Br | OCH$_2$CH=CH$_2$ |
| A-432 | Cl | H | Cl | OCH$_2$CH=CH$_2$ |
| A-433 | Cl | Cl | Cl | OCH$_2$CH=CH$_2$ |
| A-434 | Cl | F | Cl | OCH$_2$CH=CH$_2$ |
| A-435 | Cl | Br | Cl | OCH$_2$CH=CH$_2$ |
| A-436 | Cl | H | Br | OCH$_2$CH=CH$_2$ |
| A-437 | Br | H | Br | OCH$_2$CH=CH$_2$ |
| A-438 | Br | F | Br | OCH$_2$CH=CH$_2$ |
| A-439 | Br | Cl | Br | OCH$_2$CH=CH$_2$ |
| A-440 | CF$_3$ | H | F | OCH$_2$CH=CH$_2$ |
| A-441 | CF$_3$ | H | Cl | OCH$_2$CH=CH$_2$ |
| A-442 | CF$_3$ | H | Br | OCH$_2$CH=CH$_2$ |
| A-443 | CF$_3$ | H | CF$_3$ | OCH$_2$CH=CH$_2$ |
| A-444 | CF$_3$ | F | F | OCH$_2$CH=CH$_2$ |
| A-445 | CF$_3$ | Cl | Cl | OCH$_2$CH=CH$_2$ |
| A-446 | CF$_3$ | Br | Br | OCH$_2$CH=CH$_2$ |
| A-447 | SF$_5$ | H | F | OCH$_2$CH=CH$_2$ |
| A-448 | SF$_5$ | H | Cl | OCH$_2$CH=CH$_2$ |
| A-449 | SF$_5$ | H | Br | OCH$_2$CH=CH$_2$ |
| A-450 | SF$_5$ | H | CF$_3$ | OCH$_2$CH=CH$_2$ |
| A-451 | F | H | F | O—$^c$C$_3$H$_5$* |
| A-452 | F | F | F | O—$^c$C$_3$H$_5$* |
| A-453 | F | Cl | F | O—$^c$C$_3$H$_5$* |
| A-454 | F | Br | F | O—$^c$C$_3$H$_5$* |
| A-455 | F | H | Cl | O—$^c$C$_3$H$_5$* |
| A-456 | F | H | Br | O—$^c$C$_3$H$_5$* |
| A-457 | Cl | H | Cl | O—$^c$C$_3$H$_5$* |
| A-458 | Cl | Cl | Cl | O—$^c$C$_3$H$_5$* |
| A-459 | Cl | F | Cl | O—$^c$C$_3$H$_5$* |
| A-460 | Cl | Br | Cl | O—$^c$C$_3$H$_5$* |
| A-461 | Cl | H | Br | O—$^c$C$_3$H$_5$* |
| A-462 | Br | H | Br | O—$^c$C$_3$H$_5$* |
| A-463 | Br | F | Br | O—$^c$C$_3$H$_5$* |
| A-464 | Br | Cl | Br | O—$^c$C$_3$H$_5$* |
| A-465 | CF$_3$ | H | F | O—$^c$C$_3$H$_5$* |
| A-466 | CF$_3$ | H | Cl | O—$^c$C$_3$H$_5$* |
| A-467 | CF$_3$ | H | Br | O—$^c$C$_3$H$_5$* |
| A-468 | CF$_3$ | H | CF$_3$ | O—$^c$C$_3$H$_5$* |
| A-469 | CF$_3$ | F | F | O—$^c$C$_3$H$_5$* |
| A-470 | CF$_3$ | Cl | Cl | O—$^c$C$_3$H$_5$* |
| A-471 | CF$_3$ | Br | Br | O—$^c$C$_3$H$_5$* |
| A-472 | SF$_5$ | H | F | O—$^c$C$_3$H$_5$* |
| A-473 | SF$_5$ | H | Cl | O—$^c$C$_3$H$_5$* |
| A-474 | SF$_5$ | H | Br | O—$^c$C$_3$H$_5$* |
| A-475 | SF$_5$ | H | CF$_3$ | O—$^c$C$_3$H$_5$* |
| A-476 | F | H | F | OCHF$_2$ |
| A-477 | F | F | F | OCHF$_2$ |
| A-478 | F | Cl | F | OCHF$_2$ |
| A-479 | F | Br | F | OCHF$_2$ |
| A-480 | F | H | Cl | OCHF$_2$ |
| A-481 | F | H | Br | OCHF$_2$ |
| A-482 | Cl | H | Cl | OCHF$_2$ |
| A-483 | Cl | Cl | Cl | OCHF$_2$ |
| A-484 | Cl | F | Cl | OCHF$_2$ |
| A-485 | Cl | Br | Cl | OCHF$_2$ |
| A-486 | Cl | H | Br | OCHF$_2$ |
| A-487 | Br | H | Br | OCHF$_2$ |
| A-488 | Br | F | Br | OCHF$_2$ |
| A-489 | Br | Cl | Br | OCHF$_2$ |
| A-490 | CF$_3$ | H | F | OCHF$_2$ |
| A-491 | CF$_3$ | H | Cl | OCHF$_2$ |
| A-492 | CF$_3$ | H | Br | OCHF$_2$ |
| A-493 | CF$_3$ | H | CF$_3$ | OCHF$_2$ |
| A-494 | CF$_3$ | F | F | OCHF$_2$ |
| A-495 | CF$_3$ | Cl | Cl | OCHF$_2$ |
| A-496 | CF$_3$ | Br | Br | OCHF$_2$ |
| A-497 | SF$_5$ | H | F | OCHF$_2$ |
| A-498 | SF$_5$ | H | Cl | OCHF$_2$ |
| A-499 | SF$_5$ | H | Br | OCHF$_2$ |
| A-500 | SF$_5$ | H | CF$_3$ | OCHF$_2$ |
| A-501 | F | H | F | OCF$_3$ |
| A-502 | F | F | F | OCF$_3$ |
| A-503 | F | Cl | F | OCF$_3$ |
| A-504 | F | Br | F | OCF$_3$ |
| A-505 | F | H | Cl | OCF$_3$ |
| A-506 | F | H | Br | OCF$_3$ |
| A-507 | Cl | H | Cl | OCF$_3$ |
| A-508 | Cl | Cl | Cl | OCF$_3$ |
| A-509 | Cl | F | Cl | OCF$_3$ |
| A-510 | Cl | Br | Cl | OCF$_3$ |
| A-511 | Cl | H | Br | OCF$_3$ |
| A-512 | Br | H | Br | OCF$_3$ |
| A-513 | Br | F | Br | OCF$_3$ |
| A-514 | Br | Cl | Br | OCF$_3$ |
| A-515 | CF$_3$ | H | F | OCF$_3$ |
| A-516 | CF$_3$ | H | Cl | OCF$_3$ |
| A-517 | CF$_3$ | H | Br | OCF$_3$ |
| A-518 | CF$_3$ | H | CF$_3$ | OCF$_3$ |
| A-519 | CF$_3$ | F | F | OCF$_3$ |
| A-520 | CF$_3$ | Cl | Cl | OCF$_3$ |
| A-521 | CF$_3$ | Br | Br | OCF$_3$ |
| A-522 | SF$_5$ | H | F | OCF$_3$ |
| A-523 | SF$_5$ | H | Cl | OCF$_3$ |
| A-524 | SF$_5$ | H | Br | OCF$_3$ |
| A-525 | SF$_5$ | H | CF$_3$ | OCF$_3$ |
| A-526 | F | H | F | OCH$_2$CF$_3$ |
| A-527 | F | F | F | OCH$_2$CF$_3$ |
| A-528 | F | Cl | F | OCH$_2$CF$_3$ |
| A-529 | F | Br | F | OCH$_2$CF$_3$ |
| A-530 | F | H | Cl | OCH$_2$CF$_3$ |
| A-531 | F | H | Br | OCH$_2$CF$_3$ |
| A-532 | Cl | H | Cl | OCH$_2$CF$_3$ |
| A-533 | Cl | Cl | Cl | OCH$_2$CF$_3$ |
| A-534 | Cl | F | Cl | OCH$_2$CF$_3$ |

TABLE A-continued

| No. | $R^{2a}$ | $R^{2b}$ | $R^{2c}$ | $R^4$ |
|---|---|---|---|---|
| A-535 | Cl | Br | Cl | OCH$_2$CF$_3$ |
| A-536 | Cl | H | Br | OCH$_2$CF$_3$ |
| A-537 | Br | H | Br | OCH$_2$CF$_3$ |
| A-538 | Br | F | Br | OCH$_2$CF$_3$ |
| A-539 | Br | Cl | Br | OCH$_2$CF$_3$ |
| A-540 | CF$_3$ | H | F | OCH$_2$CF$_3$ |
| A-541 | CF$_3$ | H | Cl | OCH$_2$CF$_3$ |
| A-542 | CF$_3$ | H | Br | OCH$_2$CF$_3$ |
| A-543 | CF$_3$ | H | CF$_3$ | OCH$_2$CF$_3$ |
| A-544 | CF$_3$ | F | F | OCH$_2$CF$_3$ |
| A-545 | CF$_3$ | Cl | Cl | OCH$_2$CF$_3$ |
| A-546 | CF$_3$ | Br | Br | OCH$_2$CF$_3$ |
| A-547 | SF$_5$ | H | F | OCH$_2$CF$_3$ |
| A-548 | SF$_5$ | H | Cl | OCH$_2$CF$_3$ |
| A-549 | SF$_5$ | H | Br | OCH$_2$CF$_3$ |
| A-550 | SF$_5$ | H | CF$_3$ | OCH$_2$CF$_3$ |
| A-551 | F | H | F | SCH$_3$ |
| A-552 | F | F | F | SCH$_3$ |
| A-553 | F | Cl | F | SCH$_3$ |
| A-554 | F | Br | F | SCH$_3$ |
| A-555 | F | H | Cl | SCH$_3$ |
| A-556 | F | H | Br | SCH$_3$ |
| A-557 | Cl | H | Cl | SCH$_3$ |
| A-558 | Cl | Cl | Cl | SCH$_3$ |
| A-559 | Cl | F | Cl | SCH$_3$ |
| A-560 | Cl | Br | Cl | SCH$_3$ |
| A-561 | Cl | H | Br | SCH$_3$ |
| A-562 | Br | H | Br | SCH$_3$ |
| A-563 | Br | F | Br | SCH$_3$ |
| A-564 | Br | Cl | Br | SCH$_3$ |
| A-565 | CF$_3$ | H | F | SCH$_3$ |
| A-566 | CF$_3$ | H | Cl | SCH$_3$ |
| A-567 | CF$_3$ | H | Br | SCH$_3$ |
| A-568 | CF$_3$ | H | CF$_3$ | SCH$_3$ |
| A-569 | CF$_3$ | F | F | SCH$_3$ |
| A-570 | CF$_3$ | Cl | Cl | SCH$_3$ |
| A-571 | CF$_3$ | Br | Br | SCH$_3$ |
| A-572 | SF$_5$ | H | F | SCH$_3$ |
| A-573 | SF$_5$ | H | Cl | SCH$_3$ |
| A-574 | SF$_5$ | H | Br | SCH$_3$ |
| A-575 | SF$_5$ | H | CF$_3$ | SCH$_3$ |
| A-576 | F | H | F | SCH$_2$CH$_3$ |
| A-577 | F | F | F | SCH$_2$CH$_3$ |
| A-578 | F | Cl | F | SCH$_2$CH$_3$ |
| A-579 | F | Br | F | SCH$_2$CH$_3$ |
| A-580 | F | H | Cl | SCH$_2$CH$_3$ |
| A-581 | F | H | Br | SCH$_2$CH$_3$ |
| A-582 | Cl | H | Cl | SCH$_2$CH$_3$ |
| A-583 | Cl | Cl | Cl | SCH$_2$CH$_3$ |
| A-584 | Cl | F | Cl | SCH$_2$CH$_3$ |
| A-585 | Cl | Br | Cl | SCH$_2$CH$_3$ |
| A-586 | Cl | H | Br | SCH$_2$CH$_3$ |
| A-587 | Br | H | Br | SCH$_2$CH$_3$ |
| A-588 | Br | F | Br | SCH$_2$CH$_3$ |
| A-589 | Br | Cl | Br | SCH$_2$CH$_3$ |
| A-590 | CF$_3$ | H | F | SCH$_2$CH$_3$ |
| A-591 | CF$_3$ | H | Cl | SCH$_2$CH$_3$ |
| A-592 | CF$_3$ | H | Br | SCH$_2$CH$_3$ |
| A-593 | CF$_3$ | H | CF$_3$ | SCH$_2$CH$_3$ |
| A-594 | CF$_3$ | F | F | SCH$_2$CH$_3$ |
| A-595 | CF$_3$ | Cl | Cl | SCH$_2$CH$_3$ |
| A-596 | CF$_3$ | Br | Br | SCH$_2$CH$_3$ |
| A-597 | SF$_5$ | H | F | SCH$_2$CH$_3$ |
| A-598 | SF$_5$ | H | Cl | SCH$_2$CH$_3$ |
| A-599 | SF$_5$ | H | Br | SCH$_2$CH$_3$ |
| A-600 | SF$_5$ | H | CF$_3$ | SCH$_2$CH$_3$ |
| A-601 | F | H | F | SCH(CH$_3$)$_2$ |
| A-602 | F | F | F | SCH(CH$_3$)$_2$ |
| A-603 | F | Cl | F | SCH(CH$_3$)$_2$ |
| A-604 | F | Br | F | SCH(CH$_3$)$_2$ |
| A-605 | F | H | Cl | SCH(CH$_3$)$_2$ |
| A-606 | F | H | Br | SCH(CH$_3$)$_2$ |
| A-607 | Cl | H | Cl | SCH(CH$_3$)$_2$ |
| A-608 | Cl | Cl | Cl | SCH(CH$_3$)$_2$ |
| A-609 | Cl | F | Cl | SCH(CH$_3$)$_2$ |
| A-610 | Cl | Br | Cl | SCH(CH$_3$)$_2$ |
| A-611 | Cl | H | Br | SCH(CH$_3$)$_2$ |
| A-612 | Br | H | Br | SCH(CH$_3$)$_2$ |
| A-613 | Br | F | Br | SCH(CH$_3$)$_2$ |
| A-614 | Br | Cl | Br | SCH(CH$_3$)$_2$ |
| A-615 | CF$_3$ | H | F | SCH(CH$_3$)$_2$ |
| A-616 | CF$_3$ | H | Cl | SCH(CH$_3$)$_2$ |
| A-617 | CF$_3$ | H | Br | SCH(CH$_3$)$_2$ |
| A-618 | CF$_3$ | H | CF$_3$ | SCH(CH$_3$)$_2$ |
| A-619 | CF$_3$ | F | F | SCH(CH$_3$)$_2$ |
| A-620 | CF$_3$ | Cl | Cl | SCH(CH$_3$)$_2$ |
| A-621 | CF$_3$ | Br | Br | SCH(CH$_3$)$_2$ |
| A-622 | SF$_5$ | H | F | SCH(CH$_3$)$_2$ |
| A-623 | SF$_5$ | H | Cl | SCH(CH$_3$)$_2$ |
| A-624 | SF$_5$ | H | Br | SCH(CH$_3$)$_2$ |
| A-625 | SF$_5$ | H | CF$_3$ | SCH(CH$_3$)$_2$ |
| A-626 | F | H | F | SCH$_2$CH=CH$_2$ |
| A-627 | F | F | F | SCH$_2$CH=CH$_2$ |
| A-628 | F | Cl | F | SCH$_2$CH=CH$_2$ |
| A-629 | F | Br | F | SCH$_2$CH=CH$_2$ |
| A-630 | F | H | Cl | SCH$_2$CH=CH$_2$ |
| A-631 | F | H | Br | SCH$_2$CH=CH$_2$ |
| A-632 | Cl | H | Cl | SCH$_2$CH=CH$_2$ |
| A-633 | Cl | Cl | Cl | SCH$_2$CH=CH$_2$ |
| A-634 | Cl | F | Cl | SCH$_2$CH=CH$_2$ |
| A-635 | Cl | Br | Cl | SCH$_2$CH=CH$_2$ |
| A-636 | Cl | H | Br | SCH$_2$CH=CH$_2$ |
| A-637 | Br | H | Br | SCH$_2$CH=CH$_2$ |
| A-638 | Br | F | Br | SCH$_2$CH=CH$_2$ |
| A-639 | Br | Cl | Br | SCH$_2$CH=CH$_2$ |
| A-640 | CF$_3$ | H | F | SCH$_2$CH=CH$_2$ |
| A-641 | CF$_3$ | H | Cl | SCH$_2$CH=CH$_2$ |
| A-642 | CF$_3$ | H | Br | SCH$_2$CH=CH$_2$ |
| A-643 | CF$_3$ | H | CF$_3$ | SCH$_2$CH=CH$_2$ |
| A-644 | CF$_3$ | F | F | SCH$_2$CH=CH$_2$ |
| A-645 | CF$_3$ | Cl | Cl | SCH$_2$CH=CH$_2$ |
| A-646 | CF$_3$ | Br | Br | SCH$_2$CH=CH$_2$ |
| A-647 | SF$_5$ | H | F | SCH$_2$CH=CH$_2$ |
| A-648 | SF$_5$ | H | Cl | SCH$_2$CH=CH$_2$ |
| A-649 | SF$_5$ | H | Br | SCH$_2$CH=CH$_2$ |
| A-650 | SF$_5$ | H | CF$_3$ | SCH$_2$CH=CH$_2$ |
| A-651 | F | H | F | S—$^c$C$_3$H$_5$* |
| A-652 | F | F | F | S—$^c$C$_3$H$_5$* |
| A-653 | F | Cl | F | S—$^c$C$_3$H$_5$* |
| A-654 | F | Br | F | S—$^c$C$_3$H$_5$* |
| A-655 | F | H | Cl | S—$^c$C$_3$H$_5$* |
| A-656 | F | H | Br | S—$^c$C$_3$H$_5$* |
| A-657 | Cl | H | Cl | S—$^c$C$_3$H$_5$* |
| A-658 | Cl | Cl | Cl | S—$^c$C$_3$H$_5$* |
| A-659 | Cl | F | Cl | S—$^c$C$_3$H$_5$* |
| A-660 | Cl | Br | Cl | S—$^c$C$_3$H$_5$* |
| A-661 | Cl | H | Br | S—$^c$C$_3$H$_5$* |
| A-662 | Br | H | Br | S—$^c$C$_3$H$_5$* |
| A-663 | Br | F | Br | S—$^c$C$_3$H$_5$* |
| A-664 | Br | Cl | Br | S—$^c$C$_3$H$_5$* |
| A-665 | CF$_3$ | H | F | S—$^c$C$_3$H$_5$* |
| A-666 | CF$_3$ | H | Cl | S—$^c$C$_3$H$_5$* |
| A-667 | CF$_3$ | H | Br | S—$^c$C$_3$H$_5$* |
| A-668 | CF$_3$ | H | CF$_3$ | S—$^c$C$_3$H$_5$* |
| A-669 | CF$_3$ | F | F | S—$^c$C$_3$H$_5$* |
| A-670 | CF$_3$ | Cl | Cl | S—$^c$C$_3$H$_5$* |
| A-671 | CF$_3$ | Br | Br | S—$^c$C$_3$H$_5$* |
| A-672 | SF$_5$ | H | F | S—$^c$C$_3$H$_5$* |
| A-673 | SF$_5$ | H | Cl | S—$^c$C$_3$H$_5$* |
| A-674 | SF$_5$ | H | Br | S—$^c$C$_3$H$_5$* |
| A-675 | SF$_5$ | H | CF$_3$ | S—$^c$C$_3$H$_5$* |
| A-676 | F | H | F | SCF$_3$ |
| A-677 | F | F | F | SCF$_3$ |
| A-678 | F | Cl | F | SCF$_3$ |
| A-679 | F | Br | F | SCF$_3$ |
| A-680 | F | H | Cl | SCF$_3$ |
| A-681 | F | H | Br | SCF$_3$ |
| A-682 | Cl | H | Cl | SCF$_3$ |
| A-683 | Cl | Cl | Cl | SCF$_3$ |
| A-684 | Cl | F | Cl | SCF$_3$ |
| A-685 | Cl | Br | Cl | SCF$_3$ |
| A-686 | Cl | H | Br | SCF$_3$ |
| A-687 | Br | H | Br | SCF$_3$ |
| A-688 | Br | F | Br | SCF$_3$ |
| A-689 | Br | Cl | Br | SCF$_3$ |
| A-690 | CF$_3$ | H | F | SCF$_3$ |

TABLE A-continued

| No. | $R^{2a}$ | $R^{2b}$ | $R^{2c}$ | $R^4$ |
|---|---|---|---|---|
| A-691 | $CF_3$ | H | Cl | $SCF_3$ |
| A-692 | $CF_3$ | H | Br | $SCF_3$ |
| A-693 | $CF_3$ | H | $CF_3$ | $SCF_3$ |
| A-694 | $CF_3$ | F | F | $SCF_3$ |
| A-695 | $CF_3$ | Cl | Cl | $SCF_3$ |
| A-696 | $CF_3$ | Br | Br | $SCF_3$ |
| A-697 | $SF_5$ | H | F | $SCF_3$ |
| A-698 | $SF_5$ | H | Cl | $SCF_3$ |
| A-699 | $SF_5$ | H | Br | $SCF_3$ |
| A-700 | $SF_5$ | H | $CF_3$ | $SCF_3$ |
| A-701 | F | H | F | $SCH_2CF_3$ |
| A-702 | F | F | F | $SCH_2CF_3$ |
| A-703 | F | Cl | F | $SCH_2CF_3$ |
| A-704 | F | Br | F | $SCH_2CF_3$ |
| A-705 | F | H | Cl | $SCH_2CF_3$ |
| A-706 | F | H | Br | $SCH_2CF_3$ |
| A-707 | Cl | H | Cl | $SCH_2CF_3$ |
| A-708 | Cl | Cl | Cl | $SCH_2CF_3$ |
| A-709 | Cl | F | Cl | $SCH_2CF_3$ |
| A-710 | Cl | Br | Cl | $SCH_2CF_3$ |
| A-711 | Cl | H | Br | $SCH_2CF_3$ |
| A-712 | Br | H | Br | $SCH_2CF_3$ |
| A-713 | Br | F | Br | $SCH_2CF_3$ |
| A-714 | Br | Cl | Br | $SCH_2CF_3$ |
| A-715 | $CF_3$ | H | F | $SCH_2CF_3$ |
| A-716 | $CF_3$ | H | Cl | $SCH_2CF_3$ |
| A-717 | $CF_3$ | H | Br | $SCH_2CF_3$ |
| A-718 | $CF_3$ | H | $CF_3$ | $SCH_2CF_3$ |
| A-719 | $CF_3$ | F | F | $SCH_2CF_3$ |
| A-720 | $CF_3$ | Cl | Cl | $SCH_2CF_3$ |
| A-721 | $CF_3$ | Br | Br | $SCH_2CF_3$ |
| A-722 | $SF_5$ | H | F | $SCH_2CF_3$ |
| A-723 | $SF_5$ | H | Cl | $SCH_2CF_3$ |
| A-724 | $SF_5$ | H | Br | $SCH_2CF_3$ |
| A-725 | $SF_5$ | H | $CF_3$ | $SCH_2CF_3$ |

*$^cC_3H_5$ = cyclopropyl

Among the above compounds, preference is given to compounds Ia.1, Ia.13, Ia.17, Ia.19 and Ia.20 and especially to Ia.13.

The compounds of the formula (I) can be prepared by novel methods as described below or and in the synthesis descriptions of the working examples, or by standard methods of organic chemistry, e.g. by the methods described hereinafter or in the synthesis descriptions of the working examples. The substituents, variables and indices are as defined above for formula (I), if not otherwise specified.

The invention relates to a method for preparing compounds of formula I as defined in any of the preceding claims, where however $R^{3b}$ is hydrogen, which method comprises dehydrating a compound of formula II

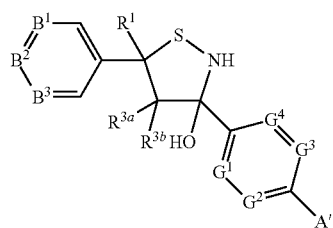
(II)

wherein $B^1$, $B^2$, $B^3$, $G^1$, $G^2$, $G^3$, $G^4$, $R^1$, $R^{3a}$ and $R^{3b}$ are as defined above and A' is A or a precursor of A;

to give a compound I'

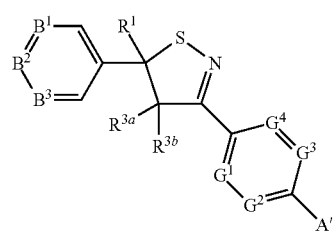
(I')

and, if necessary (i.e. if A' is a precursor of A), converting the group A' into a group A.

A' as a precursor of A is typically a halogen atom, CN, carboxy, tert-butoxycarbonyl, an acetale group, a protected aldehyde group or —$OSO_2$—$R^{z1}$, where $R^{z1}$ is $C_1$-$C_4$-alkyl, $C_1$-$C_4$-haloalkyl or phenyl which may be substituted by 1, 2 or 3 radicals selected from $C_1$-$C_4$-alkyl, $C_1$-$C_4$-haloalkyl $C_1$-$C_4$-alkoxy or $C_1$-$C_4$-haloalkoxy. A' as a precursor of A is preferably a halogen atom or —$OSO_2$—$R^{z1}$, where $R^{z1}$ is as defined above, and is more preferably a halogen atom or Otriflate.

Dehydration either occurs spontaneously or with the help of dehydrating agents, such as molecular sieves, acid-washed molecular sieves, magnesium sulfate, sodium sulfate, silica gel, $SOCl_2$, $POCl_3$, Burgess reagent, trifluoroacetic anhydride, p-toluene sulfonic acid, anhydrous HCl or sulfuric acid. Preferably, p-toluene sulfonic acid or acid-washed molecular sieves are used. The water formed may alternatively be removed, e.g. by azeotropic distillation, e.g. with benzene/toluene as entrainer, e.g. using a Dean Stark trap.

The compound of formula II, in which $R^{3b}$ is hydrogen, is preferably obtained by reacting a compound of formula IV

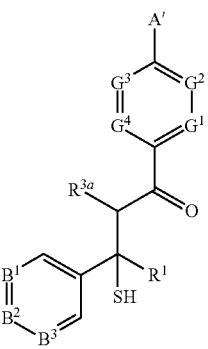
(IV)

with an amination agent to give a compound of formula I with an amination agent to give a compound of formula III

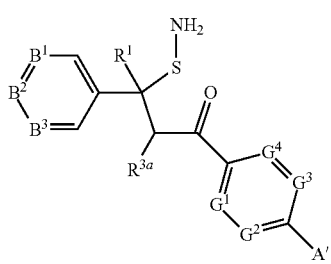
(III)

which reacts spontaneously to the compound II;
wherein $B^1$, $B^2$, $B^3$, $G^1$, $G^2$, $G^3$, $G^4$, $R^1$ and $R^{3a}$ are as defined above and A' is A or a precursor of A.

Depending on the amination agents used, amination can the carried out in a one step reaction, wherein compound IV reacts directly to compound III, or as a two step reaction, wherein the SH group of compound IV is first oxidized to a S—Cl group, which then further reacts to a S—NH$_2$ group, thus giving compound III.

Suitable amination agents for the one step reaction are for example HOSA (hydroxylamine-O-sulfonic acid), which is generally used in the presence of a base (suitable bases being for example sodium hydrogen phosphate, potassium hydrogen phosphate, sodium hydroxide, potassium hydroxide, sodium carbonate, potassium carbonate, sodium methanolate, triethylamine and the like), O-(diphenylphosphoryl)hydroxylamine, which is generally also used in the presence of a base (suitable bases being for example sodium hydrogen phosphate, potassium hydrogen phosphate, sodium hydroxide, potassium hydroxide, sodium carbonate, potassium carbonate, sodium methanolate, triethylamine and the like), 2,4-dinitrophenylhydroxyl amine, O-mesitylensulfonylhydroxylamine and 2-oxa-1-azaspiro[2.5]octane, among which HOSA and O-(diphenylphosphoryl)hydroxylamine are preferred.

The amination is preferably carried out in a solvent, suitable solvents being for example chlorinated alkanes, such as methylene chloride or chloroform, aromatic solvents, such as benzene, toluene, the xylenes, chlorobenzene or dichlorobenzene, and ethers, such as diethylether, dipropylether, methyl tert-butylether, methyl isobutylether, ethylenegylcol dimethylether, tetrahydrofuran (THF) or dioxane and the like.

The reaction is suitably carried out low temperature, e.g. at from −100 to 0° C. or −78 to 0° C.

Generally, the compound IV is dispersed in a solvent and cooled to the desired temperature and the base is added followed by the amination agent, or the amination agent is added followed by the base, or base and amination agent are added simultaneously.

In a preferred embodiment, HOSA is used in combination with an amine base, such as triethylamine. In this case, it is preferred to cool compound IV to −30 to 0° C., preferably −20 to −10° C., to add the amine base at this temperature and then HOSA and keep the reaction at approximately −10 to 0° C.

In an alternatively preferred embodiment, O-(diphenylphosphoryl)hydroxylamine is used in combination with a base, preferably with an inorganic base, such as sodium hydrogen phosphate, potassium hydrogen phosphate, sodium hydroxide, potassium hydroxide, sodium carbonate or potassium carbonate and specifically sodium hydrogen phosphate. In this case, it is preferred to cool compound IV to −80 to −30° C., preferably −80 to −70° C., to add the base at this temperature and then O-(diphenylphosphoryl)hydroxylamine and keep the reaction at approximately 0° C. to room temperature.

In the two step reaction, the compound IV is first reacted with a chlorination agent which converts the SH group into an S—Cl group. Suitable chlorination agents are for example sulfurylchloride, N-chloro succinimide (NCS), sodium hypochlorite, monochloroamine (NH$_2$Cl) or chlorine, which is preferably used in the presence of FeCl$_3$. The chlorination can be carried out in analogy to the method described in Synthesis 1987, 1987, 683-688, Tetrahedron 66(36), 2010, 7279-7287, J. Org. Chem. 59(4), 1994, 914-921, J. Org. Chem. 63, 1998, 4878-4888 or J. Chem. Soc. 1938, 2114-2117.

The chlorination is generally carried out in a solvent. Suitable solvents are for example ethers, such as diethylether, dipropylether, methyl tert-butylether, methyl isobutylether, ethylenegylcol dimethylether, tetrahydrofuran or dioxane.

The reaction temperature can vary over wide ranges and is generally from 0° C. to the boiling point of the reaction mixture (if a solvent is used).

The chlorinated compound is then reacted without isolation with ammonia or ammonium hydroxide.

If anhydrous ammonia is used, the reaction is generally carried out at from −78 to −33° C. If aqueous ammonia or ammonium hydroxide is used, the reaction can also be carried out at higher temperatures, such as 0 to 25° C.

The reaction is generally carried out in a solvent. Suitable solvents are for example the above-listed ethers, among which the water-miscible ethers, such as THF and dioxane, are preferred. In general, the chlorinated compound is dissolved in a solvent to which ammonia or ammonium hydroxide is added. The reaction can be carried out as described, for example, in Synthesis, 1987, 8, 683-688.

The chlorination/amination can also be carried as a one pot reaction. For example, the thiol IV is reacted simultaneously with a chlorinating agent (such as NCS or aqueous sodium hypochlorite) and anhydrous or aqueous ammonia in ethereal solvents (such as THF or Et$_2$O) or water. Preferred is the reaction with NCS in a mixture of THF and anhydrous liquid ammonia at −33° C. For instance, a solution of the thiol IV in THF is added to a solution of NCS(N-chlorosuccinimide) in THF/liquid ammonia at −78° C. The solution is warmed to −30° C. and stirred until the ammonia has evaporated. Alternatively, at 0° C., a solution of the sodium thiolate (NaSR) in water is added to a mixture of aqueous ammonia (25%) and aqueous sodium hypochlorite (1 N). The one pot chlorination/amination reaction can be carried out as described, for example, in Tetrahedron 2010, 66, 7279-7287 or in J. Org. Chem. 1994, 59, 914-921.

Compound III can virtually not be isolated as it generally reacts spontaneously in a ring-closing reaction to compound II.

The compound of formula IV is preferably prepared by reacting a compound of formula V

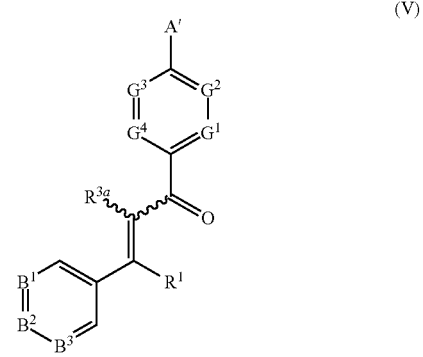

(V)

wherein $B^1$, $B^2$, $B^3$, $G^1$, $G^2$, $G^3$, $G^4$, $R^1$ and $R^{3a}$ are as defined in any of claims 1 to 32 and A' is A or a precursor of A;
with a sulfur source.

Suitable sulfur sources are for example $H_2S$, metal hydrogen sulfides, such as NaSH or KSH, metal sulfides, such as $Na_2S$, $K_2S$ $Li_2S$, $Cu_2S$, MgS, CaS, CuS, FeS and the like, ammonium sulfide [$(NH_4)_2S$], tetraalkylammonium sulfides ($R_4NSH$), such as tetramethylammonium sulfide, tetraethylammonium sulfide, tetrapropylammonium sulfide and the like, or bistrimethylsilyl sulfide.

$H_2S$ as a sulfur source is generally used in the presence of a base, such as $Na_2CO_3$, $K_2CO_3$, $Cs_2CO_3$, sodium acetate, potassium acetate, cesium acetate, amines, such as diethylamine, dipropylamine, triethylamine, diisopropylethylamine and the like, or basic nitrogen-containing heterocycles, such as pyrrolidine, piperidine, piperazine, pyridine, lutidine and the like.

Alternatively, $H_2S$ as a sulfur source can be used in the presence of a Lewis acid, such as $AlCl_3$ or $FeCl_3$.

The reaction of compound V with a sulfur source is generally carried out in a solvent, suitable solvents being for example chlorinated alkanes, such as methylene chloride or chloroform, and aromatic solvents, such as benzene, toluene, the xylenes, chlorobenzene or dichlorobenzene.

The reaction temperature can vary over a wide range, such as −78° C. to room temperature.

In general, compound V is dissolved in a solvent, optionally cooled, then the base (if used) and subsequently the sulfur source is added The compound V can alternatively be reacted with a sulfur source which provides a compound IV which is protected at the thiol group SH by a protective group (S-PG).

This is advantageous if compound IV is for example subjected to harsher purification conditions or is derivatized, e.g. for converting the precursor group A' into a group A or for modifying group A' at this stage. Moreover, purification of the protected product is easier.

Suitable sulfuration reagents which give such protected thiols are for example thiourea ($NH_2$—C(=S)—$NH_2$), optionally substituted benzyl thiols, such as benzylthiol, o- or p-methoxy-benzylthiol, o- or p-hydroxybenzylthiol, o- or p-acetoxybenzylthiol, o- or p-nitrobenzylthiol or 2,4,6-trimethylbenzylthiol, pyridin-4-yl-methylthiol, quinolin-2-yl-methylthiol, benzyl metal sulfides, such as sodium benzylsulfide, phenylthiol, 2,4-dinitrophenylthiol, tritylthiol, tert-butylthiol, compounds of formula R—C(=O)—NH—$CH_3$—SH, wherein R is methyl, tert-butyl, allyl, phenyl or benzyl, 2-trimethylsilanyl-ethanethiol, 2-(2,4-dinitrophenyl)-ethanethiol, 2-phenylsulfonyl-ethanethiol, acylated thiols, such as methylcarbonylthiol or phenylcarbonylthiol, and thiocarbamates R—NH—C(=O)—SH, wherein R is e.g. methyl or ethyl.

The benzyl and alkyl thiols are generally used in the presence of a base, such as sodium hydroxide, potassium hydroxide, sodium phosphate, potassium phosphate, sodium hydrogenphosphate, potassium hydrogenphosphate, sodium carbonate, potassium carbonate, caesium carbonate, sodium hydride, potassium hydride, lithium diisopropyl amide (LDA), sodium methanolate, sodium ethanolate, potassium tert-butoxide, aqueous sodium tetraborate, n-butyllithium, tert-butyllithium, tetrabutylammoniumfluoride (TBAF), NaHMDS and the like, or in the presence of a Lewis or Bronsted acid, such as $FeCl_3$, $Zn(ClO_4)_2$, $Cu(BF_4)_2$, $HBF_4$ or $HClO_4$.

The reaction is preferably carried out in a solvent, suitable solvents being for example chlorinated alkanes, such as methylene chloride or chloroform, and ethers, such as diethylether, dipropylether, methyl tert-butylether, methyl isobutylether, ethylenegylcol dimethylether, tetrahydrofuran (THF) or dioxane and the like.

The reaction temperature can vary over a wide range, such as from −25° C. to the boiling point of the reaction mixture.

The acylated thiols can be reacted neat or in a solvent, suitable solvents being for example chlorinated alkanes, such as methylene chloride or chloroform, and ethers, such as diethylether, dipropylether, methyl tert-butylether, methyl isobutylether, ethylenegylcol dimethylether, tetrahydrofuran (THF) or dioxane and the like. They can be used with or without a base.

The S-protected compound IV can then be deprotected to the free thiol IV under conditions generally known for the respective protective group, such as described, for example, in Peter G. M. Wuts, Theodora Greene, *Protective Groups in Organic Synthesis*, 4$^{th}$ edition, John Wiley & Sons, Inc., 2007, Chapter 6.

Among the above sulfur sources, preference is given to $H_2S$, especially used in the presence of a base, such as $Na_2CO_3$, $K_2CO_3$, $Cs_2CO_3$, sodium acetate, potassium acetate, cesium acetate, amines, such as diethylamine, dipropylamine, triethylamine, diisopropylethylamine and the like, or basic nitrogen-containing heterocycles, such as pyrrolidine, piperidine, piperazine, pyridine, lutidine and the like, and preferably in the presence of an amine, such as triethylamine.

In a preferred embodiment of the method of the invention, the reaction of compound IV to compound I' via compounds III and II is carried out as a one-pot reaction.

In an alternatively preferred embodiment of the method of the invention, the reaction of compound V to compound I' via compounds IV, III and II is carried out as a one-pot reaction.

Compound V can be prepared in analogy to the method described in EP-A-2172462.

Compounds II (in which $R^{3b}$ is not necessarily hydrogen) can be prepared alternatively by reacting a compound of formula VII

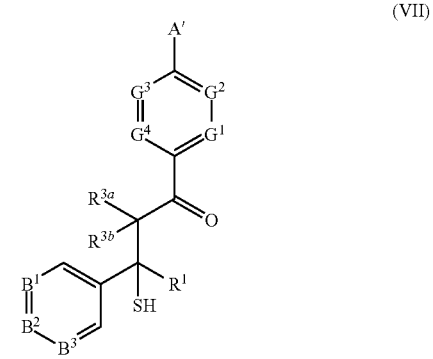

(VII)

with an amination agent to give a compound of formula VI

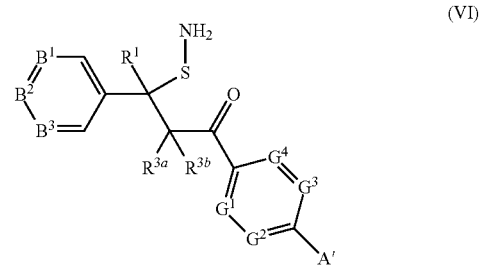

(VI)

which reacts spontaneously to the compound II;
wherein $B^1$, $B^2$, $B^3$, $G^1$, $G^2$, $G^3$, $G^4$, $R^1$, $R^{3a}$ and $R^{3b}$ are as defined above and A' is A or a precursor of A.

The reaction can be carried out in analogy to that of compounds IV and III.

The compound of formula VII is preferably obtained by reacting a compound of formula VIII with a compound of formula IX

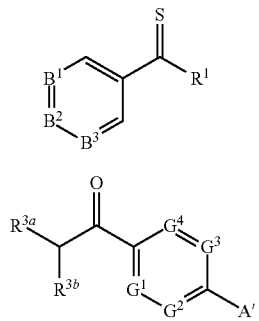

(VIII)

(IX)

The reaction is preferably carried out as a Mukaiyama aldol reaction. To this purpose, the trialklysilyl-enolate derivative of IX is reacted with VIII in the presence of a Lewis acid, such as $TiCl_4$ or $BF_3[O(C_2H_5)_2]$. Alternatively, the reaction can be carried out in the presence of a strong base, such as lithium diisopropylamide (LDA), sodium bistrimethylsilylamide (sodium hexamethyldisilazide; NaH-MDS) and amines, such as triethylamine, tripropylamine or diisopropylethylamine.

The reaction is generally carried out in a solvent.

If a lithium or sodium base is used, the solvent is suitably an ether, such as diethylether, dipropylether, methyl tert-butylether, methyl isobutylether, ethylenegylcol dimethylether, tetrahydrofuran (THF) or dioxane and the like. Suitable reaction temperatures range from −78 to 25° C.

If an amine base is used, the solvent is suitably an ether, such as diethylether, dipropylether, methyl tert-butylether, methyl isobutylether, ethylenegylcol dimethylether, tetrahydrofuran (THF) or dioxane, or an alkane, such as pentane, hexane or heptane. Suitable reaction temperatures range from 25 to 100° C.

The compound of formula VIII can be obtained by reacting a compound of formula X with a sulfuration agent, such as Lawesson's reagent or $P_2S_5$

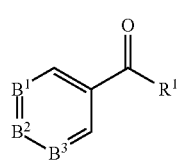

(X)

The reaction is generally carried out in a solvent, suitable solvents being for example aromatic solvents, such as benzene, toluene, the xylenes, chlorobenzene or dichlorobenzene, ethers, such as diethylether, dipropylether, methyl tert-butylether, methyl isobutylether, ethylenegylcol dimethylether, tetrahydrofuran (THF) or dioxane, and hexamethyl phosphoric acid triamide (HMPA).

The reaction is generally carried out at a temperature of from 25° C. to the boiling point of the reaction mixture.

The invention further relates to a method for preparing compounds of formula I as defined above, wherein $R^1$ is $CF_3$, which method comprises reacting a compound of formula XI

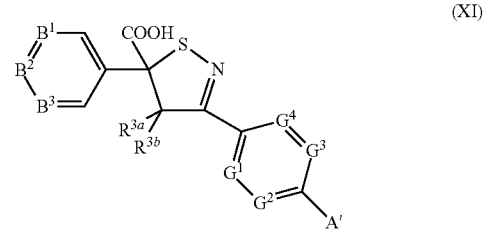

(XI)

wherein $B^1$, $B^2$, $B^3$, $G^1$, $G^2$, $G^3$, $G^4$, $R^{3a}$ and $R^{3b}$ are as defined above and A' is A or a precursor of A;
with a fluorinating agent
to give a compound I"

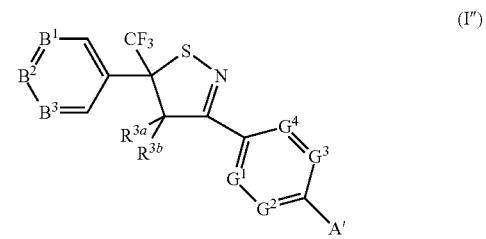

(I")

and, if necessary (i.e. if A' is a precursor of A), converting the group A' into a group A.

Suitable fluorinating agents are, for example, $SF_4$, preferably in combination with HF or $BF_3[O(C_2H_5)_2]$, phenylsulfur trifluoride (Ph-$SF_3$), preferably in combination with HF and pyridine, 4-tert-butyl-2,6-dimethylphenylsulfur trifluoride ("Fluoled"), and bis(2-methoxyethyl)aminosulfur trifluoride [$(CH_3OCH_2CH_2)_2NSF_3$]. Among these, preference is given to $SF_4$ in combination with HF.

If $SF_4$ in combination with HF is used, the reaction is carried out neat, i.e. without any further solvent. The reaction is generally carried out under elevated pressure stemming from the reactants, e.g. at a pressure of from 2 to 10 bar, preferably from 5 to 8 bar. The reaction temperature can vary over wide ranges, such as from 25 to 120° C., preferably from 60 to 100° C.

Alternatively, fluorination can be carried out by a two step method, in which the carboxyl group on the isothiazoline ring is first converted into a $CCl_3$ group, and this is subsequently fluorinated to the $CF_3$ group.

The conversion of the COOH group to the $CCl_3$ group is preferably carried out by reacting the compound VI with $PCl_5$ and phenyl-phosphoroxy dichloride (Ph-P(=O)$Cl_2$).

The reaction can be carried out neat, i.e. without any further solvent. Suitably, the reaction is carried out at elevated temperatures, for example at from 50° to reflux and preferably at reflux.

Fluorination agents for converting the $CCl_3$ group into a CF3 group are those mentioned above, and further HF and HF in combination with $SbCl_5$ and HF in combination with $Cl_2$ and $SbF_3$.

The reaction can be carried out neat, i.e. without any further solvent. The reaction temperature can vary over wide ranges, for examples from 25 to 300° C., preferably from 50 to 200° C. and in particular from 80 to 120° C. If the fluorination agent is HF or HF in combination with a further agent, the reaction generally takes place at the pressure stemming from HF and ranging generally from 2 to 10 bar, preferably from 5 to 8 bar.

The compound of formula XI is preferably obtained by hydrolyzing a compound of formula XII

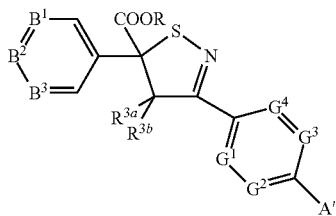
(XII)

wherein $B^1$, $B^2$, $B^3$, $G^1$, $G^2$, $G^3$, $G^4$, $R^{3a}$ and $R^{3b}$ are as defined above, A' is A or a precursor of A and R is $C_1$-$C_4$-alkyl.

Hydrolysis can be carried out by any suitable means known for hydrolyzing ester groups, such as acidic conditions, e.g. using hydrochloric acid, hydrobromic acid, sulfuric acid, trifluoroacetic acid, etc., or by basic conditions, e.g. using an alkali metal hydroxide, such as LiOH, NaOH or KOH, or an alkali metal carbonate, such as sodium or potassium carbonate.

The compound of formula XII is in turn preferably obtained by reacting a compound XIII with a compound XIV

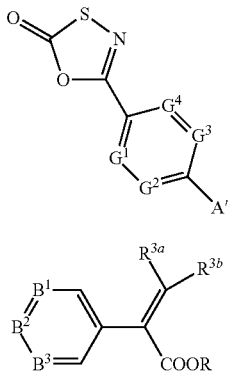
(XIII)

(XIV)

wherein $B^1$, $B^2$, $B^3$, $G^1$, $G^2$, $G^3$, $G^4$, $R^1$, $R^{3a}$ and $R^{3b}$ are as defined above, A' is A or a precursor of A and R is $C_1$-$C_4$-alkyl.

The reaction is carried out at elevated temperature, e.g. at from 90 to 200° C., preferably from 100 to 180° C. and in particular from 120 to 160° C., e.g. at about 140° C.

The compound of formula XIII can in turn be obtained by reacting a compound XVI with a compound XVII

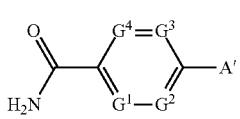
(XVI)

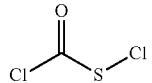
(XVII)

The reaction is generally carried out in a solvent, suitable solvents being for example aromatic solvents, such as benzene, toluene, the xylenes, chlorobenzene and dichlorobenzene. The reaction temperature is preferably from 80 to 140° C., more preferably from 100 to 120° C.

The invention further relates to a method for preparing compounds of formula I as defined above, wherein however $R^1$ is $CF_3$, which method comprises reacting a compound of formula XIII as defined above with a compound of formula XV (XV)

wherein $B^1$, $B^2$, $B^3$, $R^{3a}$ and $R^{3b}$ are as defined above, to give a compound I"

(I")

and, if necessary, converting the group A' into a group A.

The reaction is carried out at elevated temperature, e.g. at from 90 to 200° C., preferably from 100 to 180° C. and in particular from 120 to 160° C., e.g. at about 140° C.

Compounds I' or I", in which A' is a precursor of A can be converted as shown below into the different groups $A^1$ to $A^4$.

Compounds I' or I", in which A' is Cl, Br, I or —OSO$_2$—$R^{z1}$, where $R^{z1}$ is as defined above, can be converted to compounds I wherein A is a group $A^1$, wherein A is an imino group —C(=NR$^6$)R$^8$, by reaction with carbon monoxide and a hydride source, such as triethylsilane, in the presence of a transition metal complex catalyst, preferably a palladium catalyst, to a carbonyl compound XVIII. This reaction converts the starting group A' into a carbonyl group —C(=O)H.

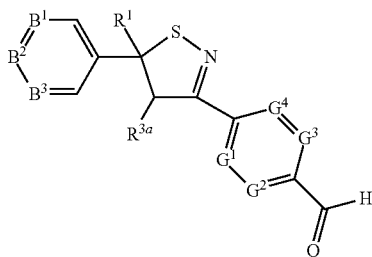

(XVIII)

The aldehyde XVIII can also be obtained by reducing the methyl ester XXI (see below; R=methyl) with diisobutyl-aluminium hydride (DIBAL-H) either directly to the aldehyde XVIII or via the corresponding alcohol, which is then oxidized to the aldehyde.

For obtaining compounds in which $R^8$ in the imino group is H, such carbonyl compounds XVIII are then reacted with an amine (derivative) $NH_2R^6$. Alternatively, the compound I' or I", in which A' is Cl, Br, I or $-OSO_2-R^{z1}$, where $R^{z1}$ is as defined above, can be reacted in a one pot reaction with carbon monoxide and hydrogen in the presence of a transition metal complex catalyst and the amine $NH_2R^6$.

For obtaining compounds in which $R^8$ in the imino group is not H, the carbonyl compounds are reacted with a Grignard reagent $R^8$—MgHal, where Hal is Cl, Br or I, or an organolithium compound $R^8$—Li to obtain an alcohol of formula XIX

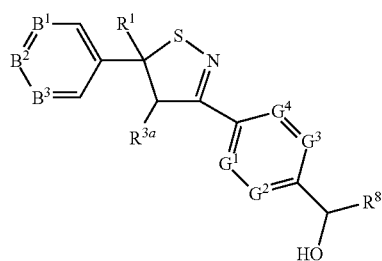

(XIX)

which is then oxidized to a carbonyl compound of the formula XX

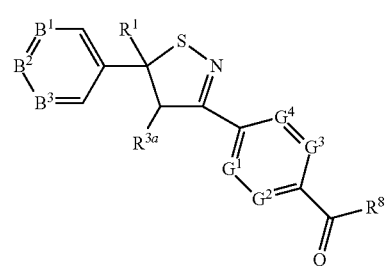

(XX)

This is then reacted with an amine $NH_2R^6$ to the respective imine compound.

These reactions can be carried out in analogy to the methods described in PCT/EP 2011/060388 or in WO 2010/072781 and the references cited therein, especially WO 2006135763, Fattorusso et al, J. Med. Chem. 2008, 51, 1333-1343 and WO 2008/122375.

Compounds I wherein A is a group $A^1$, wherein $A^1$ is $-S(O)_nR^9$ or $-N(R^5)R^6$, can for example be prepared by reacting a compound I' or I" wherein A' is Cl, Br or I in a Ullmann-type reaction with an amine $NHR^5R^6$ or a thiol $SHR^9$ in the presence of a Cu(I) catalyst. To obtain a compound wherein A is $-S(O)_nR^9$ wherein n is not 0 the thiol can then be oxidized, e.g. with hydrogen peroxide. Amine and thiol groups can further be introduced in a Buchwald-Hartwig reaction by reacting a compound I' or I" wherein A' is Cl, Br or I with an amine $NHR^5R^6$ or a thiol $HSR^9$ in the presence of a palladium catalyst, such as $PdCl_2$(dppf) in the presence of a base, such as cesium carbonate or N,N-diisopropylethyl amine, and optionally in the presence of a phosphine ligand, such as Xantphos ("4,5-Bis(diphenylphosphino)-9,9-dimethylxanthene").

Thioethers ($A^1=-SR^9$) can further be introduced by reacting a compound I' or I" wherein A' is F in an $S_NAr$ reaction (nucleophilic aromatic substitution reaction) with a thiol $HSR^9$ in the presence of a base, such as potassium carbonate ($K_2CO_3$), or with a thiolate (e.g. $NaSR^9$).

Compounds I wherein A is a group $A^2$, wherein W is O and Y is $OR^9$ can be prepared by reacting a compound I' or I" wherein A' is Cl, Br, I or Otriflate with carbon monoxide in the presence of a palladium catalyst and an alcohol $R^9OH$. Compounds I wherein A is a group $A^2$, wherein W is O and Y is $NR^5R^6$ can be prepared by reacting a compound I' or I" wherein A' is Cl, Br, I or Otriflate with carbon monoxide in the presence of a palladium catalyst and an alcohol ROH, wherein R is $C_1$-$C_4$-alkyl, to a compound of formula XXI. Suitable palladium catalysts are for example those described in PCT/EP 2011/060388.

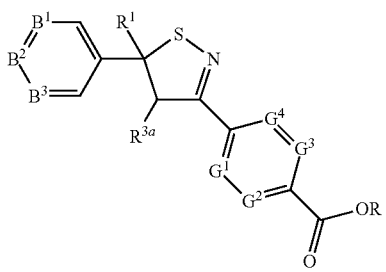

(XXI)

This ester is then hydrolyzed to the respective carboxylic acid, which is the reacted under standard amidation conditions with an amine $NHR^5R^6$. Hydrolyzation can be carried out under standard conditions, e.g. under acidic conditions using for example hydrochloric acid, sulfuric acid or trifluoroacetic acid, or under basic conditions using for example an alkali metal hydroxide, such as LiOH, NaOH or KOH. Amidation is preferably carried out by activation of the carboxylic acids with oxalylchloride [$(COCl)_2$] or thionylchloride ($SOCl_2$) to the respective acid chlorides, followed by reaction with an amine $NHR^5R^6$. Alternatively, amidation is carried out in in the presence of a coupling reagent. Suitable coupling reagent (activators) are well known and are for instance selected from carbodiimides, such as DCC (dicyclohexylcarbodiimide) and DCI (diisopropylcarbodiimide), benzotriazol derivatives, such as HATU (O-(7-azabenzotriazol-1-yl)N,N,N',N'-tetramethyluronium hexafluorophosphate), HBTU (1H-benzotriazol-1-yl)N,N,N',N'-tetramethyluronium hexafluorophosphate) and HCTU (1H-benzotriazolium-1-[bis(dimethylamino)methylene]-5-chloro tetrafluoroborate) and phosphonium-derived activators, such as BOP ((benzotriazol-1-yloxy)-tris(dimethylamino)phosphonium hexafluorophosphate), Py-BOP ((benzotriazol-1-yloxy)-tripyrrolidinphosphonium hexafluorophosphate) and Py-BrOP (bromotripyrrolidinphosphonium hexafluorophosphate). Generally, the activator is used in excess. The benzotriazol and phosphonium coupling reagents are generally used in a basic medium.

Compounds I wherein A is a group $A^2$, wherein W is S and Y is $NR^5R^6$ or $OR^9$, can be prepared by reacting the corresponding oxo-compound (W is O) with Lawesson's reagent (CAS19172-47-5), see for example Jesberger et al., Synthesis, 2003, 1929-1958 and references therein. For compounds wherein Y is $NR^5R^6$, solvents such as HMPA or THF at an elevated temperature such as 60° C. to 100° C. can be used. Preferred reaction conditions are THF at 65° C. For compounds wherein Y is $OR^9$, solvent free conditions or solvents such as toluene at temperatures such as 100° C. to 200° C., preferably 140° C., are suitable reaction conditions.

Compounds I wherein A is a group $A^3$, wherein $R^{7a}$ and $R^{7b}$ are hydrogen, can be prepared by reducing a compound XXI or XVIII for example with LAH (lithium aluminium hydride) or DIBAL-H (diisobutyl aluminium hydride) to a compound XXII.

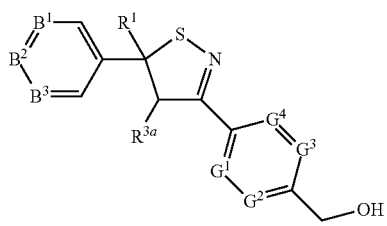

(XXII)

This is then reacted in an $S_N$ reaction with an amine $NHR^5R^6$. For this purpose, the OH group can first be converted into a better leaving group, e.g. into a sulfonate (for example mesylate, tosylate or a triflate group). If $R^6$ is a group $—C(O)R^8$, it is alternatively possible to react compound XXII with an amine $NH_2R^5$ and react then the resulting benzylic amine with an acid $R^8$—COOH or a derivative thereof, such as its acid chloride $R^8$—COCl, in an amidation reaction.

Compounds I wherein A is a group $A^3$, wherein $R^{7a}$ is optionally substituted alkyl or optionally substituted cycloalkyl and $R^{7b}$ is hydrogen, can be prepared by subjecting a ketone XX, in which $R^8$ corresponds to $R^{7a}$ which is optionally substituted $C_1$-$C_6$-alkyl or optionally substituted $C_3$-$C_8$-cycloalkyl, to a reductive amination to furnish compounds XXIII. Typical conditions for the reductive amination are: Reacting ketone XX with an amine $H_2NR^5$ to yield the corresponding imine which is reduced to amine XIII with a reducing agent reagent such as $Na(CN)BH_3$. The reaction from ketone XX to amine XXIII may also be carried out as a one pot procedure.

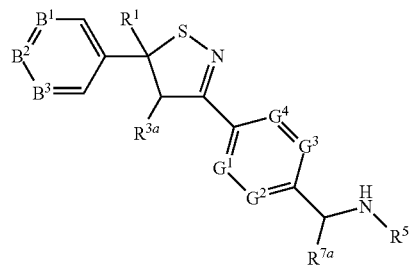

(XXIII)

For obtaining compounds in which $R^{7a}$ and $R^{7b}$ are optionally substituted alkyl, optionally substituted cycloalkyl, optionally substituted alkenyl or optionally substituted alkynyl, carbonyl compounds such as XX, in which $R^8$ corresponds to $R^{7a}$ which is optionally substituted $C_1$-$C_6$-alkyl, optionally substituted $C_3$-$C_8$-cycloalkyl, optionally substituted $C_2$-$C_6$-alkenyl or optionally substituted $C_2$-$C_6$-alkynyl, is reacted with a Grignard reagent $R^{7b}$—MgHal, where Hal is Cl, Br or I, or an organolithium compound $R^{7b}$—Li, where $R^{7b}$ is optionally substituted $C_1$-$C_6$-alkyl, optionally substituted $C_3$-$C_8$-cycloalkyl, optionally substituted $C_2$-$C_6$-alkenyl or optionally substituted $C_2$-$C_6$-alkynyl, to obtain an alcohol of formula XXIV.

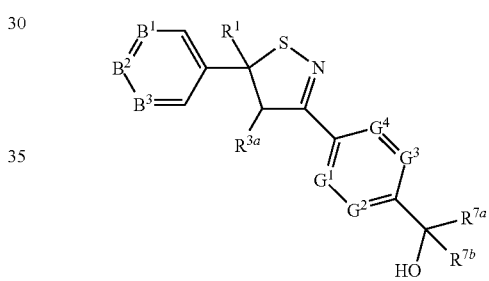

(XXIV)

Alcohol XXIV can then be converted into amine XXV via the corresponding azide, as described, for example, in Organic Letters, 2001, 3(20), 3145-3148.

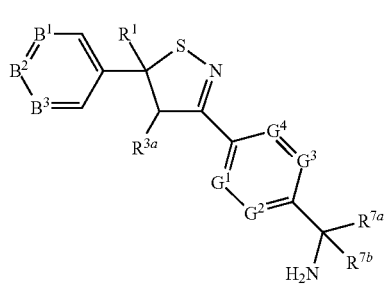

(XXV)

If desired, this can be converted into compounds I wherein $R^5$ and $R^6$ are different from hydrogen, for example by standard alkylation reactions.

Compounds I wherein A is a group $A^3$, wherein $R^{7a}$ is optionally substituted alkyl, alkenyl, alkynyl, cycloalkyl or CN and $R^{7b}$ is hydrogen, can be prepared by converting an aldehyde XVIII into an imine XXVI by reaction with an amine derivative $NH_2R^6$, wherein $R^6$ is tert-butyl sulfinyl, or, for preparing a compound with $R^{7a}$=CN, tosylate.

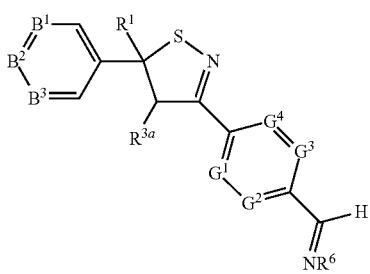

(XXVI)

This imine is then reacted with a compound H—$R^{7a}$ in an addition reaction under conditions as described for example in J. Am. Chem. Soc. 2009, 3850-3851 and the references cited therein, or, for introducing CN as a group $R^{7a}$, Chemistry—A European Journal 2009, 15, 11642-11659.

Compounds I wherein A is a group $A^3$, wherein both $R^{7a}$ and $R^{7b}$ are optionally substituted alkyl, alkenyl, alkynyl, cycloalkyl or CN, can be prepared analogously by converting a ketone XX, wherein $R^8$ is has the meaning desired for $R^{7b}$ and is optionally substituted alkyl, alkenyl, alkynyl, cycloalkyl or CN, into an imine by reaction with an amine derivative $NH_2R^6$, wherein $R^6$ is tert-butyl sulfinyl, or, for preparing a compound with $R^{7a}$=CN, tosylate.

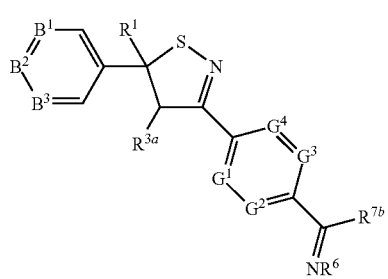

(XXVII)

This imine is then reacted with a compound H—$R^{7a}$ in an addition reaction under conditions as described for example in J. Org. Chem. 2002, 67, 7819-7832 and the references cited therein, or, for introducing CN as a group $R^{7a}$, Chemistry—A European Journal 2009, 15, 11642-11659.

If desired, $R^6$ can then be removed to yield an amino group $NH_2$.

Compounds I wherein A is $A^4$ can be prepared by standard ring coupling reactions. For example, compounds, wherein $A^4$ is an N-bound heterocyclic ring can be prepared by reacting a compound I' or I" wherein A' is Cl, Br or I with the respective ring $A^4$-H (H being on the nitrogen ring atom to be coupled) under Ullmann coupling conditions, such as described, for example, in WO 2007/075459. Typically, copper(I) iodide or copper(I) oxide and a ligand such as 1,2-cyclohexyldiamine is used, see for example Kanemasa et al., European Journal of Organic Chemistry, 2004, 695-709. If A' is F, the reaction is typically run in a polar aprotic solvent such as N,N-dimethylformamide, N,N-dimethylacetamide or N-methylpyrrolidone, and in the presence of an inorganic base such as sodium, potassium or cesium carbonate.

Compounds, wherein $A^4$ is a C-bound heterocyclic ring can be prepared by reacting a compound I' or I" wherein A' is Br or I with the boronic acid of the respective ring $A^4$-$B(OH)_2$ or the boronate ester of the respective ring $A^4$-$B(OR_2)$ under Suzuki reaction conditions via Pd-catalyzed cross coupling, such as described, for example, in WO 2007/075459. A typical catalyst is tetrakis(triphenylphosphine)palladium(0). Solvents such as tetrahydrofuran, acetonitrile, diethyl ether and dioxane are suitable. The boronic acids $A^4$-$B(OH)_2$ are either commercially available or can be prepared by known methods. Other methods for introduction of the heterocyclic groups $A^4$ are the Heck, Stille, Kumada and Buchwald-Hartwig coupling procedures; see for example Tetrahedron, 2004, 60, 8991-9016.

As a rule, the compounds of formula (I) including their stereoisomers, salts, and N-oxides, and their precursors in the synthesis process, can be prepared by the methods described above. If individual compounds can not be prepared via the above-described routes, they can be prepared by derivatization of other compounds (I) or the respective precursor or by customary modifications of the synthesis routes described. For example, in individual cases, certain compounds of formula (I) can advantageously be prepared from other compounds of formula (I) by derivatization, e.g. by ester hydrolysis, amidation, esterification, ether cleavage, olefination, reduction, oxidation and the like, or by customary modifications of the synthesis routes described.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

Due to their excellent activity, the compounds of the present invention may be used for controlling invertebrate pests.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of the present invention or a composition as defined above.

Preferably, the method of the invention serves for protecting plant propagation material (such as seed) and the plant which grows therefrom from invertebrate pest attack or infestation and comprises treating the plant propagation material (such as seed) with a pesticidally effective amount of a compound of the present invention as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In the sense of the present invention, "invertebrate pests" are preferably selected from arthropods and nematodes, more preferably from harmful insects, arachnids and nematodes, and even more preferably from insects, acarids and nematodes. In the sense of the present invention, "invertebrate pests" are most preferably insects.

The invention further provides an agricultural composition for combating invertebrate pests, which comprises such an amount of at least one compound according to the invention and at least one inert liquid and/or solid agronomically acceptable carrier that has a pesticidal action and, if desired, at least one surfactant.

Such a composition may comprise a single active compound of the present invention or a mixture of several active compounds of the present invention. The composition according to the present invention may comprise an individual isomer or mixtures of isomers or a salt as well as individual tautomers or mixtures of tautomers.

The compounds of the present invention, including their salts, stereoisomers and tautomers, are in particular suitable for efficiently controlling arthropodal pests such as arachnids, myriapedes and insects as well as nematodes. They are especially suitable for efficiently combating or controlling the following pests:

Insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Pieris rapae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*; beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica* 12-punctata *Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria*;

flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa*;

thrips (Thysanoptera), e.g. *Dichromothrips corbetti, Dichromothrips* ssp., *Frankliniella fusca, Frankliniella occidentalis, Frankliniella tritici, Scirtothrips citri, Thrips oryzae, Thrips palmi* and *Thrips tabaci*, termites (Isoptera), e.g. *Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis,* and *Coptotermes formosanus*;

cockroaches (Blattaria—Blattodea), e.g. *Blattella germanica, Blattella asahinae, Periplaneta americana, Periplaneta japonica, Periplaneta brunnea, Periplaneta fulligginosa, Periplaneta australasiae,* and *Blatta orientalis*;

bugs, aphids, leafhoppers, whiteflies, scale insects, cicadas (Hemiptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schnideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium*

*dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma* spp., and *Arilus critatus;* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina;* arachnoidea, such as arachnids (Acarina), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis;* Araneida, e.g. *Latrodectus mactans,* and *Loxosceles reclusa;* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp.,

Earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

Collembola (springtails), e.g. *Onychiurus* ssp.

The compounds of the present invention, including their salts, stereoisomers and tautomers, are also suitable for controlling nematodes:plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of the present invention, including their salts, stereoisomers and tautomers, are particularly useful for controlling insects, preferably sucking or piercing and chewing and biting insects such as insects from the genera Lepidoptera, Coleoptera and Hemiptera, in particular Lepidoptera, Coleoptera and true bugs.

The compounds of the present invention, including their salts, stereoisomers and tautomers, are moreover useful for controlling insects of the orders Thysanoptera, Diptera (especially flies, mosquitos), Hymenoptera (especially ants) and Isoptera (especially termites).

The compounds of the present invention, including their salts, stereoisomers and tautomers, are particularly useful for controlling insects of the orders Lepidoptera and Coleoptera.

The invention also relates to agrochemical compositions comprising an auxiliary and at least one compound I according to the invention.

An agrochemical composition comprises a pesticidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the species to be controlled, the treated cultivated plant or material, the climatic conditions and the specific compound I used.

The compounds I, their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Inform a, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof.

Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
i) Water-Soluble concentrates (SL, LS)
10-60 wt % of a compound I according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)
5-25 wt % of a compound I according to the invention and 1-10 wt % dispersant (e.g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of a compound I according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I according to the invention are comminuted with addition of 2-10 wt % dispersants and wetting agents (e.g. sodium lignosulfonate and alcohol ethoxylate), 0, 1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound I according to the invention are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alkohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to 1-10 wt %. The wt % relate to the total CS composition.

ix) Dustable Powders (DP, DS)

1-10 wt % of a compound I according to the invention are ground finely and mixed intimately with solid carrier (e.g. finely divided kaolin) ad 100 wt %.

x) Granules (GR, FG)

0.5-30 wt % of a compound I according to the invention is ground finely and associated with solid carrier (e.g. silicate) ad 100 wt %. Granulation is achieved by extrusion, spray-drying or the fluidized bed.

xi) Ultra-Low Volume Liquids (UL)

1-50 wt % of a compound I according to the invention are dissolved in organic solvent (e.g. aromatic hydrocarbon) ad 100 wt %.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required. When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate. In a further embodiment, either individual components of the composition according to the invention or partially premixed components, e.g. components comprising compounds I and/or active substances from the groups M) or F) (see below), may be mixed by the user in a spray tank and further auxiliaries and additives may be added, if appropriate.

In a further embodiment, either individual components of the composition according to the invention or partially premixed components, e.g. components comprising compounds I and/or active substances from the groups M) or F) (see below), can be applied jointly (e.g. after tank mix) or consecutively.

The following categorized list M of pesticides represents insecticidal mixture partners, which are, whenever possible, classified according to the Insecticide Resistance Action Committee (IRAC), and together with which the compounds according to the present invention may be used. The combined use of the compounds of the present invention with the following pesticides may result in potential synergistic effects. The following examples of insecticidal mixing partners are provided with the intention to illustrate the possible combinations, but not to impose any limitation to the obtainable mixtures:

M.1 Acetylcholine esterase (AChE) inhibitors from the class of

M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as:

M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zetacypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, meperfluthrin, metofluthrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of

M.4A neonicotinoids, for example acteamiprid, chlothianidin, dinotefuran, imidacloprid, nitenpyram, thiacloprid and thiamethoxam; or M.4B nicotine.

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as

M.7A juvenile hormone analogues as hydroprene, kinoprene and methoprene; or others as M.7B fenoxycarb, or M.7C pyriproxyfen;

M.8 miscellaneous non-specific (multi-site) inhibitors, for example

M.8A alkyl halides as methyl bromide and other alkyl halides, or

M.8B chloropicrin, or

M.8C sulfuryl fluoride, or

M.8D borax, or

M.8E tartar emetic;

M.9 Selective homopteran feeding blockers, for example

M.9B pymetrozine, or

M.9C flonicamid;

M.10 Mite growth inhibitors, for example

M.10A clofentezine, hexythiazox and diflovidazin, or

M.10B etoxazole;

M.11 Microbial disruptors of insect midgut membranes, for example *bacillus thuringiensis* or *bacillus sphaericus* and the insecticdal proteins they produce such as *bacillus thuringiensis* subsp. *israelensis, bacillus sphaericus, bacillus thuringiensis* subsp. *aizawai, bacillus thuringiensis* subsp. *kurstaki* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example
M.12A diafenthiuron, or
M.12B organotin miticides such as azocyclotin, cyhexatin or fenbutatin oxide, or M.12C propargite, or
M.12D tetradifon;
M.13 Uncouplers of oxidative phosphorylation via disruption of the proton gradient, for example chlorfenapyr, DNOC or sulfluramid;
M.14 Nicotinic acetylcholine receptor (nAChR) channel blockers, for example nereistoxin analogues as bensultap, cartap hydrochloride, thiocyclam or thiosultap sodium;
M.15 Inhibitors of the chitin biosynthesis type 0, such as benzoylureas as for example bistrifluoron, chlorfluazuron, diflubenzuron, flucycloxuron, flufenoxuron, hexaflumuron, lufenuron, novaluron, noviflumuron, teflubenzuron or triflumuron;
M.16 Inhibitors of the chitin biosynthesis type 1, as for example buprofezin;
M.17 Moulting disruptors, Dipteran, as for example cyromazine;
M.18 Ecdyson receptor agonists such as diacylhydrazines, for example methoxyfenozide, tebufenozide, halofenozide, fufenozide or chromafenozide;
M.19 Octopamin receptor agonists, as for example amitraz;
M.20 Mitochondrial complex III electron transport inhibitors, for example
M.20A hydramethylnon, or
M.20B acequinocyl, or
M.20C fluacrypyrim;
M.21 Mitochondrial complex I electron transport inhibitors, for example
M.21A METI acaricides and insecticides such as fenazaquin, fenpyroximate, pyrimidifen, pyridaben, tebufenpyrad or tolfenpyrad, or
M.21B rotenone;
M.22 Voltage-dependent sodium channel blockers, for example
M.22A indoxacarb, or
M.22B metaflumizone;
M.23 Inhibitors of the of acetyl CoA carboxylase, such as Tetronic and Tetramic acid derivatives, for example spirodiclofen, spiromesifen or spirotetramat;
M.24 Mitochondrial complex IV electron transport inhibitors, for example
M.24A phosphine such as aluminium phosphide, calcium phosphide, phosphine or zinc phosphide, or
M.24B cyanide.
M.25 Mitochondrial complex II electron transport inhibitors, such as beta-ketonitrile derivatives, for example cyenopyrafen or cyflumetofen;
M.28 Ryanodine receptor-modulators from the class of diamides, as for example flubendiamide, chloranthraniliprole (Rynaxypyr®), cyanthraniliprole (Cyazypyr®), or the phthalamide compounds
M.28.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and
M.28.2: (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, or the compound
M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide, or the compound
M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate;

M.X insecticidal active compounds of unknown or uncertain mode of action, as for example azadirachtin, amidoflumet, benzoximate, bifenazate, bromopropylate, chinomethionat, cryolite, dicofol, flufenerim, flometoquin, fluensulfone, flupyradifurone, piperonyl butoxide, pyridalyl, pyrifluquinazon, sulfoxaflor, or the compound
M.X.1: 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide, or the compound
M.X.2: cyclopropaneacetic acid, 1,1'-[(3S,4R,4aR,6S,6aS, 12R,12aS,12bS)-4-[[(2-cyclopropylacetyl)oxy]methyl]-1,3,4,4a,5,6,6a,12,12a,12b-decahydro-[2-hydroxy-4,6a, 12b-trimethyl-11-oxo-9-(3-pyridinyl)-2H,11H-naphtho [2,1-b]pyrano[3,4-e]pyran-3,6-diyl]ester, or the compound
M.X.3: 11-(4-chloro-2,6-dimethylphenyl)-12-hydroxy-1,4-dioxa-9-azadispiro[4.2.4.2]-tetradec-11-en-10-one, or the compound
M.X.4: 3-(4'-fluoro-2,4-dimethylbiphenyl-3-yl)-4-hydroxy-8-oxa-1-azaspiro[4.5]dec-3-en-2-one, or the compound
M.X.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of bacillus firmus (Votivo, 1-1582).

The commercially available compounds of the group M listed above may be found in The Pesticide Manual, 15th Edition, C. D. S. Tomlin, British Crop Protection Council (2011) among other publications.

The phthalamides M.28.1 and M.28.2 are both known from WO 2007/101540. The anthranilamide M.28.3 has been described in WO2005/077943. The hydrazide compound M.28.4 has been described in WO 2007/043677.— The quinoline derivative flometoquin is shown in WO2006/013896. The aminofuranone compounds flupyradifurone is known from WO 2007/115644. The sulfoximine compound sulfoxaflor is known from WO2007/149134. The isoxazoline compound M.X.1 has been described in WO2005/085216. The pyripyropene derivative M.X.2 has been described in WO 2006/129714. The spiroketal-substituted cyclic ketoenol derivative M.X.3 is known from WO2006/089633 and the biphenyl-substituted spirocyclic ketoenol derivative M.X.4 from WO2008/067911. Finally triazoylphenylsulfide like M.X.5 have been described in WO2006/043635 and biological control agents on basis of bacillus firmus in WO2009/124707.

The following list F of active substances, in conjunction with which the compounds according to the invention can be used, is intended to illustrate the possible combinations but does not limit them:

F.I) Respiration Inhibitors
F.I-1) Inhibitors of complex III at Qo site (e.g. strobilurins) strobilurins: azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, triclopyricarb/chlorodincarb, trifloxystrobin, 2-[2-(2,5-dimethyl-phenoxymethyl)-phenyl]-3-methoxy-acrylic acid methyl ester and 2 (2-(3-(2,6-dichlorophenyl)-1-methyl-allylideneaminooxymethyl)phenyl)-2-methoxyimino-N methyl-acetamide;
oxazolidinediones and imidazolinones: famoxadone, fenamidone;

F.I-2) Inhibitors of complex II (e.g. carboxamides):
carboxanilides: benodanil, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2 yl)-3-difluoromethyl-1-methyl-1H-pyrazole-4 carboxamide, N-(4'-trifluoromethylthiobiphenyl-2-yl)-3 difluoromethyl-1-methyl-1H pyrazole-4-carboxamide and N-(2-(1,3,3-trimethyl-butyl)-phenyl)-1,3-dimethyl-5 fluoro-1H-pyrazole-4 carboxamide;

F.I-3) Inhibitors of complex III at Qi site: cyazofamid, amisulbrom;

F.I-4) Other respiration inhibitors (complex I, uncouplers) diflumetorim; tecnazen; ferimzone; ametoctradin; silthiofam;

nitrophenyl derivates: binapacryl, dinobuton, dinocap, fluazinam, nitrthal-isopropyl, organometal compounds: fentin salts, such as fentin-acetate, fentin chloride or fentin hydroxide;

F.II) Sterol biosynthesis inhibitors (SBI fungicides)

F.II-1) C14 demethylase inhibitors (DMI fungicides, e.g. triazoles, imidazoles)

triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole; imidazoles: imazalil, pefurazoate, oxpoconazole, prochloraz, triflumizole; pyrimidines, pyridines and piperazines: fenarimol, nuarimol, pyrifenox, triforine;

F.II-2) Delta 14-reductase inhitors (Amines, e.g. morpholines, piperidines) morpholines: aldimorph, dodemorph, dodemorph-acetate, fenpropimorph, tridemorph;
piperidines: fenpropidin, piperalin;
spiroketalamines: spiroxamine;

F.II-3) Inhibitors of 3-keto reductase: hydroxyanilides: fenhexamid;

F.III) Nucleic acid synthesis inhibitors

F.III-1) RNA, DNA synthesis
phenylamides or acyl amino acid fungicides: benalaxyl, benalaxyl-M, kiralaxyl, metalaxyl, metalaxyl-M (mefenoxam), ofurace, oxadixyl;
isoxazoles and iosothiazolones: hymexazole, octhilinone;

F.III-2) DNA topisomerase inhibitors: oxolinic acid;

F.III-3) Nucleotide metabolism (e.g. adenosin-deaminase) hydroxy (2-amino)-pyrimidines: bupirimate;

F.IV) Inhibitors of cell division and or cytoskeleton

F.IV-1) Tubulin inhibitors: benzimidazoles and thiophanates: benomyl, carbendazim, fuberidazole, thiabendazole, thiophanate-methyl;
triazolopyrimidines: 5-chloro-7 (4-methylpiperidin-1-yl)-6-(2,4,6-trifluorophenyl)-[1,2,4]triazolo[1,5a]pyrimidine F.IV-2) Other cell division inhibitors benzamides and phenyl acetamides: diethofencarb, ethaboxam, pencycuron, fluopicolide, zoxamide;

F.IV-3) Actin inhibitors: benzophenones: metrafenone;

F.V) Inhibitors of amino acid and protein synthesis

F.V-1) Mmethionine synthesis inhibitors (anilino-pyrimidines)
anilino-pyrimidines: cyprodinil, mepanipyrim, nitrapyrin, pyrimethanil;

F.V-2) Protein synthesis inhibitors (anilino-pyrimidines) antibiotics: blasticidin-S, kasugamycin, kasugamycin hydrochloride-hydrate, mildiomycin, streptomycin, oxytetracyclin, polyoxine, validamycin A;

F.VI) Signal transduction inhibitors

F.VI-1) MAP/Histidine kinase inhibitors (e.g. anilino-pyrimidines)
dicarboximides: fluoroimid, iprodione, procymidone, vinclozolin;
phenylpyrroles: fenpiclonil, fludioxonil;

F.VI-2) G protein inhibitors: quinolines: quinoxyfen;

F.VII) Lipid and membrane synthesis inhibitors

F.VII-1) Phospholipid biosynthesis inhibitors
organophosphorus compounds: edifenphos, iprobenfos, pyrazophos;
dithiolanes: isoprothiolane;

F.VII-2) Lipid peroxidation
aromatic hydrocarbons: dicloran, quintozene, tecnazene, tolclofos-methyl, biphenyl, chloroneb, etridiazole;

F.VII-3) Carboxyl acid amides (CAA fungicides)
cinnamic or mandelic acid amides: dimethomorph, flumorph, mandiproamid, pyrimorph;
valinamide carbamates: benthiavalicarb, iprovalicarb, pyribencarb, valifenalate and N-(1-(1-(4-cyano-phenyl)ethanesulfonyl)-but-2-yl)carbamic acid-(4-fluorophenyl) ester;

F.VII-4) Compounds affecting cell membrane permeability and fatty acides carbamates: propamocarb, propamocarb-hydrochlorid F.VIII) Inhibitors with Multi Site Action F.VIII-1) Inorganic active substances: Bordeaux mixture, copper acetate, copper hydroxide, copper oxychloride, basic copper sulfate, sulfur;

F.VIII-2) Thio- and dithiocarbamates: ferbam, mancozeb, maneb, metam, methasulphocarb, metiram, propineb, thiram, zineb, ziram;

F.VIII-3) Organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;

F.VIII-4) Guanidines: guanidine, dodine, dodine free base, guazatine, guazatineacetate, iminoctadine, iminoctadine-triacetate, iminoctadine-tris(albesilate);

F.VIII-5) Ahtraquinones: dithianon;

F.IX) Cell wall synthesis inhibitors

F.IX-1) Inhibitors of glucan synthesis: validamycin, polyoxin B;

F.IX-2) Melanin synthesis inhibitors: pyroquilon, tricyclazole, carpropamide, dicyclomet, fenoxanil;

F.X) Plant defence inducers

F.X-1) Salicylic acid pathway: acibenzolar-S-methyl;

F.X-2) Others: probenazole, isotianil, tiadinil, prohexadione-calcium;
phosphonates: fosetyl, fosetyl-aluminum, phosphorous acid and its salts;

F.XI) Unknown mode of action:
bronopol, chinomethionat, cyflufenamid, cymoxanil, dazomet, debacarb, diclomezine, difenzoquat, difenzoquat-methylsulfate, diphenylamin, flumetover, flusulfamide, flutianil, methasulfocarb, oxin-copper, proquinazid, tebufloquin, tecloftalam, triazoxide, 2-butoxy-6-iodo-3-propylchromen-4-one,
N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N'(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-

(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-chloro-phenyl)-2,3-dimethyl-isoxazolidin-3 yl]-pyridine, pyrisoxazole, 5-amino-2-isopropyl-3-oxo-4-ortho-tolyl-2,3-dihydro-pyrazole-1 carbothioic acid S-allyl ester, N-(6-methoxy-pyridin-3-yl)cyclopropanecarboxylic acid amide, 5-chloro-1(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

F.XI) Growth regulators:

abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;

F.XII) Biological control agents antifungal biocontrol agents: *Bacillus* substilis strain with NRRL No. B-21661 (e.g. RHAPSODY®, SERENADE® MAX and SERENADE® ASO from AgraQuest, Inc., USA.), *Bacillus pumilus* strain with NRRL No. B-30087 (e.g. SONATA® and BALLAD® Plus from AgraQuest, Inc., USA), Ulocladium oudemansii (e.g. the product BOTRYZEN from BotriZen Ltd., New Zealand), Chitosan (e.g. ARMOUR-ZEN from BotriZen Ltd., New Zealand).

The invertebrate pest (also referred to as "animal pest"), i.e. the insects, arachnids and nematodes, the plant, soil or water in which the plant is growing or may grow can be contacted with the compounds of the present invention or composition(s) comprising them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant).

The compounds of the present invention or the pesticidal compositions comprising them may be used to protect growing plants and crops from attack or infestation by animal pests, especially insects, acaridae or arachnids by contacting the plant/crop with a pesticidally effective amount of compounds of the present invention. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the insects or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

Moreover, invertebrate pests may be controlled by contacting the target pest, its food supply, habitat, breeding ground or its locus with a pesticidally effective amount of compounds of the present invention. As such, the application may be carried out before or after the infection of the locus, growing crops, or harvested crops by the pest.

The compounds of the present invention can also be applied preventively to places at which occurrence of the pests is expected.

The compounds of the present invention may be also used to protect growing plants from attack or infestation by pests by contacting the plant with a pesticidally effective amount of compounds of the present invention. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 $m^2$, preferably from 0.001 to 20 g per 100 $m^2$.

Customary application rates in the protection of materials are, for example, from 0.01 g to 1000 g of active compound per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 5 g to 500 g per hectare, more desirably from 5 g to 200 g per hectare.

The compounds of the present invention are effective through both contact (via soil, glass, wall, bed net, carpet, plant parts or animal parts), and ingestion (bait, or plant part).

The compounds of the present invention may also be applied against non-crop insect pests, such as ants, termites, wasps, flies, mosquitos, crickets, or cockroaches. For use against said non-crop pests, compounds of the present invention are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics. The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active ingredient.

Formulations of compounds of the present invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the present invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the present invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata*, *Vitex rotundifolia*, *Cymbopogan martinii*, *Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets. The compounds of the present invention and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of the present invention are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of the present invention are also suitable for the treatment of plant propagation material, especially seeds, in order to protect them from insect pest, in particular from soil-living insect pests and the resulting plant's roots and shoots against soil pests and foliar insects.

The compounds of the present invention are particularly useful for the protection of the seed from soil pests and the resulting plant's roots and shoots against soil pests and foliar insects. The protection of the resulting plant's roots and shoots is preferred.

More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the present invention, including a salt thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A 242 236, EP-A 242 246) (WO 92/00377) (EP-A 257 993, U.S. Pat. No. 5,013,659) or in transgenic crop plants, for example cotton, with the capability of producing Bacillus thuringiensis toxins (Bt toxins) which make the plants resistant to certain pests (EP-A 142 924, EP-A 193 259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a Gelling Agent is Carrageen (Satiagel®)

In the treatment of seed, the application rates of the compounds of the present invention are generally from 0.01 g to 10 kg per 100 kg of seed, preferably from 0.05 g to 5 kg per 100 kg of seed, more preferably from 0.1 g to 1000 g per 100 kg of seed and in particular from 0.1 g to 200 g per 100 kg of seed.

The invention therefore also relates to seed comprising a compound of the present invention, including an agriculturally useful salt of it, as defined herein. The amount of the compound of the present invention, including an agriculturally useful salt thereof will in general vary from 0.01 g to 10 kg per 100 kg of seed, preferably from 0.05 g to 5 kg per 100 kg of seed, in particular from 0.1 g to 1000 g per 100 kg of seed. For specific crops such as lettuce the rate can be higher.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of the present invention into contact with each other, and "seed dressing" to methods of seed treatment which provide the seeds with an amount of the compounds of the present invention, i.e. which generate a seed comprising a compound of the present invention. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of the present invention, including their stereoisomers, veterinarily acceptable salts or N-oxides, are in particular also suitable for being used for combating parasites in and on animals.

An object of the present invention is therfore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions comprising a parasiticidally effective amount of compounds of the present invention, including their stereoisomers, veterinarily acceptable salts or N-oxides, and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of the present invention, including its stereoisomers, veterinarily acceptable salts or N-oxides, or a composition comprising it.

The invention also provides a process for the preparation of a composition for treating, controlling, preventing or protecting animals against infestation or infection by parasites which comprises a parasiticidally effective amount of a compound of the present invention, including its stereoisomers, veterinarily acceptable salts or N-oxides, or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula (I) and their stereoisomers, veterinarily acceptable salts, tautomers and N-oxides, are suitable for combating endo- and ectoparasites in and on animals.

The compounds of the present invention, especially compounds of formula (I) and their stereoisomers, veterinarily acceptable salts, tautomers and N-oxides, and compositions comprising them are preferably used for controlling and preventing infestations of and infections in animals including warm-blooded animals (including humans) and fish.

They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in furbearing animals such as mink, chinchilla and raccoon, birds such as hens, geese, turkeys and ducks and fish such as fresh- and salt-water fish such as trout, carp and eels. Compounds of the present invention, including their stereoisomers, veterinarily acceptable salts or N-oxides, and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the present invention, including their stereoisomers, veterinarily acceptable salts or N-oxides, and compositions comprising them are suitable for systemic and/or non-systemic control of ecto- and/or endoparasites. They are active against all or some stages of development.

The compounds of the present invention are especially useful for combating parasites of the following orders and species, respectively: fleas (Siphonaptera), e.g. *Ctenocephalides felis, Ctenocephalides canis, Xenopsylla cheopis, Pulex irritans, Tunga penetrans*, and *Nosopsyllus fasciatus*, cockroaches (Blattaria—Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora* vicina, *Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*. ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,*

Actinedida (Prostigmata) und Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., Oesophagostomum spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi,* and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The present invention relates to the therapeutic and the non-therapeutic use of compounds of the present invention and compositions comprising them for controlling and/or combating parasites in and/or on animals. The compounds of the present invention and compositions comprising them may be used to protect the animals from attack or infestation by parasites by contacting them with a parasiticidally effective amount of compounds of the present invention and compositions containing them.

The compounds of the present invention and compositions comprising them can be effective through both contact (via soil, glass, wall, bed net, carpet, blankets or animal parts) and ingestion (e.g. baits). As such, "contacting" includes both direct contact (applying the pesticidal mixtures/compositions containing the compounds of the present invention directly on the parasite, which may include an indirect contact at its locus-P, and optionally also administrating the pesticidal mixtures/composition directly on the animal to be protected) and indirect contact (applying the compounds/compositions to the locus of the parasite). The contact of the parasite through application to its locus is an example of a non-therapeutic use of compounds of the present invention. "Locus-P" as used above means the habitat, food supply, breeding ground, area, material or environment in which a parasite is growing or may grow outside of the animal.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions of the present invention. A parasiticidally effective amount of the compositions will also vary according to the prevailing conditions such as desired parasiticidal effect and duration, target species, mode of application, and the like.

The compounds of the present invention can also be applied preventively to places at which occurrence of the pests or parasites are expected.

Administration can be carried out both prophylactically and therapeutically.

Administration of the active compounds is carried out directly or in the form of suitable preparations, orally, topically/dermally or parenterally.

The compounds of the invention have a distinctly shorter half live in the soil and thus are significantly less persistent than isoxazoline compounds of similar structure and insecticidal activity.

EXAMPLES

The present invention is now illustrated in further details by the following examples, without imposing any limitation thereto.

Preparation Examples

Compounds can be characterized e.g. by coupled High Performance Liquid Chromatography/mass spectrometry (HPLC/MS), by $^1$H-NMR and/or by their melting points.

Analytical HPLC column:

Method A: Analytical UPLC column: RP-18 column Chromolith Speed ROD, 50×4.6 mm, from Merck KgaA, Germany). Elution: acetonitrile+0.1% trifluoroacetic acid (TFA)/water+0.1% trifluoroacetic acid (TFA) in a ratio of from 5:95 to 95:5 in 5 minutes at 40° C. Flow: 1.8 mL/min. MS-method: ESI positive.

Method B: Analytical UPLC column: Phenomenex Kinetex 1.7 μm XB-C18 100A; 50×2.1 mm from Phenomenex, Germany. Elution: acetonitrile+0.1% trifluoroacetic acid (TFA)/water+0.1% trifluoroacetic acid (TFA) in a ratio from 5:95 to 100:0 in 1.5 min at 60° C. Flow: 0.8 mL/min to 1 mL/min in 1.5 min. MS-method: ESI positive.

1H-NMR, respectively $^{13}$C-NMR: The signals are characterized by chemical shift (ppm, δ [delta]) vs. tetramethylsilane, respectively CDCl$_3$ for $^{13}$C-NMR, by their multiplicity and by their integral (relative number of hydrogen atoms given). The following abbreviations are used to characterize the multiplicity of the signals: m=multiplett, q=quartett, t=triplett, d=doublet and s=singulett.

Abbreviations used are: h for hour(s), min for minute(s), r.t./room temperature for 20-25° C., THF for tetrahydrofuran, OAc for acetate.

C.1 Compound Examples 1

Compound examples 1-1 to 1-20 correspond to compounds of formula C.1:

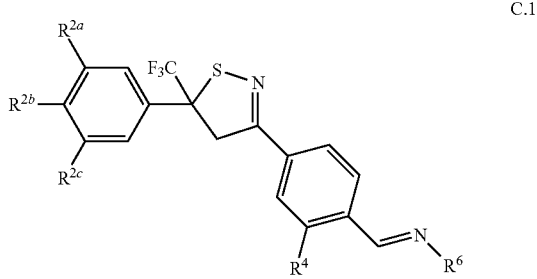

C.1 wherein $R^{2a}$, $R^{2b}$, $R^{2c}$, $R^4$, and $R^6$ of each synthesized compound is defined in one row of table C.1 below.

The compounds were synthesized in analogy to Synthesis Example S.1.

TABLE C.1

| Ex. | $R^{2a}$, $R^{2b}$, $R^{2c}$ | $R^4$ | $R^6$ | HPLC-MS: Method, R$_t$ (min) & [M + H]$^+$ or 1H-NMR | | |
|---|---|---|---|---|---|---|
| 1-1 | Cl, H, Cl | CH$_3$ | NHC(=O)—NHCH$_2$CF$_3$ | A | 4.052 | 557.0 |
| 1-2 | Cl, H, Cl | CH$_3$ | NHC(=O)—NHCH$_3$ | A | 4.420 | 489.1 |
| 1-3 | Cl, H, Cl | CH$_3$ | NHC(=O)—NH-(cyclopropyl) | 1H NMR (400 MHz, CDCl$_3$): δ 9.5 (s, 1H), 8.0 (s, 1H), 7.8 (d, 1H), 7.7-7.5 (m, 2H), 7.4 (s, 1H), 7.3 (s, 2H), 6.2 (s, 1H), 4.2 (d, 1H), 3.8 (d, 1H), 2.8-2.7 (m, 1H), 2.5 (s, 3H), 2.0-0.5 (m, 4H) | | |
| 1-4 | Cl, H, Cl | CH$_3$ | NHC(=O)—NHCH$_2$-(cyclopropyl) | B | 1.681 | 531.0 |
| 1-5 | Cl, H, Cl | CH$_3$ | NHC(=O)—NHCH$_2$CH$_3$ | B | 1.681 | 503.2 |
| 1-6 | Cl, H, Cl | CH$_3$ | NHC(=O)—NH$_2$ | A | 4.065 | 474.9 |
| 1-7 | Cl, H, Cl | Cl | NHC(=O)—NHCH$_3$ | B | 1.446 | 509.0 |
| 1-8 | Cl, H, Cl | Cl | NHC(=O)—NHCH$_2$CF$_2$H | B | 1.475 | 560.9 |
| 1-9 | Cl, H, Cl | Cl | NHC(=O)—NHCH$_2$CF$_3$ | B | 1.502 | 578.9 |
| 1-10 | Cl, H, Cl | Cl | NHC(=O)—NHCH$_2$CH$_3$ | B | 1.319 | 523.0 |
| 1-11 | Cl, H, Cl | Cl | NH-(2-pyridyl) | A | 3.891 | 530.9 |
| 1-12 | Cl, H, Cl | Cl | NHC(=O)—OCH$_3$ | B | 1.471 | 512.1 |
| 1-13 | Cl, H, Cl | Cl | NHC(=O)—NHOCH$_3$ | 1H NMR (400 MHz, CDCl$_3$): δ 8.5-8.2 (m, 2H), 8.2 (s, 1H), 8.0 (d, 1H), 7.8 (s, 1H), 7.7 (d, 1H), 7.4 (s, 1H), 7.3 (s, 2H), 4.2 (d, 1H), 3.8-3.9 (m, 4H) | | |
| 1-14 | Cl, H, Cl | Cl | NHC(=S)—NHCH$_3$ | B | 1.509 | 527.1 |
| 1-15 | Cl, H, Cl | Cl | NHC(=O)—CH$_2$CH$_3$ | A | 4.466 | 509.9 |
| 1-16 | Cl, H, Cl | Cl | N(CH$_3$)$_2$ | B | 1.687 | 480.1 |
| 1-17 | Cl, Cl, Cl | OCH$_3$ | NHC(=O)—NHCH$_3$ | B | 1.448 | 540.8 |
| 1-18 | Cl, Cl, Cl | OCH$_3$ | NHC(=O)—NHCH$_2$CF$_3$ | B | 1.503 | 608.9 |
| 1-19 | Cl, Cl, Cl | OCH$_3$ | NHC(=O)—NHCH$_2$CCH | B | 1.459 | 564.8 |
| 1-20 | Cl, H, Cl | Cl | OH | 1H NMR (400 MHz, CDCl$_3$): δ 8.5 s, 1H), 7.9 (d, 1H, 7.8 (s, 1H), 7.6 d, 1H), 7.5 (s, 1H, 7.4 (s, 1H), 7.3 s, 2H), 4.2 (d, 1H, 3.8 (d, 1H) | | |

C.2 Compound Examples 2

Compound examples 2-1 to 2-233 correspond to compounds of formula C.2:

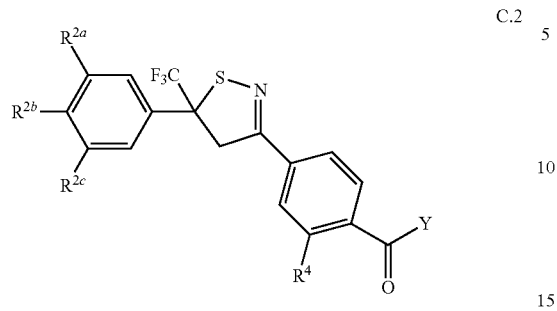

wherein $R^{2a}$, $R^{2b}$, $R^{2c}$, $R^4$, and Y of each synthesized compound is defined in one row of table C.2 below.

The compounds were synthesized in analogy to Synthesis Example S.2.

TABLE C.2

| Ex. | $R^{2a}$, $R^{2b}$, $R^{2c}$ | $R^4$ | Y | HPLC-MS: Method, $R_t$ (min) & $[M + H]^+$ or 1H-NMR | | |
|---|---|---|---|---|---|---|
| 2-1 | Cl, H, Cl | CH$_3$ | NHCH$_2$C(=O)—NHCH$_2$CF$_3$ | A | 4.242 | 572.0 |
| 2-2 | Cl, H, Cl | CH$_3$ | NHCH$_2$C(=O)—NHCH$_2$(cyclopropyl) | B | 1.348 | 530.1 |
| 2-3 | Cl, H, Cl | CH$_3$ | NHCH$_2$-(2-F—C$_6$H$_4$) | B | 1.521 | 541.0 |
| 2-4 | Cl, H, Cl | CH$_3$ | NHCH$_2$-(2-pyridyl) | B | 1.167 | 525.9 |
| 2-5 | Cl, H, Cl | CH$_3$ | NH-(3-thiethanyl) | B | 1.473 | 506.8 |
| 2-6 | Cl, H, Cl | CH$_3$ | NHCH$_2$CF$_3$ | B | 1.487 | 515.0 |
| 2-7 | Cl, H, Cl | CH$_3$ | NHCH$_2$-(4-(OCH$_3$)—C$_6$H$_4$) | B | 1.508 | 554.9 |
| 2-8 | Cl, H, Cl | CH$_3$ | NHCH$_2$-(3-(OCH$_3$)—C$_6$H$_4$) | B | 1.518 | 553.1 |
| 2-9 | Cl, H, Cl | CH$_3$ | NHCH$_2$-(2-thienyl) | B | 1.511 | 530.7 |
| 2-10 | Cl, H, Cl | CH$_3$ | NHCH$_2$-(cyclopropyl) | B | 1.491 | 487.1 |
| 2-11 | Cl, H, Cl | CH$_3$ | NH-(1-oxo-thiethan-3-yl) | B | 1.307 | 521.1 |
| 2-12 | Cl, H, Cl | CH$_3$ | NHCH$_2$-(4-thiazolyl) | B | 1.396 | 530.0 |
| 2-13 | Cl, H, Cl | CH$_3$ | NH-(1,1-dioxo-thiethan-3-yl) | A | 4.172 | 537.0 |
| 2-14 | Cl, H, Cl | CH$_3$ | H | B | 1.526 | 418.0 |
| 2-15 | Cl, H, Cl | CH$_3$ | NHCH$_2$—C$_6$H$_5$ | B | 1.501 | 523.3 |
| 2-16 | Cl, H, Cl | CH$_3$ | OCH$_3$ | B | 1.596 | 448.0 |
| 2-17 | Cl, H, Cl | F | OH | 1H NMR (400 MHz, CDCl$_3$): δ 8.2-8.0 (m, 1H), 7.7-7.5 (m, 2H), 7.4 (s, 1H), 7.3 (s, 2H), 4.2 (d, 1H), 3.9 (d, 1H) | | |
| 2-18 | Cl, H, Cl | F | NHCH$_2$C(=O)—NHCH$_2$CF$_3$ | B | 1.397 | 576.2 |
| 2-19 | Cl, H, Cl | F | NHCH$_2$-(2-pyridyl) | B | 1.207 | 528.2 |
| 2-20 | Cl, H, Cl | F | NH-(3-thiethanyl) | B | 1.479 | 509.1 |
| 2-21 | Cl, H, Cl | F | NHCH$_2$CF$_3$ | B | 1.478 | 519.2 |
| 2-22 | Cl, H, Cl | F | OCH$_3$ | B | 1.544 | 452.2 |
| 2-23 | Cl, H, Cl | F | NH-(1,1-dioxo-thiethan-3-yl) | B | 1.361 | 541.2 |
| 2-24 | Cl, H, Cl | Cl | OCH$_3$ | B | 1.583 | 470.0 |
| 2-25 | Cl, H, Cl | Cl | OH | 1H NMR (400 MHz, CDCl$_3$): δ 8.1-8.0 (m, 1H), 7.9 (s, 1H), 7.8-7.7 (m, 1H), 7.4 (s, 1H), 7.3 (s, 2H), 4.2 (d, 1H), 3.9 (d, 1H) | | |
| 2-26 | Cl, H, Cl | Cl | NHCH$_2$-(2-pyridyl) | B | 1.194 | 544.0 |
| 2-27 | Cl, H, Cl | Cl | NHCH$_2$C(=O)—NHCH$_2$CF$_3$ | B | 1.397 | 594.0 |
| 2-28 | Cl, H, Cl | Cl | NH-(3-thiethanyl) | B | 1.460 | 526.9 |
| 2-29 | Cl, H, Cl | Cl | NHCH$_2$CF$_3$ | B | 1.462 | 536.8 |
| 2-30 | Cl, H, Cl | Cl | NH-(1-oxo-thiethan-3-yl) | B | 1.310 | 543.0 |
| 2-31 | Cl, H, Cl | Cl | pyrrolidin-1-yl | B | 1.514 | 509.1 |
| 2-32 | Cl, H, Cl | Cl | NHCH$_2$-(4-thiazolyl) | B | 1.412 | 552.0 |
| 2-33 | Cl, H, Cl | F | NH-(1-oxo-thiethan-3-yl) | B | 1.304 | 526.9 |
| 2-34 | Cl, H, Cl | F | pyrrolidin-1-yl | B | 1.473 | 492.9 |
| 2-35 | Cl, H, Cl | Cl | NHCH$_2$-(3-pyridyl) | B | 1.162 | 545.9 |
| 2-36 | Cl, H, Cl | Cl | H | 1H NMR (400 MHz, CDCl$_3$): δ 10.5 (s, 1H), 8.0 (d, 1H), 7.8 (s, 1H), 7.7 (d, 1H), 7.4 (s, 1H), 7.3 (s, 2H), 4.2 (d, 1H), 3.9 (d, 1H) | | |
| 2-37 | Cl, H, Cl | Cl | NHCH$_2$-(4-pyridyl) | B | 1.150 | 544.2 |
| 2-38 | Cl, H, Cl | Cl | NH—C$_6$H$_5$ | B | 1.508 | 530.9 |
| 2-39 | Cl, H, Cl | Cl | NHCH$_2$-(6-Cl-pyrid-3-yl) | B | 1.447 | 580.0 |
| 2-40 | Cl, H, Cl | Cl | NH-(1,1-dioxo-thiethan-3-yl) | B | 1.196 | 557.0 |
| 2-41 | Cl, H, Cl | F | NHCH$_2$-(4-thiazolyl) | B | 1.396 | 534.0 |

TABLE C.2-continued

| Ex. | $R^{2a}, R^{2b}, R^{2c}$ | $R^4$ | Y | HPLC-MS: Method | $R_t$ (min) | $[M + H]^+$ or 1H-NMR |
|---|---|---|---|---|---|---|
| 2-42 | Cl, H, Cl | Cl | NH-(3-pyridyl) | B | 1.202 | 531.9 |
| 2-43 | Cl, H, Cl | $CH_3$ | $NHCH_2$-(3,3-difluoro-cyclobut-1-yl) | B | 1.466 | 537.3 |
| 2-44 | Cl, H, Cl | Cl | NH-(2-pyridyl) | B | 1.429 | 531.8 |
| 2-45 | Cl, H, Cl | Cl | NH-(4-pyridyl) | B | 1.170 | 532.0 |
| 2-46 | Cl, H, Cl | $CH_3$ | NH—$CH_2$-(2-nitrophenyl) | B | 1.485 | 568.3 |
| 2-47 | Cl, H, Cl | Cl | $N(CH_3)$—$CH_2$-(2-pyridyl) | B | 1.314 | 560.0 |
| 2-48 | Cl, H, Cl | Cl | $NHCH_2$-(4-pyrimidyl) | B | 1.343 | 546.8 |
| 2-49 | Cl, H, Cl | Cl | $N(CH_2CH_3)$—$CH_2$-(2-pyridyl) | B | 1.338 | 573.8 |
| 2-50 | Cl, H, Cl | Cl | $NHCH_2$-(2-pyrimidyl) | B | 1.374 | 547.4 |
| 2-51 | Cl, H, Cl | $CH_3$ | $NHCH_2$-(cyclobutyl) | B | 1.511 | 501.1 |
| 2-52 | Cl, H, Cl | $CH_3$ | $NHCH_2$-(cyclopentyl) | B | 1.546 | 516.8 |
| 2-53 | Cl, H, Cl | $CH_3$ | $NHCH_2$-(2-pyrazinyl) | B | 1.353 | 525.0 |
| 2-54 | Cl, H, Cl | $CH_3$ | $NHCH_2$-(3-pyridyl) | B | 1.128 | 524.3 |
| 2-55 | Cl, H, Cl | $CH_3$ | $NHCH_2$-(4-pyridyl) | B | 1.130 | 524.2 |
| 2-56 | Cl, H, Cl | $CH_3$ | NH-(2-pyridyl) | B | 1.351 | 510.3 |
| 2-57 | Cl, H, Cl | $CH_3$ | NH-(3-pyridyl) | B | 1.183 | 510.3 |
| 2-58 | Cl, H, Cl | $CH_3$ | NH-(4-pyridyl) | B | 1.174 | 510.3 |
| 2-59 | Cl, H, Cl | $CH_3$ | $NHCH_2$-(2-pyrimidyl) | B | 1.355 | 525.3 |
| 2-60 | Cl, H, Cl | $CH_3$ | $NHCH_2$-(4-pyrimidyl) | B | 1.331 | 525.3 |
| 2-61 | Cl, H, Cl | $CH_3$ | NH—$C_6H_5$ | B | 1.514 | 509.3 |
| 2-62 | Cl, H, Cl | $CH_3$ | $N(CH_3)$—$CH_2$-(2-pyridyl) | B | 1.274 | 538.3 |
| 2-63 | Cl, H, Cl | $CH_3$ | $N(CH_2CH_3)$—$CH_2$-(2-pyridyl) | B | 1.305 | 552.3 |
| 2-64 | Cl, H, Cl | $CH_3$ | $N(CH_2CCH)$—$CH_2$-(2-pyridyl) | B | 1.331 | 562.3 |
| 2-65 | Cl, H, Cl | $CH_3$ | $N(CH_3)$—$CH_2$-(4-thiazolyl) | B | 1.438 | 544.3 |
| 2-66 | Cl, H, Cl | $CH_3$ | $N(CH_3)$—$OCH_3$ | B | 1.448 | 477.0 |
| 2-67 | Cl, H, Cl | $CH_3$ | NH—$CH_2$-(2-oxazolyl) | B | 1.363 | 514.1 |
| 2-68 | Cl, H, Cl | $CH_3$ | NH-(3-oxetanyl) | B | 1.223 | 489.1 |
| 2-69 | Cl, H, Cl | $CH_3$ | pyrrolidin-1-yl | B | 1.463 | 487.3 |
| 2-70 | Cl, H, Cl | $CH_3$ | azetidin-1-yl | B | 1.422 | 474.8 |
| 2-71 | Cl, H, Cl | $CH_3$ | NH-cyclobutyl | B | 1.467 | 487.0 |
| 2-72 | Cl, H, Cl | $CH_3$ | NH—$CH_2$-(3-isoxazolyl) | B | 1.383 | 514.1 |
| 2-73 | Cl, H, Cl | $CH_3$ | $N(CH_2CH_3)$—$CH_2$-(4-thiazolyl) | B | 1.467 | 558.2 |
| 2-74 | Cl, H, Cl | $CH_3$ | $NHCH_2$-(2-thiazolyl) | B | 1.380 | 530.2 |
| 2-75 | Cl, H, Cl | $CH_3$ | aziridin-1-yl | B | 1.502 | 459.2 |
| 2-76 | Cl, H, Cl | $CH_3$ | morpholino | B | 1.408 | 503.0 |
| 2-77 | Cl, H, Cl | $CH_3$ | thiazolidin-3-yl | B | 1.476 | 505.1 |
| 2-78 | Cl, H, Cl | $CH_3$ | thiomorpholino | B | 1.489 | 519.0 |
| 2-79 | Cl, H, Cl | $CH_3$ | 1,1-dioxo-1,4-thiazinan-4-yl | B | 1.356 | 551.2 |
| 2-80 | Cl, H, Cl | $CH_3$ | 1-piperidyl | B | 1.533 | 501.3 |
| 2-81 | Cl, H, Cl | $CH_3$ | NH-[1-cyano-cycloprop-1-yl] | B | 1.391 | 498.0 |
| 2-82 | Cl, H, Cl | $CH_3$ | NH-(cyclopropyl) | B | 1.409 | 473.0 |
| 2-83 | Cl, H, Cl | $CH_3$ | $NHCH_2CF_2H$ | B | 1.418 | 497.0 |
| 2-84 | Cl, H, Cl | $CH_3$ | $NHCH_2CH_2CF_3$ | B | 1.460 | 529.0 |
| 2-85 | Cl, H, Cl | $CH_3$ | $NHCH_2$-[1-cyano-cycloprop-1-yl] | B | 1.392 | 512.1 |
| 2-86 | Cl, H, Cl | $CH_3$ | $NHCH_2CH_3$ | B | 1.245 | 461.0 |
| 2-87 | Cl, H, Cl | $CH_3$ | $NHCH_3$ | B | 1.359 | 447.0 |
| 2-88 | Cl, H, Cl | $CH_3$ | $NHCH_2CCH$ | B | 1.396 | 471.0 |
| 2-89 | Cl, H, Cl | $CH_3$ | $NHCH_2CH=CH_2$ | B | 1.423 | 473.0 |
| 2-90 | Cl, H, Cl | $CH_3$ | $NHCH_2CH_2CF=CF_2$ | B | 1.477 | 541.0 |
| 2-91 | Cl, H, Cl | $CH_3$ | $NHCH(CH_3)_2$ | B | 1.445 | 475.0 |
| 2-92 | Cl, H, Cl | $CH_3$ | $NHCH_2C(CH_3)_3$ | B | 1.529 | 504.8 |
| 2-93 | Cl, H, Cl | $CH_3$ | $NHCH_2CH_2CH_3$ | B | 1.445 | 475.4 |
| 2-94 | Cl, H, Cl | $CH_3$ | $NHCH_2CH(CH_3)_2$ | B | 1.487 | 489.0 |
| 2-95 | Cl, H, Cl | $CH_3$ | $NHCH_2CN$ | B | 1.365 | 472.0 |
| 2-96 | Cl, H, Cl | $CH_3$ | $NHCH(CF_3)_2$ | B | 1.546 | 583.0 |
| 2-97 | Cl, H, Cl | $CH_3$ | $NHCH_2CH_2SCH_2CH_3$ | B | 1.476 | 521.0 |
| 2-98 | Cl, H, Cl | $CH_3$ | $NHC(CH_3)_2CH_2SCH_3$ | B | 1.534 | 535.1 |
| 2-99 | Cl, H, Cl | $CH_3$ | $NHCH(CH_3)CF_3$ | B | 1.481 | 529.3 |
| 2-100 | Cl, H, Cl | $CH_3$ | NH-(3,3-difluoro-cyclobut-1-yl) | B | 1.451 | 523.3 |
| 2-101 | Cl, H, Cl | $CH_3$ | $NHCH_2$-(1,2,3-thiadiazol-4-yl) | B | 1.386 | 532.7 |
| 2-102 | Cl, H, Cl | $CH_3$ | $NHCH_2$-(1,3,4-thiadiazol-2-yl) | B | 1.334 | 531.0 |
| 2-103 | Cl, H, Cl | $CH_3$ | $N=S[CH(CH_3)_2]_2$ | B | 1.355 | 549.3 |
| 2-104 | Cl, H, Cl | $CH_3$ | $N=S(CH_2CH_3)_2$ | B | 1.308 | 521.3 |
| 2-105 | Cl, H, Cl | $CH_3$ | $NHCH_2$-[2,2-dichloro-cycloprop-1-yl] | B | 1.510 | 557.2 |

TABLE C.2-continued

| Ex. | $R^{2a}$, $R^{2b}$, $R^{2c}$ | $R^4$ | Y | HPLC-MS: Method, $R_t$ (min) & $[M + H]^+$ or 1H-NMR | | |
|---|---|---|---|---|---|---|
| 2-106 | Cl, H, Cl | $CH_3$ | $NHCH_2$-(1-methylimidazol-2-yl) | B | 1.120 | 527.3 |
| 2-107 | Cl, H, Cl | $CH_3$ | $NHCH_2$-(5-oxazolyl) | B | 1.349 | 514.3 |
| 2-108 | Cl, H, Cl | $CH_3$ | $NHCH_2CH_2SCH_3$ | B | 1.544 | 507.0 |
| 2-109 | Cl, H, Cl | $CH_3$ | $NHCH(CH_3)CH_2SCH_3$ | B | 1.551 | 521.0 |
| 2-110 | Cl, H, Cl | $CH_3$ | $NHCH_2$-(2-Cl—$C_6H_4$) | B | 1.533 | 557.0 |
| 2-111 | Cl, H, Cl | $CH_3$ | $NHCH_2$-(2-$OCH_3$ $C_6H_4$) | B | 1.501 | 557.0 |
| 2-112 | Cl, H, Cl | $CH_3$ | $NHCH(CH_3)CH_2SO_2CH_3$ | B | 1.340 | 553.0 |
| 2-113 | Cl, H, Cl | $CH_3$ | 1-oxo-1,4-thiazinan-4-yl | B | 1.279 | 535.0 |
| 2-114 | Cl, H, Cl | $CH_3$ | $N(CH_2CN)$ $CH_2$-(2-pyridyl) | B | 1.392 | 564.9 |
| 2-115 | Cl, H, Cl | $CH_3$ | $NHCH_2$-(1-$CH_3$-pyrazol-3-yl) | B | 1.368 | 527.3 |
| 2-116 | Cl, H, Cl | $CH_3$ | $NHCH_2$-(2-$CH_3$-pyrazol-3-yl) | B | 1.364 | 527.3 |
| 2-117 | Cl, H, Cl | $CH_3$ | $NHCH_2$-(1-$CH_3$-imidazol-4-yl) | B | 1.124 | 527.3 |
| 2-118 | Cl, H, Cl | $CH_3$ | $NHCH_2$-(4-oxazolyl) | B | 1.361 | 514.3 |
| 2-119 | Cl, H, Cl | $CH_3$ | $NHCH_2$-(2-oxetanyl) | B | 1.376 | 503.3 |
| 2-120 | Cl, H, Cl | $CH_3$ | NH-(3-tetrahydrofuranyl) | B | 1.358 | 503.0 |
| 2-121 | Cl, H, Cl | $CH_3$ | NH-[(2-pyridyl)cycloprop-1-yl] | B | 1.234 | 550.1 |
| 2-122 | Cl, Cl, Cl | $CH_3$ | $OC(CH_3)_3$ | 1H NMR (400 MHz, $CDCl_3$): δ 7.8 (d, 1H), 7.6-7.5 (m, 1H), 7.4 (s, 2H), 4.2 (d, 1H), 3.9 (d, 1H), 2.6 (s, 3H), 1.6 (s, 9H) | | |
| 2-123 | Cl, H, Cl | $CH_3$ | $NHCH_2$-(2-$SCH_3$—$C_6H_4$) | B | 1.539 | 569.5 |
| 2-124 | Cl, H, Cl | $CH_3$ | $NHCH_2CH_2SO_2CH_3$ | B | 1.323 | 539.4 |
| 2-125 | Cl, H, Cl | $CH_3$ | $NHCH_2$-(2-$SO_2CH_3$—$C_6H_4$) | B | 1.435 | 601.5 |
| 2-126 | Cl, Cl, Cl | $CH_3$ | NH-(1,1-dioxo-thiethan-3-yl) | B | 1.389 | 571.9 |
| 2-127 | Cl, Cl, Cl | $CH_3$ | $NHCH_2C(=O)$—$NHCH_2CF_3$ | B | 1.439 | 606.8 |
| 2-128 | Cl, Cl, Cl | $CH_3$ | $NHCH_2$-(2-pyridyl) | B | 1.251 | 558.8 |
| 2-129 | Cl, H, Cl | $CH_3$ | NH-[(1R)-(2-pyridyl)eth-1-yl] | B | 1.233 | 538.3 |
| 2-130 | Cl, H, Cl | $CH_3$ | NH-[(1S)-(2-pyridyl)eth-1-yl] | B | 1.221 | 538.3 |
| 2-131 | Cl, Cl, Cl | $CH_3$ | $NHCH_2CF_3$ | B | 1.500 | 549.7 |
| 2-132 | Cl, Cl, Cl | $CH_3$ | $NHCH_2$-(4-thiazolyl) | B | 1.426 | 564.9 |
| 2-133 | Cl, Cl, Cl | $CH_3$ | NH-(3-thiethanyl) | B | 1.492 | 539.0 |
| 2-134 | Cl, H, Cl | $CH_3$ | $NHCH_2$-(3-pyridazinyl) | B | 1.302 | 525.3 |
| 2-135 | Cl, H, Cl | $CH_3$ | $NHCH_2$-(4-isoxazolyl) | B | 1.376 | 514.2 |
| 2-136 | Cl, H, Cl | $CH_3$ | $NHCH_2$-(5-thiazolyl) | B | 1.354 | 530.3 |
| 2-137 | Cl, Cl, Cl | $SCH_3$ | $NHCH_2$-(2-pyridyl) | B | 1.243 | 592.1 |
| 2-138 | Cl, Cl, Cl | $SCH_3$ | $NHCH_2CF_3$ | B | 1.500 | 581.1 |
| 2-139 | Cl, Cl, Cl | $SCH_3$ | NH-(1,1-dioxo-thiethan-3-yl) | B | 1.403 | 605.1 |
| 2-140 | Cl, Cl, Cl | $SCH_3$ | $NHCH_2C(=O)$—$NHCH_2CF_3$ | B | 1.434 | 640.0 |
| 2-141 | Cl, Cl, Cl | $SCH_3$ | $NHCH_2$-(4-thiazolyl) | B | 1.442 | 598.0 |
| 2-142 | Cl, Cl, Cl | $SCH_3$ | $NHCH_2$-(2-thiazolyl) | B | 1.444 | 598.0 |
| 2-143 | Cl, Cl, Cl | $CH_3$ | $NHCH_2$-(2-thiazolyl) | B | 1.449 | 566.1 |
| 2-144 | Cl, H, Cl | $CH_3$ | $NHCH(CH_3)C(=O)$—$NHCH_2CF_3$ | B | 1.402 | 586.2 |
| 2-145 | Cl, H, Cl | $CH_3$ | $NHCH_2C(=O)$—$NHCH_2CH_3$ | B | 1.326 | 518.2 |
| 2-146 | Cl, H, Cl | $CH_3$ | $NHCH_2C(=O)$—$NHCH(CH_3)_2$ | B | 1.362 | 532.2 |
| 2-147 | Cl, H, Cl | $CH_3$ | $NHCH_2C(=O)$—$NHCH_3$ | B | 1.281 | 504.2 |
| 2-148 | Cl, H, Cl | $CH_3$ | $NHCH_2C(=O)$—$NHCH_2CH_2CH_3$ | B | 1.355 | 532.3 |
| 2-149 | Cl, H, Cl | $CH_3$ | $NHCH_2$-(1,3-dioxolan-2-yl) | B | 1.368 | 519.2 |
| 2-150 | Cl, Cl, Cl | Cl | $NHCH_2$-(2-pyridyl) | B | 1.245 | 580.1 |
| 2-151 | Cl, Cl, Cl | Cl | $NHCH_2$-(2-pyrimidyl) | B | 1.433 | 581.1 |
| 2-152 | Cl, Cl, Cl | Cl | $NHCH_2$-(2-thiazolyl) | B | 1.450 | 586.1 |
| 2-153 | Cl, Cl, Cl | Cl | $NHCH_2C(=O)$—$NHCH_2CF_3$ | B | 1.440 | 628.1 |
| 2-154 | Cl, Cl, Cl | Cl | $NHCH_2CF_3$ | B | 1.508 | 571.1 |
| 2-155 | Cl, Cl, Cl | Cl | NH-(1,1-dioxo-thiethan-3-yl) | 1H NMR (400 MHz, $CDCl_3$): δ 7.8 (s, 1H), 7.8-7.6 (m, 2H), 7.4 (s, 2H), 7.1 (d, 1H), 5.0-4.8 (m, 1H), 4.7-4.6 (m, 2H), 4.2 (d, 1H), 4.2-4.0 (m, 2H), 3.9 (d, 1H) | | |
| 2-156 | Cl, H, Cl | $CH_3$ | OH | B | 1.419 | 434.1 |
| 2-157 | Cl, Cl, Cl | $CH_3$ | OH | B | 1.472 | 470.1 |

TABLE C.2-continued

| Ex. | $R^{2a}, R^{2b}, R^{2c}$ | $R^4$ | Y | HPLC-MS: Method, $R_t$ (min) & $[M + H]^+$ or 1H-NMR | | |
|---|---|---|---|---|---|---|
| 2-158 | Cl, Cl, Cl | SCH$_3$ | OH | B | 1.466 | 500.1 |
| 2-159 | Cl, Cl, Cl | Cl | OH | B | 1.477 | 490.0 |
| 2-160 | Cl, F, Cl | CH$_3$ | OC(CH$_3$)$_3$ | B | 1.678 | 508.2 |
| 2-161 | Cl, F, Cl | CH$_3$ | OH | B | 1.417 | 454.0 |
| 2-162 | Cl, F, Cl | CH$_3$ | NHCH$_2$C(=O)—NHCH$_2$CF$_3$ | B | 1.373 | 590.2 |
| 2-163 | Cl, F, Cl | CH$_3$ | NH-(1,1-dioxo-thiethan-3-yl) | B | 1.344 | 555.2 |
| 2-164 | Cl, F, Cl | CH$_3$ | NHCH$_2$-(2-pyridyl) | B | 1.190 | 542.3 |
| 2-165 | Cl, F, Cl | CH$_3$ | NHCH$_2$CF$_3$ | B | 1.451 | 533.3 |
| 2-166 | Cl, F, Cl | CH$_3$ | NHCH$_2$-(2-thiazolyl) | B | 1.391 | 548.1 |
| 2-167 | Cl, Cl, Cl | OCH$_3$ | OC(CH$_3$)$_3$ | B | 1.651 | 542.2 |
| 2-168 | Cl, Cl, Cl | OCH$_3$ | OH | B | 1.424 | 484.2 |
| 2-169 | Cl, Cl, Cl | OCH$_3$ | NHCH$_2$C(=O)—NHCH$_2$CF$_3$ | B | 1.434 | 624.1 |
| 2-170 | Cl, Cl, Cl | OCH$_3$ | NH-(1,1-dioxo-thiethan-3-yl) | B | 1.410 | 589.1 |
| 2-171 | Cl, Cl, Cl | OCH$_3$ | NHCH$_2$-(2-pyridyl) | B | 1.245 | 574.1 |
| 2-172 | Cl, Cl, Cl | OCH$_3$ | NHCH$_2$-(2-thiazolyl) | B | 1.469 | 580.1 |
| 2-173 | Cl, Cl, Cl | OCH$_3$ | NHCH$_2$CH$_2$CF$_3$ | B | 1.537 | 579.1 |
| 2-174 | Cl, H, CF$_3$ | CH$_3$ | OC(CH$_3$)$_3$ | B | 1.657 | 524.3 |
| 2-175 | Cl, Cl, Cl | H | OC(CH$_3$)$_3$ | B | 1.687 | 512.1 |
| 2-176 | Cl, H, CF$_3$ | CH$_3$ | OH | B | 1.413 | 468.2 |
| 2-177 | Cl, Cl, Cl | H | OH | B | 1.435 | 456.1 |
| 2-178 | Cl, H, Cl | CH$_3$ | NHNH-(2-pyridyl) | B | 1.153 | 525.2 |
| 2-179 | Cl, H, Cl | CH$_3$ | NHN(CH$_3$)-(2-pyridyl) | B | 1.201 | 539.2 |
| 2-180 | Cl, H, Cl | CH$_3$ | NHCH$_2$CH$_2$CH$_3$ | B | 1.480 | 489.2 |
| 2-181 | Cl, H, CF$_3$ | CH$_3$ | NHCH$_2$C(=O)—NHCH$_2$CF$_3$ | B | 1.358 | 606.3 |
| 2-182 | Cl, H, CF$_3$ | CH$_3$ | NHCH$_2$-(2-pyridyl) | B | 1.185 | 558.4 |
| 2-183 | Cl, H, CF$_3$ | CH$_3$ | NH-(1,1-dioxo-thiethan-3-yl) | B | 1.343 | 571.2 |
| 2-184 | Cl, H, CF$_3$ | CH$_3$ | NHCH$_2$-(2-thiazolyl) | B | 1.384 | 564.2 |
| 2-185 | Cl, H, CF$_3$ | CH$_3$ | NHCH$_2$CF$_3$ | B | 1.450 | 563.2 |
| 2-186 | Cl, Cl, Cl | H | NHCH$_2$C(=O)—NHCH$_2$CF$_3$ | B | 1.393 | 594.2 |
| 2-187 | Cl, Cl, Cl | H | NH-(1,1-dioxo-thiethan-3-yl) | 1H NMR (400 MHz, CDCl$_3$): δ 8.1-7.7 (m, 4H), 7.4 (s, 2H), 6.9-6.8 (m, 1H), 5.0-4.8 (m, 1H), 4.8-4.6 (m, 2H), 4.2 (d, 1H), 4.2-4.0 (m, 2H), 3.9 (d, 1H) | | |
| 2-188 | Cl, Cl, Cl | H | NHCH$_2$-(2-pyridyl) | B | 1.211 | 544.1 |
| 2-189 | Cl, Cl, Cl | H | NHCH$_2$-(2-thiazolyl) | B | 1.409 | 552.1 |
| 2-190 | Cl, Cl, Cl | H | NHCH$_2$CF$_3$ | B | 1.470 | 550.3 |
| 2-191 | Cl, H, Cl | CH$_3$ | NHCH$_2$-(6-CF$_3$-pyrid-2-yl) | B | 1.310 | 592.3 |
| 2-192 | Cl, H, Cl | CH$_3$ | NHNHC(=O)—NHCH$_2$CF$_3$ | B | 1.317 | 573.3 |
| 2-193 | Cl, H, Cl | CH$_3$ | NH-(2-oxotetrahydrofuran-3-yl) | B | 1.335 | 517.2 |
| 2-194 | Cl, H, Cl | CH$_3$ | OCH$_2$-(2-pyridyl) | B | 1.420 | 525.3 |
| 2-195 | Cl, H, Cl | CH$_3$ | NH-[2-oxo-1-(2,2,2-trifluoroethyl)pyrrolidin-3-yl] | B | 1.388 | 598.2 |
| 2-196 | Cl, H, Cl | CH$_3$ | OCH$_2$CH$_2$CF$_3$ | B | 1.593 | 530.2 |
| 2-197 | Cl, H, Cl | CH$_3$ | NH-(2-pyrazinyl) | B | 1.421 | 511.2 |
| 2-198 | Cl, H, Cl | CH$_3$ | NH$_2$ | B | 1.310 | 433.2 |
| 2-199 | Cl, H, Cl | CH$_3$ | NHCH=NOCH$_3$ | B | 1.459 | 490.3 |
| 2-200 | Cl, H, Cl | CH$_3$ | NH-(1-acetylazetidin-3-yl) | B | 1.284 | 530.3 |
| 2-201 | Cl, H, Cl | CH$_3$ | NH-(1-methyl-2-oxo-pyrrolidin-3-yl) | B | 1.296 | 530.3 |
| 2-202 | Cl, H, Cl | CH$_3$ | NHCH$_2$CH$_2$OH | A | 3.705 | 477.0 |
| 2-203 | Cl, H, Cl | CH$_3$ | NHCH$_2$CH$_2$OCH$_2$CH$_3$ | A | 4.141 | 505.0 |
| 2-204 | Cl, H, Cl | CH$_3$ | NHCH$_2$CH$_2$OCH$_2$CF$_3$ | A | 4.277 | 559.0 |
| 2-205 | Cl, H, Cl | CH$_3$ | NH2 | B | 1.398 | 434.2 |
| 2-206 | Cl, H, Cl | CH$_3$ | NHCH$_2$CH$_2$OCH$_3$ | B | 1.353 | 491.4 |
| 2-207 | Cl, H, Cl | CH$_3$ | NHCH(CH$_3$)CH$_2$OCH$_3$ | B | 1.393 | 505.3 |
| 2-208 | Cl, H, Cl | CH$_3$ | NHCH$_2$CH$_2$CH$_2$CF$_3$ | B | 1.459 | 543.0 |
| 2-209 | Cl, H, Cl | CH$_3$ | NHCH$_2$CF$_2$CF$_3$ | B | 1.494 | 565.2 |
| 2-210 | Cl, H, Cl | CH$_3$ | NHCH$_2$CH$_2$SCF$_3$ | B | 1.487 | 561.4 |
| 2-211 | Cl, H, Cl | CH$_3$ | NHCH$_2$CH$_2$OCF$_3$ | B | 1.447 | 545.3 |
| 2-212 | Cl, H, Cl | CH$_3$ | N(CH$_3$)—CH$_2$C(=O)—NHCH$_2$CF$_3$ | B | 1.377 | 586.4 |
| 2-213 | Cl, H, Cl | SCH$_3$ | NHCH$_2$CF$_3$ | B | 1.444 | 547.1 |
| 2-214 | Cl, H, Cl | SCH$_3$ | pyrrolidin-1-yl | B | 1.463 | 519.2 |
| 2-215 | Cl, H, Cl | SCH$_3$ | NHCH$_2$-(2-pyridyl) | B | 1.200 | 556.2 |
| 2-216 | Cl, H, Cl | SCH$_3$ | NHCH$_2$C(=O)—NHCH$_2$CF$_3$ | B | 1.369 | 604.2 |
| 2-217 | Cl, H, Cl | SCH$_3$ | NHCH$_2$-(2-pyrimidyl) | B | 1.346 | 557.2 |
| 2-218 | Cl, H, Cl | SCH$_3$ | NHCH$_2$-(2-thiazolyl) | B | 1.371 | 564.0 |
| 2-219 | Cl, H, Cl | SCH$_3$ | NH-(1,1-dioxo-thiethan-3-yl) | B | 1.331 | 569.2 |
| 2-220 | Cl, H, Cl | SCH$_3$ | NH-(3-thietanyl) | B | 1.425 | 538.9 |
| 2-221 | Cl, H, Cl | CH$_3$ | NHCH$_2$C(=O)—NHCH$_2$CCH | B | 1.319 | 528.4 |
| 2-222 | Cl, H, Cl | CH$_3$ | NHCH$_2$C(=O)—N(CH$_3$)—CH$_2$CF$_3$ | B | 1.402 | 586.4 |
| 2-223 | Cl, H, Cl | CH$_3$ | NH-(4-CF$_3$-thiazol-2-yl) | B | 1.407 | 584.4 |

TABLE C.2-continued

| Ex. | $R^{2a}, R^{2b}, R^{2c}$ | $R^4$ | Y | HPLC-MS: Method, $R_t$ (min) & $[M + H]^+$ or 1H-NMR | | |
|---|---|---|---|---|---|---|
| 2-224 | Cl, Cl, Cl | $CH_3$ | $NHCH_2$-(2-pyrimidyl) | B | 1.397 | 561.1 |
| 2-225 | Cl, F, Cl | $CH_3$ | $NHCH_2$-(2-pyrimidyl) | B | 1.340 | 543.2 |
| 2-226 | Cl, H, Cl | $CH_3$ | $NHCH_2$-(5-Cl-pyrid-2-yl) | B | 1.400 | 560.1 |
| 2-227 | Cl, H, $CF_3$ | $CH_3$ | $NHCH_2$-(2-pyrimidyl) | B | 1.382 | 559.2 |
| 2-228 | Cl, H, Cl | $CH_3$ | NHNH-(2-pyrimidyl) | B | 1.341 | 526.2 |
| 2-229 | Cl, H, Cl | $CH_3$ | NH-(5-pyrimidyl) | B | 1.382 | 511.0 |
| 2-230 | Cl, H, Cl | $CH_3$ | NH-(2-pyrimidyl) | B | 1.349 | 511.0 |
| 2-231 | Cl, H, Cl | $CH_3$ | $NHCH=NOCH_2CF_3$ | B | 1.527 | 557.9 |
| 2-232 | Cl, H, Cl | $CH_3$ | $NHNHC(=O)-NHCH_2CHF_2$ | B | 1.318 | 555.4 |
| 2-233 | Cl, H, Cl | $CH_3$ | $NHCH_2C(=O)-NHCH_2CN$ | B | 1.300 | 529.3 |
| 2-234 | Cl, H, Cl | $CH_3$ | NH-(3-oxo-isoxazolidin-4-yl) | B | 1.282 | 519.9 |

C.3 Compound Examples 3

Compound examples 3-1 to 3-28 correspond to compounds of formula C.3:

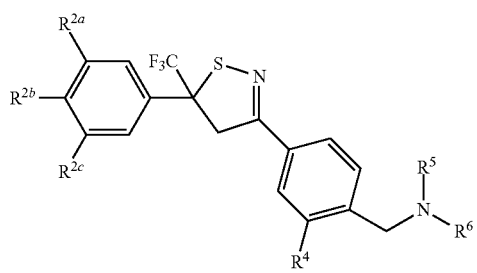

C.3 wherein $R^{2a}$, $R^{2b}$, $R^{2c}$, $R^4$, $R^5$ and $R^6$ of each synthesized compound is defined in one row of table C.3 below.

The compounds were synthesized in analogy to Synthesis Example S.3.

TABLE C.3

| Ex. | $R^{2a}, R^{2b}, R^{2c}$ | $R^4$ | $R^5$ | $R^6$ | HPLC-MS: Method, $R_t$ (min) and $[M + H]^+$ | | |
|---|---|---|---|---|---|---|---|
| 3-1 | Cl, H, Cl | $CH_3$ | H | $C(=O)CH_2SCH_2CH_3$ | B | 1.503 | 521.1 |
| 3-2 | Cl, H, Cl | $CH_3$ | $C_2H_5$ | H | B | 1.142 | 447.3 |
| 3-3 | Cl, H, Cl | $CH_3$ | $C_2H_5$ | $C(=O)CH_2SCH_2CH_3$ | A | 4.639 | 549.0 |
| 3-4 | Cl, H, Cl | $CH_3$ | $C_2H_5$ | $C(=O)$-(cyclopropyl) | A | 4.547 | 515.0 |
| 3-5 | Cl, H, Cl | $CH_3$ | $C_2H_5$ | $C(=O)CH_2SO_2CH_3$ | A | 4.214 | 567.0 |
| 3-6 | Cl, H, Cl | Cl | H | H | B | 1.085 | 440.8 |
| 3-7 | Cl, H, Cl | Cl | H | $C(=O)CH_2SCH_2CH_3$ | B | 1.511 | 542.9 |
| 3-8 | Cl, H, Cl | Cl | H | $C(=O)CH_2SO_2CH_3$ | B | 1.376 | 560.9 |
| 3-9 | Cl, H, Cl | Cl | H | $C(=O)$ (cyclopropyl) | B | 1.461 | 508.9 |
| 3-10 | Cl, H, Cl | Cl | $C_2H_5$ | $C(=O)CH_2CF_3$ | B | 1.555 | 579.2 |
| 3-11 | Cl, H, Cl | Cl | $C_2H_5$ | $C(=O)CH_3$ | B | 1.513 | 511.1 |
| 3-12 | Cl, H, Cl | Cl | $C_2H_5$ | $C(=O)C_2H_5$ | B | 1.560 | 525.1 |
| 3-13 | Cl, H, Cl | Cl | $C_2H_5$ | $C(=O)$-pyrid-3-yl | B | 1.395 | 574.1 |
| 3-14 | Cl, H, Cl | Cl | $C_2H_5$ | $C(=O)$-pyrid-2-yl | B | 1.534 | 574.1 |
| 3-15 | Cl, H, Cl | Cl | $C_2H_5$ | $C(=O)$-2,3-difluorophenyl | B | 1.601 | 609.2 |
| 3-16 | Cl, H, Cl | Cl | $C_2H_5$ | $C(=O)C_6H_5$ | B | 1.598 | 573.1 |
| 3-17 | Cl, H, Cl | Cl | $C_2H_5$ | $C(=O)$-(cyclopropyl) | B | 1.566 | 537.1 |
| 3-18 | Cl, H, Cl | Cl | $C_2H_5$ | $C(=O)CH_2SO_2CH_3$ | B | 1.455 | 589.1 |
| 3-19 | Cl, H, Cl | Cl | $C_2H_5$ | $C(=O)CH_2SCH_2CH_3$ | B | 1.596 | 571.0 |
| 3-20 | Cl, H, Cl | Cl | $C_2H_5$ | $C(=O)CH_2SCF_3$ | B | 1.603 | 611.0 |
| 3-21 | Cl, H, Cl | Cl | H | $C(=O)C_2H_5$ | B | 1.430 | 497.2 |
| 3-22 | Cl, H, Cl | Cl | H | $C(=O)NHCH_2CF_3$ | B | 1.424 | 566.2 |
| 3-23 | Cl, H, Cl | Cl | H | $C(=O)CH_3$ | B | 1.379 | 481.1 |
| 3-24 | Cl, H, Cl | Cl | H | $C(=O)CH_2CF_3$ | B | 1.462 | 551.2 |
| 3-25 | Cl, H, Cl | Cl | $C_2H_5$ | $C(=O)CH(CH_3)_2$ | B | 1.591 | 537.2 |
| 3-26 | Cl, H, Cl | Cl | H | $C(=O)NHCH_2CH_3$ | B | 1.399 | 512.1 |
| 3-27 | Cl, H, Cl | Cl | H | $C(=O)CH(CH_3)_2$ | B | 1.497 | 509.2 |
| 3-28 | Cl, H, Cl | Cl | $C_2H_5$ | $C(=O)$-(1,1-dioxothietan-3-yl) | B | 1.495 | 601.2 |

C.4 Compound Examples 4

Compound example 4-1 corresponds to compounds of formula C.4:

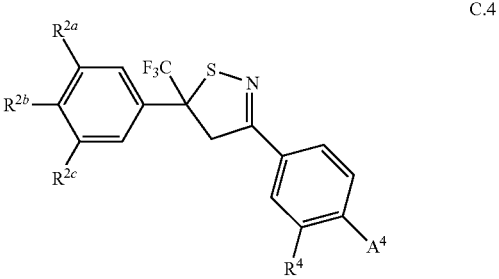

C.4 wherein $R^{2a}$, $R^{2b}$, $R^{2c}$, $R^4$, and $A^4$ of each synthesized compound is defined in one row of table C.4 below.

Compound 4-1 was synthesized in analogy to Synthesis Example S.2. The starting material (2-(1,2,4-triazol-1-yl)-5-[(Z)-4,4,4-trifluoro-3-(3,4,5-trichlorophenyl)but-2-enoyl] benzonitrile) was prepared in analogy to the method described in EP-A-2172462.

TABLE C.4

| Ex. | $R^{2a}, R^{2b}, R^{2c}$ | —$R^4$ | $A^4$ | HPLC-MS: Method, $R_t$ (min) and $[M + H]^+$ | | |
|---|---|---|---|---|---|---|
| 4-1 | Cl, Cl, Cl | —CN | 1,2,4-triazol-1-yl | B | 1.463 | 504.1 |

C.5 Compound Examples 5

Compound examples 5-1 to 5-15 correspond to compounds of formula C.5:

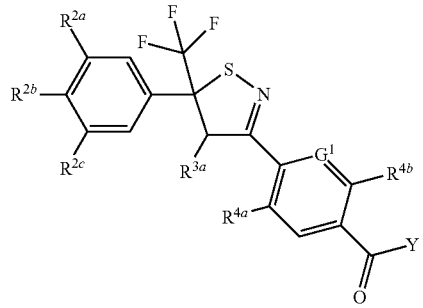

wherein $R^{2a}$, $R^{2b}$, $R^{2c}$, $R^{3a}$, $G^1$, $R^{4a}$, $R^{4b}$, and Y of each synthesized compound is defined in one row of table C.5 below.

Compounds 5-1 to 5-3 were synthesized in analogy to Synthesis Example S.4.

Compounds 5-4 to 5-15 were synthesized in analogy to Synthesis Example S.2.

TABLE C.5

| Ex. | $R^{2a}, R^{2b}, R^{2c}$ | $R^{3a}$ | $G^1$ | $R^{4a}$ | $R^{4b}$ | Y | HPLC-MS: Method, $R_t$ (min) & $[M + H]^+$ or $^1$H-NMR | | |
|---|---|---|---|---|---|---|---|---|---|
| 5-1 | Cl, H, Cl | F | CH | H | CH$_3$ | NHCH$_2$C(=O)—NHCH$_2$CF$_3$ | B | 1.364 | 590.2 |
| 5-2 | Cl, H, Cl | F | CH | H | CH$_3$ | NHCH$_2$-(2-pyridyl) | B | 1.192 | 543.9 |
| 5-3 | Cl, H, Cl | F | CH | H | CH$_3$ | NH-(1,1-dioxo-thiethan-3-yl) | 1H NMR (400 MHz, CDCl$_3$): δ 7.8-7.7 (m, 2H), 7.5-7.4 (m, 2H), 7.3 (s, 2H), 6.5 (d, 1H), 6.3 (d, 1H, CHF), 5.0-4.8 (m, 1H), 4.7-4.5 (m, 2H), 4.1-3.9 (m, 2H), 2.5 (s, 3H) | | |
| 5-4 | Cl, Cl, Cl | H | N | H | CH$_3$ | NHCH$_2$C(=O)—NHCH$_2$CF$_3$ | B | 1.432 | 608.8 |
| 5-5 | Cl, Cl, Cl | H | N | H | CH$_3$ | NHCH$_2$-(2-pyridyl) | B | 1.254 | 559.2 |
| 5-6 | Cl, Cl, Cl | H | N | H | CH$_3$ | NHCH$_2$-(2-pyrimidyl) | B | 1.396 | 561.8 |
| 5-7 | Cl, Cl, Cl | H | N | H | CH$_3$ | NH-(1,1-dioxo-thiethan-3-yl) | B | 1.376 | 573.7 |
| 5-8 | Cl, Cl, Cl | H | N | H | CH$_3$ | NHCH$_2$CH$_2$CF$_3$ | B | 1.504 | 563.9 |
| 5-9 | Cl, Cl, Cl | H | CCH$_3$ | CH$_3$ | H | OCH$_3$ | 1H NMR (400 MHz, CDCl$_3$): δ 7.7 (s, 2H), 7.4 (s, 2H), 4.0 (d, 1H), 3.9 (s, 3H), 3.6 (d, 1H), 2.3 (s, 6H) | | |
| 5-10 | Cl, Cl, Cl | H | CCH$_3$ | CH$_3$ | H | NHCH$_2$C(=O)—NHCH$_2$CF$_3$ | B | 1.445 | 621.8 |
| 5-11 | Cl, Cl, Cl | H | CCH$_3$ | CH$_3$ | H | NHCH$_2$-(2-pyridyl) | B | 1.256 | 574.1 |
| 5-12 | Cl, Cl, Cl | H | CCH$_3$ | CH$_3$ | H | NHCH$_2$CF$_3$ | B | 1.512 | 564.9 |
| 5-13 | Cl, Cl, Cl | H | CCH$_3$ | CH$_3$ | H | NHCH$_2$-(2-thiazolyl) | B | 1.447 | 579.8 |
| 5-14 | Cl, Cl, Cl | H | CCH$_3$ | CH$_3$ | H | NHCH$_2$-(2-pyrimidyl) | B | 1.415 | 574.8 |
| 5-15 | Cl, Cl, Cl | H | CCH$_3$ | CH$_3$ | H | NH-(1,1-dioxo-thiethan-3-yl) | B | 1.436 | 585.1 |

C.6 Compound Examples 6

Intermediates

Intermediates 6-1 to 6-7 correspond to compounds of formula C.6:

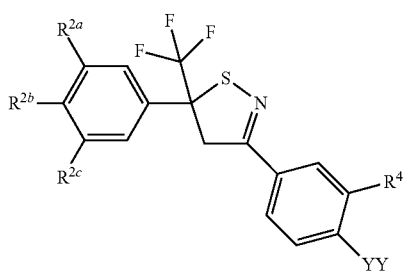

C.6 wherein $R^{2a}$, $R^{2b}$, $R^{2c}$, $R^4$, and YY of each synthesized compound is defined in one row of table C.6 below.

| Ex. | $R^{2a}, R^{2b}, R^{2c}$ | $R^4$ | YY | HPLC-MS: Method, $R_t$ (min) & $[M + H]^+$ or 1H-NMR |
|---|---|---|---|---|
| 6-1 | Cl, H, Cl | CH₃ | Br | 1H NMR (400 MHz, CDCl₃): δ 7.7-7.5 (m, 2H), 7.5-7.3 (m, 2H), 7.3 (s, 2H), 4.2 (d, 1H), 3.8 (d, 1H), 2.4 (s, 3H) |
| 6-2 | Cl, H, Cl | Cl | Br | B    1.676    489.8 |
| 6-3 | Cl, H, Cl | F | Br | 1H NMR (400 MHz, CDCl₃): δ 7.7-7.5 (m, 2H), 7.5-7.3 (m, 2H), 7.3 (s, 2H), 4.2 (d, 1H), 3.8 (d, 1H) |
| 6-4 | Cl, H, Cl | Cl | CH₂OH | 1H NMR (400 MHz, CDCl₃): δ 7.8 (s, 1H), 7.7-7.5 (m, 2H), 7.4 (s, 1H), 7.3, (s, 2H), 4.8 (s, 2H), 4.2 (d, 1H), 3.8 (d, 1H), 1.7 (br. s, 1H) |
| 6-5 | Cl, Cl, Cl | OCH₃ | CH₂OH | 1H NMR (400 MHz, CDCl₃): δ 7.5-7.4 (m, 3H), 7.3 (d, 1H), 7.2 (d, 1H), 4.7 (s, 2H), 4.2 (d, 1H), 3.9 (s, 3H), 3.8 (d, 1H) |
| 6-6 | Cl, H, Cl | Cl | CH₂N₃ | 1H NMR (400 MHz, CDCl₃): δ 7.8 (s, 1 H), 7.7 (d, 1H), 7.5 (d, 1H), 7.4 (s, 1H), 7.3, (s, 2H), 4.5 (s, 2H), 4.2 (d, 1H), 3.8 (d, 1H) |
| 6-7 | Cl, H, Cl | CH₃ | CH₂OH | 1H NMR (400 MHz, CDCl₃): δ 7.7-7.5 (m, 2H), 7.5 (d, 1H), 7.4 (s, 1H), 7.3, (s, 2H), 4.7 (s, 2H), 4.2 (d, 1H), 3.8 (d, 1H), 2.4 (s, 3H), 1.7 (br. s, 1H) |

Synthesis Example S.1

1-[(E)-[4-[5-(3,5-dichlorophenyl)-5-(trifluoromethyl)-4H-isothiazol-3-yl]-2-methyl-phenyl]methyleneamino]-3-ethyl-urea (Compound example 1-5; compound of formula IA, wherein $R^{2a}$ and $R^{2c}$ are Cl, $R^2$ is H, $R^4$ is methyl and A is $A^1$=—CH(=N—NH—C(=O)—NH—CH₂CH₃).

Step 1: 1-(4-Bromo-3-methyl-phenyl)-3-(3,5-dichlorophenyl)-3-sulfanyl-butan-1-one 1-(4-Bromo-3-methyl-phenyl)-3-(3,5-dichlorophenyl) but-2-en-1-one (21.5 g, 4:1-mixture of E/Z-isomers) in CH₂Cl₂ (400 mL) was treated with triethylamine (68 mL). At 0° C., gaseous hydrogen sulfide (H₂S) was bubbled through the solution for 10 min. The mixture was stirred for another 20 min at 0° C., and then diluted with CH₂Cl₂ (300 mL). The organic layer was washed with 6% aqueous hydrochloric acid (300 mL), dried (MgSO₄), filtered, and concentrated.

The product was obtained as a yellowish oil (23.1 g, 99.7%).

HPLC-MS (method B): 1.557 min, M=472.90.

Step 2: 3-(4-Bromo-3-methyl-phenyl)-5-(3,5-dichlorophenyl)-5-methyl-4H-isothiazole At −15° C., the product of step 1 (23 g) in CH₂Cl₂ (400 mL) was treated with triethylamine (27.1 mL) and with a solution of hydroxylamine-O-sulfonic acid ("HOSA", 6.23 g) in water (10 mL). The reaction was warmed to 0° C. and stirred at 0° C. for 45 min, and then diluted with CH₂Cl₂ (400 mL). The organic layer was washed with saturated aqueous NH₄Cl solution (3×), dried (MgSO₄), and filtered. To the obtained solution, acid washed molecular sieves (AW 300, 150 g) were added and the mixture was stirred vigorously for 90 min at room temperature. Then, the molecular sieves were filtered off, and the filtrate concentrated to afford a residue that was purified by flash chromatography on silica gel (ethyl acetate/cyclohexane). The obtained pale yellow solid (19.5 g) was titurated with hexanes (3×) to afford the product as a white solid (15.6 g, 68%).

HPLC-MS (method B): 1.697 min, M=469.90.

Step 3: Methyl 4-[5-(3,5-dichlorophenyl)-5-methyl-4H-isothiazol-3-yl]-2-methyl-benzoate The product of step 2 (14.6 g) in methanol/THF (63 mL/6 mL) was treated with [1,1'-bis(diphenylphosphino)ferrocene]dichloropalladium(II) ("Pd(dppf)Cl₂", 5.08 g), Pd(OAc)₂ (0.42 g), NaOAc (3.7 g). The reaction was subsequently pressurized twice with N₂ (3.5 bar) and three times with carbon monoxide (5 bar). Then, the mixture was pressurized with carbon monoxide (7.5 bar) and heated at 80° C. (internal temperature) for 13 h. Thereby, the carbon monoxide pressure was adjusted several times back to 7.5 bar. Then, the reaction was cooled to room temperature, filtered over celite (CH₂Cl₂) and subsequently filtered over a plug of silica gel. The product was obtained as a pale yellow foam (13.1 g, 89%).

HPLC-MS (method A): 3.974 min, M=566.00.

Step 4: [4-[5-(3,5-Dichlorophenyl)-5-(trifluoromethyl)-4H-isothiazol-3-yl]-2-methyl-phenyl]methanol To a solution of the product of step 3 (4.9 g) in CH₂Cl₂ (100 mL) at 0° C. was added a solution of DIBAL-H in toluene (1.5 M, 16 mL). The resulting solution was stirred at 0° C. for 90 min and quenched by adding MeOH (10 mL). A saturated solution of Rochelle's salt (potassium sodium tartrate, CAS 304-59-6) (100 mL) was added, followed by vigorous stirring at r.t. for 2 h. Then, $CH_2Cl_2$ (300 mL) was added, and the organic layer was washed with water, dried ($Na_2SO_4$), filtered, and concentrated to afford a residue that was purified by flash chromatography on silica gel (ethyl acetate/hexanes).

The product was obtained as pale yellow solid (3.45 g, 75%).

HPLC-MS (methode A): 4.390 min, M=419.95.

Step 5: 4-[5-(3,5-Dichlorophenyl)-5-(trifluoromethyl)-4H-isothiazol-3-yl]-2-methylbenzaldehyde To a solution of the product of step 1 (1 g) in $CH_2Cl_2$ (40 mL) at r.t. was added DessMartin-Periodane (CAS 87413-09-0) (1.11 g). The reaction was stirred overnight, filtered and concentrated. The residue was purified by flash chromatography on silica gel (ethyl acetate/cyclohexane). The product was obtained as a viscous oil (0.81 g, 81%).

HPLC-MS (method A): 4.036 min, M=417.90.

Step 6: 1-[(E)-[4-[5-(3,5-Dichlorophenyl)-5-(trifluoromethyl)-4H-isothiazol-3-yl]-2-methyl-phenyl]methyleneamino]-3-ethyl-urea A solution of the product of step 2 (0.15 g) and 1-ammonium-3-ethyl urea hydrochloride (60 mg) in EtOH (4 mL) and acetic acid (0.14 mL) was stirred at 70° C. overnight, and concentrated. The residue was purified by flash chromatography on silica gel (ethyl acetate/cyclohexane). The product was obtained as a pale yellow foam (0.10 g, 55%).

HPLC-MS (method B): 1.484 min, M=505.0.

Synthesis Example S.2

4-[5-(3,5-Dichlorophenyl)-5-trifluoromethyl-4H-isothiazol-3-yl]-2-methyl-N-[2-oxo-2-(2,2,2-trifluoroethylamino)ethyl]benzamide (Compound example 2-1; compound of formula IA, wherein $R^{2a}$ and $R^{2c}$ are Cl, $R^2$ is H, $R^4$ is methyl and A is $A^2$=—C(=O)—NH—$CH_2$—C(=O)—NH—$CH_2CF_3$)

Step 1: 4-[5-(3,5-dichlorophenyl)-5-methyl-4H-isothiazol-3-yl]-2-methyl-benzoic acid To a solution of methyl 4-[5-(3,5-dichlorophenyl)-5-methyl-4H-isothiazol-3-yl]-2-methyl-benzoate (=the product of step 3 of example 1) (2.4 g) in THF (50 mL) was added a solution of LiOH (0.51 g) in water (50 mL). The reaction was stirred for 16 h at room temperature, then diluted with water (300 mL) and washed with $CH_2Cl_2$ (3×). The aqueous phase was acidified with aqueous 1 M HCl to pH 1-2 and extracted with $CH_2Cl_2$ (3×). The combined organic layers were washed with water, dried ($Na_2SO_4$), filtered, and concentrated. The product was obtained as a pale yellow solid (2.24 g, 96%).

HPLC-MS (method A): 4.458 min, M=433.95.

Step 2: 4-[5-(3,5-Dichlorophenyl)-5-trifluoromethyl-4H-isothiazol-3-yl]-2-methyl-N-[2-oxo-2-(2,2,2-trifluoroethylamino)ethyl]benzamide To a solution of the product of step 1 (2.2 g), [2-oxo-2-(2,2,2-trifluoroethylamino)ethyl]ammonium chloride (1.22 g) and bromotripyrrolidinophosphonium hexafluorophosphate ("PyBroP", 2.95 g) in $CH_2Cl_2$ (100 mL) at room temperature was added N,N-diisopropylethylamine (3.53 mL). The reaction was stirred at room temperature for 16 h, then concentrated and redissolved in ethyl acetate (200 mL). The organic layer was washed with 5% aqueous HCl (2×) and 5% aqueous $K_2CO_3$ (2×), dried ($Na_2SO_4$), filtered, and concentrated to afford a residue that was purified by flash chromatography on silica gel (ethyl acetate/cyclohexane). The product was obtained as amorphous white foam (2.45 g, 84%).

HPLC-MS (method A): 4.045 min, M=572.00.

Synthesis Example S.3

N-[[4-[5-(3,5-Dichlorophenyl)-5-(trifluoromethyl)-4H-isothiazol-3-yl]-2-methyl-phenyl]methyl]-N-ethyl-2-ethylsulfanyl-acetamide (Compound example 3-3; compound of formula IA, wherein $R^{2a}$ and $R^{2c}$ are Cl, $R^2$ is H, $R^4$ is methyl and A is $A^3$=—$CH_2$—N($CH_2CH_3$)—C(=O)—$CH_2SCH_2CH_3$).

Step 1: N—[[4-[5-(3,5-dichlorophenyl)-5-(trifluoromethyl)-4H-isothiazol-3-yl]-2-methyl-phenyl]methyl]ethanamine To a solution of [4-[5-(3,5-dichlorophenyl)-5-(trifluoromethyl)-4H-isothiazol-3-yl]-2-methyl-phenyl]methanol (i.e. the product of example 1, step 4) (1.5 g) in $CH_2Cl_2$ (50 mL) was added triethylamine (0.75 mL) and methansulfonylchloride (0.63 g) at r.t. The reaction was stirred at r.t. overnight, then diluted with ethyl acetate (200 mL), and washed with water (3×), dried ($Na_2SO_4$), filtered, and concentrated to afford the crude mesylate (1.19 g) that was re-dissolved in acetonitrile (30 mL) and treated with a solution of ethylamine in THF (2 M, 8.8 mL). The reaction was stirred overnight at r.t. The residue was taken up in ethyl acetate and washed with 5% aqueous potassium carbonate solution (3×), dried ($Na_2SO_4$), filtered, and concentrated to afford the product as a solid (0.98 g, 59%).

HPLC-MS (method B): 1.139 min, M=447.3.

Step 2: N—[[4-[5-(3,5-Dichlorophenyl)-5-(trifluoromethyl)-4H-isothiazol-3-yl]-2-methyl-phenyl]methyl]-N-ethyl-2-ethylsulfanyl-acetamide To a solution of the product of step 1 (0.30 g), (ethylthio)acetic acid (0.10 g) and bromotripyrrolidinophosphonium hexafluorophosphate ("PyBroP", 0.39 g) in $CH_2Cl_2$ (20 mL) at r.t. was added N,N-diisopropylethylamine (0.47 mL). The reaction was stirred at r.t. for 16 h, then concentrated to afford a residue that was purified by flash chromatography on silica gel (ethyl acetate/cyclohexane). The product was obtained as amorphous foam (330 mg, 90%).

HPLC-MS (method A): 4.639 min, M=549.00.

Synthesis Example S.4

4-[5-(3,5-dichlorophenyl)-4-fluoro-5-(trifluoromethyl)-4H-isothiazol-3-yl]-2-methyl-N-[2-oxo-2-(2,2,2-trifluoroethylamino)ethyl]benzamide (Compound example 5-1; compound of formula C.5, wherein $R^{2a}$ and $R^{2c}$ are Cl, $R^{2b}$ is H, $R^{3a}$ is F, G is CH, $R^{4a}$ is H, $R^{4b}$ is methyl and Y is —NH$CH_2$—C(=O)—NH$CH_2CF_3$).

Step 1: tert-butyl 4-[5-(3,5-dichlorophenyl)-4-fluoro-5-(trifluoromethyl)-4H-isothiazol-3-yl]-2-methyl-benzoate To a solution of [tert-butyl 4-[5-(3,5-dichlorophenyl)-5-(trifluoromethyl)-4H-isothiazol-3-yl]-2-methyl-benzoate (prepared from "tert-butyl 4-[(Z)-3-(3,5-dichlorophenyl)-4,4,4-trifluoro-but-2-enoyl]-2-methyl-benzoate" in analogy to Synthesis Example S.1, step 1 and step 2) (2.55 g) in THF (40 mL) under nitrogen at −78° C. was added LiHMDS (5.7 mL, 1M solution in THF) and the mixture was stirred for 1.5 h at −78° C. Then, N-fluorobenzenesulfonimide ("NFSI", 2.1 g) was added at −78° C. in one portion and the mixture was stirred at −78° C. for another 2 h. Then, the reaction was quenched with saturated aqueous NH$_4$Cl solution. EtOAc was added and the organic layer was washed with water (3×), dried (Na$_2$SO$_4$), filtered, and concentrated to afford a residue that was purified by flash chromatography on silica gel (ethyl acetate/cyclohexane). The product was obtained as yellow oil (1.65 g, 62%).

1H NMR (400 MHz, CDCl$_3$, signals of major diastereomer): δ 7.9 (d, 1H), 7.7-7.6 (m, 2H), 7.5 (s, 1H), 7.4 (s, 2H), 6.4 (d, 1H, CHF), 2.6 (s, 3H), 1.6 (s, 9H).

Step 2: 4-[5-(3,5-dichlorophenyl)-4-fluoro-5-(trifluoromethyl)-4H-isothiazol-3-yl]-2-methyl-benzoic acid To a solution of the product of step 1 (0.36 g) in CH$_2$Cl$_2$ (20 mL) at 0° C. was added trifluoroacetic acid ("TFA", 10 mL), and the mixture was stirred at r.t. overnight. Then, the reaction was concentrated, azeotroped with CH$_2$Cl$_2$ (5×) and triturated with petroleum ether/EtOAc (40:1) to obtain the product as a pale yellow solid (0.28 g, 87%).

1H NMR (400 MHz, d6-DMSO, signals of major diastereomer): δ 8.0-7.8 (m, 4H), 7.7 (s, 2H), 7.5 (d, 1H, CHF), 2.6 (s, 3H).

Step 3: 4-[5-(3,5-dichlorophenyl)-4-fluoro-5-(trifluoromethyl)-4H-isothiazol-3-yl]-2-methyl-N-[2-oxo-2-(2,2,2-trifluoroethylamino)ethyl]benzamide To a solution of the product of step 2 (0.25 g) in toluene/CH$_2$Cl$_2$ (1:1, 20 mL) was added N,N-dimethylformamide ("DMF", 1 drop) and oxalyl chloride (0.14 mL). The reaction was stirred overnight, concentrated, and azeotroped with CH$_2$Cl$_2$ (5×). The obtained residue (0.26 g) was dissolved in THF (30 mL) and added to a solution of 2-amino-N-(2,2,2-trifluoroethyl)acetamide hydrochloride and triethylamine (0.22 g) in THF (30 mL). The reaction was stirred overnight, filtered and concentrated to afford a residue that was purified by flash chromatography on silica gel (ethyl acetate/cyclohexane). The product was obtained as amorphous foam (0.13 g, 40%).

HPLC-MS (method B): 1.364 min, M=590.2.

II. Evaluation of Pesticidal Activity:

The activity of the compounds of formula I of the present invention can be demonstrated and evaluated by the following biological test.

B.1 Cotton Aphid (*Aphis gossypii*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants at the cotyledon stage were infested with aphids prior to treatment by placing a heavily infested leaf from the main aphid colony on top of each cotyledon. Aphids were allowed to transfer overnight to accomplish an infestation of 80-100 aphids per plant and the host leaf was removed. The infested plants were then sprayed by an automated electrostatic plant sprayer equipped with an atomizing spray nozzle. The plants were dried in the sprayer fume hood, removed from the sprayer, and then maintained in a growth room under fluorescent lighting in a 24-hr photoperiod at 25° C. and 20-40% relative humidity. Aphid mortality on the treated plants, relative to mortality on untreated control plants, was determined after 5 days.

In this test, the compounds 2-4, 2-10, 2-12, 2-15, 2-19, 2-26, 2-27, 2-28, 2-29, 2-31, 2-32, 2-35, 2-37, 2-38, 2-42, 2-43, 2-47, 2-48, 2-49, 2-50, 2-53, 2-57, 2-59, 2-62, 2-63, 2-65, 2-68, 2-71, 2-72, 2-73, 2-74, 2-75, 2-82, 2-83, 2-86, 2-88, 2-93, 2-99, 2-109, 2-118, 2-137, 2-138, 2-142, 2-143, 2-145, 2-149, 2-150, 2-151, 2-152, 2-153, 2-162, 2-163, 2-164, 2-166, 2-171, 2-178, 2-182, 2-183, 2-185, 2-195, 2-199, 3-11, and 3-12 at 100 ppm, respectively, showed a mortality of at least 75% in comparison with untreated controls.

B.2 Cowpea Aphid (*Aphis craccivora*)

Potted cowpea plants colonized with approximately 100-150 aphids of various stages were sprayed after the pest population had been recorded. Population reduction was assessed after 24, 72, and 120 hours.

In this test, the compounds 1-13, 2-1, 2-2, 2-4, 2-8, 2-9, 2-10, 2-11, 2-12, 2-15, 2-19, 2-26, 2-28, 2-32, 2-33, 2-34, 2-35, 2-36, 2-38, 2-47, 2-51, 2-54, 2-55, 2-59, 2-69, 2-137, 2-142, 2-150, 2-151, 2-152, 2-162, 2-164, 2-165, 2-166, 2-178, 2-180, 2-181, 2-182, 2-184, 2-185, 2-197, 2-199, 2-200, 2-215, 2-217, 2-218, 2-220, 2-223, 2-224, 2-225, 2-227, 3-1, 3-2, 3-8, 3-9, 3-11, 3-12, 3-21, 3-23, 4-1, and 5-2 at 500 ppm, respectively, showed a mortality of at least 75% in comparison with untreated controls.

B.3 Diamond Back Moth (*Plutella xylostella*)

Leaves of Chinese cabbage were dipped in test solution and air-dried. Treated leaves were placed in petri dished lined with moist filter paper. Mortality was recorded 24, 72, and 120 hours after treatment.

In this test, the compounds 1-1, 1-2, 1-4, 1-5, 1-6, 1-7, 1-8, 1-9, 1-10, 1-11, 1-12, 1-13, 1-15, 2-1, 2-2, 2-3, 2-4, 2-5, 2-6, 2-7, 2-8, 2-9, 2-10, 2-11, 2-12, 2-13, 2-15, 2-18, 2-19, 2-20, 2-21, 2-22, 2-23, 2-26, 2-27, 2-28, 2-29, 2-30, 2-31, 2-32, 2-33, 2-34, 2-35, 2-36, 2-37, 2-38, 2-39, 2-40, 2-41, 2-42, 2-43, 2-44, 2-45, 2-46, 2-47, 2-48, 2-49, 2-50, 2-51, 2-52, 2-53, 2-54, 2-55, 2-56, 2-57, 2-58, 2-59, 2-60, 2-61, 2-62, 2-63, 2-64, 2-65, 2-66, 2-67, 2-68, 2-69, 2-70, 2-71, 2-72, 2-73, 2-74, 2-75, 2-76, 2-77, 2-78, 2-80, 2-81, 2-82, 2-83, 2-84, 2-85, 2-86, 2-87, 2-88, 2-89, 2-90, 2-91, 2-92, 2-93, 2-94, 2-95, 2-96, 2-97, 2-98, 2-99, 2-100, 2-101, 2-102, 2-103, 2-104, 2-105, 2-106, 2-107, 2-108, 2-109, 2-111, 2-112, 2-114, 2-115, 2-116, 2-117, 2-118, 2-119, 2-120, 2-121, 2-123, 2-124, 2-125, 2-126, 2-127, 2-128, 2-129, 2-130, 2-131, 2-132, 2-133, 2-134, 2-135, 2-136, 2-137, 2-138, 2-139, 2-140, 2-141, 2-142, 2-143, 2-144, 2-145, 2-146, 2-147, 2-148, 2-149, 2-150, 2-151, 2-152, 2-153, 2-154, 2-155, 2-162, 2-163, 2-164, 2-165, 2-166, 2-169, 2-170, 2-171, 2-172, 2-173, 2-178, 2-179, 2-180, 2-181, 2-182, 2-183, 2-184, 2-185, 2-186, 2-188, 2-189, 2-190, 2-191, 2-192, 2-193, 2-194, 2-195, 2-197, 2-198, 2-199, 2-200, 2-201, 2-202, 2-203, 2-204, 2-206, 2-207, 2-208, 2-209, 2-210, 2-211, 2-212, 2-213, 2-214, 2-215, 2-216, 2-217, 2-218, 2-219, 2-220, 2-221, 2-222, 2-223, 2-224, 2-225, 2-226, 2-227, 3-1, 3-2, 3-3, 3-4, 3-5, 3-6, 3-7, 3-8, 3-9, 3-10, 3-11, 3-12, 3-13, 3-14, 3-16, 3-17, 3-18, 3-19, 3-20, 3-21, 3-22, 3-23, 3-24, 3-25, 3-26, 3-27, 4-1, 5-1, 5-2, 5-3, 5-4, 5-5, 5-6, 5-7, and 5-8 at 500 ppm, respectively, showed a mortality of at least 75% in comparison with untreated controls.

B.4 Green Peach Aphid (*Myzus persicae*)

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications.

After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, the compounds 1-1, 1-2, 1-3, 1-4, 1-5, 1-7, 1-8, 1-9, 1-10, 1-12, 1-13, 1-14, 1-15, 2-1, 2-2, 2-3, 2-4, 2-5, 2-6, 2-7, 2-8, 2-9, 2-10, 2-11, 2-12, 2-13, 2-15, 2-18, 2-19, 2-20, 2-21, 2-23, 2-24, 2-26, 2-27, 2-28, 2-29, 2-30, 2-31, 2-32, 2-33, 2-35, 2-37, 2-38, 2-39, 2-40, 2-41, 2-42, 2-43, 2-44, 2-45, 2-46, 2-47, 2-48, 2-49, 2-51, 2-52, 2-53, 2-54, 2-55, 2-56, 2-57, 2-58, 2-59, 2-60, 2-61, 2-62, 2-63, 2-64, 2-65, 2-66, 2-67, 2-68, 2-69, 2-70, 2-71, 2-72, 2-73, 2-74, 2-75, 2-76, 2-77, 2-81, 2-82, 2-83, 2-84, 2-85, 2-86, 2-87, 2-88, 2-89, 2-90, 2-91, 2-92, 2-93, 2-94, 2-95, 2-96, 2-97, 2-98, 2-99, 2-100, 2-101, 2-102, 2-103, 2-104, 2-105, 2-106, 2-107, 2-108, 2-109, 2-110, 2-111, 2-112, 2-113, 2-114, 2-115, 2-116, 2-117, 2-118, 2-119, 2-120, 2-121, 2-123, 2-124, 2-125, 2-126, 2-127, 2-128, 2-129, 2-130, 2-131, 2-132, 2-133, 2-134, 2-135, 2-136, 2-137, 2-138, 2-139, 2-140, 2-141, 2-142, 2-143, 2-145, 2-146, 2-147, 2-148, 2-149, 2-150, 2-151, 2-152, 2-153, 2-154, 2-155, 2-159, 2-160, 2-162, 2-163, 2-164, 2-165, 2-166, 2-167, 2-168, 2-169, 2-170, 2-171, 2-172, 2-173, 2-177, 2-178, 2-179, 2-180, 2-181, 2-182, 2-183, 2-184, 2-185, 2-186, 2-187, 2-188, 2-189, 2-190, 2-191, 2-192, 2-193, 2-194, 2-195, 2-196, 2-197, 2-199, 2-200, 2-201, 2-202, 2-203, 2-204, 2-206, 2-207, 2-208, 2-209, 2-210, 2-211, 2-215, 2-216, 2-217, 2-218, 2-219, 2-220, 2-221, 2-222, 2-223, 2-224, 2-225, 2-226, 2-227, 3-3, 3-4, 3-5, 3-6, 3-7, 3-8, 3-9, 3-10, 3-11, 3-12, 3-13, 3-14, 3-16, 3-17, 3-18, 3-19, 3-20, 3-21, 3-22, 3-23, 3-24, 3-25, 3-26, 3-27, 3-28, 4-1, 5-1, 5-2, 5-3, 5-4, 5-5, 5-6, 5-7, and 5-8 at 2500 ppm, respectively, showed a mortality of at least 75% in comparison with untreated controls.

B.5 Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs.

The compounds were formulated using a solution containing 75% v/v water and 25% v/v DMSO. Different concentrations of formulated compounds were sprayed onto the insect diet at 5 μl, using a custom built micro atomizer, at two replications.

After application, microtiter plates were incubated at about 28±1° C. and about 80±5% relative humidity for 5 days. Egg and larval mortality was then visually assessed.

In this test, the compounds 1-1, 1-2, 1-3, 1-4, 1-5, 1-6, 1-7, 1-8, 1-9, 1-10, 1-11, 1-12, 1-13, 1-14, 2-1, 2-2, 2-3, 2-4, 2-5, 2-6, 2-7, 2-8, 2-9, 2-10, 2-11, 2-12, 2-13, 2-15, 2-18, 2-19, 2-20, 2-21, 2-23, 2-26, 2-27, 2-28, 2-29, 2-30, 2-31, 2-32, 2-33, 2-34, 2-35, 2-37, 2-38, 2-39, 2-40, 2-41, 2-42, 2-43, 2-44, 2-45, 2-46, 2-47, 2-48, 2-49, 2-51, 2-52, 2-53, 2-54, 2-55, 2-56, 2-57, 2-58, 2-59, 2-60, 2-61, 2-62, 2-63, 2-64, 2-65, 2-66, 2-67, 2-68, 2-69, 2-70, 2-71, 2-72, 2-73, 2-74, 2-75, 2-76, 2-77, 2-78, 2-80, 2-81, 2-82, 2-83, 2-84, 2-85, 2-86, 2-87, 2-88, 2-89, 2-90, 2-91, 2-92, 2-93, 2-94, 2-95, 2-96, 2-97, 2-98, 2-99, 2-100, 2-101, 2-103, 2-104, 2-105, 2-106, 2-107, 2-108, 2-109, 2-111, 2-112, 2-114, 2-115, 2-116, 2-117, 2-118, 2-119, 2-120, 2-121, 2-123, 2-124, 2-125, 2-126, 2-127, 2-128, 2-129, 2-130, 2-131, 2-132, 2-133, 2-135, 2-138, 2-140, 2-141, 2-142, 2-143, 2-146, 2-147, 2-148, 2-149, 2-150, 2-151, 2-152, 2-153, 2-154, 2-155, 2-162, 2-163, 2-164, 2-165, 2-166, 2-169, 2-170, 2-171, 2-172, 2-178, 2-179, 2-180, 2-181, 2-182, 2-183, 2-184, 2-185, 2-186, 2-187, 2-188, 2-189, 2-190, 2-191, 2-192, 2-194, 2-195, 2-197, 2-198, 2-199, 2-200, 2-201, 2-202, 2-203, 2-206, 2-207, 2-209, 2-212, 2-215, 2-216, 2-217, 2-218, 2-220, 2-221, 2-222, 2-223, 2-224, 2-225, 2-226, 2-227, 3-3, 3-4, 3-5, 3-6, 3-7, 3-8, 3-9, 3-10, 3-11, 3-12, 3-13, 3-14, 3-16, 3-17, 3-18, 3-19, 3-20, 3-21, 3-22, 3-23, 3-24, 3-25, 3-26, 3-27, 3-28, 4-1, 5-1, 5-2, 5-3, 5-4, and 5-7 at 2500 ppm, respectively, showed a mortality of at least 75% in comparison with untreated controls.

B.6 Orchid Thrips (*Dichromothrips corbetti*)

*Dichromothrips corbetti* adults used for bioassay were obtained from a colony maintained continuously under laboratory conditions. For testing purposes, the test compound was diluted to a concentration of 500 ppm (wt compound: vol diluent) in a 1:1 mixture of acetone:water (vol:vol), plus 0.01% vol/vol Kinetic® surfactant.

Thrips potency of each compound was evaluated by using a floral-immersion technique. Plastic petri dishes were used as test arenas. All petals of individual, intact orchid flowers were dipped into treatment solution and allowed to dry. Treated flowers were placed into individual petri dishes along with 10-15 adult thrips. The petri dishes were then covered with lids. All test arenas were held under continuous light and a temperature of about 28° C. for duration of the assay. After 4 days, the numbers of live thrips were counted on each flower, and along inner walls of each petri dish. The level of thrips mortality was extrapolated from pre-treatment thrips numbers.

In this test, the compounds 1-1, 1-2, 1-5, 1-7, 1-8, 1-9, 1-10, 1-13 2-1, 2-2, 2-3, 2-4, 2-5, 2-6, 2-7, 2-8, 2-9, 2-10, 2-11, 2-12, 2-13, 2-15, 2-18, 2-19, 2-20, 2-21, 2-22, 2-23, 2-26, 2-27, 2-28, 2-29, 2-30, 2-31, 2-33, 2-34, 2-35, 2-37, 2-38, 2-39, 2-40, 2-41, 2-42, 2-43, 2-45, 2-46, 2-47, 2-48, 2-49, 2-50, 2-51, 2-52, 2-53, 2-54, 2-55, 2-56, 2-57, 2-58, 2-59, 2-60, 2-61, 2-62, 2-63, 2-64, 2-65, 2-66, 2-67, 2-68, 2-69, 2-70, 2-71, 2-72, 2-73, 2-74, 2-75, 2-76, 2-77, 2-78, 2-80, 2-81, 2-82, 2-83, 2-84, 2-85, 2-86, 2-87, 2-88, 2-89, 2-90, 2-91, 2-92, 2-93, 2-94, 2-95, 2-96, 2-97, 2-98, 2-99, 2-100, 2-101, 2-102, 2-103, 2-104, 2-105, 2-106, 2-107, 2-108, 2-109, 2-111, 2-112, 2-113, 2-114, 2-115, 2-116, 2-117, 2-118, 2-119, 2-120, 2-121, 2-123, 2-124, 2-125, 2-126, 2-127, 2-128, 2-129, 2-130, 2-131, 2-132, 2-133, 2-134, 2-135, 2-136, 2-137, 2-138, 2-139, 2-140, 2-141, 2-142, 2-143, 2-144, 2-145, 2-146, 2-147, 2-148, 2-149, 2-150, 2-151, 2-152, 2-153, 2-154, 2-155, 2-162, 2-163, 2-164, 2-165, 2-166, 2-169, 2-170, 2-171, 2-172, 2-173, 2-178, 2-179, 2-180, 2-181, 2-182, 2-183, 2-184, 2-185, 2-186, 2-187, 2-188, 2-189, 2-190, 2-192, 2-193, 2-195, 2-197, 2-198, 2-199, 2-200, 2-201, 2-202, 2-203, 2-204, 2-206, 2-207, 2-208, 2-209, 2-210, 2-211, 2-212, 2-213, 2-214, 2-215, 2-216, 2-217, 2-218, 2-219, 2-220, 2-221, 2-222, 2-223, 2-224, 2-225, 2-226, 2-227, 3-1, 3-2, 3-3, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 3-26, 3-27, 4-1, 5-1, 5-2, 5-3, 5-4, 5-5, 5-6, 5-7, and 5-8 at 500 ppm, respectively, showed a mortality of at least 75% in comparison with untreated controls.

B.7 Rice Green Leafhopper (*Nephotettix virescens*)

Rice seedlings were cleaned and washed 24 hours before spraying. The active compounds were formulated in 50:50 acetone:water (vol:vol), and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, the compounds 1-7, 2-1, 2-2, 2-4, 2-5, 2-6, 2-9, 2-10, 2-11, 2-13, 2-15, 2-19, 2-23, 2-26, 2-27, 2-28, 2-29, 2-30, 2-31, 2-32, 2-33, 2-35, 2-37, 2-38, 2-40, 2-41, 2-42, 2-43, 2-45, 2-47, 2-48, 2-49, 2-50, 2-51, 2-52, 2-53, 2-54, 2-55, 2-56, 2-57, 2-58, 2-59, 2-60, 2-61, 2-62, 2-63, 2-64, 2-67, 2-68, 2-69, 2-70, 2-71, 2-72, 2-73, 2-74, 2-81, 2-82, 2-83, 2-84, 2-85, 2-86, 2-88, 2-89, 2-91, 2-93, 2-94, 2-95, 2-97, 2-99, 2-100, 2-101, 2-102, 2-104, 2-107, 2-108, 2-109, 2-112, 2-114, 2-115, 2-116, 2-118, 2-119, 2-120, 2-121, 2-124, 2-126, 2-127, 2-128, 2-129, 2-131, 2-132, 2-133, 2-134, 2-135, 2-136, 2-137, 2-138, 2-139, 2-140, 2-141, 2-142, 2-143, 2-145, 2-146, 2-147, 2-148, 2-149, 2-150, 2-151, 2-152, 2-153, 2-154, 2-155, 2-162, 2-163, 2-164, 2-165, 2-166, 2-170, 2-178, 2-179, 2-180, 2-181, 2-182, 2-183, 2-184, 2-185, 2-193, 2-195, 2-197, 2-199, 2-200, 2-201, 2-203, 2-204, 2-206, 2-207, 2-208, 2-209, 2-210, 2-211, 2-212, 2-213, 2-214, 2-215, 2-216, 2-217, 2-218, 2-219, 2-220, 2-222, 2-224, 2-225, 2-226, 2-227, 3-3, 3-4, 3-6, 3-7, 3-8, 3-10, 3-11, 3-12, 3-17, 3-18, 3-19, 3-21, 3-23, 3-24, 3-25, 3-26, 4-1, 5-2, and 5-3 at 500 ppm, respectively, showed a mortality of at least 75% in comparison with untreated controls.

B.8 Silverleaf Whitefly (*Bemisia argentifolii*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding. Cups were covered with a reusable screened lid. Test plants were maintained in a growth room at about 25° C. and about 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, the compounds 1-7, 1-9, 1-10, 2-2, 2-3, 2-4, 2-5, 2-10, 2-11, 2-12, 2-13, 2-15, 2-23, 2-26, 2-28, 2-29, 2-31, 2-33, 2-35, 2-37, 2-38, 2-39, 2-40, 2-41, 2-42, 2-43, 2-47, 2-48, 2-49, 2-50, 2-53, 2-57, 2-58, 2-59, 2-62, 2-63, 2-65, 2-66, 2-67, 2-68, 2-71, 2-72, 2-73, 2-74, 2-75, 2-77, 2-81, 2-82, 2-83, 2-84, 2-86, 2-87, 2-88, 2-90, 2-91, 2-92, 2-93, 2-95, 2-96, 2-99, 2-100, 2-109, 2-110, 2-114, 2-115, 2-121, 2-123, 2-128, 2-130, 2-134, 2-136, 2-137, 2-138, 2-139, 2-140, 2-142, 2-143, 2-145, 2-146, 2-148, 2-149, 2-150, 2-151, 2-152, 2-153, 2-154, 2-155, 2-162, 2-163, 2-164, 2-165, 2-166, 2-169, 2-171, 2-172, 2-173, 2-178, 2-179, 2-181, 2-182, 2-183, 2-185, 2-186, 2-188, 2-189, 2-190, 2-195, 2-199, 3-1, 3-4, 3-6, 3-7, 3-9, 3-10, 3-11, 3-12, and 3-19 at 100 ppm, respectively, showed a mortality of at least 75% in comparison with untreated controls.

B.9 Southern Armyworm (*Spodoptera eridania*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Lima bean plants (variety Sieva) were grown 2 plants to a pot and selected for treatment at the $1^{st}$ true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the compounds 1-1, 1-2, 1-5, 1-7, 1-8, 1-9, 1-10, 1-11, 1-13, 1-14, 2-1, 2-2, 2-3, 2-4, 2-5, 2-6, 2-7, 2-8, 2-9, 2-10, 2-11, 2-12, 2-13, 2-15, 2-18, 2-19, 2-20, 2-21, 2-23, 2-26, 2-27, 2-28, 2-29, 2-30, 2-31, 2-32, 2-33, 2-35, 2-37, 2-38, 2-39, 2-40, 2-41, 2-42, 2-43, 2-44, 2-45, 2-46, 2-47, 2-48, 2-49, 2-50, 2-51, 2-52, 2-53, 2-54, 2-55, 2-56, 2-57, 2-58, 2-59, 2-60, 2-61, 2-62, 2-63, 2-64, 2-65, 2-66, 2-67, 2-68, 2-69, 2-70, 2-71, 2-72, 2-73, 2-74, 2-75, 2-76, 2-77, 2-81, 2-82, 2-83, 2-84, 2-85, 2-86, 2-87, 2-88, 2-89, 2-90, 2-91, 2-92, 2-93, 2-94, 2-95, 2-96, 2-97, 2-98, 2-99, 2-100, 2-101, 2-102, 2-103, 2-104, 2-105, 2-106, 2-107, 2-108, 2-109, 2-110, 2-112, 2-114, 2-115, 2-116, 2-117, 2-118, 2-119, 2-120, 2-121, 2-123, 2-124, 2-125, 2-126, 2-127, 2-128, 2-129, 2-130, 2-131, 2-132, 2-133, 2-134, 2-135, 2-136, 2-137, 2-138, 2-139, 2-140, 2-141, 2-142, 2-143, 2-144, 2-145, 2-146, 2-147, 2-148, 2-149, 2-150, 2-151, 2-152, 2-153, 2-154, 2-155, 2-162, 2-163, 2-164, 2-165, 2-166, 2-169, 2-170, 2-171, 2-172, 2-173, 2-178, 2-179, 2-180, 2-181, 2-182, 2-183, 2-184, 2-185, 2-186, 2-187, 2-188, 2-189, 2-190, 2-191, 2-192, 2-193, 2-195, 2-197, 2-198, 2-199, 2-200, 2-202, 2-203, 2-204, 2-206, 2-207, 2-208, 2-209, 2-210, 2-212, 2-214, 2-216, 2-221, 2-222, 2-224, 2-225, 2-226, 2-227, 3-1, 3-2, 3-3, 3-4, 3-5, 3-6, 3-7, 3-8, 3-9, 3-10, 3-11, 3-12, 3-13, 3-17, 3-18, 3-19, 3-20, 3-21, 3-22, 3-23, 3-24, 3-25, 3-26, 3-27, 4-1, 5-2, 5-3, 5-6 and 5-7 at 1 ppm, respectively, showed a mortality of at least 75% in comparison with untreated controls.

B.10 Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 μl, using a custom built micro atomizer, at two replications.

After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, the compounds 1-1, 1-2, 1-3, 1-4, 1-5, 1-7, 1-8, 1-9, 1-10, 1-12, 1-13, 1-15, 2-1, 2-2, 2-3, 2-4, 2-5, 2-6, 2-7, 2-8, 2-9, 2-10, 2-11, 2-12, 2-13, 2-15, 2-19, 2-20, 2-21, 2-23, 2-24, 2-26, 2-27, 2-28, 2-29, 2-30, 2-31, 2-32, 2-33, 2-35, 2-36, 2-37, 2-38, 2-39, 2-40, 2-41, 2-42, 2-43, 2-44, 2-45, 2-46, 2-47, 2-48, 2-49, 2-51, 2-52, 2-53, 2-54, 2-55, 2-56, 2-57, 2-58, 2-59, 2-60, 2-61, 2-62, 2-63, 2-64, 2-65, 2-66, 2-67, 2-68, 2-69, 2-70, 2-71, 2-72, 2-73, 2-74, 2-75, 2-77, 2-79, 2-81, 2-82, 2-83, 2-84, 2-85, 2-86, 2-87, 2-88, 2-89, 2-90, 2-91, 2-92, 2-93, 2-94, 2-95, 2-96, 2-97, 2-98, 2-99, 2-100, 2-101, 2-102, 2-104, 2-105, 2-106, 2-107, 2-108, 2-109, 2-110, 2-111, 2-112, 2-114, 2-115, 2-116, 2-117, 2-118, 2-119, 2-120, 2-121, 2-123, 2-124, 2-125, 2-126, 2-127, 2-128, 2-129, 2-130, 2-131, 2-132, 2-133, 2-134, 2-135, 2-136, 2-137, 2-138, 2-139, 2-140, 2-141, 2-142, 2-143, 2-145, 2-146, 2-147, 2-148, 2-149, 2-150, 2-151, 2-152, 2-153, 2-154, 2-155, 2-159, 2-162, 2-163, 2-164, 2-165, 2-166, 2-170, 2-171, 2-172, 2-173, 2-178, 2-179, 2-180, 2-181, 2-182, 2-183, 2-184, 2-185, 2-186, 2-188, 2-189, 2-190, 2-191, 2-192, 2-193, 2-194, 2-195, 2-197, 2-198, 2-199, 2-200, 2-201, 2-202, 2-203, 2-204, 2-206, 2-207, 2-208, 2-209, 2-210, 2-211, 2-213, 2-214, 2-215, 2-216, 2-217, 2-218, 2-219, 2-220, 2-221, 2-222, 2-223, 2-224, 2-225, 2-226, 2-227, 3-6, 3-7, 3-8, 3-9, 3-10, 3-11, 3-12, 3-13, 3-14, 3-16, 3-17, 3-18, 3-19, 3-20, 3-21, 3-22, 3-23, 3-24, 3-25, 3-26, 3-27, 3-28, 4-1, 5-1, 5-2, 5-3, 5-4, 5-5, 5-6, 5-7, and 5-8 at 2500 ppm, respectively, showed a mortality of at least 75% in comparison with untreated controls.

B.11 Tobacco Budworm (*Heliothis virescens*) I

For evaluating control of tobacco budworm (*Heliothis virescens*) the test unit consisted of 96-well-microtiter plates containing an insect diet and 15-25 *H. virescens* eggs. The compounds were formulated using a solution containing 75% v/v water and 25% v/v DMSO. Different concentrations of formulated compounds were sprayed onto the insect diet at 10 µl, using a custom built micro atomizer, at two replications.

After application, microtiter plates were incubated at about 28±1° C. and about 80±5% relative humidity for 5 days. Egg and larval mortality was then visually assessed.

In this test, the compounds 1-1, 1-2, 1-3, 1-4, 1-5, 1-7, 1-8, 1-9, 1-10, 1-11, 1-12, 1-13, 1-14, 1-15, 2-1, 2-2, 2-3, 2-4, 2-5, 2-6, 2-7, 2-8, 2-9, 2-10, 2-11, 2-12, 2-13, 2-15, 2-17, 2-18, 2-19, 2-20, 2-21, 2-22, 2-23, 2-26, 2-27, 2-28, 2-29, 2-30, 2-31, 2-32, 2-33, 2-34, 2-35, 2-36, 2-37, 2-38, 2-39, 2-40, 2-41, 2-42, 2-43, 2-44, 2-45, 2-46, 2-47, 2-48, 2-49, 2-51, 2-52, 2-53, 2-54, 2-55, 2-56, 2-57, 2-58, 2-59, 2-60, 2-61, 2-62, 2-63, 2-64, 2-65, 2-66, 2-67, 2-68, 2-69, 2-70, 2-71, 2-72, 2-73, 2-74, 2-75, 2-77, 2-78, 2-81, 2-82, 2-83, 2-84, 2-85, 2-86, 2-87, 2-88, 2-89, 2-90, 2-91, 2-92, 2-93, 2-94, 2-95, 2-96, 2-97, 2-98, 2-99, 2-100, 2-101, 2-102, 2-103, 2-104, 2-105, 2-106, 2-107, 2-108, 2-109, 2-110, 2-111, 2-112, 2-114, 2-115, 2-116, 2-117, 2-118, 2-119, 2-120, 2-121, 2-122, 2-123, 2-124, 2-125, 2-126, 2-127, 2-128, 2-129, 2-130, 2-131, 2-132, 2-133, 2-134, 2-135, 2-136, 2-137, 2-138, 2-139, 2-140, 2-141, 2-142, 2-143, 2-145, 2-146, 2-147, 2-148, 2-149, 2-150, 2-151, 2-152, 2-153, 2-154, 2-155, 2-156, 2-157, 2-158, 2-160, 2-161, 2-162, 2-163, 2-164, 2-165, 2-166, 2-167, 2-169, 2-170, 2-171, 2-172, 2-173, 2-174, 2-175, 2-177, 2-178, 2-179, 2-180, 2-181, 2-182, 2-183, 2-184, 2-185, 2-186, 2-187, 2-188, 2-189, 2-190, 2-191, 2-192, 2-193, 2-194, 2-195, 2-196, 2-197, 2-198, 2-199, 2-200, 2-201, 2-202, 2-203, 2-204, 2-206, 2-207, 2-208, 2-209, 2-210, 2-211, 2-212, 2-213, 2-215, 2-216, 2-217, 2-218, 2-219, 2-220, 2-221, 2-222, 2-223, 2-224, 2-225, 2-226, 2-227, 3-3, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 3-26, 3-27, 3-28, 4-1, 5-1, 5-2, 5-3, 5-4, 5-5, 5-6, 5-7, and 5-8 at 2500 ppm, respectively, showed a mortality of at least 75% in comparison with untreated controls.

B.12 Boll Weevil (*Anthonomus grandis*)

For evaluating control of boll weevil (Anthonomusgrandis) the test unit consisted of 24-well-microtiter plates containing an insect diet and 20-30 *A. grandis* eggs.

The compounds were formulated using a solution containing 75% v/v water and 25% v/v DMSO. Different concentrations of formulated compounds were sprayed onto the insect diet at 20 µl, using a custom built micro atomizer, at two replications.

After application, microtiter plates were incubated at about 23±1° C. and about 50±5% relative humidity for 5 days. Egg and larval mortality was then visually assessed.

In this test, the compounds 1-1, 1-2, 1-3, 1-4, 1-5, 1-7, 1-8, 1-9, 1-10, 1-11, 1-12, 1-13, 1-14, 1-15, 2-1, 2-2, 2-3, 2-4, 2-5, 2-6, 2-7, 2-8, 2-9, 2-10, 2-11, 2-12, 2-13, 2-15, 2-18, 2-19, 2-20, 2-21, 2-22, 2-23, 2-26, 2-27, 2-28, 2-29, 2-30, 2-31, 2-32, 2-33, 2-34, 2-35, 2-36, 2-37, 2-38, 2-39, 2-40, 2-41, 2-42, 2-43, 2-44, 2-45, 2-46, 2-47, 2-48, 2-49, 2-51, 2-52, 2-53, 2-54, 2-55, 2-56, 2-57, 2-58, 2-59, 2-60, 2-61, 2-62, 2-63, 2-64, 2-65, 2-66, 2-67, 2-68, 2-69, 2-70, 2-71, 2-72, 2-73, 2-74, 2-75, 2-76, 2-77, 2-78, 2-79, 2-80, 2-81, 2-82, 2-83, 2-84, 2-85, 2-86, 2-87, 2-88, 2-89, 2-90, 2-91, 2-92, 2-93, 2-94, 2-95, 2-96, 2-97, 2-98, 2-99, 2-100, 2-101, 2-102, 2-103, 2-104, 2-105, 2-106, 2-107, 2-108, 2-109, 2-110, 2-111, 2-112, 2-113, 2-114, 2-115, 2-116, 2-117, 2-118, 2-119, 2-120, 2-121, 2-123, 2-124, 2-125, 2-126, 2-127, 2-128, 2-129, 2-130, 2-131, 2-132, 2-133, 2-134, 2-135, 2-136, 2-137, 2-138, 2-139, 2-140, 2-141, 2-142, 2-143, 2-145, 2-146, 2-147, 2-148, 2-149, 2-150, 2-151, 2-152, 2-153, 2-154, 2-155, 2-157, 2-158, 2-160, 2-162, 2-163, 2-164, 2-165, 2-166, 2-167, 2-168, 2-169, 2-170, 2-171, 2-172, 2-173, 2-178, 2-179, 2-180, 2-181, 2-182, 2-183, 2-184, 2-185, 2-186, 2-187, 2-188, 2-189, 2-190, 2-191, 2-192, 2-193, 2-194, 2-195, 2-196, 2-197, 2-198, 2-199, 2-200, 2-201, 2-202, 2-203, 2-204, 2-206, 2-207, 2-208, 2-209, 2-210, 2-211, 2-212, 2-213, 2-214, 2-215, 2-216, 2-217, 2-218, 2-219, 2-220, 2-221, 2-222, 2-223, 2-224, 2-225, 2-226, 2-227, 3-3, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 3-26, 3-27, 3-28, 4-1, 5-1, 5-2, 5-3, 5-4, 5-5, 5-6, 5-7, and 5-8 at 2500 ppm, respectively, showed a mortality of at least 75% in comparison with untreated controls.

B.13 Colorado Potato Beetle (*Leptinotarsa decemlineata*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Eggplants were grown 2 plants to a pot and were selected for treatment at the 1$^{st}$ true leaf stage. Test solutions were sprayed onto the foliage by an automated electrostatic plant sprayer equipped with an atomizing spray nozzle. The plants were dried in the sprayer fume hood and then removed from the sprayer. The treated foliage was then cut and removed from the pot and placed in a 5-inch Petri dish lined with moistened filter paper. Five beetle larvae were introduced into each Petri dish and the dish was covered by a Petri dish lid. Petri dishes were maintained in a growth room at 25° C. and 20-40% relative humidity for 4 days, avoiding direct exposure to fluorescent light (24 hour photoperiod) to prevent trapping of heat inside the dishes. Mortality and reduced feeding were assessed 4 days after treatment, compared to untreated control plants.

In this test, the compounds 1-2, 2-1, 2-4, 2-5, 2-6, 2-10, 2-11, 2-12, 2-13, 2-19, 2-20, 2-26, 2-27, 2-28, 2-31, 2-32, 2-33, 2-35, 2-37, 2-38, 2-40, 2-43, 2-49, 2-50, 2-53, 2-57, 2-58, 2-59, 2-61, 2-67, 2-68, 2-71, 2-72, 2-73, 2-74, 2-82, 2-83, 2-88, 2-89, 2-93, 2-108, 2-112, 2-116, 2-118, 2-119, 2-120, 2-124, 2-126, 2-127, 2-128, 2-129, 2-131, 2-132, 2-133, 2-135, 2-137, 2-138, 2-141, 2-143, 2-147, 2-148, 2-149, 2-150, 2-151, 2-153, 2-154, 2-155, 2-162, 2-163, 2-165, 2-170, 2-178, 2-179, 2-180, 2-181, 2-182, 2-185, 2-186, 2-187, 2-193, 2-197, 2-199, 2-200, 3-4, 3-5, 3-7, 3-8, 3-9, 3-17, and 3-18 at 1 ppm, respectively, showed a mortality of at least 75% in comparison with untreated controls.

B.14 Red Spider Mite (*Tetranychus kanzawai*)

The active compound was dissolved at the desired concentration in a mixture of 1:1 (v/v) distilled water:acetone. A surfactant (Alkamuls® EL 620) was added at the rate of 0.1% (v/v).

Potted cowpea beans of 7-10 days of age were cleaned with tap water and sprayed with 5 ml of the test solution using air driven hand atomizer. The treated plants were allowed to air dry and afterwards inculated with 20 or more mites by clipping a cassava leaf section with known mite population. Treated plants were placed inside a holding room at about 25-27° C. and about 50-60% relatice humidity.

Mortality was determined by counting the live mites 72 HAT. Percent mortality was assessed after 72 h.

In this test, the compounds 2-1, 2-2, 2-4, 2-5, 2-6, 2-7, 2-8, 2-9, 2-10, 2-12, 2-13, 2-15, 2-26, 2-27, 2-28, 2-29, 2-30, 2-32, 2-37, 2-40, 2-43, 2-48, 2-51, 2-54, 2-55, 2-59, 2-60, 2-68, 2-70, 2-71, 2-72, 2-73, 2-75, 2-77, 2-82, 2-86, 2-97, 2-98, 2-99, 2-100, 2-108, 2-116, 2-118, 2-119, 2-120, 2-124, 2-126, 2-127, 2-128, 2-129, 2-131, 2-132, 2-133, 2-134, 2-135, 2-136, 2-137, 2-138, 2-139, 2-140, 2-141, 2-142, 2-143, 2-145, 2-146, 2-147, 2-148, 2-149, 2-151, 2-153, 2-162, 2-165, 2-166, 2-178, 2-179, 2-180, 2-181, 2-182, 2-183, 2-184, 2-185, 2-186, 2-193, 2-195, 2-199, 2-200, 2-201, 2-202, 2-203, 2-204, 2-206, 2-207, 2-208, 2-209, 2-210, 2-211, 2-213, 2-214, 2-215, 2-216, 2-217, 2-218, 2-219, 2-220, 2-221, 2-222, 2-224, 2-225, 2-226, 3-1, 3-7, 3-8, 3-10, 3-11, 3-12, 3-21, 3-22, 3-23, 3-24, 5-1, 5-2, and 5-3 at 500 ppm, respectively, showed a mortality of at least 75% in comparison with untreated controls.

We claim:

1. A compound of formula I

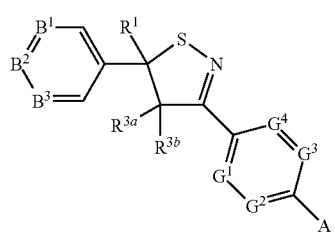

wherein
A is a group $A^1$ or $A^3$;
wherein
$A^1$ is selected from the group consisting of —C(=NR$^6$)R$^8$, and —S(O)$_n$R$^9$;
$A^3$ is a group of following formula:

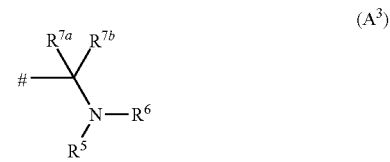

wherein
# denotes the bond to the aromatic ring of formula (I);
$B^1$, $B^2$ and $B^3$ are each independently selected from the group consisting of N and CR$^2$, with the proviso that at most two of $B^1$, $B^2$ and $B^3$ are N;
$G^1$, $G^2$, $G^3$ and $G^4$ are each independently selected from the group consisting of N and CR$^4$, with the proviso that at most two of $G^1$, $G^2$, $G^3$ and $G^4$ are N;
$R^1$ is CF$_3$;
each $R^2$ is independently selected from the group consisting of hydrogen, halogen, cyano, azido, nitro, —SCN, —SF$_5$, C$_1$-C$_6$-alkyl, C$_3$-C$_8$-cycloalkyl, C$_2$-C$_6$-alkenyl, C$_2$-C$_6$-alkynyl, wherein the four last mentioned aliphatic and cycloaliphatic radicals may be partially or fully halogenated and/or may be substituted by one or more radicals R$^8$, —Si(R$^{12}$)$_3$, —OR$^9$, —S(O)$_n$R$^9$, —NR$^{10a}$R$^{10b}$, phenyl which may be substituted by 1, 2, 3, 4 or 5 radicals R$^{11}$, and a 3-, 4-, 5-, 6-, 7-, 8-, 9- or 10-membered saturated, partially unsaturated or maximally unsaturated heteromonocyclic or heterobicyclic ring containing 1, 2, 3 or 4 heteroatoms or heteroatom groups selected from the group consisting of N, O, S, NO, SO and SO$_2$, as ring members, where the heteromono- or heterobicyclic ring may be substituted by one or more radicals R$^{11}$;
$R^{3a}$, $R^{3b}$ are each independently selected from the group consisting of hydrogen, halogen, hydroxyl, —CO$_2$R$^{3d}$, C$_1$-C$_3$-alkyl, C$_1$-C$_3$-haloalkyl, C$_2$-C$_3$-alkenyl, C$_2$-C$_3$-alkynyl, C$_1$-C$_3$-alkoxy, C$_1$-C$_3$-haloalkoxy, C$_1$-C$_3$-alkylthio, C$_1$-C$_3$-haloalkylthio, C$_1$-C$_3$-alkylsulfonyl and C$_1$-C$_3$-haloalkylsulfonyl; or
$R^{3a}$ and $R^{3b}$ together form a group =O, =C(R$^{3c}$)$_2$, =NOH or =NOCH$_3$;
each $R^{3c}$ is independently selected from the group consisting of hydrogen, halogen, CH$_3$ and CF$_3$;
$R^{3d}$ is selected from the group consisting of hydrogen, C$_1$-C$_6$-alkyl and C$_1$-C$_3$-alkyloxy-C$_1$-C$_3$-alkyl-;
each $R^4$ is independently selected from the group consisting of hydrogen, halogen, cyano, azido, nitro, —SCN, —SF$_5$, C$_1$-C$_6$-alkyl which may be partially or fully halogenated and/or may be substituted by one or more radicals R$^8$, C$_3$-C$_8$-cycloalkyl which may be partially or fully halogenated and/or may be substituted by one or more radicals R$^8$, C$_2$-C$_6$-alkenyl which may be partially or fully halogenated and/or may be substituted by one or more radicals R$^8$, C$_2$-C$_6$-alkynyl which may be partially or fully halogenated and/or may be substituted by one or more radicals R$^8$, —Si(R$^{12}$)$_3$, —OR$^9$, —S(O)R$^9$, —NR$^{10a}$R$^{10b}$, phenyl which may be substituted by 1, 2, 3, 4 or 5 radicals $R^{11}$, and a 3-, 4-, 5-, 6-, 7-, 8-, 9- or 10-membered saturated, partially unsaturated or maximally unsaturated heteromonocyclic or heterobicyclic ring containing 1, 2, 3 or 4 heteroatoms or heteroatom groups selected from the group consisting of N, O, S, NO, SO and $SO_2$, as ring members, where the heteromonocyclic or heterobicyclic ring may be substituted by one or more radicals $R^{11}$;

each $R^5$ is independently selected from the group consisting of hydrogen, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted with one or more substituents $R^8$, and —$S(O)_nR^9$, each $R^6$ is independently selected from the group consisting of hydrogen, cyano, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted by one or more substituents $R^8$, —$OR^9$, —$NR^{10a}R^{10b}$, —$S(O)_nR^9$, —$C(=O)NR^{10a}N(R^{10a}R^{10b})$, —$Si(R^{12})_3$, —$C(=O)R^8$, phenyl which may be substituted with 1, 2, 3, 4, or 5 substituents $R^{11}$, and a 3-, 4-, 5-, 6-, 7-, 8-, 9- or 10-membered saturated, partially unsaturated or maximally unsaturated heteromonocyclic or heterobicyclic ring containing 1, 2, 3 or 4 heteroatoms or heteroatom groups independently selected from the group consisting of N, O, S, NO, SO and $SO_2$, as ring members, where the heteromonocyclic or heterobicyclic ring may be substituted with one or more substituents $R^{11}$;

or $R^5$ and $R^6$, together with the nitrogen atom to which they are bound, form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from the group consisting of O, S, N, SO, $SO_2$, C=O and C=S as ring members, wherein the heterocyclic ring may be substituted with 1, 2, 3, 4 or 5 substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the aliphatic or cycloaliphatic moieties in the twelve last-mentioned radicals may be substituted by one or more radicals $R^8$, and phenyl which may be substituted with 1, 2, 3, 4 or 5 substituents $R^{11}$;

or $R^5$ and $R^6$ together form a group =$C(R^8)_2$, =$S(O)_m(R^9)_2$, =$NR^{10a}$ or =$NOR^9$;

$R^{7a}$, $R^{7b}$ are each independently selected from the group consisting of hydrogen, halogen, cyano, $C_1$-$C_6$-alkyl, $C_3$-$C_8$-cycloalkyl, $C_2$-$C_6$-alkenyl and $C_2$-$C_6$-alkynyl, wherein the four last-mentioned aliphatic and cycloaliphatic radicals may be partially or fully halogenated and/or may be substituted by one or more radicals $R^8$;

each $R^8$ is independently selected from the group consisting of cyano, azido, nitro, —SCN, —$SF_5$, $C_3$-$C_8$-cycloalkyl, $C_3$-$C_8$-halocycloalkyl, where the cycloaliphatic moieties in the two last-mentioned radicals may be substituted by one or more radicals $R^{13}$;

—$Si(R^{12})_3$, —$OR^9$, —$OSO_2R^9$, —$S(O)_nR^9$, —$N(R^{10a})R^{10b}$, —$C(=O)N(R^{10a})R^{10b}$, —$C(=S)N(R^{10a})R^{10b}$, —$C(=O)OR^9$, phenyl, optionally substituted with 1, 2, 3, 4 or 5 substituents $R^{16}$, and a 3-, 4-, 5-, 6- or 7-membered saturated, partially unsaturated or maximally unsaturated heterocyclic ring comprising 1, 2 or 3 heteroatoms or heteroatom groups selected from the group consisting of N, O, S, NO, SO and $SO_2$, as ring members, where the heterocyclic ring is optionally substituted with one or more substituents $R^{16}$, or two $R^8$ present on the same carbon atom of an alkyl, alkenyl, alkynyl or cycloalkyl group together form a group =O, =$C(R^{13})_2$; =S; =$S(O)_m(R^{15})_2$, =$S(O)_mR^{15}N(R^{14a})R^{14b}$, =$NR^{10a}$, =$NOR^9$; or =$NN(R^{10a})R^{10b}$;

or two radicals $R^8$, together with the carbon atoms of an alkyl, alkenyl, alkynyl or cycloalkyl group which they are bonded to, form a 3-, 4-, 5-, 6-, 7- or 8-membered saturated or partially unsaturated carbocyclic or heterocyclic ring, where the heterocyclic ring comprises 1, 2, 3 or 4 heteroatoms or heteroatom groups independently selected from N, O, S, NO, SO and $SO_2$, as ring members, and where the carbocyclic or heterocyclic ring is optionally substituted with one or more substituents $R^{16}$; and $R^8$ as a substituent on a cycloalkyl ring is additionally selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl and $C_2$-$C_6$-haloalkynyl, where the aliphatic moieties in these six radicals may be substituted by one or more radicals $R^{13}$; and $R^8$ in the groups —$C(=NR^6)R^8$, —$C(=O)R^8$ and =$C(R^8)_2$ is additionally selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl and $C_2$-$C_6$-haloalkynyl, where the aliphatic moieties in the six last-mentioned radicals may be substituted by one or more radicals $R^{13}$;

each $R^9$ is independently selected from the group consisting of hydrogen, cyano, $C_1$-$C_6$-alkyl, $C_1$-$C_6$-haloalkyl, $C_3$-$C_8$-cycloalkyl, $C_3$-$C_8$-cycloalkyl-$C_1$-$C_4$-alkyl-, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, where the aliphatic and cycloaliphatic moieties in the nine last-mentioned radicals may be substituted by one or more radicals $R^{13}$, —$C_1$-$C_6$-alkyl-$C(=O)OR^{15}$, —$C_1$-$C_6$-alkyl-$C(=O)N(R^{14a})R^{14b}$,
—$C_1$-$C_6$-alkyl-$C(=S)N(R^{14a})R^{14b}$, —$C_1$-$C_6$-alkyl-$C(=NR^{14})N(R^{14a})R^{14b}$,
—$Si(R^{12})_3$, —$S(O)_nR^{15}$, —$S(O)_nN(R^{14a})R^{14b}$,
—$N(R^{10a})R^{10b}$, —$N=C(R^{13})_2$, —$C(=O)R^{13}$,
—$C(=O)N(R^{14a})R^{14b}$, —$C(=S)N(R^{14a})R^{14b}$,
—$C(=O)OR^{15}$, phenyl, optionally substituted with one or more substituents $R^{16}$; and a 3-, 4-, 5-, 6- or 7-membered saturated, partially unsaturated or maximally unsaturated heterocyclic ring comprising 1, 2 or 3 heteroatoms or heteroatom groups selected from the group consisting of N, O, S, NO, SO and $SO_2$, as ring members, where the heterocyclic ring is optionally substituted with one or more substituents $R^{16}$; and R$^9$ in the groups —S(O)$_n$R$^9$ and —OSO$_2$R$^9$ is additionally selected from the group consisting of C$_1$-C$_6$-alkoxy and C$_1$-C$_6$-haloalkoxy;

R$^{10a}$, R$^{10b}$ are selected independently from one another from the group consisting of hydrogen, C$_1$-C$_6$-alkyl, C$_1$-C$_6$-haloalkyl, C$_3$-C$_8$-cycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$-haloalkynyl, where the aliphatic and cycloaliphatic moieties in the eight last-mentioned radicals may be substituted by one or more radicals R$^{13}$;

—C$_1$-C$_6$-alkyl-C(=O)OR$^{15}$, —C$_1$-C$_6$-alkyl-C(=O)N(R$^{14a}$)R$^{14b}$, —C$_1$-C$_6$-alkyl-C(=S)N(R$^{14a}$)R$^{14b}$, —C$_1$-C$_6$-alkyl-C(=NR$^{14}$)N(R$^{14a}$)R$^{14b}$, C$_1$-C$_6$-alkoxy, C$_1$-C$_6$-haloalkoxy, C$_1$-C$_6$-alkylthio, C$_1$-C$_6$-haloalkylthio, —S(O)$_n$R$^{15}$, —S(O)$_n$N(R$^{14a}$)R$^{14b}$, —C(=O)R$^{13}$, —C(=O)OR$^{15}$, —C(=O)N(R$^{14a}$)R$^{14b}$, —C(=S)R$^{13}$, —C(=S)SR$^{15}$, —C(=S)N(R$^{14a}$)R$^{14b}$, —C(=NR$^{14}$)R$^{13}$;

phenyl, optionally substituted with 1, 2, 3 or 4, substituents R$^{16}$; and a 3-, 4-, 5-, 6- or 7-membered saturated, partially unsaturated or maximally unsaturated heterocyclic ring comprising 1, 2, 3 or 4 heteroatoms or heteroatom groups selected from N, O, S, NO, SO and SO$_2$, as ring members, where the heterocyclic ring is optionally substituted with one or more substituents R$^{16}$;

or

R$^{10a}$ and R$^{10b}$ form together with the nitrogen atom they are bonded to a 3-, 4-, 5-, 6-, 7- or 8-membered saturated, partially unsaturated or maximally unsaturated heterocyclic ring, wherein the heterocyclic ring may additionally contain one or two heteroatoms or heteroatom groups selected from N, O, S, NO, SO and SO$_2$, as ring members, where the heterocyclic ring optionally carries one or more substituents selected from halogen, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, C$_3$-C$_8$-cycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$-haloalkynyl, phenyl, optionally substituted with 1, 2, 3, 4 or 5 substituents R$^{16}$, and a 3-, 4-, 5-, 6,- or 7-membered saturated, partially unsaturated or maximally unsaturated heterocyclic ring comprising 1, 2 or 3 heteroatoms or heteroatom groups selected from the group consisting of N, O, S, NO, SO and SO$_2$, as ring members, where the heterocyclic ring optionally carries one or more substituents R$^{16}$;

or R$^{10a}$ and R$^{10b}$ together form a group =C(R$^{13}$)$_2$, =S(O)$_m$(R$^{15}$)$_2$, =S(O)$_m$R$^{15}$N(R$^{14a}$)R$^{14b}$, =NR$^{14}$ or =NOR$^{15}$;

R$^{11}$ is independently selected from the group consisting of halogen, cyano, azido, nitro, —SCN, —SF$_5$, C$_1$-C$_{10}$-alkyl, C$_3$-C$_8$-cycloalkyl, C$_2$-C$_{10}$-alkenyl, C$_2$-C$_{10}$-alkynyl, wherein the four last-mentioned aliphatic and cycloaliphatic radicals may be partially or fully halogenated and/or may be substituted with one or more radicals R$^8$, —OR$^9$, —NR$^{10a}$R$^{10b}$, —S(O)$_n$R$^9$, —Si(R$^{12}$)$_3$;

phenyl, optionally substituted with 1, 2, 3, 4, or 5 substituents selected independently from R$^{16}$; and a 3-, 4-, 5-, 6- or 7-membered saturated, partially unsaturated or maximally unsaturated aromatic heterocyclic ring comprising 1, 2, 3 or 4 heteroatoms or heteroatom groups selected from the group consisting of N, O, S, NO, SO and SO$_2$, as ring members, where the heterocyclic ring is optionally substituted with one or more substituents selected independently from R$^{16}$;

or two R$^{11}$ present on the same ring carbon atom of a saturated or partially unsaturated heterocyclic ring may together form a group =O, =C(R$^{13}$)$_2$; =S; =S(O)$_m$(R$^{15}$)$_2$; =S(O)$_m$R$^{15}$N(R$^{14a}$)R$^{14b}$, —NR$^{14}$, —NOR$^{15}$, or =NN(R$^{14a}$)R$^{14b}$;

or two R$^{11}$ bound on adjacent ring atoms form together with the ring atoms to which they are bound a saturated 3-, 4-, 5-, 6-, 7-, 8- or 9-membered ring, wherein the ring may contain 1 or 2 heteroatoms or heteroatom groups selected from O, S, N, NR$^{14}$, NO, SO and SO$_2$ and/or 1 or 2 groups selected from C=O, C=S and C=NR$^{14}$ as ring members, and wherein the ring may be substituted by one or more radicals selected from the group consisting of halogen, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, C$_3$-C$_8$-cycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$-haloalkynyl, phenyl which may be substituted by 1, 2, 3, 4 or 5 radicals R$^{16}$, and a 3-, 4-, 5-, 6- or 7-membered saturated, partially unsaturated or maximally unsaturated heterocyclic ring containing 1, 2 or 3 heteroatoms or heteroatom groups selected from the group consisting of N, O, S, NO, SO and SO$_2$, as ring members, where the heterocyclic ring may be substituted by one or more radicals R$^{16}$;

each R$^{12}$ is independently selected from the group consisting of hydrogen, halogen, C$_1$-C$_6$-alkyl, C$_1$-C$_6$-haloalkyl, C$_1$-C$_6$-alkoxy, C$_1$-C$_6$-haloalkoxy, C$_2$-C$_6$-alkenyl, C$_2$-C$_6$-haloalkenyl, C$_2$-C$_6$-alkynyl, C$_2$-C$_6$-haloalkynyl, C$_3$-C$_8$-cycloalkyl, C$_3$-C$_8$-halocycloalkyl, C$_1$-C$_6$-alkoxy-C$_1$-C$_6$-alkyl, C$_1$-C$_6$-haloalkoxy-C$_1$-C$_6$-alkyl, and phenyl, optionally substituted with 1, 2, 3, 4, or 5 substituents R$^{16}$;

each R$^{13}$ is independently selected from the group consisting of cyano, nitro, —OH, —SH, —SCN, —SF$_5$, C$_1$-C$_6$-alkoxy, C$_1$-C$_6$-haloalkoxy, C$_1$-C$_6$-alkylthio, C$_1$-C$_6$-haloalkylthio, C$_1$-C$_6$-alkylsulfinyl, C$_1$-C$_6$-haloalkylsulfinyl, C$_1$-C$_6$-alkylsulfonyl, C$_1$-C$_6$-haloalkylsulfonyl, trimethylsilyl, triethylsilyl, tert-butyldimethylsilyl, C$_3$-C$_8$-cycloalkyl which may be unsubstituted, partially or fully halogenated and/or may carry 1 or 2 radicals selected from C$_1$-C$_4$-alkyl, C$_3$-C$_4$-cycloalkyl, C$_1$-C$_4$-alkoxy, C$_1$-C$_4$-haloalkoxy and oxo; phenyl, benzyl, phenoxy, where the phenyl moiety in the three last-mentioned radicals may be unsubstituted or carry 1, 2, 3, 4 or 5 substituents R$^{16}$; and a 3-, 4-, 5-, 6-, or 7-membered saturated, partially unsaturated or maximally unsaturated heterocyclic ring containing 1, 2 or 3 heteroatoms or heteroatom groups selected from the group consisting of N, O, S, NO, SO and SO$_2$, as ring members, where the heterocyclic ring may be substituted by 1, 2 or 3 substituents R$^{16}$;

or two R$^{13}$ present on the same carbon atom of an alkyl, alkenyl, alkynyl or cycloalkyl group may together be =O, =CH(C$_1$-C$_4$-alkyl), =C(C$_1$-C$_4$-alkyl)C$_1$-C$_4$-alkyl, =N(C$_1$-C$_6$-alkyl) or =NO(C$_1$-C$_6$-alkyl);

and

R$^{13}$ as a substituent on a cycloalkyl ring is additionally selected from the group consisting of C$_1$-C$_6$-alkyl, C$_2$-C$_6$-alkenyl and C$_2$-C$_6$-alkynyl, wherein the three last-mentioned aliphatic radicals may be unsubstituted, partially or fully halogenated and/or may carry 1 or 2 substituents selected from CN, $C_3$-$C_4$-cycloalkyl, $C_1$-$C_4$-alkoxy, $C_1$-$C_4$-haloalkoxy and oxo;
and $R^{13}$ in the groups $=C(R^{13})_2$, $-N=C(R^{13})_2$, $-C(=O)R^{13}$, $-C(=S)R^{13}$ and $-C(=NR^{14})R^{13}$ is additionally selected from the group consisting of hydrogen, halogen, $C_1$-$C_6$-alkyl, $C_2$-$C_6$-alkenyl and $C_2$-$C_6$-alkynyl, wherein the three last-mentioned aliphatic radicals may be unsubstituted, partially or fully halogenated and/or may carry 1 or 2 radicals selected from CN, $C_3$-$C_4$-cycloalkyl, $C_1$-$C_4$-alkoxy, $C_1$-$C_4$-haloalkoxy and oxo;

each $R^{14}$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from oxo, CN, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_3$-$C_4$-cycloalkyl which may be substituted by 1 or 2 substituents selected from halogen and cyano;

$C_3$-$C_8$-cycloalkyl which may be unsubstituted, partially or fully halogenated and/or may carry 1 or 2 radicals selected from oxo $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_3$-$C_4$-cycloalkyl, $C_3$-$C_4$-cycloalkyl-$C_1$-$C_4$-alkyl-, where the cycloalkyl moiety in the two last-mentioned radicals may be substituted by 1 or 2 substituents selected from halogen and cyano;

phenyl, benzyl, pyridyl, phenoxy, wherein the cyclic moieties in the four last-mentioned radicals may be unsubstituted or carry 1, 2 or 3 substituents selected from halogen, $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl; and a 3-, 4-, 5- or 6-membered saturated, partially unsaturated or maximally unsaturated heterocyclic ring comprising 1 or 2 heteroatoms or heteroatom groups selected from the group consisting of N, O, S, NO, SO and $SO_2$, as ring members, where the heterocyclic ring is optionally substituted with one or more substituents $R^{16}$;

$R^{14a}$ and $R^{14b}$, independently of each other, have one of the meanings given for $R^{14}$; or $R^{14a}$ and $R^{14b}$, together with the nitrogen atom to which they are bound, form a 3-, 4-, 5-, 6- or 7-membered saturated, partially unsaturated or maximally unsaturated heterocyclic ring, wherein the heterocyclic ring may additionally contain 1 or 2 heteroatoms or heteroatom groups selected from the group consisting of N, O, S, NO, SO and $SO_2$, as ring members, where the heterocyclic ring optionally carries one or more substituents selected from halogen, $C_1$-$C_4$-alkyl, $C_1$-$C_4$-haloalkyl, $C_1$-$C_4$-alkoxy and $C_1$-$C_4$-haloalkoxy;

or $R^{14a}$ and $R^{14}$ or $R^{14b}$ and $R^{14}$, together with the nitrogen atoms to which they are bound in the group $-C(=NR^{14})N(R^{14a})R^{14b}$, form a 3-, 4-, 5-, 6- or 7-membered partially unsaturated or maximally unsaturated heterocyclic ring, wherein the heterocyclic ring may additionally contain 1 or 2 heteroatoms or heteroatom groups selected from the group consisting of N, O, S, NO, SO and $SO_2$, as ring members, where the heterocyclic ring optionally carries one or more substituents selected from halogen, $C_1$-$C_4$-haloalkyl, $C_1$-$C_4$-alkoxy and $C_1$-$C_4$-haloalkoxy;

each $R^{15}$ is independently selected from the group consisting of hydrogen, cyano, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from $C_3$-$C_4$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl and oxo;

$C_3$-$C_8$-cycloalkyl which may be unsubstituted, partially or fully halogenated and/or may carry 1 or 2 radicals selected from $C_1$-$C_4$-alkyl, $C_3$-$C_4$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl and oxo;

phenyl, benzyl, pyridyl and phenoxy, wherein the four last-mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl;

each $R^{16}$ is independently selected from the group consisting of halogen, nitro, cyano, $-OH$, $-SH$, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, trimethylsilyl, triethylsilyl, tert-butyldimethylsilyl;

$C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from $C_3$-$C_4$-cycloalkyl, $C_1$-$C_4$-alkoxy, $C_1$-$C_4$-haloalkoxy and oxo;

$C_3$-$C_8$-cycloalkyl which may be unsubstituted, partially or fully halogenated and/or may carry 1 or 2 radicals selected from $C_1$-$C_4$-alkyl, $C_3$-$C_4$-cycloalkyl, $C_1$-$C_4$-alkoxy, $C_1$-$C_4$-haloalkoxy and oxo;

phenyl, benzyl, pyridyl and phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl;

or two $R^{16}$ present together on the same atom of a saturated or partially unsaturated ring may be $=O$, $=S$, $=N(C_1$-$C_6$-alkyl), $=NO(C_1$-$C_6$-alkyl), $=CH(C_1$-$C_4$-alkyl) or $=C(C_1$-$C_4$-alkyl)$C_1$-$C_4$-alkyl;

or two $R^{16}$ on two adjacent carbon atoms form together with the carbon atoms they are bonded to a 4-, 5-, 6-, 7- or 8-membered saturated, partially unsaturated or maximally unsaturated ring, wherein the ring may contain 1 or 2 heteroatoms or heteroatom groups selected from the group consisting of N, O, S, NO, SO and $SO_2$, as ring members, and wherein the ring optionally carries one or more substituents selected from halogen, $C_1$-$C_4$-haloalkyl, $C_1$-$C_4$-alkoxy and $C_1$-$C_4$-haloalkoxy;

each n is independently 0, 1 or 2; and each m is independently 0 or 1;

an N-oxide, stereoisomer or agriculturally or veterinarily acceptable salt thereof.

2. The compound as claimed in claim 1, where A is $A^1$ and $A^1$ is $-C(=NR^6)R^8$.

3. The compound as claimed in claim 2, where $R^6$ in $-C(=NR^6)R^8$ is selected from hydrogen, cyano, $C_3$-$C_8$- cycloalkyl, $C_2$-$C_{10}$-alkenyl, $C_2$-$C_{10}$-alkynyl, wherein the four last-mentioned aliphatic and cycloaliphatic radicals each independently may be partially or fully halogenated and/or may be substituted with 1, 2, 3, 4, 5 or 6 substituents $R^8$; —$OR^9$ and —$NR^{10a}R^{10b}$.

4. The compound as claimed in claim 3, where $R^6$ in —C(=$NR^6$)$R^8$ is selected from —$OR^9$ and —$NR^{10a}R^{10b}$.

5. The compound as claimed in claim 2, where $R^9$ is selected from hydrogen, $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl and $C_2$-$C_6$-haloalkynyl.

6. The compound as claimed in claim 2, where $R^6$ in —C(=$NR^6$)$R^8$ is
—$NR^{10a}R^{10b}$, where
$R^{10a}$ and $R^{10b}$, independently of each other, are selected from the group consisting of hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkylcarbonyl, $C_1$-$C_6$-haloalkylcarbonyl,
—C(=O)$OR^{15}$, —C(=O)N($R^{14a}$)$R^{14b}$, —C(=S)N($R^{14a}$)$R^{14b}$, phenyl which is optionally substituted with 1, 2, 3 or 4, substituents $R^{16}$, and a 3-, 4-, 5-, 6- or 7-membered saturated, partially unsaturated or maximally unsaturated heterocyclic ring comprising 1, 2, 3 or 4 heteroatoms or heteroatom groups selected from N, O, S, NO, SO and $SO_2$, as ring members, where the heterocyclic ring is optionally substituted with one or more substituents $R^{16}$;
or $R^{10a}$ and $R^{10b}$ form together with the nitrogen atom they are bonded to a 3-, 4-, 5-, 6-, 7- or 8-membered saturated, partially unsaturated or maximally unsaturated heterocyclic ring, wherein the heterocyclic ring may additionally contain one or two heteroatoms or heteroatom groups selected from the group consisting of N, O, S, NO, SO and $SO_2$, as ring members, where the heterocyclic ring optionally carries one or more substituents selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl and $C_2$-$C_6$-haloalkynyl.

7. The compound as claimed in claim 6, where
$R^{10a}$ is selected from hydrogen, $C_1$-$C_6$-alkyl and $C_1$-$C_6$-haloalkyl; and
$R^{10b}$ is selected from $C_1$-$C_6$-alkyl, $C_1$-$C_6$-haloalkyl, $C_1$-$C_6$-alkylcarbonyl, $C_1$-$C_6$-haloalkylcarbonyl, —C(=O)$OR^{15}$, —C(=O)N($R^{14a}$)$R^{14b}$, —C(=S)N($R^{14a}$)$R^{14b}$, phenyl which is optionally substituted with 1, 2, 3 or 4, substituents $R^{16}$, and a 5- or 6-membered heteroaromatic ring comprising 1, 2 or 3 heteroatoms selected from N, O and S, as ring members, where the heteroaromatic ring is optionally substituted with one or more substituents $R^{16}$.

8. The compound as claimed in claim 6, where
$R^{14a}$ is selected from hydrogen, $C_1$-$C_6$-alkyl and $C_1$-$C_6$-haloalkyl; and
$R^{14b}$ is selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_3$-$C_6$-cycloalkyl-$C_1$-$C_4$-alkyl-, $C_1$-$C_6$-alkyl substituted with a CN group, $C_1$-$C_6$-alkoxyl, $C_1$-$C_6$-haloalkoxy, phenyl which is optionally substituted with 1, 2, or 3, substituents each independently selected from the group consisting of halogen, $C_1$-$C_4$-alkyl, $C_1$-$C_4$-haloalkyl, $C_1$-$C_4$-alkoxy, and $C_1$-$C_4$-haloalkoxy; and a heterocyclic ring selected from rings of formulae E-1 to E-34 and E-43 to E-51

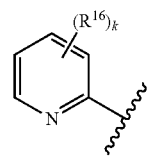 E-1

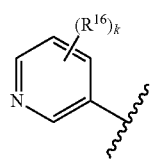 E-2

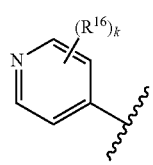 E-3

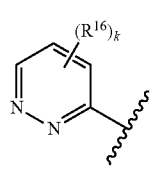 E-4

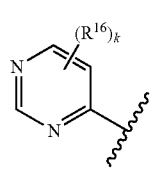 E-5

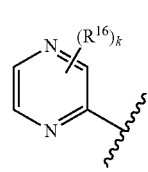 E-6

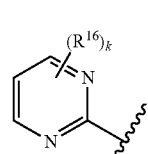 E-7

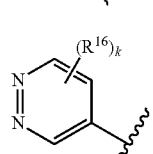 E-8

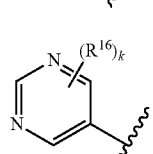 E-9

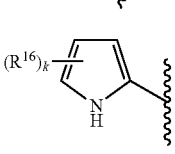 E-10

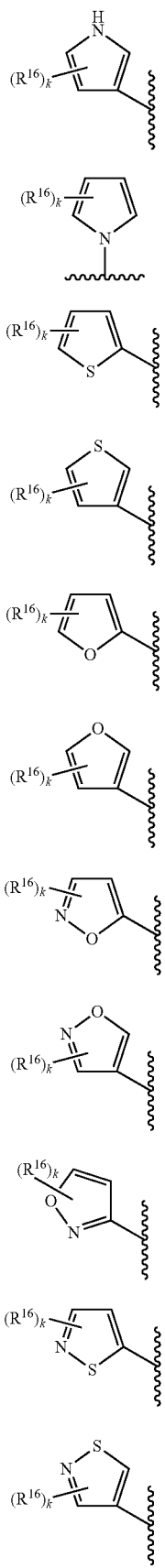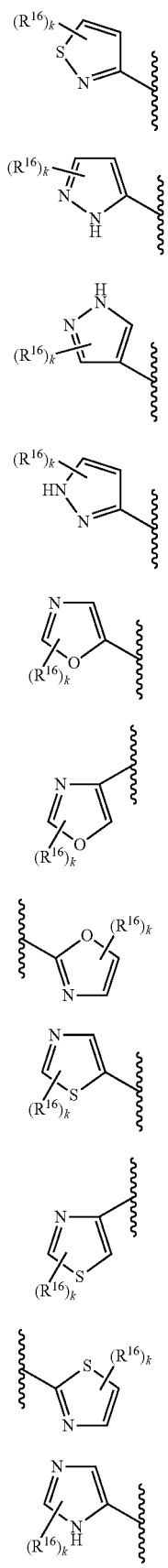

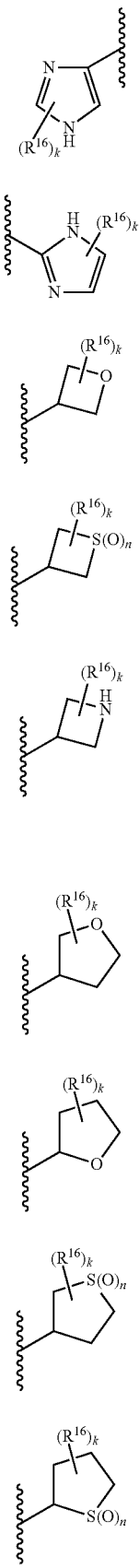

wherein
k is 0, 1, 2 or 3,
n is 0, 1 or 2; and
each $R^{16}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or
two $R^{16}$ present on the same carbon atom of a saturated ring may form together =O or =S.

9. The compound as claimed in claim 4, where $R^6$ in —C(=NR$^6$)R$^8$ is
—NR$^{10a}$R$^{10b}$, where
$R^{10a}$ and $R^{10b}$, independently of each other, are selected from the group consisting of hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkylcarbonyl, $C_1$-$C_6$-haloalkylcarbonyl,
—C(=O)N(R$^{14a}$)R$^{14b}$, —C(=S)N(R$^{14a}$)R$^{14b}$, phenyl which is optionally substituted with 1, 2, 3 or 4, substituents $R^{16}$, and a 3-, 4-, 5-, 6- or 7-membered saturated, partially unsaturated or maximally unsaturated heterocyclic ring comprising 1, 2, 3 or 4 heteroatoms or heteroatom groups selected from the group consisting of N, O, S, NO, SO and SO$_2$, as ring members, where the heterocyclic ring is optionally substituted with one or more substituents $R^{16}$;
or $R^{10a}$ and $R^{10b}$ form together with the nitrogen atom they are bonded to a 3-, 4-, 5-, 6-, 7- or 8-membered saturated, partially unsaturated or maximally unsaturated heterocyclic ring, wherein the heterocyclic ring may additionally contain one or two heteroatoms or heteroatom groups selected from N, O, S, NO, SO and SO$_2$, as ring members, where the heterocyclic ring optionally carries one or more substituents selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl and $C_2$-$C_6$-haloalkynyl.

10. The compound as claimed in claim 9, where
$R^{10a}$ is selected from hydrogen, $C_1$-$C_6$-alkyl and $C_1$-$C_6$-haloalkyl; and
$R^{10b}$ is selected from —C(=O)N(R$^{14a}$)R$^{14b}$, —C(=S)N(R$^{14a}$)R$^{14b}$, phenyl which is optionally substituted with 1, 2, 3 or 4, substituents $R^{16}$, and a 5- or 6-membered heteroaromatic ring comprising 1, 2 or 3 heteroatoms selected from the group consisting of N, O and S, as ring members, where the heteroaromatic ring is optionally substituted with one or more substituents $R^{16}$.

11. The compound as claimed in claim 9, where

R$^{14a}$ is selected from the group consisting of hydrogen, C$_1$-C$_6$-alkyl and C$_1$-C$_6$-haloalkyl; and R$^{14b}$ is selected from the group consisting of hydrogen, C$_1$-C$_6$-alkyl, C$_1$-C$_6$-haloalkyl, C$_2$-C$_6$-alkenyl, C$_2$-C$_6$-haloalkenyl, C$_3$-C$_6$-cycloalkyl, C$_3$-C$_6$-halocycloalkyl, C$_1$-C$_6$-alkyl substituted with a CN group, phenyl which is optionally substituted with 1, 2, or 3, substituents each independently selected from the group consisting of halogen, C$_1$-C$_6$-alkyl, C$_1$-C$_6$-alkoxy, C$_1$-C$_6$-haloalkoxy and (C$_1$-C$_6$-alkoxy)carbonyl; and a heterocyclic ring selected from rings of formulae E-1 to E-34 and E-43 to E-51

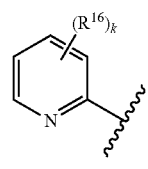
E-1

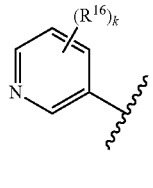
E-2

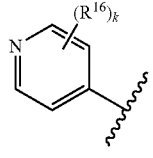
E-3

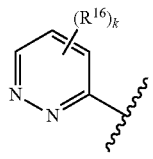
E-4

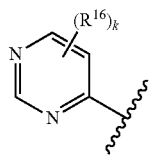
E-5

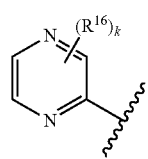
E-6

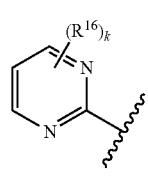
E-7

-continued

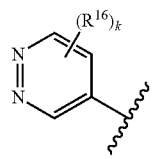
E-8

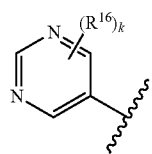
E-9

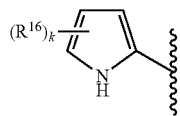
E-10

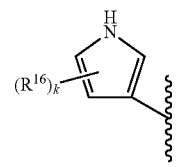
E-11

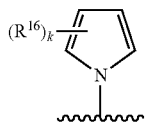
E-12

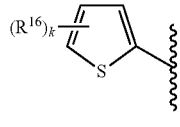
E-13

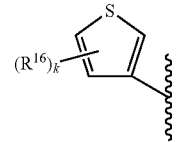
E-14

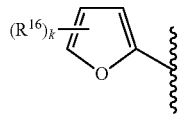
E-15

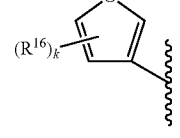
E-16

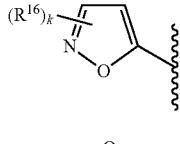
E-17

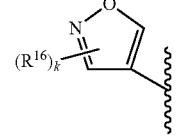
E-18

E-19 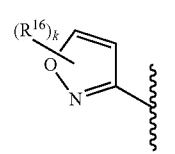
E-20 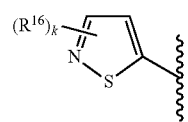
E-21 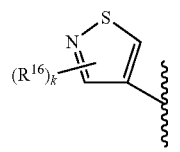
E-22 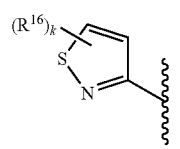
E-23 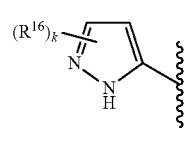
E-24 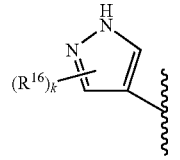
E-25 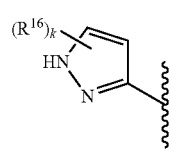
E-26 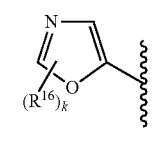
E-27 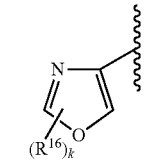
E-28 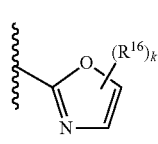
E-29 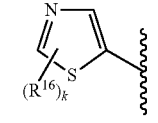
E-30 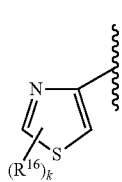
E-31 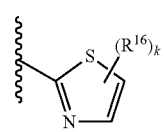
E-32 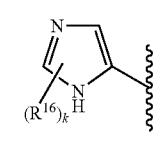
E-33 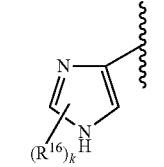
E-34 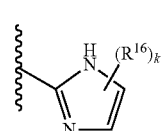
E-43 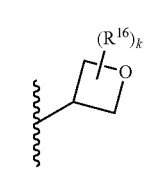
E-44 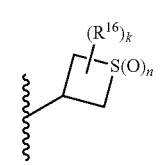
E-45 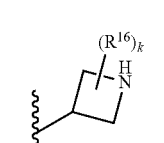
E-46 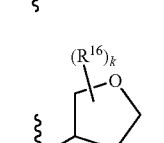
E-47 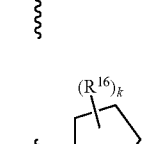

-continued

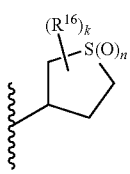
E-48

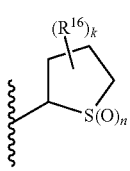
E-49

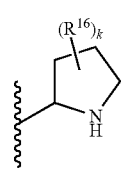
E-50

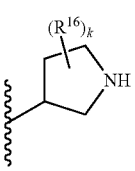
E-51 wherein
k is 0, 1, 2 or 3,
n is 0, 1 or 2; and
each $R^{16}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or
two $R^{16}$ present on the same carbon atom of a saturated ring may form together =O or =S.

12. The compound as claimed in claim 2, where $R^8$ in —C(=NR$^6$)R$^8$ as a meaning for A$^1$ is selected from hydrogen and NR$^{10a}$R$^{10b}$.

13. The compound as claimed in claim 1, where A is A$^3$ and in A$^3$ R$^{7a}$ and R$^{7b}$ are independently of each other selected from hydrogen, $C_1$-$C_4$-alkyl and $C_1$-$C_4$-haloalkyl.

14. The compound as claimed in claim 1, where in A$^3$
$R^5$ is selected from the group consisting of hydrogen, $C_1$-$C_6$-alkyl, $C_3$-$C_6$-cycloalkyl, $C_2$-$C_6$-alkenyl, $C_2$-$C_6$-alkynyl, wherein the four last-mentioned aliphatic and cycloaliphatic radicals may be partially or fully halogenated and/or may be substituted with one or more substituents $R^8$; and
$R^6$ is selected from hydrogen, $C_1$-$C_6$-alkyl, $C_3$-$C_6$-cycloalkyl, $C_2$-$C_6$-alkenyl, $C_2$-$C_6$-alkynyl, wherein the four last-mentioned aliphatic and cycloaliphatic radicals may be partially or fully halogenated and/or may be substituted by one or more substituents $R^8$, —OR$^9$, —NR$^{10a}$R$^{10b}$, —S(O)$_n$R$^9$, —C(=O)NR$^{10a}$N(R$^{10a}$R$^{10b}$), —C(=O)R$^8$,
and a 3-, 4-, 5-, 6- or 7-membered saturated, partially unsaturated or maximally unsaturated heteromonocyclic or heterobicyclic ring containing 1, 2, 3 or 4 heteroatoms or heteroatom groups independently selected from N, O, S, NO, SO and SO$_2$, as ring members, where the heteromonocyclic or heterobicyclic ring may be substituted with one or more substituents $R^{11}$;
or
$R^5$ and $R^6$, together with the nitrogen atom to which they are bound, form a 3-, 4-, 5- or 6-membered saturated, partially unsaturated or maximally unsaturated heterocyclic ring, where the ring may further contain 1, 2, 3 or 4 heteroatoms or heteroatom-containing groups selected from the group consisting of O, S, N, SO, SO$_2$, C=O and C=S as ring members, wherein the heterocyclic ring may be substituted with 1, 2, 3, 4 or 5 substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the aliphatic or cycloaliphatic moieties in the twelve last-mentioned radicals may be substituted by one or more radicals $R^8$, and phenyl which may be substituted with 1, 2, 3, 4 or 5 substituents $R^{11}$;
or
$R^5$ and $R^6$ together form a group =C(R$^8$)$_2$, =S(O)$_m$(R$^9$)$_2$, =NR$^{10a}$ or =NOR$^9$.

15. The compound as claimed in claim 14, where
$R^5$ is selected from the group consisting of hydrogen, $C_1$-$C_4$-alkyl, $C_2$-$C_3$-alkynyl, —CH$_2$—CN and $C_1$-$C_6$-alkoxy-methyl; and
$R^6$ is —C(=O)R$^8$.

16. The compound as claimed in claim 14, where $R^8$ is selected from the group consisting of $C_1$-$C_6$-alkyl, $C_1$-$C_6$-haloalkyl, $C_3$-$C_8$-cycloalkyl, $C_3$-$C_8$-halocycloalkyl, where the aliphatic and cycloaliphatic moieties in the four last-mentioned radicals may be substituted by one or more radicals $R^{13}$;
—OR$^9$, —S(O)$_n$R$^9$, —N(R$^{10a}$)R$^{10b}$,
phenyl, optionally substituted with 1, 2, 3, 4 or 5 substituents $R^{16}$, and a 3-, 4-, 5- or 6-membered saturated, partially unsaturated or maximally unsaturated heterocyclic ring comprising 1, 2 or 3 heteroatoms or heteroatom groups selected from the group consisting of N, O, S, NO, SO and SO$_2$, as ring members, where the heterocyclic ring is optionally substituted with one or more substituents $R^{16}$.

17. The compound as claimed in claim 16, where $R^8$ is selected from the group consisting of $C_1$-$C_6$-alkyl, $C_1$-$C_6$-haloalkyl, $C_1$-$C_4$-alkyl substituted by one radical $R^{13}$, $C_3$-$C_8$-cycloalkyl, $C_3$-$C_8$-halocycloalkyl, —N(R$^{10a}$)R$^{10b}$, phenyl which is optionally substituted with 1, 2, 3, 4 or 5 substituents each independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; and a heterocyclic ring selected from rings of formulae E-1 to E-51,

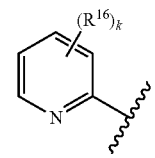
E-1

-continued
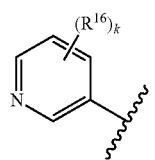   E-2
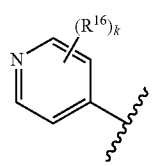   E-3
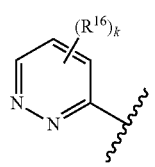   E-4
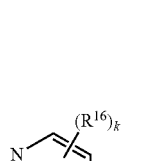   E-5
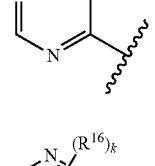   E-6
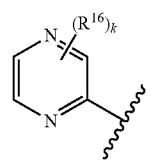   E-7
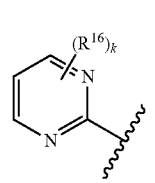   E-8
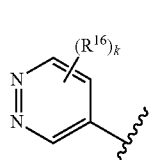   E-9
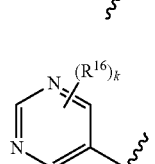
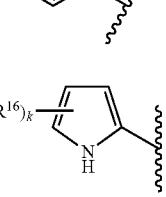   E-10
-continued
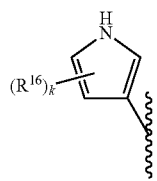   E-11
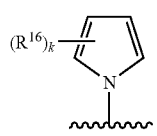   E-12
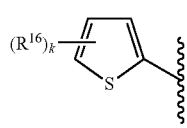   E-13
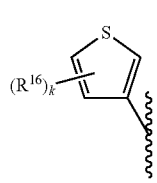   E-14
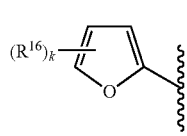   E-15
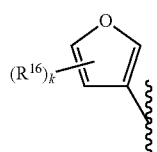   E-16
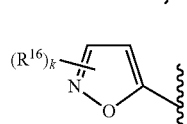   E-17
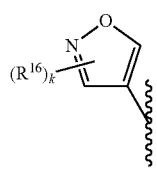   E-18
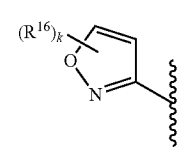   E-19
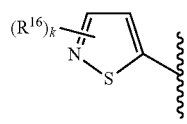   E-20

| | |
|---|---|
| 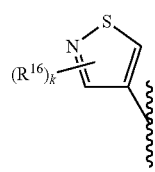 E-21 | 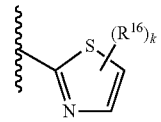 E-31 |
| 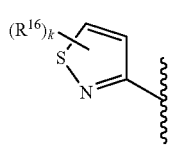 E-22 | 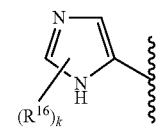 E-32 |
| 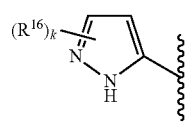 E-23 | 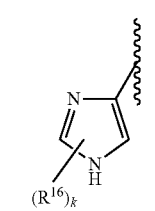 E-33 |
| 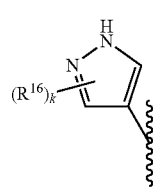 E-24 | 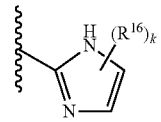 E-34 |
| 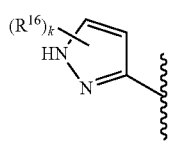 E-25 | 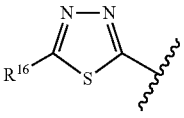 E-35 |
| 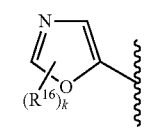 E-26 | 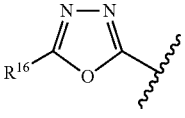 E-36 |
| 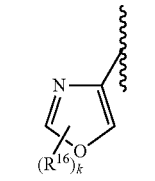 E-27 | 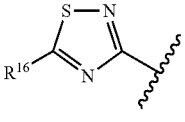 E-37 |
| 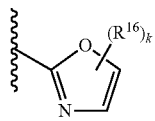 E-28 | 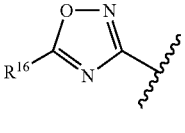 E-38 |
| 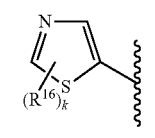 E-29 | 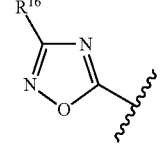 E-39 |
| 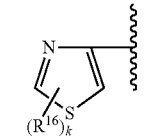 E-30 | 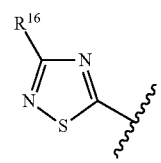 E-40 |
| | 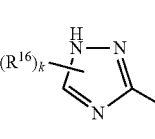 E-41 |

-continued

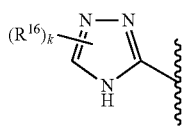
E-42

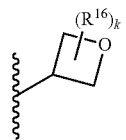
E-43

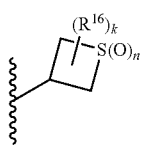
E-44

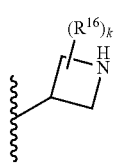
E-45

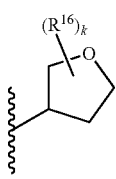
E-46

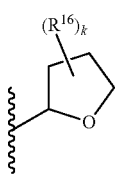
E-47

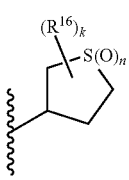
E-48

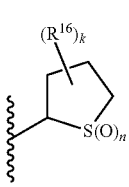
E-49

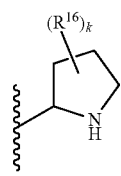
E-50

-continued

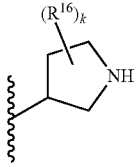
E-51 wherein
k is 0, 1, 2 or 3,
n is 0, 1 or 2;
$R^{10a}$ and $R^{10b}$, independently of each other, are selected from the group consisting of hydrogen, $C_1$-$C_4$-alkyl, $C_1$-$C_4$-haloalkyl and $C_3$-$C_6$-cycloalkyl; and
$R^{13}$ is selected from CN, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl and a heterocyclic ring selected from rings of formulae E-1 to E-51; and
each $R^{16}$ as a substituent on heterocyclic rings of formulae E-1 to E-51 is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or two $R^{16}$ present on the same carbon atom of a saturated heterocyclic ring may form together =O or =S.

18. The compound as claimed in claim 14, where $R^5$ and $R^6$ are hydrogen.

19. The compound as claimed in claim 1, where $B^1$, $B^2$ and $B^3$ are $CR^2$.

20. The compound as claimed in claim 19, where $B^1$ and $B^3$ are $CR^2$, where $R^2$ is not hydrogen, and $B^2$ is $CR^2$.

21. The compound as claimed in claim 1, where $R^2$ is selected from the group consisting of hydrogen, halogen, cyano, azido, nitro, —SCN, —SF$_5$, $C_3$-$C_8$-cycloalkyl, $C_2$-$C_6$-alkenyl, $C_2$-$C_6$-alkynyl, wherein the four last mentioned aliphatic and cycloaliphatic radicals may be partially or fully halogenated and/or may be substituted by one or more radicals $R^8$, —$OR^9$, —$S(O)_nR^9$ and —$NR^{10a}R^{10b}$.

22. The compound as claimed in claim 21, where $R^2$ is selected from the group consisting of hydrogen, halogen and $C_1$-$C_2$-haloalkyl.

23. The compound as claimed in claim 1, where $G^1$, $G^2$, $G^3$ and $G^4$ are $CR^4$; or $G^1$, $G^3$ and $G^4$ are $CR^4$ and $G^2$ is N; or $G^2$, $G^3$ and $G^4$ are $CR^4$ and $G^1$ is N.

24. The compound as claimed in claim 23, where $G^1$, $G^3$ and $G^4$ are CH and $G^2$ is $CR^4$.

25. The compound as claimed in claim 23, where $G^1$ is N or CH, $G^3$ and $G^4$ are CH and $G^2$ is $CR^4$.

26. The compound as claimed in claim 1, where $R^4$ is selected from the group consisting of hydrogen, halogen, cyano, $C_1$-$C_4$-alkyl, $C_1$-$C_4$-haloalkyl, $C_3$-$C_5$-cycloalkyl, $C_3$-$C_5$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio and $C_1$-$C_4$-haloalkylthio.

27. The compound as claimed in claim 1, where $R^{3a}$ and $R^{3b}$ are selected, independently of each other, from hydrogen and halogen.

28. An agricultural composition comprising at least one compound of the formula I, as defined in claim 1, a stereoisomer thereof or at least one agriculturally acceptable salt thereof, and at least one inert liquid and/or solid agriculturally acceptable carrier.

29. A veterinary composition comprising at least one compound of the formula I, as defined in claim 1, a stereoisomer thereof and/or at least one veterinarily acceptable salt thereof, and at least one inert liquid and/or solid veterinarily acceptable carrier.

30. A method for controlling invertebrate pests which method comprises treating the pests, their food supply, their habitat or their breeding ground or a plant, plant propagation material, soil, area, material or environment in which the pests are growing or may grow, or the materials, plants, plant propagation material, soils, surfaces or spaces to be protected from invertebrate pest attack or infestation with a pesticidally effective amount of at least one imine compound of the formula I as defined in claim 1, a stereoisomer thereof and/or at least one agriculturally acceptable salt thereof.

31. The method as claimed in claim 30, for protecting plants from attack or infestation by invertebrate pests, which method comprises treating the plants with a pesticidally effective amount of at least one compound of the formula I, a stereoisomer thereof and/or at least one agriculturally acceptable salt thereof.

32. The method as claimed in claim 30, for protecting plant propagation material and/or the plants which grow therefrom from attack or infestation by invertebrate pests, which method comprises treating the plant propagation material with a pesticidally effective amount of at least one compound of the formula I, a stereoisomer thereof and/or at least one agriculturally acceptable salt thereof.

33. Plant propagation material treated with at least one compound of the formula I as defined in claim 1, a stereoisomer thereof and/or at least one agriculturally acceptable salt thereof.

* * * * *